United States Patent
Bardelli et al.

(10) Patent No.: US 9,206,467 B2
(45) Date of Patent: Dec. 8, 2015

(54) TYROSINE KINOME

(71) Applicant: The Johns Hopkins University, Baltimore, MD (US)

(72) Inventors: Alberto Bardelli, Turin (IT); D. Williams Parsons, Bellaire, TX (US); Victor Velculescu, Dayton, MD (US); Kenneth W. Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/746,376

(22) Filed: Jan. 22, 2013

(65) Prior Publication Data

US 2013/0157299 A1    Jun. 20, 2013

Related U.S. Application Data

(62) Division of application No. 12/705,760, filed on Feb. 15, 2010, now Pat. No. 8,394,598, which is a division of application No. 10/544,536, filed as application No. PCT/US2004/004452 on Feb. 18, 2004, now abandoned.

(60) Provisional application No. 60/473,895, filed on May 29, 2003, provisional application No. 60/448,537, filed on Feb. 21, 2003.

(51) Int. Cl.
| | |
|---|---|
| *G01N 33/15* | (2006.01) |
| *C12Q 1/48* | (2006.01) |
| *C12N 9/12* | (2006.01) |
| *C12Q 1/68* | (2006.01) |
| *G01N 33/574* | (2006.01) |
| *C12Q 1/02* | (2006.01) |

(52) U.S. Cl.
CPC .............. *C12Q 1/485* (2013.01); *C12N 9/1205* (2013.01); *C12Q 1/025* (2013.01); *C12Q 1/6809* (2013.01); *C12Q 1/6827* (2013.01); *C12Q 1/6886* (2013.01); *G01N 33/574* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,242,212 B1 | 6/2001 | Croce et al. | |
| 6,593,126 B2 * | 7/2003 | Hu et al. | 435/252.3 |
| 6,861,239 B1 * | 3/2005 | Blumenberg et al. | 435/194 |

OTHER PUBLICATIONS

Burkhardt et al, Current Protocol, online posting May 2001.*
Soung et al, Dig and Liver Dis 38:283-286, IDS item #5, Jan. 22, 2013).*
Martini et al (Can Res 73: 1912-21, 2013.*
Bardelli et al, Science 300:949, May 2003.*
Dickson et al., "Tyrosine Kinase Signalling in Breast Cancer Fibroblast Growth Gactors and Their Receptors," Breast Cancer Research, 2000, vol. 3, No. 2, pp. 191-196, especially p. 192.
Laura et al., "The Kinase Homology Domain of Retinal Guanylyl Cyclases 1 and 2 Specifies the Affinity and Cooperativity of Interaction With Guanylyl Cyclase Activating Protein-2," Biochemistry, Aug. 11, 1998, vol. 37, Issue 32, pp. 11264-11271, especially p. 11270.
Eguchi et al., Blood 1999, vol. 93:1355-1363.
Bardelli, et al, "Mutational Analysis of the Tyrosine Kinome in Colorectal Cancers," Science vol. 300, May 9, 2003, pp. 949,plus supporting material.
Soung, et al., "Kinase domain mutation of MLK4 gene is uncommon in gastric and hepatocellular carcinomas," Letters to the Editor, Digestive and Liver Disease 38 (2006), pp. 283-286.
Shao, et al, "No mutations in the tyrosine kinases of human hepatic, pancreatic, and gastric cancer cell lines," Digestive & Liver Dis. 38, Letters to the Editor, Nov. 2005, p. 283.

* cited by examiner

*Primary Examiner* — Lei Yao
(74) *Attorney, Agent, or Firm* — Banner & Witcoff, Ltd.

(57) ABSTRACT

Protein kinases are important signaling molecules involved in tumorigenesis. Mutational analysis of the human tyrosine kinase gene family (98 genes) identified somatic alterations in ~20% of colorectal cancers, with the majority of mutations occurring in NTRK3, FES, GUCY2F and a previously uncharacterized tyrosine kinase gene called MCCK/MLK4. Most alterations were in conserved residues affecting key regions of the kinase domain. These data represent a paradigm for the unbiased analysis of signal transducing genes in cancer and provide useful targets for therapeutic intervention.

28 Claims, 3 Drawing Sheets

A.

```
Human NTRK3    685  CLVGANLLVKIGDFGMSRDVYS-TDYYRVGGHT--MLPIRWMPPESIMYRK---FTTE
Pig NTRK3           ............................................................
Rat NTRK3           ............................................................
Chicken NTRK3       ............................................................
Drosophila NTRK3    ...NEG.V...S....L..I..-S....QSKS-L.V....S..L.G.....
C. elegans NTRK3    ...DTRTI..A....LM.TS.G-S..KMLHRS--WM.V...SK.A.EQGR----.SEA
Human MET           .MLDEKFT...A....LA...MD-KE..S.HNK.GAK..VK..AL.LQTQ.----.K
Human BRAF          IFLHED.T.....AT.KSRWSGSHQFEQLSGSI.----.A..V.RMQDKNPYSFQ
```

B.

```
Human FES      694  KNVLKISDFGMSR--EE-ADGV-YAASGGL-RQVPVKWTAPEALNYGR---YSSESDVWSFGILLWETFSLGAS
Feline FES          .................I-.........................................
Mouse FES           .................I-.A........................................
Rat FES             N.T...............-Q.-DG....-S.S...-K.I I............
Chicken FES         ..T...............-Q.-E....-ST.-M-K.I........................VC
Drosophila FES      EHSV............-EE----IV.D.M-K.I.........F.K---.T.LC....Y...M..I..K.DT
Human NTRK2         NLLV..G.........-DVYSTDY--RV..H-TML.IR.MP..SIM.-.K--FTT......L.VV...I.TY.KQ
Human EPHA3         NL.C.V...L..VL.DDPEAA-.TTR.--KI.IR..S.--KI..-K--FT.A.....Y..V...VM.Y.ER
Human MET           .FTV..A....LA.EM--DKEY..SVHNKTGAKL....L.S.Q-TQK--FTTK......VV...LMTR..P
Human BRAF          DLTV..G.....AT.KSRWSGSHQFEQLS.----SIL.M..VIRMQDKNP..FQ....YA...V.Y.LMT-.QL
```

C.

```
Human MCCK     243  FVPILHRDLKSSNILLLEKIEHDDICNKTLKITDFGLA------REWHRTTKMST-AGTYAWMAPEVIKS
Mouse MCCK          V.............................................R..A-.......R.
Anopholes MCCK      PISVI......V.IS.S.Q.GHLL...........AY..R..A-..F..P.....
Drosophila MCCK     PMS.I......V.IY.A..GNHLQQ............MYN.QR..A-.....P....SV
Human MET           SKKFV...AAR.CM.D..F-----.V..A......RDM.DK.YYSVHNKTGAKLPVK...L.SLQT
Human BRAF          --S.I.....N..F.H.DL------.V..G..T.K--SR.SGSHQFEQLS.SIL......RM
```

Fig. 3.

SEQUENCE LISTING

<160> NUMBER OF SEQ ID NOS: 2191

<210> SEQ ID NO 1
<211> LENGTH: 52
<212> TYPE: PRT
<213> ORGANISM: Homo sapiens

<400> SEQUENCE: 1

Cys Leu Val Gly Ala Asn Leu Leu Val Lys Ile Gly Asp Phe Gly Met
1               5                   10                  15

Ser Arg Asp Val Tyr Ser Thr Asp Tyr Tyr Arg Val Gly Gly His Thr
            20                  25                  30

Met Leu Pro Ile Arg Trp Met Pro Pro Glu Ser Ile Met Tyr Arg Lys
        35                  40                  45

Phe Thr Thr Glu
    50

<210> SEQ ID NO 2
<211> LENGTH: 52
<212> TYPE: PRT
<213> ORGANISM: Drosophila melanogaster

<400> SEQUENCE: 2

Cys Leu Val Asn Glu Gly Leu Val Val Lys Ile Ser Asp Phe Gly Leu
1               5                   10                  15

Ser Arg Asp Ile Tyr Ser Ser Asp Tyr Tyr Arg Val Gln Ser Lys Ser
            20                  25                  30

Leu Leu Pro Val Arg Trp Met Pro Ser Glu Ser Ile Leu Tyr Gly Lys
        35                  40                  45

Phe Thr Thr Glu
    50

<210> SEQ ID NO 3
<211> LENGTH: 52
<212> TYPE: PRT
<213> ORGANISM: Caenorhabditis elegans

<400> SEQUENCE: 3

Cys Leu Val Gly Asp Thr Arg Thr Ile Lys Ile Ala Asp Phe Gly Leu
1               5                   10                  15

Met Arg Thr Ser Tyr Gly Ser Asp Tyr Tyr Lys Met Leu His Arg Ser
            20                  25                  30

Trp Met Pro Val Arg Trp Met Ser Lys Glu Ala Ile Glu Gln Gly Arg
        35                  40                  45

Phe Ser Glu Ala
    50

<210> SEQ ID NO 4
<211> LENGTH: 54
<212> TYPE: PRT
<213> ORGANISM: Homo sapiens

<400> SEQUENCE: 4

Cys Met Leu Asp Glu Lys Phe Thr Val Lys Val Ala Asp Phe Gly Leu
1               5                   10                  15

Ala Arg Asp Met Tyr Asp Lys Glu Tyr Tyr Ser Val His Asn Lys Thr
            20                  25                  30

Gly Ala Lys Leu Pro Val Lys Trp Met Ala Leu Glu Ser Leu Gln Thr
        35                  40                  45

Gln Lys Phe Thr Thr Lys
    50

<210> SEQ ID NO 5
<211> LENGTH: 55
<212> TYPE: PRT
<213> ORGANISM: Homo sapiens

<400> SEQUENCE: 5

Ile Phe Leu His Glu Asp Leu Thr Val Lys Ile Gly Asp Phe Gly Leu
1               5                   10                  15

Ala Thr Val Lys Ser Arg Trp Ser Gly Ser His Gln Phe Glu Gln Leu
            20                  25                  30

Ser Gly Ser Ile Leu Trp Met Ala Pro Glu Val Ile Arg Met Gln Asp
        35                  40                  45

Lys Asn Pro Tyr Ser Phe Gln
    50                  55

<210> SEQ ID NO 6
<211> LENGTH: 66
<212> TYPE: PRT
<213> ORGANISM: Homo sapiens

<400> SEQUENCE: 6

Lys Asn Val Leu Lys Ile Ser Asp Phe Gly Met Ser Arg Glu Glu Ala
1               5                   10                  15

Asp Gly Val Tyr Ala Ala Ser Gly Gly Leu Arg Gln Val Pro Val Lys
            20                  25                  30

Trp Thr Ala Pro Glu Ala Leu Asn Tyr Gly Arg Tyr Ser Ser Glu Ser
        35                  40                  45

Asp Val Trp Ser Phe Gly Ile Leu Leu Trp Glu Thr Phe Ser Leu Gly
    50                  55                  60

Ala Ser
65

<210> SEQ ID NO 7
<211> LENGTH: 66
<212> TYPE: PRT
<213> ORGANISM: Felis domesticus

<400> SEQUENCE: 7

Lys Asn Val Leu Lys Ile Ser Asp Phe Gly Met Ser Arg Glu Glu Ala
1               5                   10                  15

Asp Gly Ile Tyr Ala Ala Ser Gly Gly Leu Arg Gln Val Pro Val Lys
            20                  25                  30

Trp Thr Ala Pro Glu Ala Leu Asn Tyr Gly Arg Tyr Ser Ser Glu Ser
        35                  40                  45

Asp Val Trp Ser Phe Gly Ile Leu Leu Trp Glu Thr Phe Ser Leu Gly
    50                  55                  60

Ala Ser
65

<210> SEQ ID NO 8
<211> LENGTH: 66
<212> TYPE: PRT
<213> ORGANISM: Mus musculus

<400> SEQUENCE: 8

Lys Asn Val Leu Lys Ile Ser Asp Phe Gly Met Ser Arg Glu Glu Ala
1               5                   10                  15

Asp Gly Ile Tyr Ala Ala Ser Ala Gly Leu Arg Gln Val Pro Val Lys
                20                  25                  30

Trp Thr Ala Pro Glu Ala Leu Asn Tyr Gly Arg Tyr Ser Ser Glu Ser
            35                  40                  45

Asp Val Trp Ser Phe Gly Ile Leu Leu Trp Glu Thr Phe Ser Leu Gly
        50                  55                  60

Ala Ser
65

<210> SEQ ID NO 9
<211> LENGTH: 65
<212> TYPE: PRT
<213> ORGANISM: Rattus norvegicus

<400> SEQUENCE: 9

Asn Asn Thr Leu Lys Ile Ser Asp Phe Gly Met Ser Arg Gln Glu Asp
1               5                   10                  15

Gly Gly Val Tyr Ser Ser Ser Gly Leu Lys Gln Ile Pro Ile Lys Trp
                20                  25                  30

Thr Ala Pro Glu Ala Leu Asn Tyr Gly Arg Tyr Ser Ser Glu Ser Asp
            35                  40                  45

Val Trp Ser Phe Gly Ile Leu Leu Trp Glu Thr Phe Ser Leu Gly Val
        50                  55                  60

Cys
65

<210> SEQ ID NO 10
<211> LENGTH: 66
<212> TYPE: PRT
<213> ORGANISM: Gallus domesticus

<400> SEQUENCE: 10

Lys Asn Thr Leu Lys Ile Ser Asp Phe Gly Met Ser Arg Gln Glu Glu
1               5                   10                  15

Asp Gly Val Tyr Ala Ser Thr Gly Gly Met Lys Gln Ile Pro Val Lys
                20                  25                  30

Trp Thr Ala Pro Glu Ala Leu Asn Tyr Gly Arg Tyr Ser Ser Glu Ser
            35                  40                  45

Asp Val Trp Ser Phe Gly Ile Leu Leu Trp Glu Ala Phe Ser Leu Gly
        50                  55                  60

Val Val
65

<210> SEQ ID NO 11
<211> LENGTH: 64
<212> TYPE: PRT
<213> ORGANISM: Drosophila melanogaster

<400> SEQUENCE: 11

Glu His Ser Val Lys Ile Ser Asp Phe Gly Met Ser Arg Glu Glu Glu
1               5                   10                  15

Glu Tyr Ile Val Ser Asp Gly Met Lys Gln Ile Pro Val Lys Trp Thr
                20                  25                  30

Ala Pro Glu Ala Leu Asn Phe Gly Lys Tyr Thr Ser Leu Cys Asp Val
            35                  40                  45

Trp Ser Tyr Gly Ile Leu Met Trp Glu Ile Phe Ser Lys Gly Asp Thr
        50                  55                  60

<210> SEQ ID NO 12
<211> LENGTH: 66
<212> TYPE: PRT
<213> ORGANISM: Homo sapiens

<400> SEQUENCE: 12

Asn Leu Leu Val Lys Ile Gly Asp Phe Gly Met Ser Arg Asp Val Tyr
1               5                   10                  15

Ser Thr Asp Tyr Tyr Arg Val Gly Gly His Thr Met Leu Pro Ile Arg
            20                  25                  30

Trp Met Pro Pro Glu Ser Ile Met Tyr Arg Lys Phe Thr Thr Glu Ser
        35                  40                  45

Asp Val Trp Ser Leu Gly Val Val Leu Trp Glu Ile Phe Thr Tyr Gly
    50                  55                  60

Lys Gln
65

<210> SEQ ID NO 13
<211> LENGTH: 67
<212> TYPE: PRT
<213> ORGANISM: Homo sapiens

<400> SEQUENCE: 13

Asn Leu Val Cys Lys Val Ser Asp Phe Gly Leu Ser Arg Val Leu Glu
1               5                   10                  15

Asp Asp Pro Glu Ala Ala Tyr Thr Thr Arg Gly Gly Lys Ile Pro Ile
            20                  25                  30

Arg Trp Thr Ser Pro Glu Ala Ile Ala Tyr Arg Lys Phe Thr Ser Ala
        35                  40                  45

Ser Asp Val Trp Ser Tyr Gly Ile Val Leu Trp Glu Val Met Ser Tyr
    50                  55                  60

Gly Glu Arg
65

<210> SEQ ID NO 14
<211> LENGTH: 68
<212> TYPE: PRT
<213> ORGANISM: Homo sapiens

<400> SEQUENCE: 14

Lys Phe Thr Val Lys Val Ala Asp Phe Gly Leu Ala Arg Asp Met Tyr
1               5                   10                  15

Asp Lys Glu Tyr Tyr Ser Val His Asn Lys Thr Gly Ala Lys Leu Pro
            20                  25                  30

Val Lys Trp Met Ala Leu Glu Ser Leu Gln Thr Gln Lys Phe Thr Thr
        35                  40                  45

Lys Ser Asp Val Trp Ser Phe Gly Val Val Leu Trp Glu Leu Met Thr
    50                  55                  60

Arg Gly Ala Pro
65

<210> SEQ ID NO 15
<211> LENGTH: 68
<212> TYPE: PRT
<213> ORGANISM: Homo sapiens

<400> SEQUENCE: 15

Asp Leu Thr Val Lys Ile Gly Asp Phe Gly Leu Ala Thr Val Lys Ser
1               5                   10                  15

-continued

Arg Trp Ser Gly Ser His Gln Phe Glu Gln Leu Ser Gly Ser Ile Leu
            20                  25                  30

Trp Met Ala Pro Glu Val Ile Arg Met Gln Asp Lys Asn Pro Tyr Ser
        35                  40                  45

Phe Gln Ser Asp Val Tyr Ala Phe Gly Ile Val Leu Tyr Glu Leu Met
    50                  55                  60

Thr Gly Gln Leu
65

<210> SEQ ID NO 16
<211> LENGTH: 63
<212> TYPE: PRT
<213> ORGANISM: Homo sapiens

<400> SEQUENCE: 16

Phe Val Pro Ile Leu His Arg Asp Leu Lys Ser Ser Asn Ile Leu Leu
1               5                   10                  15

Leu Glu Lys Ile Glu His Asp Asp Ile Cys Asn Lys Thr Leu Lys Ile
            20                  25                  30

Thr Asp Phe Gly Leu Ala Arg Glu Trp His Arg Thr Thr Lys Met Ser
        35                  40                  45

Thr Ala Gly Thr Tyr Ala Trp Met Ala Pro Glu Val Ile Lys Ser
    50                  55                  60

<210> SEQ ID NO 17
<211> LENGTH: 63
<212> TYPE: PRT
<213> ORGANISM: Mus musculus

<400> SEQUENCE: 17

Val Val Pro Ile Leu His Arg Asp Leu Lys Ser Ser Asn Ile Leu Leu
1               5                   10                  15

Leu Glu Lys Ile Glu His Asp Asp Ile Cys Asn Lys Thr Leu Lys Ile
            20                  25                  30

Thr Asp Phe Gly Leu Ala Arg Glu Trp His Arg Thr Thr Arg Met Ser
        35                  40                  45

Ala Ala Gly Thr Tyr Ala Trp Met Ala Pro Glu Val Ile Arg Ser
    50                  55                  60

<210> SEQ ID NO 18
<211> LENGTH: 63
<212> TYPE: PRT
<213> ORGANISM: Anopholes funestus

<400> SEQUENCE: 18

Pro Ile Ser Val Ile His Arg Asp Leu Lys Ser Ser Asn Val Leu Ile
1               5                   10                  15

Ser Glu Ser Ile Gln His Gly His Leu Leu Asn Lys Thr Leu Lys Ile
            20                  25                  30

Thr Asp Phe Gly Leu Ala Arg Glu Ala Tyr Arg Thr Thr Arg Met Ser
        35                  40                  45

Ala Ala Gly Thr Phe Ala Trp Met Pro Pro Glu Val Ile Arg Ser
    50                  55                  60

<210> SEQ ID NO 19
<211> LENGTH: 63
<212> TYPE: PRT
<213> ORGANISM: Drosophila melanogaster

<400> SEQUENCE: 19

Pro Met Ser Ile Ile His Arg Asp Leu Lys Ser Ser Asn Val Leu Ile
1               5                   10                  15

Tyr Glu Ala Ile Glu Gly Asn His Leu Gln Gln Lys Thr Leu Lys Ile
            20                  25                  30

Thr Asp Phe Gly Leu Ala Arg Glu Met Tyr Asn Thr Gln Arg Met Ser
        35                  40                  45

Ala Ala Gly Thr Tyr Ala Trp Met Pro Pro Glu Val Ile Ser Val
    50                  55                  60

<210> SEQ ID NO 20
<211> LENGTH: 61
<212> TYPE: PRT
<213> ORGANISM: Homo sapiens

<400> SEQUENCE: 20

Ser Lys Lys Phe Val His Arg Asp Leu Ala Ala Arg Asn Cys Met Leu
1               5                   10                  15

Asp Glu Lys Phe Thr Val Lys Val Ala Asp Phe Gly Leu Ala Arg Asp
            20                  25                  30

Met Tyr Asp Lys Glu Tyr Tyr Ser Val His Asn Lys Thr Gly Ala Lys
        35                  40                  45

Leu Pro Val Lys Trp Met Ala Leu Glu Ser Leu Gln Thr
    50                  55                  60

<210> SEQ ID NO 21
<211> LENGTH: 57
<212> TYPE: PRT
<213> ORGANISM: Homo sapiens

<400> SEQUENCE: 21

Ser Ile Ile His Arg Asp Leu Lys Ser Asn Asn Ile Phe Leu His Glu
1               5                   10                  15

Asp Leu Thr Val Lys Ile Gly Asp Phe Gly Leu Ala Thr Val Lys Ser
            20                  25                  30

Arg Trp Ser Gly Ser His Gln Phe Glu Gln Leu Ser Gly Ser Ile Leu
        35                  40                  45

Trp Met Ala Pro Glu Val Ile Arg Met
    50                  55

<210> SEQ ID NO 22
<211> LENGTH: 10
<212> TYPE: DNA
<213> ORGANISM: Homo sapiens

<400> SEQUENCE: 22 cggargttca                                                                  10

<210> SEQ ID NO 23
<211> LENGTH: 10
<212> TYPE: DNA
<213> ORGANISM: Homo sapiens

<400> SEQUENCE: 23
cggaagttca                                                                  10

<210> SEQ ID NO 24
<211> LENGTH: 10
<212> TYPE: DNA
<213> ORGANISM: Homo sapiens

```
<400> SEQUENCE: 24 tgcascggga                                                            10

<210> SEQ ID NO 25
<211> LENGTH: 10
<212> TYPE: DNA
<213> ORGANISM: Homo sapiens

<400> SEQUENCE: 25
tgcaccggga                                                            10

<210> SEQ ID NO 26
<211> LENGTH: 18
<212> TYPE: DNA
<213> ORGANISM: Homo sapiens

<400> SEQUENCE: 26
atggagggct tcctggag                                                   18

<210> SEQ ID NO 27
<211> LENGTH: 18
<212> TYPE: DNA
<213> ORGANISM: Homo sapiens

<400> SEQUENCE: 27
gccatcggca ttgacaag                                                   18

<210> SEQ ID NO 28
<211> LENGTH: 20
<212> TYPE: DNA
<213> ORGANISM: Homo sapiens

<400> SEQUENCE: 28
tcgggaaaca caaaaacatc                                                 20

<210> SEQ ID NO 29
<211> LENGTH: 21
<212> TYPE: DNA
<213> ORGANISM: Homo sapiens

<400> SEQUENCE: 29
gagtacttgg cctcccagaa g                                               21

<210> SEQ ID NO 30
<211> LENGTH: 20
<212> TYPE: DNA
<213> ORGANISM: Homo sapiens

<400> SEQUENCE: 30
acgtgcacaa cctcgactac                                                 20

<210> SEQ ID NO 31
<211> LENGTH: 20
<212> TYPE: DNA
<213> ORGANISM: Homo sapiens

<400> SEQUENCE: 31
tcctgggtgt ggtttctacc                                                 20

<210> SEQ ID NO 32
<211> LENGTH: 19
<212> TYPE: DNA
```

<213> ORGANISM: Homo sapiens

<400> SEQUENCE: 32
acgacctgtg agtggcatc                                                    19

<210> SEQ ID NO 33
<211> LENGTH: 19
<212> TYPE: DNA
<213> ORGANISM: Homo sapiens

<400> SEQUENCE: 33
gacgtgagtg ctggctctg                                                    19

<210> SEQ ID NO 34
<211> LENGTH: 22
<212> TYPE: DNA
<213> ORGANISM: Homo sapiens

<400> SEQUENCE: 34
aaatcttcat tcaatgctgg tg                                                22

<210> SEQ ID NO 35
<211> LENGTH: 20
<212> TYPE: DNA
<213> ORGANISM: Homo sapiens

<400> SEQUENCE: 35
ggccttttca tttcccatac                                                   20

<210> SEQ ID NO 36
<211> LENGTH: 23
<212> TYPE: DNA
<213> ORGANISM: Homo sapiens

<400> SEQUENCE: 36
tttctttatg attctgcaca tgg                                               23

<210> SEQ ID NO 37
<211> LENGTH: 19
<212> TYPE: DNA
<213> ORGANISM: Homo sapiens

<400> SEQUENCE: 37
attcaggttg cctgccttg                                                    19

<210> SEQ ID NO 38
<211> LENGTH: 20
<212> TYPE: DNA
<213> ORGANISM: Homo sapiens

<400> SEQUENCE: 38 tgaaagggc aggcatttag                                                    20

<210> SEQ ID NO 39
<211> LENGTH: 21
<212> TYPE: DNA
<213> ORGANISM: Homo sapiens

<400> SEQUENCE: 39
ttgaaccatt tgaaccattc c                                                 21

<210> SEQ ID NO 40
<211> LENGTH: 20

<212> TYPE: DNA
<213> ORGANISM: Homo sapiens

<400> SEQUENCE: 40
ttgtgtttaa ggctgcatgg                                              20

<210> SEQ ID NO 41
<211> LENGTH: 26
<212> TYPE: DNA
<213> ORGANISM: Homo sapiens

<400> SEQUENCE: 41
ttctaagtct gtaccagcat aatgtc                                       26

<210> SEQ ID NO 42
<211> LENGTH: 20
<212> TYPE: DNA
<213> ORGANISM: Homo sapiens

<400> SEQUENCE: 42
gccgatatgg agaagtacgg                                              20

<210> SEQ ID NO 43
<211> LENGTH: 23
<212> TYPE: DNA
<213> ORGANISM: Homo sapiens

<400> SEQUENCE: 43
ttcatatgtc aagaccgtac agc                                          23

<210> SEQ ID NO 44
<211> LENGTH: 20
<212> TYPE: DNA
<213> ORGANISM: Homo sapiens

<400> SEQUENCE: 44
gttgcatgga ggattttgtg                                              20

<210> SEQ ID NO 45
<211> LENGTH: 20
<212> TYPE: DNA
<213> ORGANISM: Homo sapiens

<400> SEQUENCE: 45
tcattcctag ctccccacag                                              20

<210> SEQ ID NO 46
<211> LENGTH: 20
<212> TYPE: DNA
<213> ORGANISM: Homo sapiens

<400> SEQUENCE: 46
agcgactttg gtcagaaagg                                              20

<210> SEQ ID NO 47
<211> LENGTH: 23
<212> TYPE: DNA
<213> ORGANISM: Homo sapiens

<400> SEQUENCE: 47
ttgcgttaaa atgaacaagt gtc                                          23

<210> SEQ ID NO 48

<211> LENGTH: 20
<212> TYPE: DNA
<213> ORGANISM: Homo sapiens

<400> SEQUENCE: 48
tggctcatgt gaaggagttg                                                  20

<210> SEQ ID NO 49
<211> LENGTH: 24
<212> TYPE: DNA
<213> ORGANISM: Homo sapiens

<400> SEQUENCE: 49
caattgttcc atttaaaacc ttcc                                             24

<210> SEQ ID NO 50
<211> LENGTH: 21
<212> TYPE: DNA
<213> ORGANISM: Homo sapiens

<400> SEQUENCE: 50
aatacacctg ccttgttgtg c                                                21

<210> SEQ ID NO 51
<211> LENGTH: 20
<212> TYPE: DNA
<213> ORGANISM: Homo sapiens

<400> SEQUENCE: 51
aggctggtct caaactcctg                                                  20

<210> SEQ ID NO 52
<211> LENGTH: 20
<212> TYPE: DNA
<213> ORGANISM: Homo sapiens

<400> SEQUENCE: 52
cactgagctc atcaccaagg                                                  20

<210> SEQ ID NO 53
<211> LENGTH: 21
<212> TYPE: DNA
<213> ORGANISM: Homo sapiens

<400> SEQUENCE: 53
ggtgtaccag ccccatttta c                                                21

<210> SEQ ID NO 54
<211> LENGTH: 20
<212> TYPE: DNA
<213> ORGANISM: Homo sapiens

<400> SEQUENCE: 54
gtagggctag gagcggtagg                                                  20

<210> SEQ ID NO 55
<211> LENGTH: 20
<212> TYPE: DNA
<213> ORGANISM: Homo sapiens

<400> SEQUENCE: 55
cctcacttgg ggcctagttc                                                  20

```
<210> SEQ ID NO 56
<211> LENGTH: 19
<212> TYPE: DNA
<213> ORGANISM: Homo sapiens

<400> SEQUENCE: 56
aggacgcctg ggagatcag                                                  19

<210> SEQ ID NO 57
<211> LENGTH: 18
<212> TYPE: DNA
<213> ORGANISM: Homo sapiens

<400> SEQUENCE: 57
ggacgcctgg gagatcag                                                   18

<210> SEQ ID NO 58
<211> LENGTH: 20
<212> TYPE: DNA
<213> ORGANISM: Homo sapiens

<400> SEQUENCE: 58
acgagacaag tgagggttg                                                  20

<210> SEQ ID NO 59
<211> LENGTH: 20
<212> TYPE: DNA
<213> ORGANISM: Homo sapiens

<400> SEQUENCE: 59
tctttctggg cctcagtctc                                                 20

<210> SEQ ID NO 60
<211> LENGTH: 21
<212> TYPE: DNA
<213> ORGANISM: Homo sapiens

<400> SEQUENCE: 60
aatagctcct tgatgctgtg c                                               21

<210> SEQ ID NO 61
<211> LENGTH: 20
<212> TYPE: DNA
<213> ORGANISM: Homo sapiens

<400> SEQUENCE: 61
gggttcatgg aggtcttctg                                                 20

<210> SEQ ID NO 62
<211> LENGTH: 20
<212> TYPE: DNA
<213> ORGANISM: Homo sapiens

<400> SEQUENCE: 62
accaatgaat cccgtttctg                                                 20

<210> SEQ ID NO 63
<211> LENGTH: 22
<212> TYPE: DNA
<213> ORGANISM: Homo sapiens

<400> SEQUENCE: 63
gagatttagg gtgggaaaga gg                                              22
```

```
<210> SEQ ID NO 64
<211> LENGTH: 20
<212> TYPE: DNA
<213> ORGANISM: Homo sapiens

<400> SEQUENCE: 64
tgggaaggtg tctgtagtcg                                              20

<210> SEQ ID NO 65
<211> LENGTH: 22
<212> TYPE: DNA
<213> ORGANISM: Homo sapiens

<400> SEQUENCE: 65
ttgaggagga gagacttttg ag                                           22

<210> SEQ ID NO 66
<211> LENGTH: 23
<212> TYPE: DNA
<213> ORGANISM: Homo sapiens

<400> SEQUENCE: 66
tgggcaaaat ataaaaagca cag                                          23

<210> SEQ ID NO 67
<211> LENGTH: 20
<212> TYPE: DNA
<213> ORGANISM: Homo sapiens

<400> SEQUENCE: 67
taatcgacag ggcatgctac                                              20

<210> SEQ ID NO 68
<211> LENGTH: 20
<212> TYPE: DNA
<213> ORGANISM: Homo sapiens

<400> SEQUENCE: 68
cctgggtgct acaggacaag                                              20

<210> SEQ ID NO 69
<211> LENGTH: 20
<212> TYPE: DNA
<213> ORGANISM: Homo sapiens

<400> SEQUENCE: 69
gagcgagact ccatctcagg                                              20

<210> SEQ ID NO 70
<211> LENGTH: 22
<212> TYPE: DNA
<213> ORGANISM: Homo sapiens

<400> SEQUENCE: 70
tcaagattga agaggtgatt gg                                           22

<210> SEQ ID NO 71
<211> LENGTH: 20
<212> TYPE: DNA
<213> ORGANISM: Homo sapiens

<400> SEQUENCE: 71
ctatgatggc accactgcac                                              20
```

-continued

<210> SEQ ID NO 72
<211> LENGTH: 20
<212> TYPE: DNA
<213> ORGANISM: Homo sapiens

<400> SEQUENCE: 72
ttggagagta ggaggcttgg                                               20

<210> SEQ ID NO 73
<211> LENGTH: 20
<212> TYPE: DNA
<213> ORGANISM: Homo sapiens

<400> SEQUENCE: 73
gggcaaacag agttggagag                                               20

<210> SEQ ID NO 74
<211> LENGTH: 19
<212> TYPE: DNA
<213> ORGANISM: Homo sapiens

<400> SEQUENCE: 74
agcttcaact ccggctagg                                                19

<210> SEQ ID NO 75
<211> LENGTH: 20
<212> TYPE: DNA
<213> ORGANISM: Homo sapiens

<400> SEQUENCE: 75
cagaagtgtc cgttcattgg                                               20

<210> SEQ ID NO 76
<211> LENGTH: 20
<212> TYPE: DNA
<213> ORGANISM: Homo sapiens

<400> SEQUENCE: 76
ccgggaactg ttgacatctg                                               20

<210> SEQ ID NO 77
<211> LENGTH: 20
<212> TYPE: DNA
<213> ORGANISM: Homo sapiens

<400> SEQUENCE: 77
cttgtgtcct ctccctccac                                               20

<210> SEQ ID NO 78
<211> LENGTH: 22
<212> TYPE: DNA
<213> ORGANISM: Homo sapiens

<400> SEQUENCE: 78
aaggcagtag tctgtggagg ac                                            22

<210> SEQ ID NO 79
<211> LENGTH: 22
<212> TYPE: DNA
<213> ORGANISM: Homo sapiens

<400> SEQUENCE: 79

```
cgagggatct gaaaactgac tc                                              22

<210> SEQ ID NO 80
<211> LENGTH: 27
<212> TYPE: DNA
<213> ORGANISM: Homo sapiens

<400> SEQUENCE: 80
aattccttag aagaatagat tcagacc                                         27

<210> SEQ ID NO 81
<211> LENGTH: 20
<212> TYPE: DNA
<213> ORGANISM: Homo sapiens

<400> SEQUENCE: 81
aggccaccta aggagagagc                                                 20

<210> SEQ ID NO 82
<211> LENGTH: 20
<212> TYPE: DNA
<213> ORGANISM: Homo sapiens

<400> SEQUENCE: 82
tcagggtgac agtgaggatg                                                 20

<210> SEQ ID NO 83
<211> LENGTH: 21
<212> TYPE: DNA
<213> ORGANISM: Homo sapiens

<400> SEQUENCE: 83
ttcctgaccg attgtaagca c                                               21

<210> SEQ ID NO 84
<211> LENGTH: 20
<212> TYPE: DNA
<213> ORGANISM: Homo sapiens

<400> SEQUENCE: 84
tccctctctg cctttctcac                                                 20

<210> SEQ ID NO 85
<211> LENGTH: 23
<212> TYPE: DNA
<213> ORGANISM: Homo sapiens

<400> SEQUENCE: 85
tcacagagct atatgatggc aac                                             23

<210> SEQ ID NO 86
<211> LENGTH: 20
<212> TYPE: DNA
<213> ORGANISM: Homo sapiens

<400> SEQUENCE: 86
aacctctctc aggacgttgc                                                 20

<210> SEQ ID NO 87
<211> LENGTH: 20
<212> TYPE: DNA
<213> ORGANISM: Homo sapiens

<400> SEQUENCE: 87
```
ccccgtaggg aggaagactc                                           20

<210> SEQ ID NO 88
<211> LENGTH: 20
<212> TYPE: DNA
<213> ORGANISM: Homo sapiens

<400> SEQUENCE: 88
gaaaccttct ggctgattgg                                           20

<210> SEQ ID NO 89
<211> LENGTH: 21
<212> TYPE: DNA
<213> ORGANISM: Homo sapiens

<400> SEQUENCE: 89
aaagttgagc aatttgcaag c                                         21

<210> SEQ ID NO 90
<211> LENGTH: 20
<212> TYPE: DNA
<213> ORGANISM: Homo sapiens

<400> SEQUENCE: 90
tcaggatggg ggaaagaaac                                           20

<210> SEQ ID NO 91
<211> LENGTH: 20
<212> TYPE: DNA
<213> ORGANISM: Homo sapiens

<400> SEQUENCE: 91
aagcaggagg gctatgttcc                                           20

<210> SEQ ID NO 92
<211> LENGTH: 20
<212> TYPE: DNA
<213> ORGANISM: Homo sapiens

<400> SEQUENCE: 92
tgattcgctg ttttcaaagg                                           20

<210> SEQ ID NO 93
<211> LENGTH: 20
<212> TYPE: DNA
<213> ORGANISM: Homo sapiens

<400> SEQUENCE: 93
ctaccaaccc tggctactgc                                           20

<210> SEQ ID NO 94
<211> LENGTH: 19
<212> TYPE: DNA
<213> ORGANISM: Homo sapiens

<400> SEQUENCE: 94
tgggtgcata cagccaatc                                            19

<210> SEQ ID NO 95
<211> LENGTH: 20
<212> TYPE: DNA
<213> ORGANISM: Homo sapiens

```
<400> SEQUENCE: 95
gcatacctca gcctcagctc                                              20

<210> SEQ ID NO 96
<211> LENGTH: 20
<212> TYPE: DNA
<213> ORGANISM: Homo sapiens

<400> SEQUENCE: 96
ttgggggaga gactcagatg                                              20

<210> SEQ ID NO 97
<211> LENGTH: 22
<212> TYPE: DNA
<213> ORGANISM: Homo sapiens

<400> SEQUENCE: 97
ttcctctggg tcttcatagc tc                                           22

<210> SEQ ID NO 98
<211> LENGTH: 20
<212> TYPE: DNA
<213> ORGANISM: Homo sapiens

<400> SEQUENCE: 98
agaaaatgga caggctggtg                                              20

<210> SEQ ID NO 99
<211> LENGTH: 22
<212> TYPE: DNA
<213> ORGANISM: Homo sapiens

<400> SEQUENCE: 99
caacaagaca gactgtgctg ag                                           22

<210> SEQ ID NO 100
<211> LENGTH: 20
<212> TYPE: DNA
<213> ORGANISM: Homo sapiens

<400> SEQUENCE: 100
gggttgcttc cttcttttcc                                              20

<210> SEQ ID NO 101
<211> LENGTH: 23
<212> TYPE: DNA
<213> ORGANISM: Homo sapiens

<400> SEQUENCE: 101
tcaatctcat gtttacaggg ttc                                          23

<210> SEQ ID NO 102
<211> LENGTH: 19
<212> TYPE: DNA
<213> ORGANISM: Homo sapiens

<400> SEQUENCE: 102
gtggagggtg ggagagaag                                               19

<210> SEQ ID NO 103
<211> LENGTH: 21
<212> TYPE: DNA
<213> ORGANISM: Homo sapiens
```

-continued

```
<400> SEQUENCE: 103
ttggagatca tcatgggagt c                                              21

<210> SEQ ID NO 104
<211> LENGTH: 20
<212> TYPE: DNA
<213> ORGANISM: Homo sapiens

<400> SEQUENCE: 104
acctcacact ggtgctcctc                                                20

<210> SEQ ID NO 105
<211> LENGTH: 20
<212> TYPE: DNA
<213> ORGANISM: Homo sapiens

<400> SEQUENCE: 105
gggatgagga gaggaaatgg                                                20

<210> SEQ ID NO 106
<211> LENGTH: 19
<212> TYPE: DNA
<213> ORGANISM: Homo sapiens

<400> SEQUENCE: 106
ccaaagcagg gatcagagc                                                 19

<210> SEQ ID NO 107
<211> LENGTH: 20
<212> TYPE: DNA
<213> ORGANISM: Homo sapiens

<400> SEQUENCE: 107
cttccttccc agccattttc                                                20

<210> SEQ ID NO 108
<211> LENGTH: 21
<212> TYPE: DNA
<213> ORGANISM: Homo sapiens

<400> SEQUENCE: 108
gcttctgctt ctgtgaaatg g                                              21

<210> SEQ ID NO 109
<211> LENGTH: 21
<212> TYPE: DNA
<213> ORGANISM: Homo sapiens

<400> SEQUENCE: 109
tgcttctgct tctgtgaaat g                                              21

<210> SEQ ID NO 110
<211> LENGTH: 19
<212> TYPE: DNA
<213> ORGANISM: Homo sapiens

<400> SEQUENCE: 110
ctcatggctg ttggattgc                                                 19

<210> SEQ ID NO 111
<211> LENGTH: 19
<212> TYPE: DNA
```

```
<213> ORGANISM: Homo sapiens

<400> SEQUENCE: 111
ctggagcttg gggctagag                                            19

<210> SEQ ID NO 112
<211> LENGTH: 20
<212> TYPE: DNA
<213> ORGANISM: Homo sapiens

<400> SEQUENCE: 112
tcagtgatgt ggctcagctc                                           20

<210> SEQ ID NO 113
<211> LENGTH: 19
<212> TYPE: DNA
<213> ORGANISM: Homo sapiens

<400> SEQUENCE: 113
agacaccgac ctgatgcac                                            19

<210> SEQ ID NO 114
<211> LENGTH: 20
<212> TYPE: DNA
<213> ORGANISM: Homo sapiens

<400> SEQUENCE: 114
ccctcccatc ccctagtatc                                           20

<210> SEQ ID NO 115
<211> LENGTH: 20
<212> TYPE: DNA
<213> ORGANISM: Homo sapiens

<400> SEQUENCE: 115
gagtcacctt gggaaacagg                                           20

<210> SEQ ID NO 116
<211> LENGTH: 18
<212> TYPE: DNA
<213> ORGANISM: Homo sapiens

<400> SEQUENCE: 116
gtcccaggaa gggcactc                                             18

<210> SEQ ID NO 117
<211> LENGTH: 20
<212> TYPE: DNA
<213> ORGANISM: Homo sapiens

<400> SEQUENCE: 117
gaggtggagg ttgcaatgag                                           20

<210> SEQ ID NO 118
<211> LENGTH: 24
<212> TYPE: DNA
<213> ORGANISM: Homo sapiens

<400> SEQUENCE: 118
tgaatccagc agtttaaatg tttc                                      24

<210> SEQ ID NO 119
<211> LENGTH: 25
```

```
<212> TYPE: DNA
<213> ORGANISM: Homo sapiens

<400> SEQUENCE: 119
ctgaatccag cagtttaaat gtttc                                    25

<210> SEQ ID NO 120
<211> LENGTH: 23
<212> TYPE: DNA
<213> ORGANISM: Homo sapiens

<400> SEQUENCE: 120
tatcatataa tctgctcgca ttg                                      23

<210> SEQ ID NO 121
<211> LENGTH: 23
<212> TYPE: DNA
<213> ORGANISM: Homo sapiens

<400> SEQUENCE: 121
tgctgctttg gtagataatt tgc                                      23

<210> SEQ ID NO 122
<211> LENGTH: 20
<212> TYPE: DNA
<213> ORGANISM: Homo sapiens

<400> SEQUENCE: 122
tgatccttct ttcccctgtg                                          20

<210> SEQ ID NO 123
<211> LENGTH: 22
<212> TYPE: DNA
<213> ORGANISM: Homo sapiens

<400> SEQUENCE: 123
tgttcaaggg attagaacat gg                                       22

<210> SEQ ID NO 124
<211> LENGTH: 21
<212> TYPE: DNA
<213> ORGANISM: Homo sapiens

<400> SEQUENCE: 124
ttcccacaag cacagtatga g                                        21

<210> SEQ ID NO 125
<211> LENGTH: 24
<212> TYPE: DNA
<213> ORGANISM: Homo sapiens

<400> SEQUENCE: 125
aagcattttc atagattgat gtgc                                     24

<210> SEQ ID NO 126
<211> LENGTH: 20
<212> TYPE: DNA
<213> ORGANISM: Homo sapiens

<400> SEQUENCE: 126
tgccgttctg attctgtctg                                          20

<210> SEQ ID NO 127
```

```
<211> LENGTH: 18
<212> TYPE: DNA
<213> ORGANISM: Homo sapiens

<400> SEQUENCE: 127
cgcttttcgg ctgcttag                                                 18

<210> SEQ ID NO 128
<211> LENGTH: 20
<212> TYPE: DNA
<213> ORGANISM: Homo sapiens

<400> SEQUENCE: 128 tcctgcccctt atggaatttg                                              20

<210> SEQ ID NO 129
<211> LENGTH: 20
<212> TYPE: DNA
<213> ORGANISM: Homo sapiens

<400> SEQUENCE: 129
atggcagcta aatgctggag                                               20

<210> SEQ ID NO 130
<211> LENGTH: 21
<212> TYPE: DNA
<213> ORGANISM: Homo sapiens

<400> SEQUENCE: 130
gcttgactcc agagattttg c                                             21

<210> SEQ ID NO 131
<211> LENGTH: 19
<212> TYPE: DNA
<213> ORGANISM: Homo sapiens

<400> SEQUENCE: 131 cttttccccac cattcaagg                                               19

<210> SEQ ID NO 132
<211> LENGTH: 20
<212> TYPE: DNA
<213> ORGANISM: Homo sapiens

<400> SEQUENCE: 132
ttcccaggtg aacaaagagc                                               20

<210> SEQ ID NO 133
<211> LENGTH: 26
<212> TYPE: DNA
<213> ORGANISM: Homo sapiens

<400> SEQUENCE: 133
gccactctta aataagaaat caaagc                                        26

<210> SEQ ID NO 134
<211> LENGTH: 20
<212> TYPE: DNA
<213> ORGANISM: Homo sapiens

<400> SEQUENCE: 134
cagcctcaag gacaagaagc                                               20
```

```
<210> SEQ ID NO 135
<211> LENGTH: 23
<212> TYPE: DNA
<213> ORGANISM: Homo sapiens

<400> SEQUENCE: 135
tctacgatct gtttccagct ttc                                             23

<210> SEQ ID NO 136
<211> LENGTH: 20
<212> TYPE: DNA
<213> ORGANISM: Homo sapiens

<400> SEQUENCE: 136
ccaggagttg gaaaacgaag                                                 20

<210> SEQ ID NO 137
<211> LENGTH: 26
<212> TYPE: DNA
<213> ORGANISM: Homo sapiens

<400> SEQUENCE: 137
aaaaatccct ttaaaacatc agatac                                          26

<210> SEQ ID NO 138
<211> LENGTH: 21
<212> TYPE: DNA
<213> ORGANISM: Homo sapiens

<400> SEQUENCE: 138
tgttcagcac atgtaatcca g                                               21

<210> SEQ ID NO 139
<211> LENGTH: 22
<212> TYPE: DNA
<213> ORGANISM: Homo sapiens

<400> SEQUENCE: 139
ttcagcacat gtaatccaga ac                                              22

<210> SEQ ID NO 140
<211> LENGTH: 20
<212> TYPE: DNA
<213> ORGANISM: Homo sapiens

<400> SEQUENCE: 140
tgccgtttgc cttttatgag                                                 20

<210> SEQ ID NO 141
<211> LENGTH: 21
<212> TYPE: DNA
<213> ORGANISM: Homo sapiens

<400> SEQUENCE: 141
tggagggcag tacaaaagtt c                                               21

<210> SEQ ID NO 142
<211> LENGTH: 21
<212> TYPE: DNA
<213> ORGANISM: Homo sapiens

<400> SEQUENCE: 142
gacggagtct cactctgttg c                                               21
```

<210> SEQ ID NO 143
<211> LENGTH: 20
<212> TYPE: DNA
<213> ORGANISM: Homo sapiens

<400> SEQUENCE: 143
aggctgaggg ctatcagttg                                            20

<210> SEQ ID NO 144
<211> LENGTH: 19
<212> TYPE: DNA
<213> ORGANISM: Homo sapiens

<400> SEQUENCE: 144
agatcacgcc actgcactc                                             19

<210> SEQ ID NO 145
<211> LENGTH: 21
<212> TYPE: DNA
<213> ORGANISM: Homo sapiens

<400> SEQUENCE: 145
cgctgtccac taaggtagct c                                          21

<210> SEQ ID NO 146
<211> LENGTH: 24
<212> TYPE: DNA
<213> ORGANISM: Homo sapiens

<400> SEQUENCE: 146
ttcaatcatg gaactttat cagc                                        24

<210> SEQ ID NO 147
<211> LENGTH: 20
<212> TYPE: DNA
<213> ORGANISM: Homo sapiens

<400> SEQUENCE: 147
gttggggttg atttcattgc                                            20

<210> SEQ ID NO 148
<211> LENGTH: 20
<212> TYPE: DNA
<213> ORGANISM: Homo sapiens

<400> SEQUENCE: 148
tggcaaaacc aggacctatc                                            20

<210> SEQ ID NO 149
<211> LENGTH: 20
<212> TYPE: DNA
<213> ORGANISM: Homo sapiens

<400> SEQUENCE: 149
ttacccaccc agatgaggag                                            20

<210> SEQ ID NO 150
<211> LENGTH: 20
<212> TYPE: DNA
<213> ORGANISM: Homo sapiens

<400> SEQUENCE: 150
tagaggtccc cagacagcag                                            20

```
<210> SEQ ID NO 151
<211> LENGTH: 20
<212> TYPE: DNA
<213> ORGANISM: Homo sapiens

<400> SEQUENCE: 151
gagacccact gttgaacctg                                              20

<210> SEQ ID NO 152
<211> LENGTH: 20
<212> TYPE: DNA
<213> ORGANISM: Homo sapiens

<400> SEQUENCE: 152
ggcagatccc ttctttggag                                              20

<210> SEQ ID NO 153
<211> LENGTH: 20
<212> TYPE: DNA
<213> ORGANISM: Homo sapiens

<400> SEQUENCE: 153
agaggacaga cccacgtttg                                              20

<210> SEQ ID NO 154
<211> LENGTH: 19
<212> TYPE: DNA
<213> ORGANISM: Homo sapiens

<400> SEQUENCE: 154
cacacagcct ggtcctgag                                               19

<210> SEQ ID NO 155
<211> LENGTH: 20
<212> TYPE: DNA
<213> ORGANISM: Homo sapiens

<400> SEQUENCE: 155
ggcacagaga aggagctcag                                              20

<210> SEQ ID NO 156
<211> LENGTH: 20
<212> TYPE: DNA
<213> ORGANISM: Homo sapiens

<400> SEQUENCE: 156
cacgatgact tggaggagtc                                              20

<210> SEQ ID NO 157
<211> LENGTH: 18
<212> TYPE: DNA
<213> ORGANISM: Homo sapiens

<400> SEQUENCE: 157
aagggcaccc tgggtaag                                                18

<210> SEQ ID NO 158
<211> LENGTH: 20
<212> TYPE: DNA
<213> ORGANISM: Homo sapiens

<400> SEQUENCE: 158
```

```
aaggccagcc ctttatatcc                                            20

<210> SEQ ID NO 159
<211> LENGTH: 20
<212> TYPE: DNA
<213> ORGANISM: Homo sapiens

<400> SEQUENCE: 159
gtgccaggga ctgagagttc                                            20

<210> SEQ ID NO 160
<211> LENGTH: 20
<212> TYPE: DNA
<213> ORGANISM: Homo sapiens

<400> SEQUENCE: 160
tgaccacgct accagtgaag                                            20

<210> SEQ ID NO 161
<211> LENGTH: 23
<212> TYPE: DNA
<213> ORGANISM: Homo sapiens

<400> SEQUENCE: 161
caactaagtc ccacatcttc cag                                        23

<210> SEQ ID NO 162
<211> LENGTH: 20
<212> TYPE: DNA
<213> ORGANISM: Homo sapiens

<400> SEQUENCE: 162
ggcagaatct tgccatactg                                            20

<210> SEQ ID NO 163
<211> LENGTH: 21
<212> TYPE: DNA
<213> ORGANISM: Homo sapiens

<400> SEQUENCE: 163
tttcctcaaa ttggtccagt c                                          21

<210> SEQ ID NO 164
<211> LENGTH: 20
<212> TYPE: DNA
<213> ORGANISM: Homo sapiens

<400> SEQUENCE: 164
tgatctgcct gcaagttcac                                            20

<210> SEQ ID NO 165
<211> LENGTH: 22
<212> TYPE: DNA
<213> ORGANISM: Homo sapiens

<400> SEQUENCE: 165
catcattcaa ggcgtacttt tg                                         22

<210> SEQ ID NO 166
<211> LENGTH: 21
<212> TYPE: DNA
<213> ORGANISM: Homo sapiens

<400> SEQUENCE: 166
```

```
aggtgattgg gatcatctga g                                          21

<210> SEQ ID NO 167
<211> LENGTH: 20
<212> TYPE: DNA
<213> ORGANISM: Homo sapiens

<400> SEQUENCE: 167
ggattttcct ttgggagctg                                            20

<210> SEQ ID NO 168
<211> LENGTH: 26
<212> TYPE: DNA
<213> ORGANISM: Homo sapiens

<400> SEQUENCE: 168
tctcttgtca ccaaaaatac agaaag                                     26

<210> SEQ ID NO 169
<211> LENGTH: 20
<212> TYPE: DNA
<213> ORGANISM: Homo sapiens

<400> SEQUENCE: 169
ttttggccac aaagttcttg                                            20

<210> SEQ ID NO 170
<211> LENGTH: 20
<212> TYPE: DNA
<213> ORGANISM: Homo sapiens

<400> SEQUENCE: 170
ctttcgggaa ggttgttgag                                            20

<210> SEQ ID NO 171
<211> LENGTH: 24
<212> TYPE: DNA
<213> ORGANISM: Homo sapiens

<400> SEQUENCE: 171
ttgggactaa gtagtctgat ccac                                       24

<210> SEQ ID NO 172
<211> LENGTH: 20
<212> TYPE: DNA
<213> ORGANISM: Homo sapiens

<400> SEQUENCE: 172
gatctgaaac gggactttgc                                            20

<210> SEQ ID NO 173
<211> LENGTH: 20
<212> TYPE: DNA
<213> ORGANISM: Homo sapiens

<400> SEQUENCE: 173
ggtgtgggtt acaggcattc                                            20

<210> SEQ ID NO 174
<211> LENGTH: 21
<212> TYPE: DNA
<213> ORGANISM: Homo sapiens
```

<400> SEQUENCE: 174
ttttgctcaa cagatcagtg c                                          21

<210> SEQ ID NO 175
<211> LENGTH: 25
<212> TYPE: DNA
<213> ORGANISM: Homo sapiens

<400> SEQUENCE: 175
tgtcagttga actaagctca ttttg                                      25

<210> SEQ ID NO 176
<211> LENGTH: 26
<212> TYPE: DNA
<213> ORGANISM: Homo sapiens

<400> SEQUENCE: 176
cagttgaact aagctcattt tgaatc                                     26

<210> SEQ ID NO 177
<211> LENGTH: 20
<212> TYPE: DNA
<213> ORGANISM: Homo sapiens

<400> SEQUENCE: 177
gggatggcag accttaaatc                                            20

<210> SEQ ID NO 178
<211> LENGTH: 20
<212> TYPE: DNA
<213> ORGANISM: Homo sapiens

<400> SEQUENCE: 178
ctctgggcct tgtctgtttc                                            20

<210> SEQ ID NO 179
<211> LENGTH: 18
<212> TYPE: DNA
<213> ORGANISM: Homo sapiens

<400> SEQUENCE: 179
accagcaggg aagctgtg                                              18

<210> SEQ ID NO 180
<211> LENGTH: 23
<212> TYPE: DNA
<213> ORGANISM: Homo sapiens

<400> SEQUENCE: 180
cctttcttct cacagtggat ttg                                        23

<210> SEQ ID NO 181
<211> LENGTH: 20
<212> TYPE: DNA
<213> ORGANISM: Homo sapiens

<400> SEQUENCE: 181
caaagctgtc ttgcctgaag                                            20

<210> SEQ ID NO 182
<211> LENGTH: 20
<212> TYPE: DNA
<213> ORGANISM: Homo sapiens

```
<400> SEQUENCE: 182
gttgaacttg gcctttccag                                          20

<210> SEQ ID NO 183
<211> LENGTH: 20
<212> TYPE: DNA
<213> ORGANISM: Homo sapiens

<400> SEQUENCE: 183
acacagatga ttggcagcag                                          20

<210> SEQ ID NO 184
<211> LENGTH: 20
<212> TYPE: DNA
<213> ORGANISM: Homo sapiens

<400> SEQUENCE: 184
atgtttgggc acactgcttg                                          20

<210> SEQ ID NO 185
<211> LENGTH: 20
<212> TYPE: DNA
<213> ORGANISM: Homo sapiens

<400> SEQUENCE: 185
ttgcaagaat aaggcagcag                                          20

<210> SEQ ID NO 186
<211> LENGTH: 20
<212> TYPE: DNA
<213> ORGANISM: Homo sapiens

<400> SEQUENCE: 186
tccgagccat catgagagac                                          20

<210> SEQ ID NO 187
<211> LENGTH: 19
<212> TYPE: DNA
<213> ORGANISM: Homo sapiens

<400> SEQUENCE: 187
aaggccagac agcgagaac                                           19

<210> SEQ ID NO 188
<211> LENGTH: 20
<212> TYPE: DNA
<213> ORGANISM: Homo sapiens

<400> SEQUENCE: 188
cctgtaatga agggcgaag                                           20

<210> SEQ ID NO 189
<211> LENGTH: 26
<212> TYPE: DNA
<213> ORGANISM: Homo sapiens

<400> SEQUENCE: 189
aatattcttg cataaaagtc agaacc                                   26

<210> SEQ ID NO 190
<211> LENGTH: 20
<212> TYPE: DNA
```

```
<213> ORGANISM: Homo sapiens

<400> SEQUENCE: 190
ggtcagatgt gcaccatagc                                              20

<210> SEQ ID NO 191
<211> LENGTH: 25
<212> TYPE: DNA
<213> ORGANISM: Homo sapiens

<400> SEQUENCE: 191
cattgaaagc taataaggat tttgg                                        25

<210> SEQ ID NO 192
<211> LENGTH: 23
<212> TYPE: DNA
<213> ORGANISM: Homo sapiens

<400> SEQUENCE: 192
agagttgtat cccatttcct gtg                                          23

<210> SEQ ID NO 193
<211> LENGTH: 21
<212> TYPE: DNA
<213> ORGANISM: Homo sapiens

<400> SEQUENCE: 193
ggcagcatac acacatcctt c                                            21

<210> SEQ ID NO 194
<211> LENGTH: 22
<212> TYPE: DNA
<213> ORGANISM: Homo sapiens

<400> SEQUENCE: 194
acacacacac agacacacac ac                                           22

<210> SEQ ID NO 195
<211> LENGTH: 19
<212> TYPE: DNA
<213> ORGANISM: Homo sapiens

<400> SEQUENCE: 195
actgccacta cccccaaac                                               19

<210> SEQ ID NO 196
<211> LENGTH: 20
<212> TYPE: DNA
<213> ORGANISM: Homo sapiens

<400> SEQUENCE: 196
gggttgggtt gaattgtcag                                              20

<210> SEQ ID NO 197
<211> LENGTH: 20
<212> TYPE: DNA
<213> ORGANISM: Homo sapiens

<400> SEQUENCE: 197
cttctggact gggatgaagg                                              20

<210> SEQ ID NO 198
<211> LENGTH: 20
```

```
<212> TYPE: DNA
<213> ORGANISM: Homo sapiens

<400> SEQUENCE: 198
acttgtgatg ctcccagagg                                              20

<210> SEQ ID NO 199
<211> LENGTH: 20
<212> TYPE: DNA
<213> ORGANISM: Homo sapiens

<400> SEQUENCE: 199
tgctgaggct ccctataacc                                              20

<210> SEQ ID NO 200
<211> LENGTH: 20
<212> TYPE: DNA
<213> ORGANISM: Homo sapiens

<400> SEQUENCE: 200
agatgacagc cggttctctg                                              20

<210> SEQ ID NO 201
<211> LENGTH: 20
<212> TYPE: DNA
<213> ORGANISM: Homo sapiens

<400> SEQUENCE: 201
tctttgcagg cctctctgtc                                              20

<210> SEQ ID NO 202
<211> LENGTH: 20
<212> TYPE: DNA
<213> ORGANISM: Homo sapiens

<400> SEQUENCE: 202
ctgtgtccac ccccttactc                                              20

<210> SEQ ID NO 203
<211> LENGTH: 19
<212> TYPE: DNA
<213> ORGANISM: Homo sapiens

<400> SEQUENCE: 203
cacaccctga ctccaccac                                               19

<210> SEQ ID NO 204
<211> LENGTH: 20
<212> TYPE: DNA
<213> ORGANISM: Homo sapiens

<400> SEQUENCE: 204
gttctgtgcc caggagtgtc                                              20

<210> SEQ ID NO 205
<211> LENGTH: 20
<212> TYPE: DNA
<213> ORGANISM: Homo sapiens

<400> SEQUENCE: 205
ggctgacatc tgtgagcatc                                              20

<210> SEQ ID NO 206
```

```
<211> LENGTH: 20
<212> TYPE: DNA
<213> ORGANISM: Homo sapiens

<400> SEQUENCE: 206
tggagttgga gacagagcac                                              20

<210> SEQ ID NO 207
<211> LENGTH: 20
<212> TYPE: DNA
<213> ORGANISM: Homo sapiens

<400> SEQUENCE: 207
tggagaggtc aggagattgg                                              20

<210> SEQ ID NO 208
<211> LENGTH: 19
<212> TYPE: DNA
<213> ORGANISM: Homo sapiens

<400> SEQUENCE: 208
ccctccatct gggtctctg                                               19

<210> SEQ ID NO 209
<211> LENGTH: 20
<212> TYPE: DNA
<213> ORGANISM: Homo sapiens

<400> SEQUENCE: 209
ccctgatgct ctcctttgtc                                              20

<210> SEQ ID NO 210
<211> LENGTH: 20
<212> TYPE: DNA
<213> ORGANISM: Homo sapiens

<400> SEQUENCE: 210
ccaccacatg agtagcttgc                                              20

<210> SEQ ID NO 211
<211> LENGTH: 20
<212> TYPE: DNA
<213> ORGANISM: Homo sapiens

<400> SEQUENCE: 211
gccaggaggg taggagtatg                                              20

<210> SEQ ID NO 212
<211> LENGTH: 21
<212> TYPE: DNA
<213> ORGANISM: Homo sapiens

<400> SEQUENCE: 212
tgtgaagaag acgatggtga g                                            21

<210> SEQ ID NO 213
<211> LENGTH: 20
<212> TYPE: DNA
<213> ORGANISM: Homo sapiens

<400> SEQUENCE: 213
tcggggagag gaggtttatg                                              20
```

```
<210> SEQ ID NO 214
<211> LENGTH: 20
<212> TYPE: DNA
<213> ORGANISM: Homo sapiens

<400> SEQUENCE: 214
ggccaaggcc agatacttac                                              20

<210> SEQ ID NO 215
<211> LENGTH: 20
<212> TYPE: DNA
<213> ORGANISM: Homo sapiens

<400> SEQUENCE: 215
tcagctggtc ctttggagtc                                              20

<210> SEQ ID NO 216
<211> LENGTH: 20
<212> TYPE: DNA
<213> ORGANISM: Homo sapiens

<400> SEQUENCE: 216
aagtgtgagt cacccccatcc                                             20

<210> SEQ ID NO 217
<211> LENGTH: 23
<212> TYPE: DNA
<213> ORGANISM: Homo sapiens

<400> SEQUENCE: 217
aaaaatgcta aattccacaa tgc                                          23

<210> SEQ ID NO 218
<211> LENGTH: 23
<212> TYPE: DNA
<213> ORGANISM: Homo sapiens

<400> SEQUENCE: 218
cctggtggag gtagaggaaa tag                                          23

<210> SEQ ID NO 219
<211> LENGTH: 20
<212> TYPE: DNA
<213> ORGANISM: Homo sapiens

<400> SEQUENCE: 219
gcggccaatt gtgtctaatc                                              20

<210> SEQ ID NO 220
<211> LENGTH: 20
<212> TYPE: DNA
<213> ORGANISM: Homo sapiens

<400> SEQUENCE: 220
actgccccct gttgtcatag                                              20

<210> SEQ ID NO 221
<211> LENGTH: 27
<212> TYPE: DNA
<213> ORGANISM: Homo sapiens

<400> SEQUENCE: 221
tccaatgata agactaattt ggatagg                                      27
```

```
<210> SEQ ID NO 222
<211> LENGTH: 26
<212> TYPE: DNA
<213> ORGANISM: Homo sapiens

<400> SEQUENCE: 222
ccaatgataa gactaatttg gatagg                                          26

<210> SEQ ID NO 223
<211> LENGTH: 20
<212> TYPE: DNA
<213> ORGANISM: Homo sapiens

<400> SEQUENCE: 223
ctccatcctg ggtgacagag                                                 20

<210> SEQ ID NO 224
<211> LENGTH: 21
<212> TYPE: DNA
<213> ORGANISM: Homo sapiens

<400> SEQUENCE: 224
ttggtgtcag gcgaattaaa g                                               21

<210> SEQ ID NO 225
<211> LENGTH: 20
<212> TYPE: DNA
<213> ORGANISM: Homo sapiens

<400> SEQUENCE: 225
ctttccctct ctgcctctcc                                                 20

<210> SEQ ID NO 226
<211> LENGTH: 19
<212> TYPE: DNA
<213> ORGANISM: Homo sapiens

<400> SEQUENCE: 226
tttccctctc tgcctctcc                                                  19

<210> SEQ ID NO 227
<211> LENGTH: 20
<212> TYPE: DNA
<213> ORGANISM: Homo sapiens

<400> SEQUENCE: 227
agaccaagtc acctctgtgc                                                 20

<210> SEQ ID NO 228
<211> LENGTH: 20
<212> TYPE: DNA
<213> ORGANISM: Homo sapiens

<400> SEQUENCE: 228
cagaggtggc tgcctaaatc                                                 20

<210> SEQ ID NO 229
<211> LENGTH: 19
<212> TYPE: DNA
<213> ORGANISM: Homo sapiens

<400> SEQUENCE: 229
cccttcgcac agcttatgg                                                  19
```

```
<210> SEQ ID NO 230
<211> LENGTH: 20
<212> TYPE: DNA
<213> ORGANISM: Homo sapiens

<400> SEQUENCE: 230
aaaaggtgcg aggaatcaag                                                   20

<210> SEQ ID NO 231
<211> LENGTH: 20
<212> TYPE: DNA
<213> ORGANISM: Homo sapiens

<400> SEQUENCE: 231
acagtctcac agccatcgtg                                                   20

<210> SEQ ID NO 232
<211> LENGTH: 20
<212> TYPE: DNA
<213> ORGANISM: Homo sapiens

<400> SEQUENCE: 232
actgaggaag caccaacagc                                                   20

<210> SEQ ID NO 233
<211> LENGTH: 20
<212> TYPE: DNA
<213> ORGANISM: Homo sapiens

<400> SEQUENCE: 233
gacactcaga aaccccaac                                                    20

<210> SEQ ID NO 234
<211> LENGTH: 20
<212> TYPE: DNA
<213> ORGANISM: Homo sapiens

<400> SEQUENCE: 234
gtctgtgtgt cctgcacagc                                                   20

<210> SEQ ID NO 235
<211> LENGTH: 20
<212> TYPE: DNA
<213> ORGANISM: Homo sapiens

<400> SEQUENCE: 235
ggcctgcagt tccaattttc                                                   20

<210> SEQ ID NO 236
<211> LENGTH: 20
<212> TYPE: DNA
<213> ORGANISM: Homo sapiens

<400> SEQUENCE: 236
ggtcagacag tggggtcatc                                                   20

<210> SEQ ID NO 237
<211> LENGTH: 20
<212> TYPE: DNA
<213> ORGANISM: Homo sapiens

<400> SEQUENCE: 237
```
gagggaggtg ttagcagtgg 20

<210> SEQ ID NO 238
<211> LENGTH: 20
<212> TYPE: DNA
<213> ORGANISM: Homo sapiens

<400> SEQUENCE: 238
tccacacagc tctgaccatc 20

<210> SEQ ID NO 239
<211> LENGTH: 18
<212> TYPE: DNA
<213> ORGANISM: Homo sapiens

<400> SEQUENCE: 239
gggtggggtg agtgtgtg 18

<210> SEQ ID NO 240
<211> LENGTH: 21
<212> TYPE: DNA
<213> ORGANISM: Homo sapiens

<400> SEQUENCE: 240
aggtcatcaa gtcaggtgag g 21

<210> SEQ ID NO 241
<211> LENGTH: 20
<212> TYPE: DNA
<213> ORGANISM: Homo sapiens

<400> SEQUENCE: 241
ctgtctcact tggggcttcc 20

<210> SEQ ID NO 242
<211> LENGTH: 19
<212> TYPE: DNA
<213> ORGANISM: Homo sapiens

<400> SEQUENCE: 242
ctgcaaggtg gctgacttc 19

<210> SEQ ID NO 243
<211> LENGTH: 18
<212> TYPE: DNA
<213> ORGANISM: Homo sapiens

<400> SEQUENCE: 243
gctctgccca ggagtcac 18

<210> SEQ ID NO 244
<211> LENGTH: 20
<212> TYPE: DNA
<213> ORGANISM: Homo sapiens

<400> SEQUENCE: 244
aggtggccgt gaagaatatc 20

<210> SEQ ID NO 245
<211> LENGTH: 19
<212> TYPE: DNA
<213> ORGANISM: Homo sapiens

<400> SEQUENCE: 245

| | |
|---|---|
| caccaggggc tgtacattg | 19 |

<210> SEQ ID NO 246
<211> LENGTH: 20
<212> TYPE: DNA
<213> ORGANISM: Homo sapiens

<400> SEQUENCE: 246

| | |
|---|---|
| tccatcaagg ggaaactgag | 20 |

<210> SEQ ID NO 247
<211> LENGTH: 20
<212> TYPE: DNA
<213> ORGANISM: Homo sapiens

<400> SEQUENCE: 247

| | |
|---|---|
| tgggggagga ctcaattagg | 20 |

<210> SEQ ID NO 248
<211> LENGTH: 20
<212> TYPE: DNA
<213> ORGANISM: Homo sapiens

<400> SEQUENCE: 248

| | |
|---|---|
| ctgctctggg aggtcttctc | 20 |

<210> SEQ ID NO 249
<211> LENGTH: 20
<212> TYPE: DNA
<213> ORGANISM: Homo sapiens

<400> SEQUENCE: 249

| | |
|---|---|
| ggctgtgttt caaggtctgg | 20 |

<210> SEQ ID NO 250
<211> LENGTH: 20
<212> TYPE: DNA
<213> ORGANISM: Homo sapiens

<400> SEQUENCE: 250

| | |
|---|---|
| gagtcctgcc aacacctgac | 20 |

<210> SEQ ID NO 251
<211> LENGTH: 22
<212> TYPE: DNA
<213> ORGANISM: Homo sapiens

<400> SEQUENCE: 251

| | |
|---|---|
| caggatatga tgaacagcca ag | 22 |

<210> SEQ ID NO 252
<211> LENGTH: 19
<212> TYPE: DNA
<213> ORGANISM: Homo sapiens

<400> SEQUENCE: 252

| | |
|---|---|
| aggctgaggc aggagaatg | 19 |

<210> SEQ ID NO 253
<211> LENGTH: 19
<212> TYPE: DNA
<213> ORGANISM: Homo sapiens

```
<400> SEQUENCE: 253
aaagaggctg aggcaggag                                                19

<210> SEQ ID NO 254
<211> LENGTH: 20
<212> TYPE: DNA
<213> ORGANISM: Homo sapiens

<400> SEQUENCE: 254
ctgggtaaca gagcgagacc                                               20

<210> SEQ ID NO 255
<211> LENGTH: 21
<212> TYPE: DNA
<213> ORGANISM: Homo sapiens

<400> SEQUENCE: 255
gagaacgtgg tggtaagaag g                                             21

<210> SEQ ID NO 256
<211> LENGTH: 22
<212> TYPE: DNA
<213> ORGANISM: Homo sapiens

<400> SEQUENCE: 256
cgcatcttga tgagtgctct ac                                            22

<210> SEQ ID NO 257
<211> LENGTH: 22
<212> TYPE: DNA
<213> ORGANISM: Homo sapiens

<400> SEQUENCE: 257
cgcatcttga tgagtgctct ac                                            22

<210> SEQ ID NO 258
<211> LENGTH: 20
<212> TYPE: DNA
<213> ORGANISM: Homo sapiens

<400> SEQUENCE: 258
tgatactggg cgaaagaagc                                               20

<210> SEQ ID NO 259
<211> LENGTH: 20
<212> TYPE: DNA
<213> ORGANISM: Homo sapiens

<400> SEQUENCE: 259
acgacatgca ctcaatagcc                                               20

<210> SEQ ID NO 260
<211> LENGTH: 18
<212> TYPE: DNA
<213> ORGANISM: Homo sapiens

<400> SEQUENCE: 260
gtagcccccg aaggtgag                                                 18

<210> SEQ ID NO 261
<211> LENGTH: 19
<212> TYPE: DNA
<213> ORGANISM: Homo sapiens
```

```
<400> SEQUENCE: 261
ggagtggttg gtgatggtg                                            19

<210> SEQ ID NO 262
<211> LENGTH: 20
<212> TYPE: DNA
<213> ORGANISM: Homo sapiens

<400> SEQUENCE: 262
acattctgga agggaccac                                            20

<210> SEQ ID NO 263
<211> LENGTH: 20
<212> TYPE: DNA
<213> ORGANISM: Homo sapiens

<400> SEQUENCE: 263
ttgcccttcc ctcactaaac                                           20

<210> SEQ ID NO 264
<211> LENGTH: 20
<212> TYPE: DNA
<213> ORGANISM: Homo sapiens

<400> SEQUENCE: 264
ttgtcgtgaa ggtgctgaag                                           20

<210> SEQ ID NO 265
<211> LENGTH: 20
<212> TYPE: DNA
<213> ORGANISM: Homo sapiens

<400> SEQUENCE: 265
tgccgtatgg atccctctac                                           20

<210> SEQ ID NO 266
<211> LENGTH: 20
<212> TYPE: DNA
<213> ORGANISM: Homo sapiens

<400> SEQUENCE: 266
ctgtcattgg gctaccttcc                                           20

<210> SEQ ID NO 267
<211> LENGTH: 20
<212> TYPE: DNA
<213> ORGANISM: Homo sapiens

<400> SEQUENCE: 267
ttgcccagca tgttattgag                                           20

<210> SEQ ID NO 268
<211> LENGTH: 25
<212> TYPE: DNA
<213> ORGANISM: Homo sapiens

<400> SEQUENCE: 268
tcaatcaaat actgtcactg ctctc                                     25

<210> SEQ ID NO 269
<211> LENGTH: 23
<212> TYPE: DNA
```

<213> ORGANISM: Homo sapiens

<400> SEQUENCE: 269
tgtgtgataa gcaatgggta ctg                                            23

<210> SEQ ID NO 270
<211> LENGTH: 20
<212> TYPE: DNA
<213> ORGANISM: Homo sapiens

<400> SEQUENCE: 270
catgaaatcc cagacaatgg                                                20

<210> SEQ ID NO 271
<211> LENGTH: 25
<212> TYPE: DNA
<213> ORGANISM: Homo sapiens

<400> SEQUENCE: 271
tgggactaaa attaaaatct gatgg                                          25

<210> SEQ ID NO 272
<211> LENGTH: 24
<212> TYPE: DNA
<213> ORGANISM: Homo sapiens

<400> SEQUENCE: 272
caaggccact tataagctat cacc                                           24

<210> SEQ ID NO 273
<211> LENGTH: 20
<212> TYPE: DNA
<213> ORGANISM: Homo sapiens

<400> SEQUENCE: 273
gctctgcagc actctcactg                                                20

<210> SEQ ID NO 274
<211> LENGTH: 20
<212> TYPE: DNA
<213> ORGANISM: Homo sapiens

<400> SEQUENCE: 274
ttgtccgcac tgagttgaag                                                20

<210> SEQ ID NO 275
<211> LENGTH: 20
<212> TYPE: DNA
<213> ORGANISM: Homo sapiens

<400> SEQUENCE: 275
catccatcct gtgtcactcg                                                20

<210> SEQ ID NO 276
<211> LENGTH: 20
<212> TYPE: DNA
<213> ORGANISM: Homo sapiens

<400> SEQUENCE: 276
cacacctgtt ccacctctcc                                                20

<210> SEQ ID NO 277
<211> LENGTH: 19

```
<212> TYPE: DNA
<213> ORGANISM: Homo sapiens

<400> SEQUENCE: 277
gccctggaca agttccttc                                                  19

<210> SEQ ID NO 278
<211> LENGTH: 20
<212> TYPE: DNA
<213> ORGANISM: Homo sapiens

<400> SEQUENCE: 278
gtgtcctctc acctgcacac                                                 20

<210> SEQ ID NO 279
<211> LENGTH: 20
<212> TYPE: DNA
<213> ORGANISM: Homo sapiens

<400> SEQUENCE: 279
gcccttcctg tctgtttctg                                                 20

<210> SEQ ID NO 280
<211> LENGTH: 20
<212> TYPE: DNA
<213> ORGANISM: Homo sapiens

<400> SEQUENCE: 280
gttgcccaga taaggagacg                                                 20

<210> SEQ ID NO 281
<211> LENGTH: 19
<212> TYPE: DNA
<213> ORGANISM: Homo sapiens

<400> SEQUENCE: 281
tctccaccct cctcctctg                                                  19

<210> SEQ ID NO 282
<211> LENGTH: 20
<212> TYPE: DNA
<213> ORGANISM: Homo sapiens

<400> SEQUENCE: 282
tccaggacta acggtgcttc                                                 20

<210> SEQ ID NO 283
<211> LENGTH: 20
<212> TYPE: DNA
<213> ORGANISM: Homo sapiens

<400> SEQUENCE: 283
gggtgtcttt ggaactgtgc                                                 20

<210> SEQ ID NO 284
<211> LENGTH: 20
<212> TYPE: DNA
<213> ORGANISM: Homo sapiens

<400> SEQUENCE: 284
cagggtcctg tgcttctcag                                                 20

<210> SEQ ID NO 285
```

```
<211> LENGTH: 21
<212> TYPE: DNA
<213> ORGANISM: Homo sapiens

<400> SEQUENCE: 285
tgtcttccac aaaaccagtc c                                            21

<210> SEQ ID NO 286
<211> LENGTH: 19
<212> TYPE: DNA
<213> ORGANISM: Homo sapiens

<400> SEQUENCE: 286
agatcgcacc actgcactc                                               19

<210> SEQ ID NO 287
<211> LENGTH: 18
<212> TYPE: DNA
<213> ORGANISM: Homo sapiens

<400> SEQUENCE: 287
ccagtctggg cgacagag                                                18

<210> SEQ ID NO 288
<211> LENGTH: 21
<212> TYPE: DNA
<213> ORGANISM: Homo sapiens

<400> SEQUENCE: 288 cctttttgaga cccccctctta g                                          21

<210> SEQ ID NO 289
<211> LENGTH: 20
<212> TYPE: DNA
<213> ORGANISM: Homo sapiens

<400> SEQUENCE: 289
ctcctgacct caggtgatcc                                              20

<210> SEQ ID NO 290
<211> LENGTH: 20
<212> TYPE: DNA
<213> ORGANISM: Homo sapiens

<400> SEQUENCE: 290
gagacccacc acggtatctg                                              20

<210> SEQ ID NO 291
<211> LENGTH: 20
<212> TYPE: DNA
<213> ORGANISM: Homo sapiens

<400> SEQUENCE: 291
ggaattcacg agatggaagc                                              20

<210> SEQ ID NO 292
<211> LENGTH: 20
<212> TYPE: DNA
<213> ORGANISM: Homo sapiens

<400> SEQUENCE: 292
tgtttggaga aaatcggaag                                              20
```

```
<210> SEQ ID NO 293
<211> LENGTH: 20
<212> TYPE: DNA
<213> ORGANISM: Homo sapiens

<400> SEQUENCE: 293
aagtgcacca agaaccgact                                               20

<210> SEQ ID NO 294
<211> LENGTH: 18
<212> TYPE: DNA
<213> ORGANISM: Homo sapiens

<400> SEQUENCE: 294
tgatgaacgc cctggttc                                                 18

<210> SEQ ID NO 295
<211> LENGTH: 19
<212> TYPE: DNA
<213> ORGANISM: Homo sapiens

<400> SEQUENCE: 295
ccaggctggt cagagtcac                                                19

<210> SEQ ID NO 296
<211> LENGTH: 20
<212> TYPE: DNA
<213> ORGANISM: Homo sapiens

<400> SEQUENCE: 296
gattagggag cttggtgctg                                               20

<210> SEQ ID NO 297
<211> LENGTH: 20
<212> TYPE: DNA
<213> ORGANISM: Homo sapiens

<400> SEQUENCE: 297
aggggtccct cacttttctc                                               20

<210> SEQ ID NO 298
<211> LENGTH: 20
<212> TYPE: DNA
<213> ORGANISM: Homo sapiens

<400> SEQUENCE: 298
tcccagatgt gaagctggag                                               20

<210> SEQ ID NO 299
<211> LENGTH: 20
<212> TYPE: DNA
<213> ORGANISM: Homo sapiens

<400> SEQUENCE: 299
tccttgggtg tgtgtgtctg                                               20

<210> SEQ ID NO 300
<211> LENGTH: 20
<212> TYPE: DNA
<213> ORGANISM: Homo sapiens

<400> SEQUENCE: 300
tcttcctggt ttgaggttgg                                               20
```

```
<210> SEQ ID NO 301
<211> LENGTH: 20
<212> TYPE: DNA
<213> ORGANISM: Homo sapiens

<400> SEQUENCE: 301
cagtgtctgg ccctattgtg                                              20

<210> SEQ ID NO 302
<211> LENGTH: 21
<212> TYPE: DNA
<213> ORGANISM: Homo sapiens

<400> SEQUENCE: 302 ggagggatt tacatgtacg c                                             21

<210> SEQ ID NO 303
<211> LENGTH: 20
<212> TYPE: DNA
<213> ORGANISM: Homo sapiens

<400> SEQUENCE: 303
tgagagggaa gtgacccttg                                              20

<210> SEQ ID NO 304
<211> LENGTH: 20
<212> TYPE: DNA
<213> ORGANISM: Homo sapiens

<400> SEQUENCE: 304
gggagaggag ttggaaaagg                                              20

<210> SEQ ID NO 305
<211> LENGTH: 19
<212> TYPE: DNA
<213> ORGANISM: Homo sapiens

<400> SEQUENCE: 305
agcggaggag agtggagag                                               19

<210> SEQ ID NO 306
<211> LENGTH: 20
<212> TYPE: DNA
<213> ORGANISM: Homo sapiens

<400> SEQUENCE: 306
ggcaggtcag agtggaggag                                              20

<210> SEQ ID NO 307
<211> LENGTH: 21
<212> TYPE: DNA
<213> ORGANISM: Homo sapiens

<400> SEQUENCE: 307
caccagaaac ccaaacaact g                                            21

<210> SEQ ID NO 308
<211> LENGTH: 19
<212> TYPE: DNA
<213> ORGANISM: Homo sapiens

<400> SEQUENCE: 308
ttgcctttgc ctgctgtag                                               19
```

<210> SEQ ID NO 309
<211> LENGTH: 20
<212> TYPE: DNA
<213> ORGANISM: Homo sapiens

<400> SEQUENCE: 309
tgctggagaa ggaaggagtc         20

<210> SEQ ID NO 310
<211> LENGTH: 20
<212> TYPE: DNA
<213> ORGANISM: Homo sapiens

<400> SEQUENCE: 310
ataagccata ggcaggatgg         20

<210> SEQ ID NO 311
<211> LENGTH: 21
<212> TYPE: DNA
<213> ORGANISM: Homo sapiens

<400> SEQUENCE: 311
cagcatcttc acacacctct g        21

<210> SEQ ID NO 312
<211> LENGTH: 20
<212> TYPE: DNA
<213> ORGANISM: Homo sapiens

<400> SEQUENCE: 312
gcctagcctt tagcttgtgc         20

<210> SEQ ID NO 313
<211> LENGTH: 23
<212> TYPE: DNA
<213> ORGANISM: Homo sapiens

<400> SEQUENCE: 313
tgcctttctt cagattcatt ctc      23

<210> SEQ ID NO 314
<211> LENGTH: 20
<212> TYPE: DNA
<213> ORGANISM: Homo sapiens

<400> SEQUENCE: 314
gaaccagctg ccgttgttag         20

<210> SEQ ID NO 315
<211> LENGTH: 20
<212> TYPE: DNA
<213> ORGANISM: Homo sapiens

<400> SEQUENCE: 315
gtgccaacaa catcaaccac         20

<210> SEQ ID NO 316
<211> LENGTH: 22
<212> TYPE: DNA
<213> ORGANISM: Homo sapiens

<400> SEQUENCE: 316
cctttctgtg catttctcat tc                                        22

<210> SEQ ID NO 317
<211> LENGTH: 20
<212> TYPE: DNA
<213> ORGANISM: Homo sapiens

<400> SEQUENCE: 317
ttctctagcc cttccccaac                                           20

<210> SEQ ID NO 318
<211> LENGTH: 20
<212> TYPE: DNA
<213> ORGANISM: Homo sapiens

<400> SEQUENCE: 318
aaatgcacag gcacttttgg                                           20

<210> SEQ ID NO 319
<211> LENGTH: 20
<212> TYPE: DNA
<213> ORGANISM: Homo sapiens

<400> SEQUENCE: 319
accagggagc aactgaactg                                           20

<210> SEQ ID NO 320
<211> LENGTH: 22
<212> TYPE: DNA
<213> ORGANISM: Homo sapiens

<400> SEQUENCE: 320
tgagtaacag ggcaaacaga ag                                        22

<210> SEQ ID NO 321
<211> LENGTH: 23
<212> TYPE: DNA
<213> ORGANISM: Homo sapiens

<400> SEQUENCE: 321
atgagtaaca gggcaaacag aag                                       23

<210> SEQ ID NO 322
<211> LENGTH: 20
<212> TYPE: DNA
<213> ORGANISM: Homo sapiens

<400> SEQUENCE: 322 cccttttgcgt ttatttttgc                                          20

<210> SEQ ID NO 323
<211> LENGTH: 20
<212> TYPE: DNA
<213> ORGANISM: Homo sapiens

<400> SEQUENCE: 323
cccacagcct cactttgaac                                           20

<210> SEQ ID NO 324
<211> LENGTH: 22
<212> TYPE: DNA
<213> ORGANISM: Homo sapiens

<400> SEQUENCE: 324
tcattagcat gctttggaag tg								22

<210> SEQ ID NO 325
<211> LENGTH: 21
<212> TYPE: DNA
<213> ORGANISM: Homo sapiens

<400> SEQUENCE: 325
tccttgattc tccttcattg c								21

<210> SEQ ID NO 326
<211> LENGTH: 20
<212> TYPE: DNA
<213> ORGANISM: Homo sapiens

<400> SEQUENCE: 326
ggggagtgag tgctaactgg								20

<210> SEQ ID NO 327
<211> LENGTH: 20
<212> TYPE: DNA
<213> ORGANISM: Homo sapiens

<400> SEQUENCE: 327
gatggacacc cagcttcttc								20

<210> SEQ ID NO 328
<211> LENGTH: 21
<212> TYPE: DNA
<213> ORGANISM: Homo sapiens

<400> SEQUENCE: 328
gctttgcata tgcctaagga g								21

<210> SEQ ID NO 329
<211> LENGTH: 20
<212> TYPE: DNA
<213> ORGANISM: Homo sapiens

<400> SEQUENCE: 329
gcatctttta gcaccagcag								20

<210> SEQ ID NO 330
<211> LENGTH: 20
<212> TYPE: DNA
<213> ORGANISM: Homo sapiens

<400> SEQUENCE: 330
ttgccttctg tctctgttgc								20

<210> SEQ ID NO 331
<211> LENGTH: 23
<212> TYPE: DNA
<213> ORGANISM: Homo sapiens

<400> SEQUENCE: 331
tgagaaaaca aaaccaagag tgg							23

<210> SEQ ID NO 332
<211> LENGTH: 20
<212> TYPE: DNA
<213> ORGANISM: Homo sapiens

```
<400> SEQUENCE: 332
gttaggtggc aggattaggg                                          20

<210> SEQ ID NO 333
<211> LENGTH: 20
<212> TYPE: DNA
<213> ORGANISM: Homo sapiens

<400> SEQUENCE: 333
tatcagggca gtcctgtgtg                                          20

<210> SEQ ID NO 334
<211> LENGTH: 20
<212> TYPE: DNA
<213> ORGANISM: Homo sapiens

<400> SEQUENCE: 334
ccaaggccga gaaactctac                                          20

<210> SEQ ID NO 335
<211> LENGTH: 20
<212> TYPE: DNA
<213> ORGANISM: Homo sapiens

<400> SEQUENCE: 335
ctgggtggtg ttgctagatg                                          20

<210> SEQ ID NO 336
<211> LENGTH: 21
<212> TYPE: DNA
<213> ORGANISM: Homo sapiens

<400> SEQUENCE: 336 ggagggaac tttaagggaa c                                         21

<210> SEQ ID NO 337
<211> LENGTH: 21
<212> TYPE: DNA
<213> ORGANISM: Homo sapiens

<400> SEQUENCE: 337
aagggaactg gattgtgact g                                        21

<210> SEQ ID NO 338
<211> LENGTH: 21
<212> TYPE: DNA
<213> ORGANISM: Homo sapiens

<400> SEQUENCE: 338
tgggacatac acaaagcaat g                                        21

<210> SEQ ID NO 339
<211> LENGTH: 20
<212> TYPE: DNA
<213> ORGANISM: Homo sapiens

<400> SEQUENCE: 339
actgtgtgca agggcctatc                                          20

<210> SEQ ID NO 340
<211> LENGTH: 20
<212> TYPE: DNA
<213> ORGANISM: Homo sapiens
```

<400> SEQUENCE: 340
aggatgctca ccctctcttg                                                 20

<210> SEQ ID NO 341
<211> LENGTH: 20
<212> TYPE: DNA
<213> ORGANISM: Homo sapiens

<400> SEQUENCE: 341
tcctaggggc tgtactttgg                                                 20

<210> SEQ ID NO 342
<211> LENGTH: 20
<212> TYPE: DNA
<213> ORGANISM: Homo sapiens

<400> SEQUENCE: 342
gatccggaag tacacgatgc                                                 20

<210> SEQ ID NO 343
<211> LENGTH: 20
<212> TYPE: DNA
<213> ORGANISM: Homo sapiens

<400> SEQUENCE: 343
ggcagttaca gcggagaagg                                                 20

<210> SEQ ID NO 344
<211> LENGTH: 20
<212> TYPE: DNA
<213> ORGANISM: Homo sapiens

<400> SEQUENCE: 344
tccaggctgg tactttgagc                                                 20

<210> SEQ ID NO 345
<211> LENGTH: 20
<212> TYPE: DNA
<213> ORGANISM: Homo sapiens

<400> SEQUENCE: 345
gtatgcacct gggctctttg                                                 20

<210> SEQ ID NO 346
<211> LENGTH: 20
<212> TYPE: DNA
<213> ORGANISM: Homo sapiens

<400> SEQUENCE: 346
ggctctttgc aggtctctcc                                                 20

<210> SEQ ID NO 347
<211> LENGTH: 20
<212> TYPE: DNA
<213> ORGANISM: Homo sapiens

<400> SEQUENCE: 347
ggttaggtga aggaccaagg                                                 20

<210> SEQ ID NO 348
<211> LENGTH: 20
<212> TYPE: DNA

<213> ORGANISM: Homo sapiens

<400> SEQUENCE: 348
ctgtctcctg gcatcacatc                                                    20

<210> SEQ ID NO 349
<211> LENGTH: 20
<212> TYPE: DNA
<213> ORGANISM: Homo sapiens

<400> SEQUENCE: 349
tctaccacct gagggctttg                                                    20

<210> SEQ ID NO 350
<211> LENGTH: 19
<212> TYPE: DNA
<213> ORGANISM: Homo sapiens

<400> SEQUENCE: 350
ggctaagagc accctcctg                                                     19

<210> SEQ ID NO 351
<211> LENGTH: 20
<212> TYPE: DNA
<213> ORGANISM: Homo sapiens

<400> SEQUENCE: 351
ctctgtcctg tgtggagagc                                                    20

<210> SEQ ID NO 352
<211> LENGTH: 20
<212> TYPE: DNA
<213> ORGANISM: Homo sapiens

<400> SEQUENCE: 352
aatgtggctg tcacaaaacg                                                    20

<210> SEQ ID NO 353
<211> LENGTH: 20
<212> TYPE: DNA
<213> ORGANISM: Homo sapiens

<400> SEQUENCE: 353
tgggaccatg ttggaagttg                                                    20

<210> SEQ ID NO 354
<211> LENGTH: 20
<212> TYPE: DNA
<213> ORGANISM: Homo sapiens

<400> SEQUENCE: 354
acttccaggg cattggactc                                                    20

<210> SEQ ID NO 355
<211> LENGTH: 22
<212> TYPE: DNA
<213> ORGANISM: Homo sapiens

<400> SEQUENCE: 355
gagcctggta aaatgtcaga gc                                                 22

<210> SEQ ID NO 356
<211> LENGTH: 21

<212> TYPE: DNA
<213> ORGANISM: Homo sapiens

<400> SEQUENCE: 356
catcgttttg acttgttgca g                                              21

<210> SEQ ID NO 357
<211> LENGTH: 20
<212> TYPE: DNA
<213> ORGANISM: Homo sapiens

<400> SEQUENCE: 357
tggactcttt cagctgttgc                                                20

<210> SEQ ID NO 358
<211> LENGTH: 19
<212> TYPE: DNA
<213> ORGANISM: Homo sapiens

<400> SEQUENCE: 358
gcctaggtgc caaggagtc                                                 19

<210> SEQ ID NO 359
<211> LENGTH: 20
<212> TYPE: DNA
<213> ORGANISM: Homo sapiens

<400> SEQUENCE: 359
tccatcccac ctgagaactg                                                20

<210> SEQ ID NO 360
<211> LENGTH: 19
<212> TYPE: DNA
<213> ORGANISM: Homo sapiens

<400> SEQUENCE: 360
agcctccttt tgcttggtg                                                 19

<210> SEQ ID NO 361
<211> LENGTH: 19
<212> TYPE: DNA
<213> ORGANISM: Homo sapiens

<400> SEQUENCE: 361
taagggtggg tcccaactg                                                 19

<210> SEQ ID NO 362
<211> LENGTH: 20
<212> TYPE: DNA
<213> ORGANISM: Homo sapiens

<400> SEQUENCE: 362
ctcactgagt tgctggaacg                                                20

<210> SEQ ID NO 363
<211> LENGTH: 21
<212> TYPE: DNA
<213> ORGANISM: Homo sapiens

<400> SEQUENCE: 363
gacccaattc tttcacattc g                                              21

<210> SEQ ID NO 364

```
<211> LENGTH: 27
<212> TYPE: DNA
<213> ORGANISM: Homo sapiens

<400> SEQUENCE: 364
aatatataac cagggagaac ctgatac                                        27

<210> SEQ ID NO 365
<211> LENGTH: 23
<212> TYPE: DNA
<213> ORGANISM: Homo sapiens

<400> SEQUENCE: 365
ttttattgct ctcaaaacga agg                                            23

<210> SEQ ID NO 366
<211> LENGTH: 20
<212> TYPE: DNA
<213> ORGANISM: Homo sapiens

<400> SEQUENCE: 366
aggctgcgtg agacttaacc                                                20

<210> SEQ ID NO 367
<211> LENGTH: 20
<212> TYPE: DNA
<213> ORGANISM: Homo sapiens

<400> SEQUENCE: 367
ttccaggagt gtgtgctgtc                                                20

<210> SEQ ID NO 368
<211> LENGTH: 20
<212> TYPE: DNA
<213> ORGANISM: Homo sapiens

<400> SEQUENCE: 368
cccattgaac accaggagaa                                                20

<210> SEQ ID NO 369
<211> LENGTH: 20
<212> TYPE: DNA
<213> ORGANISM: Homo sapiens

<400> SEQUENCE: 369
caagctcccg atctcaagtg                                                20

<210> SEQ ID NO 370
<211> LENGTH: 21
<212> TYPE: DNA
<213> ORGANISM: Homo sapiens

<400> SEQUENCE: 370
cccaactgac tccaacatca c                                              21

<210> SEQ ID NO 371
<211> LENGTH: 20
<212> TYPE: DNA
<213> ORGANISM: Homo sapiens

<400> SEQUENCE: 371
tgcccgaaga atgagatcag                                                20
```

```
<210> SEQ ID NO 372
<211> LENGTH: 20
<212> TYPE: DNA
<213> ORGANISM: Homo sapiens

<400> SEQUENCE: 372
atgtccctgc cactcttcag                                              20

<210> SEQ ID NO 373
<211> LENGTH: 20
<212> TYPE: DNA
<213> ORGANISM: Homo sapiens

<400> SEQUENCE: 373
agccatccat tacaggcttc                                              20

<210> SEQ ID NO 374
<211> LENGTH: 22
<212> TYPE: DNA
<213> ORGANISM: Homo sapiens

<400> SEQUENCE: 374
tctccccagt gagataaatt cc                                           22

<210> SEQ ID NO 375
<211> LENGTH: 26
<212> TYPE: DNA
<213> ORGANISM: Homo sapiens

<400> SEQUENCE: 375
gaagaaaatg tgaaggaaat acagac                                       26

<210> SEQ ID NO 376
<211> LENGTH: 19
<212> TYPE: DNA
<213> ORGANISM: Homo sapiens

<400> SEQUENCE: 376
gtcatgtggg ctgaaatgc                                               19

<210> SEQ ID NO 377
<211> LENGTH: 21
<212> TYPE: DNA
<213> ORGANISM: Homo sapiens

<400> SEQUENCE: 377
ttaatgtgca aaccagtgtg g                                            21

<210> SEQ ID NO 378
<211> LENGTH: 20
<212> TYPE: DNA
<213> ORGANISM: Homo sapiens

<400> SEQUENCE: 378
actcagggaa gtggcttgtg                                              20

<210> SEQ ID NO 379
<211> LENGTH: 21
<212> TYPE: DNA
<213> ORGANISM: Homo sapiens

<400> SEQUENCE: 379
gcaccagtac cctattgatg g                                            21
```

<210> SEQ ID NO 380
<211> LENGTH: 21
<212> TYPE: DNA
<213> ORGANISM: Homo sapiens

<400> SEQUENCE: 380
gcaccagtac cctattgatg g           21

<210> SEQ ID NO 381
<211> LENGTH: 18
<212> TYPE: DNA
<213> ORGANISM: Homo sapiens

<400> SEQUENCE: 381
cctctccagg gtggtgtg               18

<210> SEQ ID NO 382
<211> LENGTH: 20
<212> TYPE: DNA
<213> ORGANISM: Homo sapiens

<400> SEQUENCE: 382
gccctgcatt taatttgtgg             20

<210> SEQ ID NO 383
<211> LENGTH: 20
<212> TYPE: DNA
<213> ORGANISM: Homo sapiens

<400> SEQUENCE: 383
gtgtggtgtg ccctttttacc            20

<210> SEQ ID NO 384
<211> LENGTH: 19
<212> TYPE: DNA
<213> ORGANISM: Homo sapiens

<400> SEQUENCE: 384
cacgaattcc tggtcatgc              19

<210> SEQ ID NO 385
<211> LENGTH: 20
<212> TYPE: DNA
<213> ORGANISM: Homo sapiens

<400> SEQUENCE: 385
ctggagactt ggcctttctg             20

<210> SEQ ID NO 386
<211> LENGTH: 20
<212> TYPE: DNA
<213> ORGANISM: Homo sapiens

<400> SEQUENCE: 386
tcccttcgcc ccactaatac             20

<210> SEQ ID NO 387
<211> LENGTH: 22
<212> TYPE: DNA
<213> ORGANISM: Homo sapiens

<400> SEQUENCE: 387
tcacgatcca ttttgagaag tg          22

<210> SEQ ID NO 388
<211> LENGTH: 20
<212> TYPE: DNA
<213> ORGANISM: Homo sapiens

<400> SEQUENCE: 388
gcctggaaaa atctctggtg                                                    20

<210> SEQ ID NO 389
<211> LENGTH: 20
<212> TYPE: DNA
<213> ORGANISM: Homo sapiens

<400> SEQUENCE: 389
gagaggtgct cccttcacag                                                    20

<210> SEQ ID NO 390
<211> LENGTH: 18
<212> TYPE: DNA
<213> ORGANISM: Homo sapiens

<400> SEQUENCE: 390
gagctgctct cggaaatg                                                      18

<210> SEQ ID NO 391
<211> LENGTH: 20
<212> TYPE: DNA
<213> ORGANISM: Homo sapiens

<400> SEQUENCE: 391
gcaaggattt gctgagcttc                                                    20

<210> SEQ ID NO 392
<211> LENGTH: 22
<212> TYPE: DNA
<213> ORGANISM: Homo sapiens

<400> SEQUENCE: 392
cccaaaccta aaatgaagc ag                                                  22

<210> SEQ ID NO 393
<211> LENGTH: 33
<212> TYPE: DNA
<213> ORGANISM: Homo sapiens

<400> SEQUENCE: 393
agagctatta atataatagc tgagatcaga agt                                     33

<210> SEQ ID NO 394
<211> LENGTH: 21
<212> TYPE: DNA
<213> ORGANISM: Homo sapiens

<400> SEQUENCE: 394
tgaaggcctg tcagattatg g                                                  21

<210> SEQ ID NO 395
<211> LENGTH: 20
<212> TYPE: DNA
<213> ORGANISM: Homo sapiens

<400> SEQUENCE: 395
gggtgacaga gcgagacttc                                                 20

<210> SEQ ID NO 396
<211> LENGTH: 30
<212> TYPE: DNA
<213> ORGANISM: Homo sapiens

<400> SEQUENCE: 396
cacctttaat gtataataaa gttttgtcat                                      30

<210> SEQ ID NO 397
<211> LENGTH: 20
<212> TYPE: DNA
<213> ORGANISM: Homo sapiens

<400> SEQUENCE: 397
atgaagcaac cgtgttgaag                                                 20

<210> SEQ ID NO 398
<211> LENGTH: 21
<212> TYPE: DNA
<213> ORGANISM: Homo sapiens

<400> SEQUENCE: 398
tcaggcctgc tgtgataact c                                               21

<210> SEQ ID NO 399
<211> LENGTH: 20
<212> TYPE: DNA
<213> ORGANISM: Homo sapiens

<400> SEQUENCE: 399
caggcctgct gtgataactc                                                 20

<210> SEQ ID NO 400
<211> LENGTH: 26
<212> TYPE: DNA
<213> ORGANISM: Homo sapiens

<400> SEQUENCE: 400
tgaaaaggtt tgaaaacata caaaag                                          26

<210> SEQ ID NO 401
<211> LENGTH: 20
<212> TYPE: DNA
<213> ORGANISM: Homo sapiens

<400> SEQUENCE: 401
tgcggagctt ccagataaac                                                 20

<210> SEQ ID NO 402
<211> LENGTH: 20
<212> TYPE: DNA
<213> ORGANISM: Homo sapiens

<400> SEQUENCE: 402
ccctcatacc cgactctctg                                                 20

<210> SEQ ID NO 403
<211> LENGTH: 20
<212> TYPE: DNA
<213> ORGANISM: Homo sapiens

<400> SEQUENCE: 403
aaattggcta gatgggcaag                                               20

<210> SEQ ID NO 404
<211> LENGTH: 20
<212> TYPE: DNA
<213> ORGANISM: Homo sapiens

<400> SEQUENCE: 404
tcctcgtggg agtttacagg                                               20

<210> SEQ ID NO 405
<211> LENGTH: 20
<212> TYPE: DNA
<213> ORGANISM: Homo sapiens

<400> SEQUENCE: 405
aggatgcctt ccaaaatcag                                               20

<210> SEQ ID NO 406
<211> LENGTH: 20
<212> TYPE: DNA
<213> ORGANISM: Homo sapiens

<400> SEQUENCE: 406
cctctttcca cctagggatg                                               20

<210> SEQ ID NO 407
<211> LENGTH: 21
<212> TYPE: DNA
<213> ORGANISM: Homo sapiens

<400> SEQUENCE: 407
cgcagtggtc ctttctactt g                                             21

<210> SEQ ID NO 408
<211> LENGTH: 20
<212> TYPE: DNA
<213> ORGANISM: Homo sapiens

<400> SEQUENCE: 408
cttccagccc tgtctctcag                                               20

<210> SEQ ID NO 409
<211> LENGTH: 21
<212> TYPE: DNA
<213> ORGANISM: Homo sapiens

<400> SEQUENCE: 409
cctctgagtt cctgtccctt c                                             21

<210> SEQ ID NO 410
<211> LENGTH: 21
<212> TYPE: DNA
<213> ORGANISM: Homo sapiens

<400> SEQUENCE: 410
ttcagccttg tatccatttg c                                             21

<210> SEQ ID NO 411
<211> LENGTH: 22
<212> TYPE: DNA
<213> ORGANISM: Homo sapiens

```
<400> SEQUENCE: 411
tcaaaatgtt tcacagaaat gc                                              22

<210> SEQ ID NO 412
<211> LENGTH: 25
<212> TYPE: DNA
<213> ORGANISM: Homo sapiens

<400> SEQUENCE: 412
ggcaactaaa aatgagaagt tttcc                                           25

<210> SEQ ID NO 413
<211> LENGTH: 24
<212> TYPE: DNA
<213> ORGANISM: Homo sapiens

<400> SEQUENCE: 413
tcagttgtta tccttttagg caac                                            24

<210> SEQ ID NO 414
<211> LENGTH: 21
<212> TYPE: DNA
<213> ORGANISM: Homo sapiens

<400> SEQUENCE: 414
tccacaaatg aaggaacac c                                                21

<210> SEQ ID NO 415
<211> LENGTH: 20
<212> TYPE: DNA
<213> ORGANISM: Homo sapiens

<400> SEQUENCE: 415
ccacaaatga aggaacacc                                                  20

<210> SEQ ID NO 416
<211> LENGTH: 20
<212> TYPE: DNA
<213> ORGANISM: Homo sapiens

<400> SEQUENCE: 416
gaacggtccg gacataacac                                                 20

<210> SEQ ID NO 417
<211> LENGTH: 20
<212> TYPE: DNA
<213> ORGANISM: Homo sapiens

<400> SEQUENCE: 417
tgtcactgcc agtttctgtg                                                 20

<210> SEQ ID NO 418
<211> LENGTH: 22
<212> TYPE: DNA
<213> ORGANISM: Homo sapiens

<400> SEQUENCE: 418
tgtacatctt gcaggtcaaa gg                                              22

<210> SEQ ID NO 419
<211> LENGTH: 25
<212> TYPE: DNA
<213> ORGANISM: Homo sapiens
```

```
<400> SEQUENCE: 419
aaaaattaga agacaggcaa agttc                                         25

<210> SEQ ID NO 420
<211> LENGTH: 21
<212> TYPE: DNA
<213> ORGANISM: Homo sapiens

<400> SEQUENCE: 420
aactcacagg gctttaccaa g                                             21

<210> SEQ ID NO 421
<211> LENGTH: 20
<212> TYPE: DNA
<213> ORGANISM: Homo sapiens

<400> SEQUENCE: 421
catgaccatc ttccaagcag                                               20

<210> SEQ ID NO 422
<211> LENGTH: 24
<212> TYPE: DNA
<213> ORGANISM: Homo sapiens

<400> SEQUENCE: 422
ccaaaattat cttatttggc tgtc                                          24

<210> SEQ ID NO 423
<211> LENGTH: 21
<212> TYPE: DNA
<213> ORGANISM: Homo sapiens

<400> SEQUENCE: 423
caagatgggt agacctgatg c                                             21

<210> SEQ ID NO 424
<211> LENGTH: 20
<212> TYPE: DNA
<213> ORGANISM: Homo sapiens

<400> SEQUENCE: 424
atcctgcact tcacgcactc                                               20

<210> SEQ ID NO 425
<211> LENGTH: 19
<212> TYPE: DNA
<213> ORGANISM: Homo sapiens

<400> SEQUENCE: 425
gcctcctgga tgctttagg                                                19

<210> SEQ ID NO 426
<211> LENGTH: 18
<212> TYPE: DNA
<213> ORGANISM: Homo sapiens

<400> SEQUENCE: 426
atctgctgca ggggtgtg                                                 18

<210> SEQ ID NO 427
<211> LENGTH: 18
<212> TYPE: DNA
```

```
<213> ORGANISM: Homo sapiens

<400> SEQUENCE: 427
atctgctgca ggggtgtg                                                      18

<210> SEQ ID NO 428
<211> LENGTH: 20
<212> TYPE: DNA
<213> ORGANISM: Homo sapiens

<400> SEQUENCE: 428
ggaccccgta gtcatctcag                                                    20

<210> SEQ ID NO 429
<211> LENGTH: 20
<212> TYPE: DNA
<213> ORGANISM: Homo sapiens

<400> SEQUENCE: 429
gggtcaaact cccagagagc                                                    20

<210> SEQ ID NO 430
<211> LENGTH: 20
<212> TYPE: DNA
<213> ORGANISM: Homo sapiens

<400> SEQUENCE: 430 accccttat agtgccgaag                                                     20

<210> SEQ ID NO 431
<211> LENGTH: 21
<212> TYPE: DNA
<213> ORGANISM: Homo sapiens

<400> SEQUENCE: 431
cagaagcagc ccatctacat c                                                  21

<210> SEQ ID NO 432
<211> LENGTH: 20
<212> TYPE: DNA
<213> ORGANISM: Homo sapiens

<400> SEQUENCE: 432
ggagttggcc tctgtggtag                                                    20

<210> SEQ ID NO 433
<211> LENGTH: 21
<212> TYPE: DNA
<213> ORGANISM: Homo sapiens

<400> SEQUENCE: 433
gcacctgagg cccttaacta c                                                  21

<210> SEQ ID NO 434
<211> LENGTH: 20
<212> TYPE: DNA
<213> ORGANISM: Homo sapiens

<400> SEQUENCE: 434
ttggtggaga acagtgcatc                                                    20

<210> SEQ ID NO 435
<211> LENGTH: 20
```

<212> TYPE: DNA
<213> ORGANISM: Homo sapiens

<400> SEQUENCE: 435
cctgcttcac ctcctttctg                                          20

<210> SEQ ID NO 436
<211> LENGTH: 20
<212> TYPE: DNA
<213> ORGANISM: Homo sapiens

<400> SEQUENCE: 436
gtagcatggc agggtttgac                                          20

<210> SEQ ID NO 437
<211> LENGTH: 20
<212> TYPE: DNA
<213> ORGANISM: Homo sapiens

<400> SEQUENCE: 437
catccaggga aaggttaagg                                          20

<210> SEQ ID NO 438
<211> LENGTH: 21
<212> TYPE: DNA
<213> ORGANISM: Homo sapiens

<400> SEQUENCE: 438
agtggagatg ctgtgtgtgt g                                        21

<210> SEQ ID NO 439
<211> LENGTH: 20
<212> TYPE: DNA
<213> ORGANISM: Homo sapiens

<400> SEQUENCE: 439
gtggtcgtct gctggtgtag                                          20

<210> SEQ ID NO 440
<211> LENGTH: 22
<212> TYPE: DNA
<213> ORGANISM: Homo sapiens

<400> SEQUENCE: 440
tccttgcaat tgaatgtctt tg                                       22

<210> SEQ ID NO 441
<211> LENGTH: 20
<212> TYPE: DNA
<213> ORGANISM: Homo sapiens

<400> SEQUENCE: 441
ccatgtggat ggcattattc                                          20

<210> SEQ ID NO 442
<211> LENGTH: 20
<212> TYPE: DNA
<213> ORGANISM: Homo sapiens

<400> SEQUENCE: 442
accaaatctt gtggacatgg                                          20

<210> SEQ ID NO 443

```
<211> LENGTH: 20
<212> TYPE: DNA
<213> ORGANISM: Homo sapiens

<400> SEQUENCE: 443
gtcaggagtc agggacgatg                                               20

<210> SEQ ID NO 444
<211> LENGTH: 21
<212> TYPE: DNA
<213> ORGANISM: Homo sapiens

<400> SEQUENCE: 444
ccttcatcaa gctgagtgac c                                             21

<210> SEQ ID NO 445
<211> LENGTH: 20
<212> TYPE: DNA
<213> ORGANISM: Homo sapiens

<400> SEQUENCE: 445
ccctggatcc tgctaaggtc                                               20

<210> SEQ ID NO 446
<211> LENGTH: 20
<212> TYPE: DNA
<213> ORGANISM: Homo sapiens

<400> SEQUENCE: 446
tgccataatg cacagagagg                                               20

<210> SEQ ID NO 447
<211> LENGTH: 20
<212> TYPE: DNA
<213> ORGANISM: Homo sapiens

<400> SEQUENCE: 447
tcgaggagag acacctcaag                                               20

<210> SEQ ID NO 448
<211> LENGTH: 20
<212> TYPE: DNA
<213> ORGANISM: Homo sapiens

<400> SEQUENCE: 448
tcgaggagag acacctcaag                                               20

<210> SEQ ID NO 449
<211> LENGTH: 21
<212> TYPE: DNA
<213> ORGANISM: Homo sapiens

<400> SEQUENCE: 449
tgcggttccc atattacagt c                                             21

<210> SEQ ID NO 450
<211> LENGTH: 20
<212> TYPE: DNA
<213> ORGANISM: Homo sapiens

<400> SEQUENCE: 450
atgtgtcatt gttgcggttc                                               20
```

```
<210> SEQ ID NO 451
<211> LENGTH: 20
<212> TYPE: DNA
<213> ORGANISM: Homo sapiens

<400> SEQUENCE: 451
gctcgggggt agggttatag                                               20

<210> SEQ ID NO 452
<211> LENGTH: 20
<212> TYPE: DNA
<213> ORGANISM: Homo sapiens

<400> SEQUENCE: 452
gaaaccgaga ccctggagac                                               20

<210> SEQ ID NO 453
<211> LENGTH: 20
<212> TYPE: DNA
<213> ORGANISM: Homo sapiens

<400> SEQUENCE: 453
cgcttcctca cctttctgac                                               20

<210> SEQ ID NO 454
<211> LENGTH: 20
<212> TYPE: DNA
<213> ORGANISM: Homo sapiens

<400> SEQUENCE: 454
gctcttgctt tggctactgg                                               20

<210> SEQ ID NO 455
<211> LENGTH: 19
<212> TYPE: DNA
<213> ORGANISM: Homo sapiens

<400> SEQUENCE: 455
gggtttctcc tgctcatgg                                                19

<210> SEQ ID NO 456
<211> LENGTH: 20
<212> TYPE: DNA
<213> ORGANISM: Homo sapiens

<400> SEQUENCE: 456
gagtccctcc tgggtagtcc                                               20

<210> SEQ ID NO 457
<211> LENGTH: 19
<212> TYPE: DNA
<213> ORGANISM: Homo sapiens

<400> SEQUENCE: 457
cccttccttc cttccagtg                                                19

<210> SEQ ID NO 458
<211> LENGTH: 20
<212> TYPE: DNA
<213> ORGANISM: Homo sapiens

<400> SEQUENCE: 458
ctcctgcctg ggacagtatc                                               20
```

<210> SEQ ID NO 459
<211> LENGTH: 20
<212> TYPE: DNA
<213> ORGANISM: Homo sapiens

<400> SEQUENCE: 459
agtctgctct ctggggtttg                                          20

<210> SEQ ID NO 460
<211> LENGTH: 19
<212> TYPE: DNA
<213> ORGANISM: Homo sapiens

<400> SEQUENCE: 460
ggcctcccaa agtgttgag                                           19

<210> SEQ ID NO 461
<211> LENGTH: 21
<212> TYPE: DNA
<213> ORGANISM: Homo sapiens

<400> SEQUENCE: 461
tcctgggctc aaataatacc c                                        21

<210> SEQ ID NO 462
<211> LENGTH: 27
<212> TYPE: DNA
<213> ORGANISM: Homo sapiens

<400> SEQUENCE: 462
ttaaccattt ttaagggtat agttcag                                  27

<210> SEQ ID NO 463
<211> LENGTH: 21
<212> TYPE: DNA
<213> ORGANISM: Homo sapiens

<400> SEQUENCE: 463
tgctgttgat tgaatggtct g                                        21

<210> SEQ ID NO 464
<211> LENGTH: 25
<212> TYPE: DNA
<213> ORGANISM: Homo sapiens

<400> SEQUENCE: 464
ttagttcatc actggtgata ttgac                                    25

<210> SEQ ID NO 465
<211> LENGTH: 20
<212> TYPE: DNA
<213> ORGANISM: Homo sapiens

<400> SEQUENCE: 465
gggaaggctt tactcgtttg                                          20

<210> SEQ ID NO 466
<211> LENGTH: 19
<212> TYPE: DNA
<213> ORGANISM: Homo sapiens

<400> SEQUENCE: 466
caaaaagcat ggccaaatg                                           19

<210> SEQ ID NO 467
<211> LENGTH: 20
<212> TYPE: DNA
<213> ORGANISM: Homo sapiens

<400> SEQUENCE: 467
aaacaaattg ggcaaaaagc                                            20

<210> SEQ ID NO 468
<211> LENGTH: 22
<212> TYPE: DNA
<213> ORGANISM: Homo sapiens

<400> SEQUENCE: 468
tgaggactgg taaatcacaa gc                                         22

<210> SEQ ID NO 469
<211> LENGTH: 18
<212> TYPE: DNA
<213> ORGANISM: Homo sapiens

<400> SEQUENCE: 469
acattgagcg ccttggtc                                              18

<210> SEQ ID NO 470
<211> LENGTH: 20
<212> TYPE: DNA
<213> ORGANISM: Homo sapiens

<400> SEQUENCE: 470
ttgcctgttt tgttcactgc                                            20

<210> SEQ ID NO 471
<211> LENGTH: 18
<212> TYPE: DNA
<213> ORGANISM: Homo sapiens

<400> SEQUENCE: 471
ttggcctctc caaagcac                                              18

<210> SEQ ID NO 472
<211> LENGTH: 20
<212> TYPE: DNA
<213> ORGANISM: Homo sapiens

<400> SEQUENCE: 472
gtctggagct atggggtcac                                            20

<210> SEQ ID NO 473
<211> LENGTH: 20
<212> TYPE: DNA
<213> ORGANISM: Homo sapiens

<400> SEQUENCE: 473
agccctgctg actttctgag                                            20

<210> SEQ ID NO 474
<211> LENGTH: 21
<212> TYPE: DNA
<213> ORGANISM: Homo sapiens

<400> SEQUENCE: 474
tttcattgac ggagaatcca c                                           21

<210> SEQ ID NO 475
<211> LENGTH: 20
<212> TYPE: DNA
<213> ORGANISM: Homo sapiens

<400> SEQUENCE: 475
cggagaatcc acaactatgc                                             20

<210> SEQ ID NO 476
<211> LENGTH: 18
<212> TYPE: DNA
<213> ORGANISM: Homo sapiens

<400> SEQUENCE: 476
acctggagtg tggccttg                                               18

<210> SEQ ID NO 477
<211> LENGTH: 19
<212> TYPE: DNA
<213> ORGANISM: Homo sapiens

<400> SEQUENCE: 477
tgtggatgtg caggaacac                                              19

<210> SEQ ID NO 478
<211> LENGTH: 20
<212> TYPE: DNA
<213> ORGANISM: Homo sapiens

<400> SEQUENCE: 478
tggttaatgg acagcgtagg                                             20

<210> SEQ ID NO 479
<211> LENGTH: 19
<212> TYPE: DNA
<213> ORGANISM: Homo sapiens

<400> SEQUENCE: 479
catggaggtg ggaaatgtg                                              19

<210> SEQ ID NO 480
<211> LENGTH: 20
<212> TYPE: DNA
<213> ORGANISM: Homo sapiens

<400> SEQUENCE: 480
cagggtcact ggattagcag                                             20

<210> SEQ ID NO 481
<211> LENGTH: 20
<212> TYPE: DNA
<213> ORGANISM: Homo sapiens

<400> SEQUENCE: 481
ccccaaggga ctttatcagg                                             20

<210> SEQ ID NO 482
<211> LENGTH: 20
<212> TYPE: DNA
<213> ORGANISM: Homo sapiens

<400> SEQUENCE: 482 cggcccctt tgtgtatttc                                         20

<210> SEQ ID NO 483
<211> LENGTH: 18
<212> TYPE: DNA
<213> ORGANISM: Homo sapiens

<400> SEQUENCE: 483
gggtggatgt ggatctgc                                          18

<210> SEQ ID NO 484
<211> LENGTH: 21
<212> TYPE: DNA
<213> ORGANISM: Homo sapiens

<400> SEQUENCE: 484
ttttgagcca tgttctctag c                                      21

<210> SEQ ID NO 485
<211> LENGTH: 21
<212> TYPE: DNA
<213> ORGANISM: Homo sapiens

<400> SEQUENCE: 485
tgaatcctgg aaatcaacga g                                      21

<210> SEQ ID NO 486
<211> LENGTH: 20
<212> TYPE: DNA
<213> ORGANISM: Homo sapiens

<400> SEQUENCE: 486
tgctgcttat ggacaactcc                                        20

<210> SEQ ID NO 487
<211> LENGTH: 21
<212> TYPE: DNA
<213> ORGANISM: Homo sapiens

<400> SEQUENCE: 487
tctgtcattg cttagctgtg g                                      21

<210> SEQ ID NO 488
<211> LENGTH: 20
<212> TYPE: DNA
<213> ORGANISM: Homo sapiens

<400> SEQUENCE: 488
tggaaactgc aaaactgcac                                        20

<210> SEQ ID NO 489
<211> LENGTH: 22
<212> TYPE: DNA
<213> ORGANISM: Homo sapiens

<400> SEQUENCE: 489
ccctgttaac atcatctcct tc                                     22

<210> SEQ ID NO 490
<211> LENGTH: 18
<212> TYPE: DNA
<213> ORGANISM: Homo sapiens

```
<400> SEQUENCE: 490
cctgggacag gtcacgtc                                                    18

<210> SEQ ID NO 491
<211> LENGTH: 20
<212> TYPE: DNA
<213> ORGANISM: Homo sapiens

<400> SEQUENCE: 491
cttcggggac aggacttatc                                                  20

<210> SEQ ID NO 492
<211> LENGTH: 20
<212> TYPE: DNA
<213> ORGANISM: Homo sapiens

<400> SEQUENCE: 492
gtagatgcct ggctttgagg                                                  20

<210> SEQ ID NO 493
<211> LENGTH: 20
<212> TYPE: DNA
<213> ORGANISM: Homo sapiens

<400> SEQUENCE: 493
tgactgggtt tgtcacatgg                                                  20

<210> SEQ ID NO 494
<211> LENGTH: 20
<212> TYPE: DNA
<213> ORGANISM: Homo sapiens

<400> SEQUENCE: 494
ttgccttttg agtgacaagc                                                  20

<210> SEQ ID NO 495
<211> LENGTH: 21
<212> TYPE: DNA
<213> ORGANISM: Homo sapiens

<400> SEQUENCE: 495
cacttgcctg aagaagtgtg g                                                21

<210> SEQ ID NO 496
<211> LENGTH: 22
<212> TYPE: DNA
<213> ORGANISM: Homo sapiens

<400> SEQUENCE: 496
tgaaggatga ttcacgctag tc                                               22

<210> SEQ ID NO 497
<211> LENGTH: 25
<212> TYPE: DNA
<213> ORGANISM: Homo sapiens

<400> SEQUENCE: 497
tgagttttac ttgggaaacc ataac                                            25

<210> SEQ ID NO 498
<211> LENGTH: 23
<212> TYPE: DNA
<213> ORGANISM: Homo sapiens
```

```
<400> SEQUENCE: 498
tgcagtaatc gtttcttctc tgg                                           23

<210> SEQ ID NO 499
<211> LENGTH: 21
<212> TYPE: DNA
<213> ORGANISM: Homo sapiens

<400> SEQUENCE: 499
tcaggaaatt gaatgaaatg c                                             21

<210> SEQ ID NO 500
<211> LENGTH: 21
<212> TYPE: DNA
<213> ORGANISM: Homo sapiens

<400> SEQUENCE: 500
gcctttcatt ggcttttaac c                                             21

<210> SEQ ID NO 501
<211> LENGTH: 22
<212> TYPE: DNA
<213> ORGANISM: Homo sapiens

<400> SEQUENCE: 501
tttttctgcc tgaacttgtc tg                                            22

<210> SEQ ID NO 502
<211> LENGTH: 24
<212> TYPE: DNA
<213> ORGANISM: Homo sapiens

<400> SEQUENCE: 502
tcacaaagaa gacatgaaca tctg                                          24

<210> SEQ ID NO 503
<211> LENGTH: 27
<212> TYPE: DNA
<213> ORGANISM: Homo sapiens

<400> SEQUENCE: 503
cacacctacg tacctatagt ggtattg                                       27

<210> SEQ ID NO 504
<211> LENGTH: 20
<212> TYPE: DNA
<213> ORGANISM: Homo sapiens

<400> SEQUENCE: 504
aaaccctcag gacaagatgc                                               20

<210> SEQ ID NO 505
<211> LENGTH: 20
<212> TYPE: DNA
<213> ORGANISM: Homo sapiens

<400> SEQUENCE: 505
aggcttgagc cattaagacc                                               20

<210> SEQ ID NO 506
<211> LENGTH: 20
<212> TYPE: DNA
```

```
<213> ORGANISM: Homo sapiens

<400> SEQUENCE: 506
tggcaatgtc aatgtcaagc                                              20

<210> SEQ ID NO 507
<211> LENGTH: 20
<212> TYPE: DNA
<213> ORGANISM: Homo sapiens

<400> SEQUENCE: 507
tgttgcccaa aacagaaacc                                              20

<210> SEQ ID NO 508
<211> LENGTH: 20
<212> TYPE: DNA
<213> ORGANISM: Homo sapiens

<400> SEQUENCE: 508
tcctacaacc cgaatactgc                                              20

<210> SEQ ID NO 509
<211> LENGTH: 21
<212> TYPE: DNA
<213> ORGANISM: Homo sapiens

<400> SEQUENCE: 509
tgtcaaagca acagtccaca c                                            21

<210> SEQ ID NO 510
<211> LENGTH: 20
<212> TYPE: DNA
<213> ORGANISM: Homo sapiens

<400> SEQUENCE: 510
aatgggttga tggaggaatg                                              20

<210> SEQ ID NO 511
<211> LENGTH: 20
<212> TYPE: DNA
<213> ORGANISM: Homo sapiens

<400> SEQUENCE: 511
ggccacgtat caggaaattg                                              20

<210> SEQ ID NO 512
<211> LENGTH: 20
<212> TYPE: DNA
<213> ORGANISM: Homo sapiens

<400> SEQUENCE: 512
gctgagggtg gaagtctgtc                                              20

<210> SEQ ID NO 513
<211> LENGTH: 19
<212> TYPE: DNA
<213> ORGANISM: Homo sapiens

<400> SEQUENCE: 513
gcacttctgc ccaggtgtc                                               19

<210> SEQ ID NO 514
<211> LENGTH: 20
```

```
<212> TYPE: DNA
<213> ORGANISM: Homo sapiens

<400> SEQUENCE: 514
tgggaatgtc tctgatggtg                                              20

<210> SEQ ID NO 515
<211> LENGTH: 20
<212> TYPE: DNA
<213> ORGANISM: Homo sapiens

<400> SEQUENCE: 515
catgatttcg cttccctctc                                              20

<210> SEQ ID NO 516
<211> LENGTH: 24
<212> TYPE: DNA
<213> ORGANISM: Homo sapiens

<400> SEQUENCE: 516
tctcaaacac taggaattgc aaac                                         24

<210> SEQ ID NO 517
<211> LENGTH: 20
<212> TYPE: DNA
<213> ORGANISM: Homo sapiens

<400> SEQUENCE: 517
atgagtgggc cattgagaag                                              20

<210> SEQ ID NO 518
<211> LENGTH: 20
<212> TYPE: DNA
<213> ORGANISM: Homo sapiens

<400> SEQUENCE: 518
gtcccaaagc atctgagtcc                                              20

<210> SEQ ID NO 519
<211> LENGTH: 20
<212> TYPE: DNA
<213> ORGANISM: Homo sapiens

<400> SEQUENCE: 519
ggtcccaaag catctgagtc                                              20

<210> SEQ ID NO 520
<211> LENGTH: 20
<212> TYPE: DNA
<213> ORGANISM: Homo sapiens

<400> SEQUENCE: 520
ggtaagtttg gggcacaatg                                              20

<210> SEQ ID NO 521
<211> LENGTH: 20
<212> TYPE: DNA
<213> ORGANISM: Homo sapiens

<400> SEQUENCE: 521
ccaggaggtg aaagtggttg                                              20

<210> SEQ ID NO 522
```

```
<211> LENGTH: 21
<212> TYPE: DNA
<213> ORGANISM: Homo sapiens

<400> SEQUENCE: 522
catacccctt cacctgtgtt c                                              21

<210> SEQ ID NO 523
<211> LENGTH: 19
<212> TYPE: DNA
<213> ORGANISM: Homo sapiens

<400> SEQUENCE: 523
ccccactccc cagtactcc                                                 19

<210> SEQ ID NO 524
<211> LENGTH: 19
<212> TYPE: DNA
<213> ORGANISM: Homo sapiens

<400> SEQUENCE: 524
agtgggaagg gacaagtgg                                                 19

<210> SEQ ID NO 525
<211> LENGTH: 20
<212> TYPE: DNA
<213> ORGANISM: Homo sapiens

<400> SEQUENCE: 525
aagtgacctg cagggagttg                                                20

<210> SEQ ID NO 526
<211> LENGTH: 19
<212> TYPE: DNA
<213> ORGANISM: Homo sapiens

<400> SEQUENCE: 526
gacttctggc tgggggtag                                                 19

<210> SEQ ID NO 527
<211> LENGTH: 18
<212> TYPE: DNA
<213> ORGANISM: Homo sapiens

<400> SEQUENCE: 527
gcccgggaac agtttctc                                                  18

<210> SEQ ID NO 528
<211> LENGTH: 20
<212> TYPE: DNA
<213> ORGANISM: Homo sapiens

<400> SEQUENCE: 528
agtttcctga ggcacagtcg                                                20

<210> SEQ ID NO 529
<211> LENGTH: 20
<212> TYPE: DNA
<213> ORGANISM: Homo sapiens

<400> SEQUENCE: 529
ccacaggtta ggagcagtcc                                                20
```

```
<210> SEQ ID NO 530
<211> LENGTH: 19
<212> TYPE: DNA
<213> ORGANISM: Homo sapiens

<400> SEQUENCE: 530
gattggggac tttgggatg                                              19

<210> SEQ ID NO 531
<211> LENGTH: 20
<212> TYPE: DNA
<213> ORGANISM: Homo sapiens

<400> SEQUENCE: 531
cctggtgata acacccttcc                                             20

<210> SEQ ID NO 532
<211> LENGTH: 19
<212> TYPE: DNA
<213> ORGANISM: Homo sapiens

<400> SEQUENCE: 532
ctggacttcg tcgttggag                                              19

<210> SEQ ID NO 533
<211> LENGTH: 19
<212> TYPE: DNA
<213> ORGANISM: Homo sapiens

<400> SEQUENCE: 533
gtgctggact tcgtcgttg                                              19

<210> SEQ ID NO 534
<211> LENGTH: 20
<212> TYPE: DNA
<213> ORGANISM: Homo sapiens

<400> SEQUENCE: 534
ctagctttgc cagcatcttg                                             20

<210> SEQ ID NO 535
<211> LENGTH: 21
<212> TYPE: DNA
<213> ORGANISM: Homo sapiens

<400> SEQUENCE: 535
ccattttcca atctccttca g                                           21

<210> SEQ ID NO 536
<211> LENGTH: 20
<212> TYPE: DNA
<213> ORGANISM: Homo sapiens

<400> SEQUENCE: 536
gcgtgctgtc aaacagattc                                             20

<210> SEQ ID NO 537
<211> LENGTH: 20
<212> TYPE: DNA
<213> ORGANISM: Homo sapiens

<400> SEQUENCE: 537
gacactgcgt gctgtcaaac                                             20
```

```
<210> SEQ ID NO 538
<211> LENGTH: 20
<212> TYPE: DNA
<213> ORGANISM: Homo sapiens

<400> SEQUENCE: 538
tgcagcaaat ggaaatagcc                                              20

<210> SEQ ID NO 539
<211> LENGTH: 23
<212> TYPE: DNA
<213> ORGANISM: Homo sapiens

<400> SEQUENCE: 539
ttagcatttg catatttttc ctc                                          23

<210> SEQ ID NO 540
<211> LENGTH: 23
<212> TYPE: DNA
<213> ORGANISM: Homo sapiens

<400> SEQUENCE: 540
ttgaaattga tgcaaagatt gtg                                          23

<210> SEQ ID NO 541
<211> LENGTH: 21
<212> TYPE: DNA
<213> ORGANISM: Homo sapiens

<400> SEQUENCE: 541 ccctttctg actgcttttt g                                             21

<210> SEQ ID NO 542
<211> LENGTH: 25
<212> TYPE: DNA
<213> ORGANISM: Homo sapiens

<400> SEQUENCE: 542
aataaaaatt tctgggtaag ctttg                                        25

<210> SEQ ID NO 543
<211> LENGTH: 19
<212> TYPE: DNA
<213> ORGANISM: Homo sapiens

<400> SEQUENCE: 543
aattttagcc cccatgcag                                               19

<210> SEQ ID NO 544
<211> LENGTH: 20
<212> TYPE: DNA
<213> ORGANISM: Homo sapiens

<400> SEQUENCE: 544
aggagctcca tcacatcagg                                              20

<210> SEQ ID NO 545
<211> LENGTH: 20
<212> TYPE: DNA
<213> ORGANISM: Homo sapiens

<400> SEQUENCE: 545
ctggacagct gcctctactg                                              20
```

<210> SEQ ID NO 546
<211> LENGTH: 20
<212> TYPE: DNA
<213> ORGANISM: Homo sapiens

<400> SEQUENCE: 546
ggattacagg cgtgaaccac                                            20

<210> SEQ ID NO 547
<211> LENGTH: 20
<212> TYPE: DNA
<213> ORGANISM: Homo sapiens

<400> SEQUENCE: 547
agctaagaag cccagacgag                                            20

<210> SEQ ID NO 548
<211> LENGTH: 20
<212> TYPE: DNA
<213> ORGANISM: Homo sapiens

<400> SEQUENCE: 548
tccagaagac cttcttgcag                                            20

<210> SEQ ID NO 549
<211> LENGTH: 19
<212> TYPE: DNA
<213> ORGANISM: Homo sapiens

<400> SEQUENCE: 549
gtcatggttg gggttaggg                                             19

<210> SEQ ID NO 550
<211> LENGTH: 20
<212> TYPE: DNA
<213> ORGANISM: Homo sapiens

<400> SEQUENCE: 550
aggtagggac caggaagacc                                            20

<210> SEQ ID NO 551
<211> LENGTH: 21
<212> TYPE: DNA
<213> ORGANISM: Homo sapiens

<400> SEQUENCE: 551
ccctactttc cagggttctt g                                          21

<210> SEQ ID NO 552
<211> LENGTH: 20
<212> TYPE: DNA
<213> ORGANISM: Homo sapiens

<400> SEQUENCE: 552
tccattgagc ccctactttc                                            20

<210> SEQ ID NO 553
<211> LENGTH: 20
<212> TYPE: DNA
<213> ORGANISM: Homo sapiens

<400> SEQUENCE: 553
gggatcttca ccacccactc                                                    20

<210> SEQ ID NO 554
<211> LENGTH: 21
<212> TYPE: DNA
<213> ORGANISM: Homo sapiens

<400> SEQUENCE: 554
cccatttaat cccttctcac c                                                  21

<210> SEQ ID NO 555
<211> LENGTH: 20
<212> TYPE: DNA
<213> ORGANISM: Homo sapiens

<400> SEQUENCE: 555
ctatcccaaa cccccaagac                                                    20

<210> SEQ ID NO 556
<211> LENGTH: 18
<212> TYPE: DNA
<213> ORGANISM: Homo sapiens

<400> SEQUENCE: 556
cagagggagc gtgtgacc                                                      18

<210> SEQ ID NO 557
<211> LENGTH: 20
<212> TYPE: DNA
<213> ORGANISM: Homo sapiens

<400> SEQUENCE: 557
ctgtcctcct ggttcaggtc                                                    20

<210> SEQ ID NO 558
<211> LENGTH: 20
<212> TYPE: DNA
<213> ORGANISM: Homo sapiens

<400> SEQUENCE: 558
cagaagtagt ggcgcacttg                                                    20

<210> SEQ ID NO 559
<211> LENGTH: 19
<212> TYPE: DNA
<213> ORGANISM: Homo sapiens

<400> SEQUENCE: 559
ggctgtgttg tccctctgg                                                     19

<210> SEQ ID NO 560
<211> LENGTH: 18
<212> TYPE: DNA
<213> ORGANISM: Homo sapiens

<400> SEQUENCE: 560
gagcggccct actggaac                                                      18

<210> SEQ ID NO 561
<211> LENGTH: 20
<212> TYPE: DNA
<213> ORGANISM: Homo sapiens

<400> SEQUENCE: 561

```
tttggccctg acactaggac                                              20

<210> SEQ ID NO 562
<211> LENGTH: 20
<212> TYPE: DNA
<213> ORGANISM: Homo sapiens

<400> SEQUENCE: 562
ctctctgggc atggtgctac                                              20

<210> SEQ ID NO 563
<211> LENGTH: 20
<212> TYPE: DNA
<213> ORGANISM: Homo sapiens

<400> SEQUENCE: 563
tcatccaggc tagaatgcag                                              20

<210> SEQ ID NO 564
<211> LENGTH: 21
<212> TYPE: DNA
<213> ORGANISM: Homo sapiens

<400> SEQUENCE: 564
gtcatccagg ctagaatgca g                                            21

<210> SEQ ID NO 565
<211> LENGTH: 20
<212> TYPE: DNA
<213> ORGANISM: Homo sapiens

<400> SEQUENCE: 565
gcttcttcca gtgctcatcc                                              20

<210> SEQ ID NO 566
<211> LENGTH: 20
<212> TYPE: DNA
<213> ORGANISM: Homo sapiens

<400> SEQUENCE: 566
attttcccac tggattctgg                                              20

<210> SEQ ID NO 567
<211> LENGTH: 21
<212> TYPE: DNA
<213> ORGANISM: Homo sapiens

<400> SEQUENCE: 567
ttgcactatt gcactccagt c                                            21

<210> SEQ ID NO 568
<211> LENGTH: 21
<212> TYPE: DNA
<213> ORGANISM: Homo sapiens

<400> SEQUENCE: 568
aggaacaagg agacattgtg g                                            21

<210> SEQ ID NO 569
<211> LENGTH: 19
<212> TYPE: DNA
<213> ORGANISM: Homo sapiens
```

```
<400> SEQUENCE: 569
cccactcctt ccctgtctc                                                19

<210> SEQ ID NO 570
<211> LENGTH: 20
<212> TYPE: DNA
<213> ORGANISM: Homo sapiens

<400> SEQUENCE: 570
tggactacct gcggtctagg                                               20

<210> SEQ ID NO 571
<211> LENGTH: 20
<212> TYPE: DNA
<213> ORGANISM: Homo sapiens

<400> SEQUENCE: 571
ctgaggccct gagagagaag                                               20

<210> SEQ ID NO 572
<211> LENGTH: 19
<212> TYPE: DNA
<213> ORGANISM: Homo sapiens

<400> SEQUENCE: 572
agctcacagg ccactctcc                                                19

<210> SEQ ID NO 573
<211> LENGTH: 20
<212> TYPE: DNA
<213> ORGANISM: Homo sapiens

<400> SEQUENCE: 573
ccctgaacat gaaggagctg                                               20

<210> SEQ ID NO 574
<211> LENGTH: 20
<212> TYPE: DNA
<213> ORGANISM: Homo sapiens

<400> SEQUENCE: 574
attaagaacg acgccactgc                                               20

<210> SEQ ID NO 575
<211> LENGTH: 20
<212> TYPE: DNA
<213> ORGANISM: Homo sapiens

<400> SEQUENCE: 575
tcgacccact atgggagttc                                               20

<210> SEQ ID NO 576
<211> LENGTH: 20
<212> TYPE: DNA
<213> ORGANISM: Homo sapiens

<400> SEQUENCE: 576
cagcctagca aggattcagc                                               20

<210> SEQ ID NO 577
<211> LENGTH: 20
<212> TYPE: DNA
<213> ORGANISM: Homo sapiens
```

```
<400> SEQUENCE: 577
tcatcaacct gcttggtgtc                                         20

<210> SEQ ID NO 578
<211> LENGTH: 21
<212> TYPE: DNA
<213> ORGANISM: Homo sapiens

<400> SEQUENCE: 578
aaaccttgac ctcctcctct g                                       21

<210> SEQ ID NO 579
<211> LENGTH: 21
<212> TYPE: DNA
<213> ORGANISM: Homo sapiens

<400> SEQUENCE: 579
tccccgtttc taaaccttga c                                       21

<210> SEQ ID NO 580
<211> LENGTH: 20
<212> TYPE: DNA
<213> ORGANISM: Homo sapiens

<400> SEQUENCE: 580
agaaaaccag caacgtgagg                                         20

<210> SEQ ID NO 581
<211> LENGTH: 20
<212> TYPE: DNA
<213> ORGANISM: Homo sapiens

<400> SEQUENCE: 581
agaaaaccag caacgtgagg                                         20

<210> SEQ ID NO 582
<211> LENGTH: 20
<212> TYPE: DNA
<213> ORGANISM: Homo sapiens

<400> SEQUENCE: 582
gcccagacta ccaggaggag                                         20

<210> SEQ ID NO 583
<211> LENGTH: 20
<212> TYPE: DNA
<213> ORGANISM: Homo sapiens

<400> SEQUENCE: 583
tgaccctcct atccctcatc                                         20

<210> SEQ ID NO 584
<211> LENGTH: 20
<212> TYPE: DNA
<213> ORGANISM: Homo sapiens

<400> SEQUENCE: 584
ggcatcctta ccctgaacac                                         20

<210> SEQ ID NO 585
<211> LENGTH: 20
<212> TYPE: DNA
```

<213> ORGANISM: Homo sapiens

<400> SEQUENCE: 585
caacaaactc ctggacatgg                                               20

<210> SEQ ID NO 586
<211> LENGTH: 20
<212> TYPE: DNA
<213> ORGANISM: Homo sapiens

<400> SEQUENCE: 586
tgcaagattg cagactttgg                                               20

<210> SEQ ID NO 587
<211> LENGTH: 23
<212> TYPE: DNA
<213> ORGANISM: Homo sapiens

<400> SEQUENCE: 587
ccttaccatt gatgaagacc aag                                           23

<210> SEQ ID NO 588
<211> LENGTH: 23
<212> TYPE: DNA
<213> ORGANISM: Homo sapiens

<400> SEQUENCE: 588
tgaccttacc attgatgaag acc                                           23

<210> SEQ ID NO 589
<211> LENGTH: 18
<212> TYPE: DNA
<213> ORGANISM: Homo sapiens

<400> SEQUENCE: 589
gtggagacac ggggtgag                                                 18

<210> SEQ ID NO 590
<211> LENGTH: 20
<212> TYPE: DNA
<213> ORGANISM: Homo sapiens

<400> SEQUENCE: 590
cccaagtgtt tgggtgacag                                               20

<210> SEQ ID NO 591
<211> LENGTH: 20
<212> TYPE: DNA
<213> ORGANISM: Homo sapiens

<400> SEQUENCE: 591
gaggtgtgga tgggtgagtg                                               20

<210> SEQ ID NO 592
<211> LENGTH: 20
<212> TYPE: DNA
<213> ORGANISM: Homo sapiens

<400> SEQUENCE: 592
ggctacgttc tgggcctaag                                               20

<210> SEQ ID NO 593
<211> LENGTH: 20

```
<212> TYPE: DNA
<213> ORGANISM: Homo sapiens

<400> SEQUENCE: 593
agagggtgct gtttgcagag                                           20

<210> SEQ ID NO 594
<211> LENGTH: 20
<212> TYPE: DNA
<213> ORGANISM: Homo sapiens

<400> SEQUENCE: 594
gtctgcacgg ccttgtactg                                           20

<210> SEQ ID NO 595
<211> LENGTH: 18
<212> TYPE: DNA
<213> ORGANISM: Homo sapiens

<400> SEQUENCE: 595
gtactgggcc agcctctg                                             18

<210> SEQ ID NO 596
<211> LENGTH: 21
<212> TYPE: DNA
<213> ORGANISM: Homo sapiens

<400> SEQUENCE: 596
gcttggacca gaagggttat c                                         21

<210> SEQ ID NO 597
<211> LENGTH: 19
<212> TYPE: DNA
<213> ORGANISM: Homo sapiens

<400> SEQUENCE: 597
aggtctgcct ccctcactg                                            19

<210> SEQ ID NO 598
<211> LENGTH: 20
<212> TYPE: DNA
<213> ORGANISM: Homo sapiens

<400> SEQUENCE: 598
gcattaggga aaaggcttcc                                           20

<210> SEQ ID NO 599
<211> LENGTH: 20
<212> TYPE: DNA
<213> ORGANISM: Homo sapiens

<400> SEQUENCE: 599
aggcatgctg attcctgaag                                           20

<210> SEQ ID NO 600
<211> LENGTH: 19
<212> TYPE: DNA
<213> ORGANISM: Homo sapiens

<400> SEQUENCE: 600
ctggcctcat ccatcttcc                                            19

<210> SEQ ID NO 601
```

```
<211> LENGTH: 20
<212> TYPE: DNA
<213> ORGANISM: Homo sapiens

<400> SEQUENCE: 601
cttgtgctgc ttcacctctg                                              20

<210> SEQ ID NO 602
<211> LENGTH: 21
<212> TYPE: DNA
<213> ORGANISM: Homo sapiens

<400> SEQUENCE: 602
aatgtggtga atcgaggttt g                                            21

<210> SEQ ID NO 603
<211> LENGTH: 20
<212> TYPE: DNA
<213> ORGANISM: Homo sapiens

<400> SEQUENCE: 603
gctgtgggag cttgtgtctc                                              20

<210> SEQ ID NO 604
<211> LENGTH: 19
<212> TYPE: DNA
<213> ORGANISM: Homo sapiens

<400> SEQUENCE: 604 cctggggag tttctttcc                                                19

<210> SEQ ID NO 605
<211> LENGTH: 20
<212> TYPE: DNA
<213> ORGANISM: Homo sapiens

<400> SEQUENCE: 605
tgcgtaagct ctctgtggac                                              20

<210> SEQ ID NO 606
<211> LENGTH: 20
<212> TYPE: DNA
<213> ORGANISM: Homo sapiens

<400> SEQUENCE: 606
gcactcagct gcgaagtatg                                              20

<210> SEQ ID NO 607
<211> LENGTH: 19
<212> TYPE: DNA
<213> ORGANISM: Homo sapiens

<400> SEQUENCE: 607
atggtacccg tggggacag                                               19

<210> SEQ ID NO 608
<211> LENGTH: 20
<212> TYPE: DNA
<213> ORGANISM: Homo sapiens

<400> SEQUENCE: 608
caggatttgg agcctcagtc                                              20
```

```
<210> SEQ ID NO 609
<211> LENGTH: 19
<212> TYPE: DNA
<213> ORGANISM: Homo sapiens

<400> SEQUENCE: 609
tgcatccttg tggagatgc                                                19

<210> SEQ ID NO 610
<211> LENGTH: 19
<212> TYPE: DNA
<213> ORGANISM: Homo sapiens

<400> SEQUENCE: 610
tcccacccca caactcttc                                                19

<210> SEQ ID NO 611
<211> LENGTH: 20
<212> TYPE: DNA
<213> ORGANISM: Homo sapiens

<400> SEQUENCE: 611
tgtcatgaag caggttaggc                                               20

<210> SEQ ID NO 612
<211> LENGTH: 21
<212> TYPE: DNA
<213> ORGANISM: Homo sapiens

<400> SEQUENCE: 612
ttggtctttt gatcattttg c                                             21

<210> SEQ ID NO 613
<211> LENGTH: 22
<212> TYPE: DNA
<213> ORGANISM: Homo sapiens

<400> SEQUENCE: 613
tccaggtgtc aatttctctg tc                                            22

<210> SEQ ID NO 614
<211> LENGTH: 20
<212> TYPE: DNA
<213> ORGANISM: Homo sapiens

<400> SEQUENCE: 614
aacgcaaggg attcatcaag                                               20

<210> SEQ ID NO 615
<211> LENGTH: 21
<212> TYPE: DNA
<213> ORGANISM: Homo sapiens

<400> SEQUENCE: 615
tggcattttc agaattcctt g                                             21

<210> SEQ ID NO 616
<211> LENGTH: 20
<212> TYPE: DNA
<213> ORGANISM: Homo sapiens

<400> SEQUENCE: 616
ggaaaaatgg acaccacacc                                               20
```

<210> SEQ ID NO 617
<211> LENGTH: 24
<212> TYPE: DNA
<213> ORGANISM: Homo sapiens

<400> SEQUENCE: 617
tggattctct ctctgcatta caac                                    24

<210> SEQ ID NO 618
<211> LENGTH: 20
<212> TYPE: DNA
<213> ORGANISM: Homo sapiens

<400> SEQUENCE: 618
tcacgtagcc acaagaccac                                         20

<210> SEQ ID NO 619
<211> LENGTH: 21
<212> TYPE: DNA
<213> ORGANISM: Homo sapiens

<400> SEQUENCE: 619
tgcctccaaa gataattgtg c                                       21

<210> SEQ ID NO 620
<211> LENGTH: 23
<212> TYPE: DNA
<213> ORGANISM: Homo sapiens

<400> SEQUENCE: 620
ttccctctct ttctctgttc aag                                     23

<210> SEQ ID NO 621
<211> LENGTH: 20
<212> TYPE: DNA
<213> ORGANISM: Homo sapiens

<400> SEQUENCE: 621
tttagagcac ttgggggttg                                         20

<210> SEQ ID NO 622
<211> LENGTH: 21
<212> TYPE: DNA
<213> ORGANISM: Homo sapiens

<400> SEQUENCE: 622
gctaagccca cacattgaaa g                                       21

<210> SEQ ID NO 623
<211> LENGTH: 19
<212> TYPE: DNA
<213> ORGANISM: Homo sapiens

<400> SEQUENCE: 623
gggatccctc actctgacc                                          19

<210> SEQ ID NO 624
<211> LENGTH: 20
<212> TYPE: DNA
<213> ORGANISM: Homo sapiens

<400> SEQUENCE: 624
gcgtccttgc cttatttctg                                         20

```
<210> SEQ ID NO 625
<211> LENGTH: 20
<212> TYPE: DNA
<213> ORGANISM: Homo sapiens

<400> SEQUENCE: 625
gtgcacgaag caagaatagc                                              20

<210> SEQ ID NO 626
<211> LENGTH: 20
<212> TYPE: DNA
<213> ORGANISM: Homo sapiens

<400> SEQUENCE: 626
gaaggtgtgc aagcacagag                                              20

<210> SEQ ID NO 627
<211> LENGTH: 20
<212> TYPE: DNA
<213> ORGANISM: Homo sapiens

<400> SEQUENCE: 627
ccagggctcc actataatcc                                              20

<210> SEQ ID NO 628
<211> LENGTH: 20
<212> TYPE: DNA
<213> ORGANISM: Homo sapiens

<400> SEQUENCE: 628
agttgcccag tccctaatcc                                              20

<210> SEQ ID NO 629
<211> LENGTH: 20
<212> TYPE: DNA
<213> ORGANISM: Homo sapiens

<400> SEQUENCE: 629
agaaaagttg cagcctggtg                                              20

<210> SEQ ID NO 630
<211> LENGTH: 20
<212> TYPE: DNA
<213> ORGANISM: Homo sapiens

<400> SEQUENCE: 630
tgccatgaac tggttacagc                                              20

<210> SEQ ID NO 631
<211> LENGTH: 20
<212> TYPE: DNA
<213> ORGANISM: Homo sapiens

<400> SEQUENCE: 631
aggacacagt gagtggcttg                                              20

<210> SEQ ID NO 632
<211> LENGTH: 19
<212> TYPE: DNA
<213> ORGANISM: Homo sapiens

<400> SEQUENCE: 632
```

-continued tgcaagcagc agaggaaac                                              19

<210> SEQ ID NO 633
<211> LENGTH: 20
<212> TYPE: DNA
<213> ORGANISM: Homo sapiens

<400> SEQUENCE: 633 gaagggcag agtcagtgtg                                              20

<210> SEQ ID NO 634
<211> LENGTH: 20
<212> TYPE: DNA
<213> ORGANISM: Homo sapiens

<400> SEQUENCE: 634
actgcctgct gacctctgac                                             20

<210> SEQ ID NO 635
<211> LENGTH: 20
<212> TYPE: DNA
<213> ORGANISM: Homo sapiens

<400> SEQUENCE: 635
cgagagcaac atctggtgag                                             20

<210> SEQ ID NO 636
<211> LENGTH: 20
<212> TYPE: DNA
<213> ORGANISM: Homo sapiens

<400> SEQUENCE: 636
ggtctctgtc cccctctctc                                             20

<210> SEQ ID NO 637
<211> LENGTH: 19
<212> TYPE: DNA
<213> ORGANISM: Homo sapiens

<400> SEQUENCE: 637
gagtgcctgt gggagaagg                                              19

<210> SEQ ID NO 638
<211> LENGTH: 20
<212> TYPE: DNA
<213> ORGANISM: Homo sapiens

<400> SEQUENCE: 638
aaaaggtgtc gcagaggatg                                             20

<210> SEQ ID NO 639
<211> LENGTH: 20
<212> TYPE: DNA
<213> ORGANISM: Homo sapiens

<400> SEQUENCE: 639
cctagtccca tccacaggag                                             20

<210> SEQ ID NO 640
<211> LENGTH: 20
<212> TYPE: DNA
<213> ORGANISM: Homo sapiens

<400> SEQUENCE: 640

```
tgaggtggga gagttgcttg                                              20

<210> SEQ ID NO 641
<211> LENGTH: 19
<212> TYPE: DNA
<213> ORGANISM: Homo sapiens

<400> SEQUENCE: 641
ggctgaggtg ggagagttg                                               19

<210> SEQ ID NO 642
<211> LENGTH: 20
<212> TYPE: DNA
<213> ORGANISM: Homo sapiens

<400> SEQUENCE: 642
actgaaacct ccacctcctg                                              20

<210> SEQ ID NO 643
<211> LENGTH: 20
<212> TYPE: DNA
<213> ORGANISM: Homo sapiens

<400> SEQUENCE: 643
tgagagccat cctgcaagtc                                              20

<210> SEQ ID NO 644
<211> LENGTH: 20
<212> TYPE: DNA
<213> ORGANISM: Homo sapiens

<400> SEQUENCE: 644
aaatctgatg ccggtctttg                                              20

<210> SEQ ID NO 645
<211> LENGTH: 20
<212> TYPE: DNA
<213> ORGANISM: Homo sapiens

<400> SEQUENCE: 645
atctgatgcc ggtctttgtg                                              20

<210> SEQ ID NO 646
<211> LENGTH: 19
<212> TYPE: DNA
<213> ORGANISM: Homo sapiens

<400> SEQUENCE: 646
tcaatatctg gccccttcc                                               19

<210> SEQ ID NO 647
<211> LENGTH: 19
<212> TYPE: DNA
<213> ORGANISM: Homo sapiens

<400> SEQUENCE: 647
ttgttttggg gagggaatg                                               19

<210> SEQ ID NO 648
<211> LENGTH: 20
<212> TYPE: DNA
<213> ORGANISM: Homo sapiens
```

```
<400> SEQUENCE: 648
tgatgccctt gtatgacagc                                              20

<210> SEQ ID NO 649
<211> LENGTH: 20
<212> TYPE: DNA
<213> ORGANISM: Homo sapiens

<400> SEQUENCE: 649
tggtgggaga aaaccaagtc                                              20

<210> SEQ ID NO 650
<211> LENGTH: 20
<212> TYPE: DNA
<213> ORGANISM: Homo sapiens

<400> SEQUENCE: 650
tgcacttctg gaggtagcac                                              20

<210> SEQ ID NO 651
<211> LENGTH: 20
<212> TYPE: DNA
<213> ORGANISM: Homo sapiens

<400> SEQUENCE: 651
tgggatccat gtaggagacc                                              20

<210> SEQ ID NO 652
<211> LENGTH: 22
<212> TYPE: DNA
<213> ORGANISM: Homo sapiens

<400> SEQUENCE: 652
ttgaacaata tctgccacct tg                                           22

<210> SEQ ID NO 653
<211> LENGTH: 25
<212> TYPE: DNA
<213> ORGANISM: Homo sapiens

<400> SEQUENCE: 653
ggaaaaagat aatttatttg ccatc                                        25

<210> SEQ ID NO 654
<211> LENGTH: 20
<212> TYPE: DNA
<213> ORGANISM: Homo sapiens

<400> SEQUENCE: 654
gtcccccaaa tcaggttttc                                              20

<210> SEQ ID NO 655
<211> LENGTH: 20
<212> TYPE: DNA
<213> ORGANISM: Homo sapiens

<400> SEQUENCE: 655
attaaggcca gcccaaagac                                              20

<210> SEQ ID NO 656
<211> LENGTH: 21
<212> TYPE: DNA
<213> ORGANISM: Homo sapiens
```

```
<400> SEQUENCE: 656
tggatgcagg aatttatgga g                                        21

<210> SEQ ID NO 657
<211> LENGTH: 22
<212> TYPE: DNA
<213> ORGANISM: Homo sapiens

<400> SEQUENCE: 657
gccttaccaa ttgagtcgtt tc                                       22

<210> SEQ ID NO 658
<211> LENGTH: 20
<212> TYPE: DNA
<213> ORGANISM: Homo sapiens

<400> SEQUENCE: 658
ccggtggttg tgctaaagac                                          20

<210> SEQ ID NO 659
<211> LENGTH: 20
<212> TYPE: DNA
<213> ORGANISM: Homo sapiens

<400> SEQUENCE: 659
tgtgcactTt ttcccctttg                                          20

<210> SEQ ID NO 660
<211> LENGTH: 20
<212> TYPE: DNA
<213> ORGANISM: Homo sapiens

<400> SEQUENCE: 660
gtatgttacc cccgcctctc                                          20

<210> SEQ ID NO 661
<211> LENGTH: 21
<212> TYPE: DNA
<213> ORGANISM: Homo sapiens

<400> SEQUENCE: 661
gcaagtggct gtgaaggtaa g                                        21

<210> SEQ ID NO 662
<211> LENGTH: 20
<212> TYPE: DNA
<213> ORGANISM: Homo sapiens

<400> SEQUENCE: 662
tgcccatgtt tacagaatgc                                          20

<210> SEQ ID NO 663
<211> LENGTH: 20
<212> TYPE: DNA
<213> ORGANISM: Homo sapiens

<400> SEQUENCE: 663
ctttcaaatg cctccaggtg                                          20

<210> SEQ ID NO 664
<211> LENGTH: 21
<212> TYPE: DNA
```

```
<213> ORGANISM: Homo sapiens

<400> SEQUENCE: 664
ggaaatatag ggaagggaag g                                         21

<210> SEQ ID NO 665
<211> LENGTH: 19
<212> TYPE: DNA
<213> ORGANISM: Homo sapiens

<400> SEQUENCE: 665
cctgctctcc tcctgaacc                                            19

<210> SEQ ID NO 666
<211> LENGTH: 23
<212> TYPE: DNA
<213> ORGANISM: Homo sapiens

<400> SEQUENCE: 666
tgttatggaa aagggtataa tgg                                       23

<210> SEQ ID NO 667
<211> LENGTH: 18
<212> TYPE: DNA
<213> ORGANISM: Homo sapiens

<400> SEQUENCE: 667
cagctggtgg aggtgctg                                             18

<210> SEQ ID NO 668
<211> LENGTH: 18
<212> TYPE: DNA
<213> ORGANISM: Homo sapiens

<400> SEQUENCE: 668
ctctgcctgg tgctggag                                             18

<210> SEQ ID NO 669
<211> LENGTH: 23
<212> TYPE: DNA
<213> ORGANISM: Homo sapiens

<400> SEQUENCE: 669
caggcacaga taacccacta aag                                       23

<210> SEQ ID NO 670
<211> LENGTH: 20
<212> TYPE: DNA
<213> ORGANISM: Homo sapiens

<400> SEQUENCE: 670
ccatttaggg gcttttctgg                                           20

<210> SEQ ID NO 671
<211> LENGTH: 20
<212> TYPE: DNA
<213> ORGANISM: Homo sapiens

<400> SEQUENCE: 671
gccatttagg ggcttttctg                                           20

<210> SEQ ID NO 672
<211> LENGTH: 24
```

```
<212> TYPE: DNA
<213> ORGANISM: Homo sapiens

<400> SEQUENCE: 672
ggagcagata ctataaatgg aagc                                      24

<210> SEQ ID NO 673
<211> LENGTH: 21
<212> TYPE: DNA
<213> ORGANISM: Homo sapiens

<400> SEQUENCE: 673
gggaatttca gcttctcctt g                                         21

<210> SEQ ID NO 674
<211> LENGTH: 25
<212> TYPE: DNA
<213> ORGANISM: Homo sapiens

<400> SEQUENCE: 674
tttgtaaata acatttcgct tttcc                                     25

<210> SEQ ID NO 675
<211> LENGTH: 22
<212> TYPE: DNA
<213> ORGANISM: Homo sapiens

<400> SEQUENCE: 675
gcttctttct agagctgcca ac                                        22

<210> SEQ ID NO 676
<211> LENGTH: 22
<212> TYPE: DNA
<213> ORGANISM: Homo sapiens

<400> SEQUENCE: 676
tgcctgtttc cttttatgat tc                                        22

<210> SEQ ID NO 677
<211> LENGTH: 24
<212> TYPE: DNA
<213> ORGANISM: Homo sapiens

<400> SEQUENCE: 677
aaccaaagat ttgggtcttt ttac                                      24

<210> SEQ ID NO 678
<211> LENGTH: 20
<212> TYPE: DNA
<213> ORGANISM: Homo sapiens

<400> SEQUENCE: 678
agagtgcttc ctggatttgg                                           20

<210> SEQ ID NO 679
<211> LENGTH: 20
<212> TYPE: DNA
<213> ORGANISM: Homo sapiens

<400> SEQUENCE: 679
tttgtgccag gaatagatgg                                           20

<210> SEQ ID NO 680
```

```
<211> LENGTH: 22
<212> TYPE: DNA
<213> ORGANISM: Homo sapiens

<400> SEQUENCE: 680
tgtacacaca gaggatgagc ag                                              22

<210> SEQ ID NO 681
<211> LENGTH: 20
<212> TYPE: DNA
<213> ORGANISM: Homo sapiens

<400> SEQUENCE: 681
acctttggca gttcagatgc                                                 20

<210> SEQ ID NO 682
<211> LENGTH: 20
<212> TYPE: DNA
<213> ORGANISM: Homo sapiens

<400> SEQUENCE: 682
ctttggcagt tcagatgcag                                                 20

<210> SEQ ID NO 683
<211> LENGTH: 20
<212> TYPE: DNA
<213> ORGANISM: Homo sapiens

<400> SEQUENCE: 683
ctattcggga aggtgcaatg                                                 20

<210> SEQ ID NO 684
<211> LENGTH: 20
<212> TYPE: DNA
<213> ORGANISM: Homo sapiens

<400> SEQUENCE: 684
agggtgtttc cactctctgc                                                 20

<210> SEQ ID NO 685
<211> LENGTH: 19
<212> TYPE: DNA
<213> ORGANISM: Homo sapiens

<400> SEQUENCE: 685
cggatgcttg ttggacttc                                                  19

<210> SEQ ID NO 686
<211> LENGTH: 20
<212> TYPE: DNA
<213> ORGANISM: Homo sapiens

<400> SEQUENCE: 686
tgtgaagtgg tgtccacctg                                                 20

<210> SEQ ID NO 687
<211> LENGTH: 20
<212> TYPE: DNA
<213> ORGANISM: Homo sapiens

<400> SEQUENCE: 687
acaagacccc tttggagatg                                                 20
```

```
<210> SEQ ID NO 688
<211> LENGTH: 20
<212> TYPE: DNA
<213> ORGANISM: Homo sapiens

<400> SEQUENCE: 688
cctttggaga tgcctgtatg                                                  20

<210> SEQ ID NO 689
<211> LENGTH: 20
<212> TYPE: DNA
<213> ORGANISM: Homo sapiens

<400> SEQUENCE: 689
atgtggagca ctgtgattgg                                                  20

<210> SEQ ID NO 690
<211> LENGTH: 19
<212> TYPE: DNA
<213> ORGANISM: Homo sapiens

<400> SEQUENCE: 690
gagggggtca cagcagaac                                                   19

<210> SEQ ID NO 691
<211> LENGTH: 20
<212> TYPE: DNA
<213> ORGANISM: Homo sapiens

<400> SEQUENCE: 691
ccaggctagc ttaggccttc                                                  20

<210> SEQ ID NO 692
<211> LENGTH: 20
<212> TYPE: DNA
<213> ORGANISM: Homo sapiens

<400> SEQUENCE: 692
tgtgcttctg ggcttcctac                                                  20

<210> SEQ ID NO 693
<211> LENGTH: 20
<212> TYPE: DNA
<213> ORGANISM: Homo sapiens

<400> SEQUENCE: 693
ctgaggctgt tgtgcttctg                                                  20

<210> SEQ ID NO 694
<211> LENGTH: 20
<212> TYPE: DNA
<213> ORGANISM: Homo sapiens

<400> SEQUENCE: 694
ctgaggctgt tgtgcttctg                                                  20

<210> SEQ ID NO 695
<211> LENGTH: 20
<212> TYPE: DNA
<213> ORGANISM: Homo sapiens

<400> SEQUENCE: 695
cgcatgtgac caatttcttg                                                  20
```

```
<210> SEQ ID NO 696
<211> LENGTH: 20
<212> TYPE: DNA
<213> ORGANISM: Homo sapiens

<400> SEQUENCE: 696 cagggagtc atctttttcc                                          20

<210> SEQ ID NO 697
<211> LENGTH: 20
<212> TYPE: DNA
<213> ORGANISM: Homo sapiens

<400> SEQUENCE: 697
gagccaagat cacaccactg                                         20

<210> SEQ ID NO 698
<211> LENGTH: 20
<212> TYPE: DNA
<213> ORGANISM: Homo sapiens

<400> SEQUENCE: 698
ttgcaaaatc ctcaatgctg                                         20

<210> SEQ ID NO 699
<211> LENGTH: 20
<212> TYPE: DNA
<213> ORGANISM: Homo sapiens

<400> SEQUENCE: 699
ttgcaaaatc ctcaatgctg                                         20

<210> SEQ ID NO 700
<211> LENGTH: 22
<212> TYPE: DNA
<213> ORGANISM: Homo sapiens

<400> SEQUENCE: 700
gctgctgatg gagtattgaa gg                                      22

<210> SEQ ID NO 701
<211> LENGTH: 25
<212> TYPE: DNA
<213> ORGANISM: Homo sapiens

<400> SEQUENCE: 701
gaagctttaa atttcatgcc ttatg                                   25

<210> SEQ ID NO 702
<211> LENGTH: 23
<212> TYPE: DNA
<213> ORGANISM: Homo sapiens

<400> SEQUENCE: 702
ccctaaacct gagtgatctg atg                                     23

<210> SEQ ID NO 703
<211> LENGTH: 20
<212> TYPE: DNA
<213> ORGANISM: Homo sapiens

<400> SEQUENCE: 703
ctgggggttc cgtatctttg                                         20
```

<210> SEQ ID NO 704
<211> LENGTH: 19
<212> TYPE: DNA
<213> ORGANISM: Homo sapiens

<400> SEQUENCE: 704
tgggggttcc gtatctttg                                            19

<210> SEQ ID NO 705
<211> LENGTH: 19
<212> TYPE: DNA
<213> ORGANISM: Homo sapiens

<400> SEQUENCE: 705
gaagaaatcg gggtgttgg                                            19

<210> SEQ ID NO 706
<211> LENGTH: 21
<212> TYPE: DNA
<213> ORGANISM: Homo sapiens

<400> SEQUENCE: 706
gatgggagag tgggaagaat c                                         21

<210> SEQ ID NO 707
<211> LENGTH: 21
<212> TYPE: DNA
<213> ORGANISM: Homo sapiens

<400> SEQUENCE: 707
gccaatacag cgtatcagag g                                         21

<210> SEQ ID NO 708
<211> LENGTH: 20
<212> TYPE: DNA
<213> ORGANISM: Homo sapiens

<400> SEQUENCE: 708
aagcctgggt tcccatagag                                           20

<210> SEQ ID NO 709
<211> LENGTH: 20
<212> TYPE: DNA
<213> ORGANISM: Homo sapiens

<400> SEQUENCE: 709
catggggtac tgcagtcagg                                           20

<210> SEQ ID NO 710
<211> LENGTH: 19
<212> TYPE: DNA
<213> ORGANISM: Homo sapiens

<400> SEQUENCE: 710
atggggtact gcagtcagg                                            19

<210> SEQ ID NO 711
<211> LENGTH: 20
<212> TYPE: DNA
<213> ORGANISM: Homo sapiens

<400> SEQUENCE: 711

-continued atcccatgca cagcctagag                                                     20

<210> SEQ ID NO 712
<211> LENGTH: 20
<212> TYPE: DNA
<213> ORGANISM: Homo sapiens

<400> SEQUENCE: 712
atgcaccgag agatctgagg                                                     20

<210> SEQ ID NO 713
<211> LENGTH: 21
<212> TYPE: DNA
<213> ORGANISM: Homo sapiens

<400> SEQUENCE: 713
ggagcaacac agtcaccttt c                                                   21

<210> SEQ ID NO 714
<211> LENGTH: 19
<212> TYPE: DNA
<213> ORGANISM: Homo sapiens

<400> SEQUENCE: 714
gtcctggtgt gcggtagtg                                                      19

<210> SEQ ID NO 715
<211> LENGTH: 20
<212> TYPE: DNA
<213> ORGANISM: Homo sapiens

<400> SEQUENCE: 715
gaggctggag aagtggtctg                                                     20

<210> SEQ ID NO 716
<211> LENGTH: 20
<212> TYPE: DNA
<213> ORGANISM: Homo sapiens

<400> SEQUENCE: 716
caaggtacgc accacacaac                                                     20

<210> SEQ ID NO 717
<211> LENGTH: 20
<212> TYPE: DNA
<213> ORGANISM: Homo sapiens

<400> SEQUENCE: 717
ggggagtgga gaaggagaag                                                     20

<210> SEQ ID NO 718
<211> LENGTH: 20
<212> TYPE: DNA
<213> ORGANISM: Homo sapiens

<400> SEQUENCE: 718
aagagagggg tgaacagtgc                                                     20

<210> SEQ ID NO 719
<211> LENGTH: 20
<212> TYPE: DNA
<213> ORGANISM: Homo sapiens

<400> SEQUENCE: 719 gagagggtg aacagtgcag                                            20

<210> SEQ ID NO 720
<211> LENGTH: 20
<212> TYPE: DNA
<213> ORGANISM: Homo sapiens

<400> SEQUENCE: 720
gaacattttg ccagctttgg                                           20

<210> SEQ ID NO 721
<211> LENGTH: 20
<212> TYPE: DNA
<213> ORGANISM: Homo sapiens

<400> SEQUENCE: 721
cccgattctg ctctggagtc                                           20

<210> SEQ ID NO 722
<211> LENGTH: 20
<212> TYPE: DNA
<213> ORGANISM: Homo sapiens

<400> SEQUENCE: 722
gctgaagcca aaaattccag                                           20

<210> SEQ ID NO 723
<211> LENGTH: 20
<212> TYPE: DNA
<213> ORGANISM: Homo sapiens

<400> SEQUENCE: 723
cacttgtccc tcaggcagac                                           20

<210> SEQ ID NO 724
<211> LENGTH: 20
<212> TYPE: DNA
<213> ORGANISM: Homo sapiens

<400> SEQUENCE: 724
aaacggaaat gggacctagc                                           20

<210> SEQ ID NO 725
<211> LENGTH: 20
<212> TYPE: DNA
<213> ORGANISM: Homo sapiens

<400> SEQUENCE: 725
tgtccctcaa ctttccttcc                                           20

<210> SEQ ID NO 726
<211> LENGTH: 20
<212> TYPE: DNA
<213> ORGANISM: Homo sapiens

<400> SEQUENCE: 726
tggcttcata tcctctccac                                           20

<210> SEQ ID NO 727
<211> LENGTH: 20
<212> TYPE: DNA
<213> ORGANISM: Homo sapiens

```
<400> SEQUENCE: 727
cttcctctgt gtttgggttg                                              20

<210> SEQ ID NO 728
<211> LENGTH: 22
<212> TYPE: DNA
<213> ORGANISM: Homo sapiens

<400> SEQUENCE: 728
aaaatgactt ggcgttacac ac                                           22

<210> SEQ ID NO 729
<211> LENGTH: 20
<212> TYPE: DNA
<213> ORGANISM: Homo sapiens

<400> SEQUENCE: 729
aggcatccac aacctttctg                                              20

<210> SEQ ID NO 730
<211> LENGTH: 20
<212> TYPE: DNA
<213> ORGANISM: Homo sapiens

<400> SEQUENCE: 730
accgctgtta ttcaggatgg                                              20

<210> SEQ ID NO 731
<211> LENGTH: 20
<212> TYPE: DNA
<213> ORGANISM: Homo sapiens

<400> SEQUENCE: 731
aatcagacct tggcgatgac                                              20

<210> SEQ ID NO 732
<211> LENGTH: 20
<212> TYPE: DNA
<213> ORGANISM: Homo sapiens

<400> SEQUENCE: 732
tgttcaagtc ctccctcctg                                              20

<210> SEQ ID NO 733
<211> LENGTH: 20
<212> TYPE: DNA
<213> ORGANISM: Homo sapiens

<400> SEQUENCE: 733
gtctcaggtt gcagggtctc                                              20

<210> SEQ ID NO 734
<211> LENGTH: 20
<212> TYPE: DNA
<213> ORGANISM: Homo sapiens

<400> SEQUENCE: 734
ctccctccac acacacacac                                              20

<210> SEQ ID NO 735
<211> LENGTH: 19
<212> TYPE: DNA
<213> ORGANISM: Homo sapiens
```

```
<400> SEQUENCE: 735
cggggtgctt gatgaatag                                                19

<210> SEQ ID NO 736
<211> LENGTH: 20
<212> TYPE: DNA
<213> ORGANISM: Homo sapiens

<400> SEQUENCE: 736
ccttccctca ttgagattcc                                               20

<210> SEQ ID NO 737
<211> LENGTH: 20
<212> TYPE: DNA
<213> ORGANISM: Homo sapiens

<400> SEQUENCE: 737
gcatacatca aaccccttgg                                               20

<210> SEQ ID NO 738
<211> LENGTH: 21
<212> TYPE: DNA
<213> ORGANISM: Homo sapiens

<400> SEQUENCE: 738
aaccatttca tccaccattt g                                             21

<210> SEQ ID NO 739
<211> LENGTH: 19
<212> TYPE: DNA
<213> ORGANISM: Homo sapiens

<400> SEQUENCE: 739
ctacctgggg cttttcctg                                                19

<210> SEQ ID NO 740
<211> LENGTH: 18
<212> TYPE: DNA
<213> ORGANISM: Homo sapiens

<400> SEQUENCE: 740
gggtgggcta ttgggaac                                                 18

<210> SEQ ID NO 741
<211> LENGTH: 19
<212> TYPE: DNA
<213> ORGANISM: Homo sapiens

<400> SEQUENCE: 741
gtgggaatca ccagggaag                                                19

<210> SEQ ID NO 742
<211> LENGTH: 20
<212> TYPE: DNA
<213> ORGANISM: Homo sapiens

<400> SEQUENCE: 742
aaaaatggga gttgggaag                                                20

<210> SEQ ID NO 743
<211> LENGTH: 21
<212> TYPE: DNA
```

```
<213> ORGANISM: Homo sapiens

<400> SEQUENCE: 743
ctcaccaatg acatcgtcaa g                                             21

<210> SEQ ID NO 744
<211> LENGTH: 20
<212> TYPE: DNA
<213> ORGANISM: Homo sapiens

<400> SEQUENCE: 744
tcacccatga aaagggaag                                                20

<210> SEQ ID NO 745
<211> LENGTH: 19
<212> TYPE: DNA
<213> ORGANISM: Homo sapiens

<400> SEQUENCE: 745
accacccttt gacccattg                                                19

<210> SEQ ID NO 746
<211> LENGTH: 20
<212> TYPE: DNA
<213> ORGANISM: Homo sapiens

<400> SEQUENCE: 746
gaattccccc tccatctctg                                               20

<210> SEQ ID NO 747
<211> LENGTH: 20
<212> TYPE: DNA
<213> ORGANISM: Homo sapiens

<400> SEQUENCE: 747
cccaacaaca aaaggaagg                                                20

<210> SEQ ID NO 748
<211> LENGTH: 20
<212> TYPE: DNA
<213> ORGANISM: Homo sapiens

<400> SEQUENCE: 748
aggtccttgt cagtggcatc                                               20

<210> SEQ ID NO 749
<211> LENGTH: 18
<212> TYPE: DNA
<213> ORGANISM: Homo sapiens

<400> SEQUENCE: 749
gacacgggct cctcagac                                                 18

<210> SEQ ID NO 750
<211> LENGTH: 18
<212> TYPE: DNA
<213> ORGANISM: Homo sapiens

<400> SEQUENCE: 750
gtggatgcac tggggaag                                                 18

<210> SEQ ID NO 751
<211> LENGTH: 19
```

```
<212> TYPE: DNA
<213> ORGANISM: Homo sapiens

<400> SEQUENCE: 751
cggtcaaaca aggcctcag                                        19

<210> SEQ ID NO 752
<211> LENGTH: 20
<212> TYPE: DNA
<213> ORGANISM: Homo sapiens

<400> SEQUENCE: 752
gggaggggta gaaaccacac                                       20

<210> SEQ ID NO 753
<211> LENGTH: 18
<212> TYPE: DNA
<213> ORGANISM: Homo sapiens

<400> SEQUENCE: 753
cctgaggacc cagtggag                                         18

<210> SEQ ID NO 754
<211> LENGTH: 19
<212> TYPE: DNA
<213> ORGANISM: Homo sapiens

<400> SEQUENCE: 754
ccacacctca gcactctgg                                        19

<210> SEQ ID NO 755
<211> LENGTH: 21
<212> TYPE: DNA
<213> ORGANISM: Homo sapiens

<400> SEQUENCE: 755
tgtctctcca tctgcactga g                                     21

<210> SEQ ID NO 756
<211> LENGTH: 18
<212> TYPE: DNA
<213> ORGANISM: Homo sapiens

<400> SEQUENCE: 756 aagccccta cagccaac                                          18

<210> SEQ ID NO 757
<211> LENGTH: 22
<212> TYPE: DNA
<213> ORGANISM: Homo sapiens

<400> SEQUENCE: 757
tgcagaagaa agagaaatgt gc                                    22

<210> SEQ ID NO 758
<211> LENGTH: 20
<212> TYPE: DNA
<213> ORGANISM: Homo sapiens

<400> SEQUENCE: 758
cgaatggcca cttattgttg                                       20

<210> SEQ ID NO 759
```

```
<211> LENGTH: 22
<212> TYPE: DNA
<213> ORGANISM: Homo sapiens

<400> SEQUENCE: 759
ccaccttggt acatatggct tc                                              22

<210> SEQ ID NO 760
<211> LENGTH: 20
<212> TYPE: DNA
<213> ORGANISM: Homo sapiens

<400> SEQUENCE: 760
gtaggcaggc caactcagac                                                 20

<210> SEQ ID NO 761
<211> LENGTH: 22
<212> TYPE: DNA
<213> ORGANISM: Homo sapiens

<400> SEQUENCE: 761
aagcatgatt gcataacaaa gg                                              22

<210> SEQ ID NO 762
<211> LENGTH: 21
<212> TYPE: DNA
<213> ORGANISM: Homo sapiens

<400> SEQUENCE: 762
ccacctgagt cctctaccat c                                               21

<210> SEQ ID NO 763
<211> LENGTH: 24
<212> TYPE: DNA
<213> ORGANISM: Homo sapiens

<400> SEQUENCE: 763
tcatcccttt tcatatatgt gtgg                                            24

<210> SEQ ID NO 764
<211> LENGTH: 20
<212> TYPE: DNA
<213> ORGANISM: Homo sapiens

<400> SEQUENCE: 764
tggtattcaa gggcacatca                                                 20

<210> SEQ ID NO 765
<211> LENGTH: 23
<212> TYPE: DNA
<213> ORGANISM: Homo sapiens

<400> SEQUENCE: 765
gactcattag cagacggaca ctc                                             23

<210> SEQ ID NO 766
<211> LENGTH: 21
<212> TYPE: DNA
<213> ORGANISM: Homo sapiens

<400> SEQUENCE: 766
tccctggaaa gaaaatgtgt g                                               21
```

```
<210> SEQ ID NO 767
<211> LENGTH: 20
<212> TYPE: DNA
<213> ORGANISM: Homo sapiens

<400> SEQUENCE: 767
ccaccgaaca caacaaacac                                            20

<210> SEQ ID NO 768
<211> LENGTH: 20
<212> TYPE: DNA
<213> ORGANISM: Homo sapiens

<400> SEQUENCE: 768
aggaggcttc aagggatgag                                            20

<210> SEQ ID NO 769
<211> LENGTH: 22
<212> TYPE: DNA
<213> ORGANISM: Homo sapiens

<400> SEQUENCE: 769
ggccatttaa ttcttgtcct tg                                         22

<210> SEQ ID NO 770
<211> LENGTH: 20
<212> TYPE: DNA
<213> ORGANISM: Homo sapiens

<400> SEQUENCE: 770
cttgcctgcc tcctctaatg                                            20

<210> SEQ ID NO 771
<211> LENGTH: 21
<212> TYPE: DNA
<213> ORGANISM: Homo sapiens

<400> SEQUENCE: 771
gatgattacg cagctcaaag c                                          21

<210> SEQ ID NO 772
<211> LENGTH: 19
<212> TYPE: DNA
<213> ORGANISM: Homo sapiens

<400> SEQUENCE: 772
agcaatctgt gcaccaagc                                             19

<210> SEQ ID NO 773
<211> LENGTH: 20
<212> TYPE: DNA
<213> ORGANISM: Homo sapiens

<400> SEQUENCE: 773
ccacctgttc caacacttcc                                            20

<210> SEQ ID NO 774
<211> LENGTH: 20
<212> TYPE: DNA
<213> ORGANISM: Homo sapiens

<400> SEQUENCE: 774
gtgcttggta ggcattaggg                                            20
```

<210> SEQ ID NO 775
<211> LENGTH: 20
<212> TYPE: DNA
<213> ORGANISM: Homo sapiens

<400> SEQUENCE: 775
ctaccgctcc tagccctacc                                              20

<210> SEQ ID NO 776
<211> LENGTH: 20
<212> TYPE: DNA
<213> ORGANISM: Homo sapiens

<400> SEQUENCE: 776
gttggttcag ggatctgagg                                              20

<210> SEQ ID NO 777
<211> LENGTH: 20
<212> TYPE: DNA
<213> ORGANISM: Homo sapiens

<400> SEQUENCE: 777
gtcttgtcag gaccctctcc                                              20

<210> SEQ ID NO 778
<211> LENGTH: 20
<212> TYPE: DNA
<213> ORGANISM: Homo sapiens

<400> SEQUENCE: 778
cacacctggt cccttagtgg                                              20

<210> SEQ ID NO 779
<211> LENGTH: 20
<212> TYPE: DNA
<213> ORGANISM: Homo sapiens

<400> SEQUENCE: 779
cacacctggt cccttagtgg                                              20

<210> SEQ ID NO 780
<211> LENGTH: 19
<212> TYPE: DNA
<213> ORGANISM: Homo sapiens

<400> SEQUENCE: 780
ctctcaggca cagctggag                                               19

<210> SEQ ID NO 781
<211> LENGTH: 19
<212> TYPE: DNA
<213> ORGANISM: Homo sapiens

<400> SEQUENCE: 781
gagcccagaa ttgcctctc                                               19

<210> SEQ ID NO 782
<211> LENGTH: 20
<212> TYPE: DNA
<213> ORGANISM: Homo sapiens

<400> SEQUENCE: 782
ctgcattgct tatcctggtg                                              20

```
<210> SEQ ID NO 783
<211> LENGTH: 20
<212> TYPE: DNA
<213> ORGANISM: Homo sapiens

<400> SEQUENCE: 783
cagtccaccc tacccagag                                              20

<210> SEQ ID NO 784
<211> LENGTH: 20
<212> TYPE: DNA
<213> ORGANISM: Homo sapiens

<400> SEQUENCE: 784
cctcagtggg ttgttgtgtg                                             20

<210> SEQ ID NO 785
<211> LENGTH: 22
<212> TYPE: DNA
<213> ORGANISM: Homo sapiens

<400> SEQUENCE: 785
cagaggcacg cctaacttat ag                                          22

<210> SEQ ID NO 786
<211> LENGTH: 20
<212> TYPE: DNA
<213> ORGANISM: Homo sapiens

<400> SEQUENCE: 786
cggcagaaaa cgctagaatg                                             20

<210> SEQ ID NO 787
<211> LENGTH: 20
<212> TYPE: DNA
<213> ORGANISM: Homo sapiens

<400> SEQUENCE: 787
acagtaagca ctccccaagg                                             20

<210> SEQ ID NO 788
<211> LENGTH: 20
<212> TYPE: DNA
<213> ORGANISM: Homo sapiens

<400> SEQUENCE: 788
agtctttggt ggctgaatgg                                             20

<210> SEQ ID NO 789
<211> LENGTH: 20
<212> TYPE: DNA
<213> ORGANISM: Homo sapiens

<400> SEQUENCE: 789
actgagatag ggcgcttcag                                             20

<210> SEQ ID NO 790
<211> LENGTH: 19
<212> TYPE: DNA
<213> ORGANISM: Homo sapiens

<400> SEQUENCE: 790
```

```
ccaagcccct attcccatc                                                      19

<210> SEQ ID NO 791
<211> LENGTH: 20
<212> TYPE: DNA
<213> ORGANISM: Homo sapiens

<400> SEQUENCE: 791
acaaggacgc agaggtcatc                                                     20

<210> SEQ ID NO 792
<211> LENGTH: 20
<212> TYPE: DNA
<213> ORGANISM: Homo sapiens

<400> SEQUENCE: 792
agaggaaaag gctggaggag                                                     20

<210> SEQ ID NO 793
<211> LENGTH: 20
<212> TYPE: DNA
<213> ORGANISM: Homo sapiens

<400> SEQUENCE: 793
cagcctgctc ctgtatcctc                                                     20

<210> SEQ ID NO 794
<211> LENGTH: 22
<212> TYPE: DNA
<213> ORGANISM: Homo sapiens

<400> SEQUENCE: 794
cctttttgtc atctccatgg tc                                                  22

<210> SEQ ID NO 795
<211> LENGTH: 22
<212> TYPE: DNA
<213> ORGANISM: Homo sapiens

<400> SEQUENCE: 795
cctttttgtc atctccatgg tc                                                  22

<210> SEQ ID NO 796
<211> LENGTH: 18
<212> TYPE: DNA
<213> ORGANISM: Homo sapiens

<400> SEQUENCE: 796
aggagggccc attctctg                                                       18

<210> SEQ ID NO 797
<211> LENGTH: 18
<212> TYPE: DNA
<213> ORGANISM: Homo sapiens

<400> SEQUENCE: 797
caaaagcccc tggagacc                                                       18

<210> SEQ ID NO 798
<211> LENGTH: 19
<212> TYPE: DNA
<213> ORGANISM: Homo sapiens

<400> SEQUENCE: 798
```
ccagccccac tctccttag                                                19

<210> SEQ ID NO 799
<211> LENGTH: 20
<212> TYPE: DNA
<213> ORGANISM: Homo sapiens

<400> SEQUENCE: 799
catcaactga gggcttccag                                               20

<210> SEQ ID NO 800
<211> LENGTH: 20
<212> TYPE: DNA
<213> ORGANISM: Homo sapiens

<400> SEQUENCE: 800
ctcgaaggcc ctctttaacc                                               20

<210> SEQ ID NO 801
<211> LENGTH: 22
<212> TYPE: DNA
<213> ORGANISM: Homo sapiens

<400> SEQUENCE: 801
gaggctggat tttcaacaaa ag                                            22

<210> SEQ ID NO 802
<211> LENGTH: 20
<212> TYPE: DNA
<213> ORGANISM: Homo sapiens

<400> SEQUENCE: 802
gctgcttgca gactatcagg                                               20

<210> SEQ ID NO 803
<211> LENGTH: 20
<212> TYPE: DNA
<213> ORGANISM: Homo sapiens

<400> SEQUENCE: 803
tgttcctcca agaggagtgc                                               20

<210> SEQ ID NO 804
<211> LENGTH: 20
<212> TYPE: DNA
<213> ORGANISM: Homo sapiens

<400> SEQUENCE: 804
agagaaggtg caggacaagg                                               20

<210> SEQ ID NO 805
<211> LENGTH: 20
<212> TYPE: DNA
<213> ORGANISM: Homo sapiens

<400> SEQUENCE: 805
ttctacccgg ctctcatttc                                               20

<210> SEQ ID NO 806
<211> LENGTH: 19
<212> TYPE: DNA
<213> ORGANISM: Homo sapiens

```
<400> SEQUENCE: 806
aattatgcag cccggacac                                              19

<210> SEQ ID NO 807
<211> LENGTH: 20
<212> TYPE: DNA
<213> ORGANISM: Homo sapiens

<400> SEQUENCE: 807 catcacccccc tactggtttg                                            20

<210> SEQ ID NO 808
<211> LENGTH: 20
<212> TYPE: DNA
<213> ORGANISM: Homo sapiens

<400> SEQUENCE: 808
tggagcaatc ttttgggaac                                             20

<210> SEQ ID NO 809
<211> LENGTH: 20
<212> TYPE: DNA
<213> ORGANISM: Homo sapiens

<400> SEQUENCE: 809
ctttggaagg ctgcaatctc                                             20

<210> SEQ ID NO 810
<211> LENGTH: 20
<212> TYPE: DNA
<213> ORGANISM: Homo sapiens

<400> SEQUENCE: 810
ggaaattctc cagctccatc                                             20

<210> SEQ ID NO 811
<211> LENGTH: 22
<212> TYPE: DNA
<213> ORGANISM: Homo sapiens

<400> SEQUENCE: 811
tggaggtggc tctctactct tc                                          22

<210> SEQ ID NO 812
<211> LENGTH: 20
<212> TYPE: DNA
<213> ORGANISM: Homo sapiens

<400> SEQUENCE: 812
attcgctcaa tggctaatcg                                             20

<210> SEQ ID NO 813
<211> LENGTH: 20
<212> TYPE: DNA
<213> ORGANISM: Homo sapiens

<400> SEQUENCE: 813
tcctttgtcc cagctgtttc                                             20

<210> SEQ ID NO 814
<211> LENGTH: 20
<212> TYPE: DNA
<213> ORGANISM: Homo sapiens
```

```
<400> SEQUENCE: 814
gacgacccct acaggtaagc                                              20

<210> SEQ ID NO 815
<211> LENGTH: 20
<212> TYPE: DNA
<213> ORGANISM: Homo sapiens

<400> SEQUENCE: 815
atgggaaggg atgtgctacc                                              20

<210> SEQ ID NO 816
<211> LENGTH: 20
<212> TYPE: DNA
<213> ORGANISM: Homo sapiens

<400> SEQUENCE: 816
tcttgggacc tgtgtgtgag                                              20

<210> SEQ ID NO 817
<211> LENGTH: 23
<212> TYPE: DNA
<213> ORGANISM: Homo sapiens

<400> SEQUENCE: 817
cagctcatga caacctatga atg                                          23

<210> SEQ ID NO 818
<211> LENGTH: 18
<212> TYPE: DNA
<213> ORGANISM: Homo sapiens

<400> SEQUENCE: 818
tgtggttgcc tgccattg                                                18

<210> SEQ ID NO 819
<211> LENGTH: 20
<212> TYPE: DNA
<213> ORGANISM: Homo sapiens

<400> SEQUENCE: 819
ttctgcaaac cagcattttg                                              20

<210> SEQ ID NO 820
<211> LENGTH: 22
<212> TYPE: DNA
<213> ORGANISM: Homo sapiens

<400> SEQUENCE: 820
gccaagaagt gtatgtcact cg                                           22

<210> SEQ ID NO 821
<211> LENGTH: 21
<212> TYPE: DNA
<213> ORGANISM: Homo sapiens

<400> SEQUENCE: 821
gggcctgtag gaatggtaaa c                                            21

<210> SEQ ID NO 822
<211> LENGTH: 27
<212> TYPE: DNA
```

```
<213> ORGANISM: Homo sapiens

<400> SEQUENCE: 822
tttatactgt tttctaaacc cactgag                                    27

<210> SEQ ID NO 823
<211> LENGTH: 21
<212> TYPE: DNA
<213> ORGANISM: Homo sapiens

<400> SEQUENCE: 823
gcaaacacag acaccaaact g                                          21

<210> SEQ ID NO 824
<211> LENGTH: 21
<212> TYPE: DNA
<213> ORGANISM: Homo sapiens

<400> SEQUENCE: 824
cattagcaac cctgcagttt c                                          21

<210> SEQ ID NO 825
<211> LENGTH: 20
<212> TYPE: DNA
<213> ORGANISM: Homo sapiens

<400> SEQUENCE: 825
tcagcagcat gaaaatggac                                            20

<210> SEQ ID NO 826
<211> LENGTH: 18
<212> TYPE: DNA
<213> ORGANISM: Homo sapiens

<400> SEQUENCE: 826
cccacccatt tcctctcc                                              18

<210> SEQ ID NO 827
<211> LENGTH: 19
<212> TYPE: DNA
<213> ORGANISM: Homo sapiens

<400> SEQUENCE: 827
gctctgatcc ctgctttgg                                             19

<210> SEQ ID NO 828
<211> LENGTH: 20
<212> TYPE: DNA
<213> ORGANISM: Homo sapiens

<400> SEQUENCE: 828
caaggaccct cctccttcac                                            20

<210> SEQ ID NO 829
<211> LENGTH: 20
<212> TYPE: DNA
<213> ORGANISM: Homo sapiens

<400> SEQUENCE: 829
gagagcctcc ctcctttcag                                            20

<210> SEQ ID NO 830
<211> LENGTH: 19
```

-continued

```
<212> TYPE: DNA
<213> ORGANISM: Homo sapiens

<400> SEQUENCE: 830
gcaatccaac agccatgag                                                19

<210> SEQ ID NO 831
<211> LENGTH: 19
<212> TYPE: DNA
<213> ORGANISM: Homo sapiens

<400> SEQUENCE: 831
gcaatccaac agccatgag                                                19

<210> SEQ ID NO 832
<211> LENGTH: 20
<212> TYPE: DNA
<213> ORGANISM: Homo sapiens

<400> SEQUENCE: 832
atctaccctc cctggctttc                                               20

<210> SEQ ID NO 833
<211> LENGTH: 20
<212> TYPE: DNA
<213> ORGANISM: Homo sapiens

<400> SEQUENCE: 833
ttctccgaga tccccaatac                                               20

<210> SEQ ID NO 834
<211> LENGTH: 20
<212> TYPE: DNA
<213> ORGANISM: Homo sapiens

<400> SEQUENCE: 834
cctctgctcc tacgttgagg                                               20

<210> SEQ ID NO 835
<211> LENGTH: 20
<212> TYPE: DNA
<213> ORGANISM: Homo sapiens

<400> SEQUENCE: 835
tgcaggatgg gttttgatac                                               20

<210> SEQ ID NO 836
<211> LENGTH: 20
<212> TYPE: DNA
<213> ORGANISM: Homo sapiens

<400> SEQUENCE: 836
acacacacac acgcacacac                                               20

<210> SEQ ID NO 837
<211> LENGTH: 18
<212> TYPE: DNA
<213> ORGANISM: Homo sapiens

<400> SEQUENCE: 837
cctgctggtg gctctgtg                                                 18

<210> SEQ ID NO 838
```

```
<211> LENGTH: 20
<212> TYPE: DNA
<213> ORGANISM: Homo sapiens

<400> SEQUENCE: 838
gcctctcgaa gaagttccac                                              20

<210> SEQ ID NO 839
<211> LENGTH: 20
<212> TYPE: DNA
<213> ORGANISM: Homo sapiens

<400> SEQUENCE: 839
tcaaacgctg agtccagaag                                              20

<210> SEQ ID NO 840
<211> LENGTH: 23
<212> TYPE: DNA
<213> ORGANISM: Homo sapiens

<400> SEQUENCE: 840
gcagcatgac ttgctattaa ctg                                          23

<210> SEQ ID NO 841
<211> LENGTH: 23
<212> TYPE: DNA
<213> ORGANISM: Homo sapiens

<400> SEQUENCE: 841
gcagcatgac ttgctattaa ctg                                          23

<210> SEQ ID NO 842
<211> LENGTH: 19
<212> TYPE: DNA
<213> ORGANISM: Homo sapiens

<400> SEQUENCE: 842
agaaggctgt cgcttcctc                                               19

<210> SEQ ID NO 843
<211> LENGTH: 23
<212> TYPE: DNA
<213> ORGANISM: Homo sapiens

<400> SEQUENCE: 843
aattgcattt gaacgaaaaa tag                                          23

<210> SEQ ID NO 844
<211> LENGTH: 24
<212> TYPE: DNA
<213> ORGANISM: Homo sapiens

<400> SEQUENCE: 844
tcatagaaaa cagctgccta actg                                         24

<210> SEQ ID NO 845
<211> LENGTH: 20
<212> TYPE: DNA
<213> ORGANISM: Homo sapiens

<400> SEQUENCE: 845
caaactgaag cccaagacac                                              20
```

```
<210> SEQ ID NO 846
<211> LENGTH: 22
<212> TYPE: DNA
<213> ORGANISM: Homo sapiens

<400> SEQUENCE: 846
gggcttaaaa agtcaaagaa gc                                              22

<210> SEQ ID NO 847
<211> LENGTH: 23
<212> TYPE: DNA
<213> ORGANISM: Homo sapiens

<400> SEQUENCE: 847
gactcatgaa gacaaacaaa agc                                             23

<210> SEQ ID NO 848
<211> LENGTH: 23
<212> TYPE: DNA
<213> ORGANISM: Homo sapiens

<400> SEQUENCE: 848
gaaagtcaaa tggagttcca cag                                             23

<210> SEQ ID NO 849
<211> LENGTH: 20
<212> TYPE: DNA
<213> ORGANISM: Homo sapiens

<400> SEQUENCE: 849
ttacactgaa gggcgggtag                                                 20

<210> SEQ ID NO 850
<211> LENGTH: 22
<212> TYPE: DNA
<213> ORGANISM: Homo sapiens

<400> SEQUENCE: 850
tggaatgtgt ttaagcaagg ag                                              22

<210> SEQ ID NO 851
<211> LENGTH: 20
<212> TYPE: DNA
<213> ORGANISM: Homo sapiens

<400> SEQUENCE: 851
tcttggggga ggtcacttag                                                 20

<210> SEQ ID NO 852
<211> LENGTH: 20
<212> TYPE: DNA
<213> ORGANISM: Homo sapiens

<400> SEQUENCE: 852
tgtctccagt ttggttcagg                                                 20

<210> SEQ ID NO 853
<211> LENGTH: 20
<212> TYPE: DNA
<213> ORGANISM: Homo sapiens

<400> SEQUENCE: 853
tctgccacac gagttctttg                                                 20
```

```
<210> SEQ ID NO 854
<211> LENGTH: 19
<212> TYPE: DNA
<213> ORGANISM: Homo sapiens

<400> SEQUENCE: 854
ctggccccag ctaatttgg                                            19

<210> SEQ ID NO 855
<211> LENGTH: 19
<212> TYPE: DNA
<213> ORGANISM: Homo sapiens

<400> SEQUENCE: 855
ttcacagtgc agcgaaaac                                            19

<210> SEQ ID NO 856
<211> LENGTH: 21
<212> TYPE: DNA
<213> ORGANISM: Homo sapiens

<400> SEQUENCE: 856
gacccatctc catatccact g                                         21

<210> SEQ ID NO 857
<211> LENGTH: 22
<212> TYPE: DNA
<213> ORGANISM: Homo sapiens

<400> SEQUENCE: 857
gcggacttaa aacttcttac cc                                        22

<210> SEQ ID NO 858
<211> LENGTH: 20
<212> TYPE: DNA
<213> ORGANISM: Homo sapiens

<400> SEQUENCE: 858
ggcatttgca ttatgaaacc                                           20

<210> SEQ ID NO 859
<211> LENGTH: 25
<212> TYPE: DNA
<213> ORGANISM: Homo sapiens

<400> SEQUENCE: 859
ttgctagttt gaaggaatta aaatg                                     25

<210> SEQ ID NO 860
<211> LENGTH: 20
<212> TYPE: DNA
<213> ORGANISM: Homo sapiens

<400> SEQUENCE: 860
accaccttga ccaccaactc                                           20

<210> SEQ ID NO 861
<211> LENGTH: 20
<212> TYPE: DNA
<213> ORGANISM: Homo sapiens

<400> SEQUENCE: 861
accaccttga ccaccaactc                                           20
```

<210> SEQ ID NO 862
<211> LENGTH: 21
<212> TYPE: DNA
<213> ORGANISM: Homo sapiens

<400> SEQUENCE: 862
tgtgcacatg tttttgtttg g                                              21

<210> SEQ ID NO 863
<211> LENGTH: 21
<212> TYPE: DNA
<213> ORGANISM: Homo sapiens

<400> SEQUENCE: 863
aggtgcgtag atcacttgag g                                              21

<210> SEQ ID NO 864
<211> LENGTH: 20
<212> TYPE: DNA
<213> ORGANISM: Homo sapiens

<400> SEQUENCE: 864
caccccagag aacaatccag                                                20

<210> SEQ ID NO 865
<211> LENGTH: 20
<212> TYPE: DNA
<213> ORGANISM: Homo sapiens

<400> SEQUENCE: 865
acaggcgcat tgagagaaac                                                20

<210> SEQ ID NO 866
<211> LENGTH: 20
<212> TYPE: DNA
<213> ORGANISM: Homo sapiens

<400> SEQUENCE: 866
gacagaggga gaccccattc                                                20

<210> SEQ ID NO 867
<211> LENGTH: 21
<212> TYPE: DNA
<213> ORGANISM: Homo sapiens

<400> SEQUENCE: 867
aagctgagga aaaccttgga g                                              21

<210> SEQ ID NO 868
<211> LENGTH: 20
<212> TYPE: DNA
<213> ORGANISM: Homo sapiens

<400> SEQUENCE: 868
ctcttgccac tcttggaacg                                                20

<210> SEQ ID NO 869
<211> LENGTH: 18
<212> TYPE: DNA
<213> ORGANISM: Homo sapiens

<400> SEQUENCE: 869
cacctcctca cccacctc                                                 18

<210> SEQ ID NO 870
<211> LENGTH: 20
<212> TYPE: DNA
<213> ORGANISM: Homo sapiens

<400> SEQUENCE: 870
ggcagaagag ccactaccag                                               20

<210> SEQ ID NO 871
<211> LENGTH: 20
<212> TYPE: DNA
<213> ORGANISM: Homo sapiens

<400> SEQUENCE: 871
atggagagag gaaccgaacc                                               20

<210> SEQ ID NO 872
<211> LENGTH: 20
<212> TYPE: DNA
<213> ORGANISM: Homo sapiens

<400> SEQUENCE: 872
accccaggct tagaacagac                                               20

<210> SEQ ID NO 873
<211> LENGTH: 20
<212> TYPE: DNA
<213> ORGANISM: Homo sapiens

<400> SEQUENCE: 873
atacagatac ggggcgtgag                                               20

<210> SEQ ID NO 874
<211> LENGTH: 20
<212> TYPE: DNA
<213> ORGANISM: Homo sapiens

<400> SEQUENCE: 874 tagccccctca gcttgaacac                                              20

<210> SEQ ID NO 875
<211> LENGTH: 18
<212> TYPE: DNA
<213> ORGANISM: Homo sapiens

<400> SEQUENCE: 875
gacctgtgcc cttcaagc                                                 18

<210> SEQ ID NO 876
<211> LENGTH: 18
<212> TYPE: DNA
<213> ORGANISM: Homo sapiens

<400> SEQUENCE: 876
ccaggtcagc atccatcc                                                 18

<210> SEQ ID NO 877
<211> LENGTH: 20
<212> TYPE: DNA
<213> ORGANISM: Homo sapiens

<400> SEQUENCE: 877
aagggaaaag ggagtcttgg                                          20

<210> SEQ ID NO 878
<211> LENGTH: 21
<212> TYPE: DNA
<213> ORGANISM: Homo sapiens

<400> SEQUENCE: 878
tcccttaata tccccatgct c                                        21

<210> SEQ ID NO 879
<211> LENGTH: 20
<212> TYPE: DNA
<213> ORGANISM: Homo sapiens

<400> SEQUENCE: 879
gccaggttca cttaccatcc                                          20

<210> SEQ ID NO 880
<211> LENGTH: 20
<212> TYPE: DNA
<213> ORGANISM: Homo sapiens

<400> SEQUENCE: 880
ggcagtgtac tgaccccttg                                          20

<210> SEQ ID NO 881
<211> LENGTH: 20
<212> TYPE: DNA
<213> ORGANISM: Homo sapiens

<400> SEQUENCE: 881
acaaaaaccc ccatctccac                                          20

<210> SEQ ID NO 882
<211> LENGTH: 19
<212> TYPE: DNA
<213> ORGANISM: Homo sapiens

<400> SEQUENCE: 882
cagacctttc cacccacag                                           19

<210> SEQ ID NO 883
<211> LENGTH: 20
<212> TYPE: DNA
<213> ORGANISM: Homo sapiens

<400> SEQUENCE: 883
tataggggag gggaaaggtg                                          20

<210> SEQ ID NO 884
<211> LENGTH: 20
<212> TYPE: DNA
<213> ORGANISM: Homo sapiens

<400> SEQUENCE: 884
tttctgaacg ggatccagag                                          20

<210> SEQ ID NO 885
<211> LENGTH: 20
<212> TYPE: DNA
<213> ORGANISM: Homo sapiens

```
<400> SEQUENCE: 885
gaactggtct gcatcattgc                                              20

<210> SEQ ID NO 886
<211> LENGTH: 20
<212> TYPE: DNA
<213> ORGANISM: Homo sapiens

<400> SEQUENCE: 886
tccaaagaga cagcagttgg                                              20

<210> SEQ ID NO 887
<211> LENGTH: 25
<212> TYPE: DNA
<213> ORGANISM: Homo sapiens

<400> SEQUENCE: 887
cttaatttga ctgctaaaat gtgtg                                        25

<210> SEQ ID NO 888
<211> LENGTH: 20
<212> TYPE: DNA
<213> ORGANISM: Homo sapiens

<400> SEQUENCE: 888 gatagggct gcttcctgag                                               20

<210> SEQ ID NO 889
<211> LENGTH: 23
<212> TYPE: DNA
<213> ORGANISM: Homo sapiens

<400> SEQUENCE: 889 aaagggaaa acgtgaccta aag                                           23

<210> SEQ ID NO 890
<211> LENGTH: 20
<212> TYPE: DNA
<213> ORGANISM: Homo sapiens

<400> SEQUENCE: 890
ggagaagggg gattctatgc                                              20

<210> SEQ ID NO 891
<211> LENGTH: 20
<212> TYPE: DNA
<213> ORGANISM: Homo sapiens

<400> SEQUENCE: 891
accatcatgg aagccaaaag                                              20

<210> SEQ ID NO 892
<211> LENGTH: 22
<212> TYPE: DNA
<213> ORGANISM: Homo sapiens

<400> SEQUENCE: 892
gacaataaaa ggcagcttgg ac                                           22

<210> SEQ ID NO 893
<211> LENGTH: 20
<212> TYPE: DNA
<213> ORGANISM: Homo sapiens
```

```
<400> SEQUENCE: 893
cccatgaact gcctgtcaac                                              20

<210> SEQ ID NO 894
<211> LENGTH: 20
<212> TYPE: DNA
<213> ORGANISM: Homo sapiens

<400> SEQUENCE: 894
ccagccctca gagagttcag                                              20

<210> SEQ ID NO 895
<211> LENGTH: 20
<212> TYPE: DNA
<213> ORGANISM: Homo sapiens

<400> SEQUENCE: 895
tcgtgtccat gttcacacag                                              20

<210> SEQ ID NO 896
<211> LENGTH: 23
<212> TYPE: DNA
<213> ORGANISM: Homo sapiens

<400> SEQUENCE: 896
tgcaggtagt ttgtaaggct ttg                                          23

<210> SEQ ID NO 897
<211> LENGTH: 20
<212> TYPE: DNA
<213> ORGANISM: Homo sapiens

<400> SEQUENCE: 897
cgcaggtatg gtatggtcag                                              20

<210> SEQ ID NO 898
<211> LENGTH: 20
<212> TYPE: DNA
<213> ORGANISM: Homo sapiens

<400> SEQUENCE: 898
cgcaggtatg gtatggtcag                                              20

<210> SEQ ID NO 899
<211> LENGTH: 22
<212> TYPE: DNA
<213> ORGANISM: Homo sapiens

<400> SEQUENCE: 899
aaactgattg tgcagttggt tg                                           22

<210> SEQ ID NO 900
<211> LENGTH: 21
<212> TYPE: DNA
<213> ORGANISM: Homo sapiens

<400> SEQUENCE: 900
tgctgaccct tagaagagca c                                            21

<210> SEQ ID NO 901
<211> LENGTH: 23
<212> TYPE: DNA
```

```
<213> ORGANISM: Homo sapiens

<400> SEQUENCE: 901
ttgaatacat tagggcaat gac                                             23

<210> SEQ ID NO 902
<211> LENGTH: 20
<212> TYPE: DNA
<213> ORGANISM: Homo sapiens

<400> SEQUENCE: 902
agcccacgga acaaatgtag                                                20

<210> SEQ ID NO 903
<211> LENGTH: 20
<212> TYPE: DNA
<213> ORGANISM: Homo sapiens

<400> SEQUENCE: 903
ctctggaaag ccccaagtct                                                20

<210> SEQ ID NO 904
<211> LENGTH: 20
<212> TYPE: DNA
<213> ORGANISM: Homo sapiens

<400> SEQUENCE: 904
tcccaggaca ctctggtttc                                                20

<210> SEQ ID NO 905
<211> LENGTH: 18
<212> TYPE: DNA
<213> ORGANISM: Homo sapiens

<400> SEQUENCE: 905
ggccagaggg aagagagg                                                  18

<210> SEQ ID NO 906
<211> LENGTH: 20
<212> TYPE: DNA
<213> ORGANISM: Homo sapiens

<400> SEQUENCE: 906
gcccgtgaag agattcaaac                                                20

<210> SEQ ID NO 907
<211> LENGTH: 20
<212> TYPE: DNA
<213> ORGANISM: Homo sapiens

<400> SEQUENCE: 907
ctccccaagc tgggttaaag                                                20

<210> SEQ ID NO 908
<211> LENGTH: 19
<212> TYPE: DNA
<213> ORGANISM: Homo sapiens

<400> SEQUENCE: 908
ctctgccatc agcagcaag                                                 19

<210> SEQ ID NO 909
<211> LENGTH: 20
```

```
<212> TYPE: DNA
<213> ORGANISM: Homo sapiens

<400> SEQUENCE: 909
ttgcactggc ctttatgacc                                              20

<210> SEQ ID NO 910
<211> LENGTH: 21
<212> TYPE: DNA
<213> ORGANISM: Homo sapiens

<400> SEQUENCE: 910
caattaccca ggacagagtg c                                            21

<210> SEQ ID NO 911
<211> LENGTH: 21
<212> TYPE: DNA
<213> ORGANISM: Homo sapiens

<400> SEQUENCE: 911
ggctgaaagg tgtgtttctt g                                            21

<210> SEQ ID NO 912
<211> LENGTH: 22
<212> TYPE: DNA
<213> ORGANISM: Homo sapiens

<400> SEQUENCE: 912
gcaaaccaag ttaatgggaa ag                                           22

<210> SEQ ID NO 913
<211> LENGTH: 21
<212> TYPE: DNA
<213> ORGANISM: Homo sapiens

<400> SEQUENCE: 913
gacaactcaa gctgcgaaaa c                                            21

<210> SEQ ID NO 914
<211> LENGTH: 20
<212> TYPE: DNA
<213> ORGANISM: Homo sapiens

<400> SEQUENCE: 914
atgacttggg catttgttgc                                              20

<210> SEQ ID NO 915
<211> LENGTH: 20
<212> TYPE: DNA
<213> ORGANISM: Homo sapiens

<400> SEQUENCE: 915
ttctgtctca ggggcatagg                                              20

<210> SEQ ID NO 916
<211> LENGTH: 21
<212> TYPE: DNA
<213> ORGANISM: Homo sapiens

<400> SEQUENCE: 916
ggcttgtaga ccccttgaat c                                            21

<210> SEQ ID NO 917
```

```
<211> LENGTH: 21
<212> TYPE: DNA
<213> ORGANISM: Homo sapiens

<400> SEQUENCE: 917
gcagcactgg gtacctgata g                                              21

<210> SEQ ID NO 918
<211> LENGTH: 20
<212> TYPE: DNA
<213> ORGANISM: Homo sapiens

<400> SEQUENCE: 918
tggtcctgag ttctgacctg                                                20

<210> SEQ ID NO 919
<211> LENGTH: 18
<212> TYPE: DNA
<213> ORGANISM: Homo sapiens

<400> SEQUENCE: 919
ggacaagccc ctgcaaag                                                  18

<210> SEQ ID NO 920
<211> LENGTH: 20
<212> TYPE: DNA
<213> ORGANISM: Homo sapiens

<400> SEQUENCE: 920
tggaatgaat tctgggttgg                                                20

<210> SEQ ID NO 921
<211> LENGTH: 20
<212> TYPE: DNA
<213> ORGANISM: Homo sapiens

<400> SEQUENCE: 921
cagtggcagt gcttagcttg                                                20

<210> SEQ ID NO 922
<211> LENGTH: 18
<212> TYPE: DNA
<213> ORGANISM: Homo sapiens

<400> SEQUENCE: 922
ctcttcaggg tcccatgc                                                  18

<210> SEQ ID NO 923
<211> LENGTH: 20
<212> TYPE: DNA
<213> ORGANISM: Homo sapiens

<400> SEQUENCE: 923
agggagaaca gggctgtatg                                                20

<210> SEQ ID NO 924
<211> LENGTH: 20
<212> TYPE: DNA
<213> ORGANISM: Homo sapiens

<400> SEQUENCE: 924
gcatggtggg ctagagtgtg                                                20
```

```
<210> SEQ ID NO 925
<211> LENGTH: 21
<212> TYPE: DNA
<213> ORGANISM: Homo sapiens

<400> SEQUENCE: 925
tggggtgagg gctataaaaa g                                              21

<210> SEQ ID NO 926
<211> LENGTH: 20
<212> TYPE: DNA
<213> ORGANISM: Homo sapiens

<400> SEQUENCE: 926
gctagcactg cagacaggtg                                                20

<210> SEQ ID NO 927
<211> LENGTH: 20
<212> TYPE: DNA
<213> ORGANISM: Homo sapiens

<400> SEQUENCE: 927
atctactgcc acacccaagg                                                20

<210> SEQ ID NO 928
<211> LENGTH: 20
<212> TYPE: DNA
<213> ORGANISM: Homo sapiens

<400> SEQUENCE: 928
caagccactt tcagcttgtg                                                20

<210> SEQ ID NO 929
<211> LENGTH: 20
<212> TYPE: DNA
<213> ORGANISM: Homo sapiens

<400> SEQUENCE: 929
gatagtgcag agggacagc                                                 20

<210> SEQ ID NO 930
<211> LENGTH: 20
<212> TYPE: DNA
<213> ORGANISM: Homo sapiens

<400> SEQUENCE: 930
ggacaaagga gagcatcagg                                                20

<210> SEQ ID NO 931
<211> LENGTH: 20
<212> TYPE: DNA
<213> ORGANISM: Homo sapiens

<400> SEQUENCE: 931
ggtttggaag aagggtagg                                                 20

<210> SEQ ID NO 932
<211> LENGTH: 19
<212> TYPE: DNA
<213> ORGANISM: Homo sapiens

<400> SEQUENCE: 932
cggctgactt cttccactg                                                 19
```

```
<210> SEQ ID NO 933
<211> LENGTH: 22
<212> TYPE: DNA
<213> ORGANISM: Homo sapiens

<400> SEQUENCE: 933
ctgtagttca gggactcaat gg                                             22

<210> SEQ ID NO 934
<211> LENGTH: 20
<212> TYPE: DNA
<213> ORGANISM: Homo sapiens

<400> SEQUENCE: 934
tgtcacacct ggaacacagc                                                20

<210> SEQ ID NO 935
<211> LENGTH: 20
<212> TYPE: DNA
<213> ORGANISM: Homo sapiens

<400> SEQUENCE: 935
tgtcacacct ggaacacagc                                                20

<210> SEQ ID NO 936
<211> LENGTH: 20
<212> TYPE: DNA
<213> ORGANISM: Homo sapiens

<400> SEQUENCE: 936
acaaagtgct ctcggtccag                                                20

<210> SEQ ID NO 937
<211> LENGTH: 19
<212> TYPE: DNA
<213> ORGANISM: Homo sapiens

<400> SEQUENCE: 937
tcatggagct caaggatgg                                                 19

<210> SEQ ID NO 938
<211> LENGTH: 20
<212> TYPE: DNA
<213> ORGANISM: Homo sapiens

<400> SEQUENCE: 938
gcactctgga gcactctgtg                                                20

<210> SEQ ID NO 939
<211> LENGTH: 22
<212> TYPE: DNA
<213> ORGANISM: Homo sapiens

<400> SEQUENCE: 939
tgtgcccaca aaaattaaaa ac                                             22

<210> SEQ ID NO 940
<211> LENGTH: 20
<212> TYPE: DNA
<213> ORGANISM: Homo sapiens

<400> SEQUENCE: 940
tggtggcatt tacgaatcac                                                20
```

<210> SEQ ID NO 941
<211> LENGTH: 22
<212> TYPE: DNA
<213> ORGANISM: Homo sapiens

<400> SEQUENCE: 941
gaggtacaca tgagctggtt tc                                              22

<210> SEQ ID NO 942
<211> LENGTH: 21
<212> TYPE: DNA
<213> ORGANISM: Homo sapiens

<400> SEQUENCE: 942
gctttacaaa cagcggttga c                                               21

<210> SEQ ID NO 943
<211> LENGTH: 21
<212> TYPE: DNA
<213> ORGANISM: Homo sapiens

<400> SEQUENCE: 943
caccatcatg aggacacatt c                                               21

<210> SEQ ID NO 944
<211> LENGTH: 22
<212> TYPE: DNA
<213> ORGANISM: Homo sapiens

<400> SEQUENCE: 944
tcaccttgca atactgcata cc                                              22

<210> SEQ ID NO 945
<211> LENGTH: 20
<212> TYPE: DNA
<213> ORGANISM: Homo sapiens

<400> SEQUENCE: 945
ggcttccacc tgtacctcac                                                 20

<210> SEQ ID NO 946
<211> LENGTH: 26
<212> TYPE: DNA
<213> ORGANISM: Homo sapiens

<400> SEQUENCE: 946 caattttgt aaaagaaca aaatcc                                            26

<210> SEQ ID NO 947
<211> LENGTH: 19
<212> TYPE: DNA
<213> ORGANISM: Homo sapiens

<400> SEQUENCE: 947
gtttgggggc tagcttgag                                                  19

<210> SEQ ID NO 948
<211> LENGTH: 19
<212> TYPE: DNA
<213> ORGANISM: Homo sapiens

<400> SEQUENCE: 948 gtttggggc tagcttgag                    19

<210> SEQ ID NO 949
<211> LENGTH: 20
<212> TYPE: DNA
<213> ORGANISM: Homo sapiens

<400> SEQUENCE: 949
actgccactt cacccaaaag                  20

<210> SEQ ID NO 950
<211> LENGTH: 20
<212> TYPE: DNA
<213> ORGANISM: Homo sapiens

<400> SEQUENCE: 950
gccagggagc tctgtacctc                  20

<210> SEQ ID NO 951
<211> LENGTH: 19
<212> TYPE: DNA
<213> ORGANISM: Homo sapiens

<400> SEQUENCE: 951
atcggggaga cactcgttc                   19

<210> SEQ ID NO 952
<211> LENGTH: 20
<212> TYPE: DNA
<213> ORGANISM: Homo sapiens

<400> SEQUENCE: 952
cacccacaac accctaaacc                  20

<210> SEQ ID NO 953
<211> LENGTH: 19
<212> TYPE: DNA
<213> ORGANISM: Homo sapiens

<400> SEQUENCE: 953
gagaggggca tgagaggtg                   19

<210> SEQ ID NO 954
<211> LENGTH: 20
<212> TYPE: DNA
<213> ORGANISM: Homo sapiens

<400> SEQUENCE: 954
gtaggaaatg ccagcctgtg                  20

<210> SEQ ID NO 955
<211> LENGTH: 18
<212> TYPE: DNA
<213> ORGANISM: Homo sapiens

<400> SEQUENCE: 955
cacacagagc cctgatcg                    18

<210> SEQ ID NO 956
<211> LENGTH: 20
<212> TYPE: DNA
<213> ORGANISM: Homo sapiens

<400> SEQUENCE: 956

```
gggtgtgca ctttatttcc                                              20

<210> SEQ ID NO 957
<211> LENGTH: 18
<212> TYPE: DNA
<213> ORGANISM: Homo sapiens

<400> SEQUENCE: 957
ggactcacgg tggcttcc                                               18

<210> SEQ ID NO 958
<211> LENGTH: 20
<212> TYPE: DNA
<213> ORGANISM: Homo sapiens

<400> SEQUENCE: 958
cagagaatgg tgcaggtgtg                                             20

<210> SEQ ID NO 959
<211> LENGTH: 23
<212> TYPE: DNA
<213> ORGANISM: Homo sapiens

<400> SEQUENCE: 959
tgcaccagat ttctaggaat agc                                         23

<210> SEQ ID NO 960
<211> LENGTH: 20
<212> TYPE: DNA
<213> ORGANISM: Homo sapiens

<400> SEQUENCE: 960
ggaggagcac ctagaacagg                                             20

<210> SEQ ID NO 961
<211> LENGTH: 19
<212> TYPE: DNA
<213> ORGANISM: Homo sapiens

<400> SEQUENCE: 961
cttgagggtt ggacagcag                                              19

<210> SEQ ID NO 962
<211> LENGTH: 19
<212> TYPE: DNA
<213> ORGANISM: Homo sapiens

<400> SEQUENCE: 962
agacagggat gggatctgc                                              19

<210> SEQ ID NO 963
<211> LENGTH: 20
<212> TYPE: DNA
<213> ORGANISM: Homo sapiens

<400> SEQUENCE: 963
acttgaccgg gatcttggag                                             20

<210> SEQ ID NO 964
<211> LENGTH: 20
<212> TYPE: DNA
<213> ORGANISM: Homo sapiens
```

```
<400> SEQUENCE: 964
caagagctgc ctcgattctg                                          20

<210> SEQ ID NO 965
<211> LENGTH: 18
<212> TYPE: DNA
<213> ORGANISM: Homo sapiens

<400> SEQUENCE: 965
cttcgagttg gcgctctg                                            18

<210> SEQ ID NO 966
<211> LENGTH: 20
<212> TYPE: DNA
<213> ORGANISM: Homo sapiens

<400> SEQUENCE: 966
gtccgcagaa agttcaccag                                          20

<210> SEQ ID NO 967
<211> LENGTH: 20
<212> TYPE: DNA
<213> ORGANISM: Homo sapiens

<400> SEQUENCE: 967
tttccccttg atggatcttg                                          20

<210> SEQ ID NO 968
<211> LENGTH: 20
<212> TYPE: DNA
<213> ORGANISM: Homo sapiens

<400> SEQUENCE: 968
attatgggcc aagagcttcc                                          20

<210> SEQ ID NO 969
<211> LENGTH: 18
<212> TYPE: DNA
<213> ORGANISM: Homo sapiens

<400> SEQUENCE: 969
atgcggtacc ccttctcc                                            18

<210> SEQ ID NO 970
<211> LENGTH: 20
<212> TYPE: DNA
<213> ORGANISM: Homo sapiens

<400> SEQUENCE: 970
gggacacaga gacacacagg                                          20

<210> SEQ ID NO 971
<211> LENGTH: 20
<212> TYPE: DNA
<213> ORGANISM: Homo sapiens

<400> SEQUENCE: 971
tctcgtgttg catcttcctg                                          20

<210> SEQ ID NO 972
<211> LENGTH: 19
<212> TYPE: DNA
<213> ORGANISM: Homo sapiens
```

```
<400> SEQUENCE: 972
gtgtgcattt tcccaccag                                              19

<210> SEQ ID NO 973
<211> LENGTH: 20
<212> TYPE: DNA
<213> ORGANISM: Homo sapiens

<400> SEQUENCE: 973
agccagtcca tgcttaaagg                                             20

<210> SEQ ID NO 974
<211> LENGTH: 20
<212> TYPE: DNA
<213> ORGANISM: Homo sapiens

<400> SEQUENCE: 974
aagggcatgc tgatatttcc                                             20

<210> SEQ ID NO 975
<211> LENGTH: 20
<212> TYPE: DNA
<213> ORGANISM: Homo sapiens

<400> SEQUENCE: 975
caatttgctg atgtgcttgg                                             20

<210> SEQ ID NO 976
<211> LENGTH: 20
<212> TYPE: DNA
<213> ORGANISM: Homo sapiens

<400> SEQUENCE: 976
taaagggcaa gcattttggg                                             20

<210> SEQ ID NO 977
<211> LENGTH: 20
<212> TYPE: DNA
<213> ORGANISM: Homo sapiens

<400> SEQUENCE: 977
taatgggccc tgtgaaatac                                             20

<210> SEQ ID NO 978
<211> LENGTH: 21
<212> TYPE: DNA
<213> ORGANISM: Homo sapiens

<400> SEQUENCE: 978
cacagtcctg gcagatagga g                                           21

<210> SEQ ID NO 979
<211> LENGTH: 21
<212> TYPE: DNA
<213> ORGANISM: Homo sapiens

<400> SEQUENCE: 979
aacacagtcc tggcagatag g                                           21

<210> SEQ ID NO 980
<211> LENGTH: 21
<212> TYPE: DNA
```

```
<213> ORGANISM: Homo sapiens

<400> SEQUENCE: 980
tggacataaa agcctcacac c                                         21

<210> SEQ ID NO 981
<211> LENGTH: 20
<212> TYPE: DNA
<213> ORGANISM: Homo sapiens

<400> SEQUENCE: 981 gccccttcc actacttctg                                            20

<210> SEQ ID NO 982
<211> LENGTH: 20
<212> TYPE: DNA
<213> ORGANISM: Homo sapiens

<400> SEQUENCE: 982
ttcaccatca ccaaccactc                                           20

<210> SEQ ID NO 983
<211> LENGTH: 20
<212> TYPE: DNA
<213> ORGANISM: Homo sapiens

<400> SEQUENCE: 983
tctggagttc aggcaaggac                                           20

<210> SEQ ID NO 984
<211> LENGTH: 20
<212> TYPE: DNA
<213> ORGANISM: Homo sapiens

<400> SEQUENCE: 984
agtgagggaa gggcaagaag                                           20

<210> SEQ ID NO 985
<211> LENGTH: 20
<212> TYPE: DNA
<213> ORGANISM: Homo sapiens

<400> SEQUENCE: 985
tagcagcttc caggttacgc                                           20

<210> SEQ ID NO 986
<211> LENGTH: 20
<212> TYPE: DNA
<213> ORGANISM: Homo sapiens

<400> SEQUENCE: 986
cctccccaag gaaattcaac                                           20

<210> SEQ ID NO 987
<211> LENGTH: 18
<212> TYPE: DNA
<213> ORGANISM: Homo sapiens

<400> SEQUENCE: 987
gggccaggag tgagcttg                                             18

<210> SEQ ID NO 988
<211> LENGTH: 20
```

<212> TYPE: DNA
<213> ORGANISM: Homo sapiens

<400> SEQUENCE: 988
atcaagggga agggagagag        20

<210> SEQ ID NO 989
<211> LENGTH: 21
<212> TYPE: DNA
<213> ORGANISM: Homo sapiens

<400> SEQUENCE: 989
ccatccctgt gaagctctaa g        21

<210> SEQ ID NO 990
<211> LENGTH: 20
<212> TYPE: DNA
<213> ORGANISM: Homo sapiens

<400> SEQUENCE: 990
caccgtcaac ctcactttcc        20

<210> SEQ ID NO 991
<211> LENGTH: 20
<212> TYPE: DNA
<213> ORGANISM: Homo sapiens

<400> SEQUENCE: 991
atgtgacccc accaactttc        20

<210> SEQ ID NO 992
<211> LENGTH: 23
<212> TYPE: DNA
<213> ORGANISM: Homo sapiens

<400> SEQUENCE: 992
cacgtgcatt atttcacaaa atc        23

<210> SEQ ID NO 993
<211> LENGTH: 20
<212> TYPE: DNA
<213> ORGANISM: Homo sapiens

<400> SEQUENCE: 993
gccagctgtt gtctcttgtg        20

<210> SEQ ID NO 994
<211> LENGTH: 21
<212> TYPE: DNA
<213> ORGANISM: Homo sapiens

<400> SEQUENCE: 994
gcataatgca gatgggaaat c        21

<210> SEQ ID NO 995
<211> LENGTH: 20
<212> TYPE: DNA
<213> ORGANISM: Homo sapiens

<400> SEQUENCE: 995
gaagtgtggc cttgctgaac        20

<210> SEQ ID NO 996

```
<211> LENGTH: 20
<212> TYPE: DNA
<213> ORGANISM: Homo sapiens

<400> SEQUENCE: 996
gttgccacct gggattttc                                           20

<210> SEQ ID NO 997
<211> LENGTH: 20
<212> TYPE: DNA
<213> ORGANISM: Homo sapiens

<400> SEQUENCE: 997
gacagagccc ctgctaagtg                                          20

<210> SEQ ID NO 998
<211> LENGTH: 18
<212> TYPE: DNA
<213> ORGANISM: Homo sapiens

<400> SEQUENCE: 998
ctcaatggcc aggcatcc                                            18

<210> SEQ ID NO 999
<211> LENGTH: 20
<212> TYPE: DNA
<213> ORGANISM: Homo sapiens

<400> SEQUENCE: 999
acccctccct ggactcctac                                          20

<210> SEQ ID NO 1000
<211> LENGTH: 20
<212> TYPE: DNA
<213> ORGANISM: Homo sapiens

<400> SEQUENCE: 1000
ggcaacaaga gcaaaactcc                                          20

<210> SEQ ID NO 1001
<211> LENGTH: 19
<212> TYPE: DNA
<213> ORGANISM: Homo sapiens

<400> SEQUENCE: 1001
gaggtcatca tgggcagag                                           19

<210> SEQ ID NO 1002
<211> LENGTH: 19
<212> TYPE: DNA
<213> ORGANISM: Homo sapiens

<400> SEQUENCE: 1002
attgaggggc agggaagag                                           19

<210> SEQ ID NO 1003
<211> LENGTH: 20
<212> TYPE: DNA
<213> ORGANISM: Homo sapiens

<400> SEQUENCE: 1003
cactgctttt cccaagactg                                          20
```

```
<210> SEQ ID NO 1004
<211> LENGTH: 19
<212> TYPE: DNA
<213> ORGANISM: Homo sapiens

<400> SEQUENCE: 1004
tagatgcctt ccccacctc                                                19

<210> SEQ ID NO 1005
<211> LENGTH: 20
<212> TYPE: DNA
<213> ORGANISM: Homo sapiens

<400> SEQUENCE: 1005
cctctctcct agcggcatac                                               20

<210> SEQ ID NO 1006
<211> LENGTH: 18
<212> TYPE: DNA
<213> ORGANISM: Homo sapiens

<400> SEQUENCE: 1006
cccccagaca agcagttc                                                 18

<210> SEQ ID NO 1007
<211> LENGTH: 20
<212> TYPE: DNA
<213> ORGANISM: Homo sapiens

<400> SEQUENCE: 1007
gcagccttct ctccttgaac                                               20

<210> SEQ ID NO 1008
<211> LENGTH: 20
<212> TYPE: DNA
<213> ORGANISM: Homo sapiens

<400> SEQUENCE: 1008
agtgaaggga aggcagaacc                                               20

<210> SEQ ID NO 1009
<211> LENGTH: 20
<212> TYPE: DNA
<213> ORGANISM: Homo sapiens

<400> SEQUENCE: 1009
agtgaaggga aggcagaacc                                               20

<210> SEQ ID NO 1010
<211> LENGTH: 20
<212> TYPE: DNA
<213> ORGANISM: Homo sapiens

<400> SEQUENCE: 1010
gagaaaatgg ttgggctcag                                               20

<210> SEQ ID NO 1011
<211> LENGTH: 20
<212> TYPE: DNA
<213> ORGANISM: Homo sapiens

<400> SEQUENCE: 1011
cagccaactc ctccttttc                                                20
```

```
<210> SEQ ID NO 1012
<211> LENGTH: 19
<212> TYPE: DNA
<213> ORGANISM: Homo sapiens

<400> SEQUENCE: 1012
tcagggtgca aagtgttgg                                                   19

<210> SEQ ID NO 1013
<211> LENGTH: 20
<212> TYPE: DNA
<213> ORGANISM: Homo sapiens

<400> SEQUENCE: 1013
agcagcctgt gaacacgtag                                                  20

<210> SEQ ID NO 1014
<211> LENGTH: 20
<212> TYPE: DNA
<213> ORGANISM: Homo sapiens

<400> SEQUENCE: 1014
agcagcctgt gaacacgtag                                                  20

<210> SEQ ID NO 1015
<211> LENGTH: 20
<212> TYPE: DNA
<213> ORGANISM: Homo sapiens

<400> SEQUENCE: 1015
tctcagagca accgaagtca                                                  20

<210> SEQ ID NO 1016
<211> LENGTH: 18
<212> TYPE: DNA
<213> ORGANISM: Homo sapiens

<400> SEQUENCE: 1016
ggtggagacg gtgacctg                                                    18

<210> SEQ ID NO 1017
<211> LENGTH: 20
<212> TYPE: DNA
<213> ORGANISM: Homo sapiens

<400> SEQUENCE: 1017
actcccacac catcatttcc                                                  20

<210> SEQ ID NO 1018
<211> LENGTH: 20
<212> TYPE: DNA
<213> ORGANISM: Homo sapiens

<400> SEQUENCE: 1018
ttccaagccc taccaaagag                                                  20

<210> SEQ ID NO 1019
<211> LENGTH: 20
<212> TYPE: DNA
<213> ORGANISM: Homo sapiens

<400> SEQUENCE: 1019
ctcgcattta tgccaagacc                                                  20
```

<210> SEQ ID NO 1020
<211> LENGTH: 20
<212> TYPE: DNA
<213> ORGANISM: Homo sapiens

<400> SEQUENCE: 1020
ccagaagcaa gcagacagag                                               20

<210> SEQ ID NO 1021
<211> LENGTH: 19
<212> TYPE: DNA
<213> ORGANISM: Homo sapiens

<400> SEQUENCE: 1021
ctccacggac aggtgagag                                                19

<210> SEQ ID NO 1022
<211> LENGTH: 20
<212> TYPE: DNA
<213> ORGANISM: Homo sapiens

<400> SEQUENCE: 1022
tagggccaga cactgggtag                                               20

<210> SEQ ID NO 1023
<211> LENGTH: 19
<212> TYPE: DNA
<213> ORGANISM: Homo sapiens

<400> SEQUENCE: 1023
cctcccttct tccagatgc                                                19

<210> SEQ ID NO 1024
<211> LENGTH: 20
<212> TYPE: DNA
<213> ORGANISM: Homo sapiens

<400> SEQUENCE: 1024
ctgggggaat tctgagcaag                                               20

<210> SEQ ID NO 1025
<211> LENGTH: 20
<212> TYPE: DNA
<213> ORGANISM: Homo sapiens

<400> SEQUENCE: 1025
ccttgggcta ggagaacctc                                               20

<210> SEQ ID NO 1026
<211> LENGTH: 20
<212> TYPE: DNA
<213> ORGANISM: Homo sapiens

<400> SEQUENCE: 1026
caggtacacc tgcattgtgg                                               20

<210> SEQ ID NO 1027
<211> LENGTH: 20
<212> TYPE: DNA
<213> ORGANISM: Homo sapiens

<400> SEQUENCE: 1027

-continued caggtacacc tgcattgtgg                                              20

<210> SEQ ID NO 1028
<211> LENGTH: 20
<212> TYPE: DNA
<213> ORGANISM: Homo sapiens

<400> SEQUENCE: 1028
gtgcaggagg cagagttacc                                              20

<210> SEQ ID NO 1029
<211> LENGTH: 19
<212> TYPE: DNA
<213> ORGANISM: Homo sapiens

<400> SEQUENCE: 1029
cccaggaggg agagcattc                                               19

<210> SEQ ID NO 1030
<211> LENGTH: 19
<212> TYPE: DNA
<213> ORGANISM: Homo sapiens

<400> SEQUENCE: 1030
gagggagcct cttccttcc                                               19

<210> SEQ ID NO 1031
<211> LENGTH: 19
<212> TYPE: DNA
<213> ORGANISM: Homo sapiens

<400> SEQUENCE: 1031
ggtgcagggg aagacaatc                                               19

<210> SEQ ID NO 1032
<211> LENGTH: 20
<212> TYPE: DNA
<213> ORGANISM: Homo sapiens

<400> SEQUENCE: 1032
gatgcaagag aggccaaaag                                              20

<210> SEQ ID NO 1033
<211> LENGTH: 19
<212> TYPE: DNA
<213> ORGANISM: Homo sapiens

<400> SEQUENCE: 1033
atgcctgcat tcactctgc                                               19

<210> SEQ ID NO 1034
<211> LENGTH: 20
<212> TYPE: DNA
<213> ORGANISM: Homo sapiens

<400> SEQUENCE: 1034
tttgccaaac tgccttacag                                              20

<210> SEQ ID NO 1035
<211> LENGTH: 26
<212> TYPE: DNA
<213> ORGANISM: Homo sapiens

<400> SEQUENCE: 1035

```
aaaagggaa aagaaagaat aacttc                                          26

<210> SEQ ID NO 1036
<211> LENGTH: 20
<212> TYPE: DNA
<213> ORGANISM: Homo sapiens

<400> SEQUENCE: 1036
cagatctcag gtcccacacc                                                20

<210> SEQ ID NO 1037
<211> LENGTH: 20
<212> TYPE: DNA
<213> ORGANISM: Homo sapiens

<400> SEQUENCE: 1037
gagctcttga ggtccctgtg                                                20

<210> SEQ ID NO 1038
<211> LENGTH: 22
<212> TYPE: DNA
<213> ORGANISM: Homo sapiens

<400> SEQUENCE: 1038
ccactacaca atgatgctgg tc                                             22

<210> SEQ ID NO 1039
<211> LENGTH: 23
<212> TYPE: DNA
<213> ORGANISM: Homo sapiens

<400> SEQUENCE: 1039
ggcaacttgg ttgaatctta ctg                                            23

<210> SEQ ID NO 1040
<211> LENGTH: 20
<212> TYPE: DNA
<213> ORGANISM: Homo sapiens

<400> SEQUENCE: 1040
ggttttccag gaagcatcag                                                20

<210> SEQ ID NO 1041
<211> LENGTH: 21
<212> TYPE: DNA
<213> ORGANISM: Homo sapiens

<400> SEQUENCE: 1041
tttggaatga aagaggagca g                                              21

<210> SEQ ID NO 1042
<211> LENGTH: 20
<212> TYPE: DNA
<213> ORGANISM: Homo sapiens

<400> SEQUENCE: 1042
atgaaaggtc ctgggttagg                                                20

<210> SEQ ID NO 1043
<211> LENGTH: 22
<212> TYPE: DNA
<213> ORGANISM: Homo sapiens
```

```
<400> SEQUENCE: 1043
tgccatatca tcatctttag gc                                      22

<210> SEQ ID NO 1044
<211> LENGTH: 24
<212> TYPE: DNA
<213> ORGANISM: Homo sapiens

<400> SEQUENCE: 1044
gccttaacct cctaatacct ctgc                                    24

<210> SEQ ID NO 1045
<211> LENGTH: 21
<212> TYPE: DNA
<213> ORGANISM: Homo sapiens

<400> SEQUENCE: 1045
caccatcagt tgtcatgttg c                                       21

<210> SEQ ID NO 1046
<211> LENGTH: 20
<212> TYPE: DNA
<213> ORGANISM: Homo sapiens

<400> SEQUENCE: 1046
ccaaaaagga ttgcagacag                                         20

<210> SEQ ID NO 1047
<211> LENGTH: 21
<212> TYPE: DNA
<213> ORGANISM: Homo sapiens

<400> SEQUENCE: 1047
cccttaaata aacacgcttg c                                       21

<210> SEQ ID NO 1048
<211> LENGTH: 20
<212> TYPE: DNA
<213> ORGANISM: Homo sapiens

<400> SEQUENCE: 1048
gcagcaaatg ggacaataag                                         20

<210> SEQ ID NO 1049
<211> LENGTH: 23
<212> TYPE: DNA
<213> ORGANISM: Homo sapiens

<400> SEQUENCE: 1049
tcatggttaa tgagacattc tgg                                     23

<210> SEQ ID NO 1050
<211> LENGTH: 20
<212> TYPE: DNA
<213> ORGANISM: Homo sapiens

<400> SEQUENCE: 1050
tccactcctg aaccctgaag                                         20

<210> SEQ ID NO 1051
<211> LENGTH: 20
<212> TYPE: DNA
<213> ORGANISM: Homo sapiens
```

```
<400> SEQUENCE: 1051
cctccagagc catgagaaac                                              20

<210> SEQ ID NO 1052
<211> LENGTH: 20
<212> TYPE: DNA
<213> ORGANISM: Homo sapiens

<400> SEQUENCE: 1052
aggctacttg ggaagtgctg                                              20

<210> SEQ ID NO 1053
<211> LENGTH: 19
<212> TYPE: DNA
<213> ORGANISM: Homo sapiens

<400> SEQUENCE: 1053
gagcacacta tgcgccatc                                               19

<210> SEQ ID NO 1054
<211> LENGTH: 20
<212> TYPE: DNA
<213> ORGANISM: Homo sapiens

<400> SEQUENCE: 1054
ctgcctgtac ttggacttgc                                              20

<210> SEQ ID NO 1055
<211> LENGTH: 20
<212> TYPE: DNA
<213> ORGANISM: Homo sapiens

<400> SEQUENCE: 1055
gttttctcca caccctcacg                                              20

<210> SEQ ID NO 1056
<211> LENGTH: 20
<212> TYPE: DNA
<213> ORGANISM: Homo sapiens

<400> SEQUENCE: 1056
actctggcag gaaagacagg                                              20

<210> SEQ ID NO 1057
<211> LENGTH: 25
<212> TYPE: DNA
<213> ORGANISM: Homo sapiens

<400> SEQUENCE: 1057
aaatgaggga gattttaaga aggag                                        25

<210> SEQ ID NO 1058
<211> LENGTH: 20
<212> TYPE: DNA
<213> ORGANISM: Homo sapiens

<400> SEQUENCE: 1058
ttcccagggc acacagtatc                                              20

<210> SEQ ID NO 1059
<211> LENGTH: 20
<212> TYPE: DNA
```

<213> ORGANISM: Homo sapiens

<400> SEQUENCE: 1059
ttcccagggc acacagtatc                                           20

<210> SEQ ID NO 1060
<211> LENGTH: 20
<212> TYPE: DNA
<213> ORGANISM: Homo sapiens

<400> SEQUENCE: 1060
ctgcactcct ctggaaactg                                           20

<210> SEQ ID NO 1061
<211> LENGTH: 20
<212> TYPE: DNA
<213> ORGANISM: Homo sapiens

<400> SEQUENCE: 1061
gaggcttcca ctcactttgc                                           20

<210> SEQ ID NO 1062
<211> LENGTH: 20
<212> TYPE: DNA
<213> ORGANISM: Homo sapiens

<400> SEQUENCE: 1062
gacaaaatag ccccaggatg                                           20

<210> SEQ ID NO 1063
<211> LENGTH: 20
<212> TYPE: DNA
<213> ORGANISM: Homo sapiens

<400> SEQUENCE: 1063
cctgggcaca tcaggtattc                                           20

<210> SEQ ID NO 1064
<211> LENGTH: 20
<212> TYPE: DNA
<213> ORGANISM: Homo sapiens

<400> SEQUENCE: 1064
atcagaactg ccgaccacac                                           20

<210> SEQ ID NO 1065
<211> LENGTH: 20
<212> TYPE: DNA
<213> ORGANISM: Homo sapiens

<400> SEQUENCE: 1065
gtccttcctg tcctcctagc                                           20

<210> SEQ ID NO 1066
<211> LENGTH: 20
<212> TYPE: DNA
<213> ORGANISM: Homo sapiens

<400> SEQUENCE: 1066
ttgtggacat aggggtttgc                                           20

<210> SEQ ID NO 1067
<211> LENGTH: 20

```
<212> TYPE: DNA
<213> ORGANISM: Homo sapiens

<400> SEQUENCE: 1067
ggagggcaga agaggaagtc                                               20

<210> SEQ ID NO 1068
<211> LENGTH: 20
<212> TYPE: DNA
<213> ORGANISM: Homo sapiens

<400> SEQUENCE: 1068
ggagggcaga agaggaagtc                                               20

<210> SEQ ID NO 1069
<211> LENGTH: 20
<212> TYPE: DNA
<213> ORGANISM: Homo sapiens

<400> SEQUENCE: 1069
atcctgggaa gtgcacagac                                               20

<210> SEQ ID NO 1070
<211> LENGTH: 18
<212> TYPE: DNA
<213> ORGANISM: Homo sapiens

<400> SEQUENCE: 1070
ctttcatgcc ccttgtgg                                                 18

<210> SEQ ID NO 1071
<211> LENGTH: 20
<212> TYPE: DNA
<213> ORGANISM: Homo sapiens

<400> SEQUENCE: 1071
gagggtgctc ttagccacag                                               20

<210> SEQ ID NO 1072
<211> LENGTH: 21
<212> TYPE: DNA
<213> ORGANISM: Homo sapiens

<400> SEQUENCE: 1072
gaggtaagca gacagccaca c                                             21

<210> SEQ ID NO 1073
<211> LENGTH: 19
<212> TYPE: DNA
<213> ORGANISM: Homo sapiens

<400> SEQUENCE: 1073
cagatgcatc gcctaatgc                                                19

<210> SEQ ID NO 1074
<211> LENGTH: 19
<212> TYPE: DNA
<213> ORGANISM: Homo sapiens

<400> SEQUENCE: 1074
cgcgagaccc tctcttcag                                                19

<210> SEQ ID NO 1075
```

```
<211> LENGTH: 20
<212> TYPE: DNA
<213> ORGANISM: Homo sapiens

<400> SEQUENCE: 1075
aatgtgttgc cagcactgag                                               20

<210> SEQ ID NO 1076
<211> LENGTH: 20
<212> TYPE: DNA
<213> ORGANISM: Homo sapiens

<400> SEQUENCE: 1076
agcctgggtg acagagtgag                                               20

<210> SEQ ID NO 1077
<211> LENGTH: 19
<212> TYPE: DNA
<213> ORGANISM: Homo sapiens

<400> SEQUENCE: 1077
tcgtgagaac aggctgagg                                                19

<210> SEQ ID NO 1078
<211> LENGTH: 20
<212> TYPE: DNA
<213> ORGANISM: Homo sapiens

<400> SEQUENCE: 1078
accaggaagt gaaccgaatg                                               20

<210> SEQ ID NO 1079
<211> LENGTH: 19
<212> TYPE: DNA
<213> ORGANISM: Homo sapiens

<400> SEQUENCE: 1079
ggccttttag cagctcagg                                                19

<210> SEQ ID NO 1080
<211> LENGTH: 20
<212> TYPE: DNA
<213> ORGANISM: Homo sapiens

<400> SEQUENCE: 1080
cacacccacg ctctaaccac                                               20

<210> SEQ ID NO 1081
<211> LENGTH: 19
<212> TYPE: DNA
<213> ORGANISM: Homo sapiens

<400> SEQUENCE: 1081
ctgaagagga agggggcaag                                               19

<210> SEQ ID NO 1082
<211> LENGTH: 20
<212> TYPE: DNA
<213> ORGANISM: Homo sapiens

<400> SEQUENCE: 1082
actctataca ccgcccccttg                                              20
```

```
<210> SEQ ID NO 1083
<211> LENGTH: 20
<212> TYPE: DNA
<213> ORGANISM: Homo sapiens

<400> SEQUENCE: 1083
atctcctgac ctcgtgatcc                                              20

<210> SEQ ID NO 1084
<211> LENGTH: 19
<212> TYPE: DNA
<213> ORGANISM: Homo sapiens

<400> SEQUENCE: 1084
actgcctggt ccagtcctc                                               19

<210> SEQ ID NO 1085
<211> LENGTH: 20
<212> TYPE: DNA
<213> ORGANISM: Homo sapiens

<400> SEQUENCE: 1085
ggtttcaagg gcacaaacac                                              20

<210> SEQ ID NO 1086
<211> LENGTH: 21
<212> TYPE: DNA
<213> ORGANISM: Homo sapiens

<400> SEQUENCE: 1086
tcctcacgtc ataccaactc c                                            21

<210> SEQ ID NO 1087
<211> LENGTH: 27
<212> TYPE: DNA
<213> ORGANISM: Homo sapiens

<400> SEQUENCE: 1087
tttcagacat aacatatttc aatggag                                      27

<210> SEQ ID NO 1088
<211> LENGTH: 21
<212> TYPE: DNA
<213> ORGANISM: Homo sapiens

<400> SEQUENCE: 1088
ttggaaagcc tctgttttct g                                            21

<210> SEQ ID NO 1089
<211> LENGTH: 20
<212> TYPE: DNA
<213> ORGANISM: Homo sapiens

<400> SEQUENCE: 1089
agttccctct gccctctcac                                              20

<210> SEQ ID NO 1090
<211> LENGTH: 21
<212> TYPE: DNA
<213> ORGANISM: Homo sapiens

<400> SEQUENCE: 1090
gcaaaactgc tttttgaaac c                                            21
```

-continued

<210> SEQ ID NO 1091
<211> LENGTH: 22
<212> TYPE: DNA
<213> ORGANISM: Homo sapiens

<400> SEQUENCE: 1091
tgagggcaca ttaactgctt ac                                              22

<210> SEQ ID NO 1092
<211> LENGTH: 20
<212> TYPE: DNA
<213> ORGANISM: Homo sapiens

<400> SEQUENCE: 1092
tttagacgcc caaccatttc                                                 20

<210> SEQ ID NO 1093
<211> LENGTH: 20
<212> TYPE: DNA
<213> ORGANISM: Homo sapiens

<400> SEQUENCE: 1093
tgctctgtga atgtcccttg                                                 20

<210> SEQ ID NO 1094
<211> LENGTH: 20
<212> TYPE: DNA
<213> ORGANISM: Homo sapiens

<400> SEQUENCE: 1094
tgagctcatg tgagggtgag                                                 20

<210> SEQ ID NO 1095
<211> LENGTH: 21
<212> TYPE: DNA
<213> ORGANISM: Homo sapiens

<400> SEQUENCE: 1095
gggatagctt ccagatgtgt g                                               21

<210> SEQ ID NO 1096
<211> LENGTH: 27
<212> TYPE: DNA
<213> ORGANISM: Homo sapiens

<400> SEQUENCE: 1096
tcatctactt tgatgatggt tagtcac                                         27

<210> SEQ ID NO 1097
<211> LENGTH: 20
<212> TYPE: DNA
<213> ORGANISM: Homo sapiens

<400> SEQUENCE: 1097
ttataggcat gagccaccag                                                 20

<210> SEQ ID NO 1098
<211> LENGTH: 20
<212> TYPE: DNA
<213> ORGANISM: Homo sapiens

<400> SEQUENCE: 1098
agagcaggca agaccatgag                                                 20

```
<210> SEQ ID NO 1099
<211> LENGTH: 21
<212> TYPE: DNA
<213> ORGANISM: Homo sapiens

<400> SEQUENCE: 1099
caaactattg ggggagagga g                                          21

<210> SEQ ID NO 1100
<211> LENGTH: 27
<212> TYPE: DNA
<213> ORGANISM: Homo sapiens

<400> SEQUENCE: 1100
tttagaaaat tgcctaatat caaaaag                                    27

<210> SEQ ID NO 1101
<211> LENGTH: 22
<212> TYPE: DNA
<213> ORGANISM: Homo sapiens

<400> SEQUENCE: 1101
aacccttcca aaacaaaac ag                                          22

<210> SEQ ID NO 1102
<211> LENGTH: 20
<212> TYPE: DNA
<213> ORGANISM: Homo sapiens

<400> SEQUENCE: 1102
gtggcttaag cacattttgg                                            20

<210> SEQ ID NO 1103
<211> LENGTH: 20
<212> TYPE: DNA
<213> ORGANISM: Homo sapiens

<400> SEQUENCE: 1103
cccccataca catttcaagg                                            20

<210> SEQ ID NO 1104
<211> LENGTH: 20
<212> TYPE: DNA
<213> ORGANISM: Homo sapiens

<400> SEQUENCE: 1104
gccctcatca caaggttcac                                            20

<210> SEQ ID NO 1105
<211> LENGTH: 20
<212> TYPE: DNA
<213> ORGANISM: Homo sapiens

<400> SEQUENCE: 1105
cccgggtaga aaatgtaagg                                            20

<210> SEQ ID NO 1106
<211> LENGTH: 20
<212> TYPE: DNA
<213> ORGANISM: Homo sapiens

<400> SEQUENCE: 1106
```

```
ggatcatctc caccacatcc                                              20

<210> SEQ ID NO 1107
<211> LENGTH: 20
<212> TYPE: DNA
<213> ORGANISM: Homo sapiens

<400> SEQUENCE: 1107
gggggagaag gagctgtaag                                              20

<210> SEQ ID NO 1108
<211> LENGTH: 24
<212> TYPE: DNA
<213> ORGANISM: Homo sapiens

<400> SEQUENCE: 1108
ttgctatctt taaaaacctc caac                                         24

<210> SEQ ID NO 1109
<211> LENGTH: 20
<212> TYPE: DNA
<213> ORGANISM: Homo sapiens

<400> SEQUENCE: 1109
tatctcagcg cgtaggacag                                              20

<210> SEQ ID NO 1110
<211> LENGTH: 20
<212> TYPE: DNA
<213> ORGANISM: Homo sapiens

<400> SEQUENCE: 1110
ttaaggcact tgcagtggtg                                              20

<210> SEQ ID NO 1111
<211> LENGTH: 20
<212> TYPE: DNA
<213> ORGANISM: Homo sapiens

<400> SEQUENCE: 1111
tcacagaaag ccaatgatgg                                              20

<210> SEQ ID NO 1112
<211> LENGTH: 20
<212> TYPE: DNA
<213> ORGANISM: Homo sapiens

<400> SEQUENCE: 1112
tgcgtacgcc attactcatc                                              20

<210> SEQ ID NO 1113
<211> LENGTH: 20
<212> TYPE: DNA
<213> ORGANISM: Homo sapiens

<400> SEQUENCE: 1113
ctgtcagatg gggagcagag                                              20

<210> SEQ ID NO 1114
<211> LENGTH: 20
<212> TYPE: DNA
<213> ORGANISM: Homo sapiens

<400> SEQUENCE: 1114
```

```
cccctgacgt acattcaaag                                           20

<210> SEQ ID NO 1115
<211> LENGTH: 24
<212> TYPE: DNA
<213> ORGANISM: Homo sapiens

<400> SEQUENCE: 1115
gcatatgggt ggtgatcaac ataa                                      24

<210> SEQ ID NO 1116
<211> LENGTH: 26
<212> TYPE: DNA
<213> ORGANISM: Homo sapiens

<400> SEQUENCE: 1116
aaacgctctt aagttttcc taaatg                                     26

<210> SEQ ID NO 1117
<211> LENGTH: 20
<212> TYPE: DNA
<213> ORGANISM: Homo sapiens

<400> SEQUENCE: 1117
agggatgcca aacacatacc                                           20

<210> SEQ ID NO 1118
<211> LENGTH: 27
<212> TYPE: DNA
<213> ORGANISM: Homo sapiens

<400> SEQUENCE: 1118
ttgtaccaag atactccata ccctatg                                   27

<210> SEQ ID NO 1119
<211> LENGTH: 22
<212> TYPE: DNA
<213> ORGANISM: Homo sapiens

<400> SEQUENCE: 1119 tttcccacg tggactataa cc                                         22

<210> SEQ ID NO 1120
<211> LENGTH: 21
<212> TYPE: DNA
<213> ORGANISM: Homo sapiens

<400> SEQUENCE: 1120
ggtggtggat accctaaaag c                                         21

<210> SEQ ID NO 1121
<211> LENGTH: 21
<212> TYPE: DNA
<213> ORGANISM: Homo sapiens

<400> SEQUENCE: 1121
ggtggtggat accctaaaag c                                         21

<210> SEQ ID NO 1122
<211> LENGTH: 22
<212> TYPE: DNA
<213> ORGANISM: Homo sapiens
```

<400> SEQUENCE: 1122
aaaagaaaat gcatgactac cc                                      22

<210> SEQ ID NO 1123
<211> LENGTH: 22
<212> TYPE: DNA
<213> ORGANISM: Homo sapiens

<400> SEQUENCE: 1123
caggtctcaa aaagctgagt tg                                      22

<210> SEQ ID NO 1124
<211> LENGTH: 24
<212> TYPE: DNA
<213> ORGANISM: Homo sapiens

<400> SEQUENCE: 1124
ccactacata agaggacctt tctc                                    24

<210> SEQ ID NO 1125
<211> LENGTH: 20
<212> TYPE: DNA
<213> ORGANISM: Homo sapiens

<400> SEQUENCE: 1125
tccagtccaa gttgatgctg                                         20

<210> SEQ ID NO 1126
<211> LENGTH: 20
<212> TYPE: DNA
<213> ORGANISM: Homo sapiens

<400> SEQUENCE: 1126
catgggaata agggagatg                                          20

<210> SEQ ID NO 1127
<211> LENGTH: 20
<212> TYPE: DNA
<213> ORGANISM: Homo sapiens

<400> SEQUENCE: 1127
ggcagtccac agcttctctg                                         20

<210> SEQ ID NO 1128
<211> LENGTH: 18
<212> TYPE: DNA
<213> ORGANISM: Homo sapiens

<400> SEQUENCE: 1128
gaaatatggc cgctgacc                                           18

<210> SEQ ID NO 1129
<211> LENGTH: 20
<212> TYPE: DNA
<213> ORGANISM: Homo sapiens

<400> SEQUENCE: 1129
ccaggataag gcacttgctc                                         20

<210> SEQ ID NO 1130
<211> LENGTH: 19
<212> TYPE: DNA
<213> ORGANISM: Homo sapiens

```
<400> SEQUENCE: 1130
gcggaaggat gaaaggaac                                             19

<210> SEQ ID NO 1131
<211> LENGTH: 20
<212> TYPE: DNA
<213> ORGANISM: Homo sapiens

<400> SEQUENCE: 1131
tgctagagag cagtggaagc                                            20

<210> SEQ ID NO 1132
<211> LENGTH: 25
<212> TYPE: DNA
<213> ORGANISM: Homo sapiens

<400> SEQUENCE: 1132
ttaaacagtg accatctatt taccc                                      25

<210> SEQ ID NO 1133
<211> LENGTH: 24
<212> TYPE: DNA
<213> ORGANISM: Homo sapiens

<400> SEQUENCE: 1133
gcttgaggga aatatgtaaa tctg                                       24

<210> SEQ ID NO 1134
<211> LENGTH: 23
<212> TYPE: DNA
<213> ORGANISM: Homo sapiens

<400> SEQUENCE: 1134
tttcagagtg aatgccagat aac                                        23

<210> SEQ ID NO 1135
<211> LENGTH: 26
<212> TYPE: DNA
<213> ORGANISM: Homo sapiens

<400> SEQUENCE: 1135
tctctctaat atggtggaat acaagc                                     26

<210> SEQ ID NO 1136
<211> LENGTH: 23
<212> TYPE: DNA
<213> ORGANISM: Homo sapiens

<400> SEQUENCE: 1136
gccaagaaag ttcaaaagaa tcc                                        23

<210> SEQ ID NO 1137
<211> LENGTH: 20
<212> TYPE: DNA
<213> ORGANISM: Homo sapiens

<400> SEQUENCE: 1137
ttagcagttc caggcggtag                                            20

<210> SEQ ID NO 1138
<211> LENGTH: 20
<212> TYPE: DNA
```

```
<213> ORGANISM: Homo sapiens

<400> SEQUENCE: 1138
acccacccat ccaataaatg                                              20

<210> SEQ ID NO 1139
<211> LENGTH: 21
<212> TYPE: DNA
<213> ORGANISM: Homo sapiens

<400> SEQUENCE: 1139
ttcagagact gagcaatcgt g                                            21

<210> SEQ ID NO 1140
<211> LENGTH: 21
<212> TYPE: DNA
<213> ORGANISM: Homo sapiens

<400> SEQUENCE: 1140
caacctttgc tcaacatacg g                                            21

<210> SEQ ID NO 1141
<211> LENGTH: 20
<212> TYPE: DNA
<213> ORGANISM: Homo sapiens

<400> SEQUENCE: 1141
gcacaatatt ggagggtgtc                                              20

<210> SEQ ID NO 1142
<211> LENGTH: 26
<212> TYPE: DNA
<213> ORGANISM: Homo sapiens

<400> SEQUENCE: 1142
ctaatttctg acactcagtc tttttg                                       26

<210> SEQ ID NO 1143
<211> LENGTH: 22
<212> TYPE: DNA
<213> ORGANISM: Homo sapiens

<400> SEQUENCE: 1143
caaggctctc attttacatt gc                                           22

<210> SEQ ID NO 1144
<211> LENGTH: 20
<212> TYPE: DNA
<213> ORGANISM: Homo sapiens

<400> SEQUENCE: 1144
aaaaagcacc ctcaaaatgc                                              20

<210> SEQ ID NO 1145
<211> LENGTH: 24
<212> TYPE: DNA
<213> ORGANISM: Homo sapiens

<400> SEQUENCE: 1145
tgtggtagta attgtggaaa actg                                         24

<210> SEQ ID NO 1146
<211> LENGTH: 20
```

```
<212> TYPE: DNA
<213> ORGANISM: Homo sapiens

<400> SEQUENCE: 1146
cagattccat tcccttaggc                                              20

<210> SEQ ID NO 1147
<211> LENGTH: 21
<212> TYPE: DNA
<213> ORGANISM: Homo sapiens

<400> SEQUENCE: 1147
tgcctggtac gcagtaagaa c                                            21

<210> SEQ ID NO 1148
<211> LENGTH: 20
<212> TYPE: DNA
<213> ORGANISM: Homo sapiens

<400> SEQUENCE: 1148
aacagcccaa ttctctttgg                                              20

<210> SEQ ID NO 1149
<211> LENGTH: 22
<212> TYPE: DNA
<213> ORGANISM: Homo sapiens

<400> SEQUENCE: 1149
caagaccaat tatgaccgat cc                                           22

<210> SEQ ID NO 1150
<211> LENGTH: 19
<212> TYPE: DNA
<213> ORGANISM: Homo sapiens

<400> SEQUENCE: 1150
gacaaggagg ccagcagag                                               19

<210> SEQ ID NO 1151
<211> LENGTH: 20
<212> TYPE: DNA
<213> ORGANISM: Homo sapiens

<400> SEQUENCE: 1151
ggacccgtgg tgatcattag                                              20

<210> SEQ ID NO 1152
<211> LENGTH: 19
<212> TYPE: DNA
<213> ORGANISM: Homo sapiens

<400> SEQUENCE: 1152
gaggtaaggc tgccacctg                                               19

<210> SEQ ID NO 1153
<211> LENGTH: 20
<212> TYPE: DNA
<213> ORGANISM: Homo sapiens

<400> SEQUENCE: 1153
ctaccacaga ggccaactcc                                              20

<210> SEQ ID NO 1154
```

```
<211> LENGTH: 18
<212> TYPE: DNA
<213> ORGANISM: Homo sapiens

<400> SEQUENCE: 1154
aggaggcgag gaggtgag                                                 18

<210> SEQ ID NO 1155
<211> LENGTH: 20
<212> TYPE: DNA
<213> ORGANISM: Homo sapiens

<400> SEQUENCE: 1155
agcaactggc caggttattc                                               20

<210> SEQ ID NO 1156
<211> LENGTH: 20
<212> TYPE: DNA
<213> ORGANISM: Homo sapiens

<400> SEQUENCE: 1156
ctgagacctg ccttccagag                                               20

<210> SEQ ID NO 1157
<211> LENGTH: 20
<212> TYPE: DNA
<213> ORGANISM: Homo sapiens

<400> SEQUENCE: 1157
cctggccatg ttcttcaaac                                               20

<210> SEQ ID NO 1158
<211> LENGTH: 20
<212> TYPE: DNA
<213> ORGANISM: Homo sapiens

<400> SEQUENCE: 1158
tcacatgcaa tctgatcctg                                               20

<210> SEQ ID NO 1159
<211> LENGTH: 21
<212> TYPE: DNA
<213> ORGANISM: Homo sapiens

<400> SEQUENCE: 1159
caagccaact tcttcaactc g                                             21

<210> SEQ ID NO 1160
<211> LENGTH: 20
<212> TYPE: DNA
<213> ORGANISM: Homo sapiens

<400> SEQUENCE: 1160
tccagcatcc aaatggttag                                               20

<210> SEQ ID NO 1161
<211> LENGTH: 20
<212> TYPE: DNA
<213> ORGANISM: Homo sapiens

<400> SEQUENCE: 1161
tttggtgttt gggatcttcc                                               20
```

<210> SEQ ID NO 1162
<211> LENGTH: 21
<212> TYPE: DNA
<213> ORGANISM: Homo sapiens

<400> SEQUENCE: 1162
gagcacataa ctggtggttc c                                    21

<210> SEQ ID NO 1163
<211> LENGTH: 20
<212> TYPE: DNA
<213> ORGANISM: Homo sapiens

<400> SEQUENCE: 1163
tgttacacca cgacccaatg                                      20

<210> SEQ ID NO 1164
<211> LENGTH: 20
<212> TYPE: DNA
<213> ORGANISM: Homo sapiens

<400> SEQUENCE: 1164
aaggtgtcca aaccaagctg                                      20

<210> SEQ ID NO 1165
<211> LENGTH: 20
<212> TYPE: DNA
<213> ORGANISM: Homo sapiens

<400> SEQUENCE: 1165
ggaatgaaag tgggatcagg                                      20

<210> SEQ ID NO 1166
<211> LENGTH: 20
<212> TYPE: DNA
<213> ORGANISM: Homo sapiens

<400> SEQUENCE: 1166
tgagggtgag aggagcagtc                                      20

<210> SEQ ID NO 1167
<211> LENGTH: 20
<212> TYPE: DNA
<213> ORGANISM: Homo sapiens

<400> SEQUENCE: 1167
actgggccca atatgacatc                                      20

<210> SEQ ID NO 1168
<211> LENGTH: 20
<212> TYPE: DNA
<213> ORGANISM: Homo sapiens

<400> SEQUENCE: 1168
aggatagcgg gactgatgtc                                      20

<210> SEQ ID NO 1169
<211> LENGTH: 21
<212> TYPE: DNA
<213> ORGANISM: Homo sapiens

<400> SEQUENCE: 1169
cacccatacg tcttggttca c                                    21

```
<210> SEQ ID NO 1170
<211> LENGTH: 21
<212> TYPE: DNA
<213> ORGANISM: Homo sapiens

<400> SEQUENCE: 1170
ctgtaaccca tgtgaatctg g                                            21

<210> SEQ ID NO 1171
<211> LENGTH: 20
<212> TYPE: DNA
<213> ORGANISM: Homo sapiens

<400> SEQUENCE: 1171
cagctgaatc cccacaagtc                                              20

<210> SEQ ID NO 1172
<211> LENGTH: 20
<212> TYPE: DNA
<213> ORGANISM: Homo sapiens

<400> SEQUENCE: 1172
atcctgagcc ctaagccaac                                              20

<210> SEQ ID NO 1173
<211> LENGTH: 20
<212> TYPE: DNA
<213> ORGANISM: Homo sapiens

<400> SEQUENCE: 1173
gaggagccag tgctgttgag                                              20

<210> SEQ ID NO 1174
<211> LENGTH: 20
<212> TYPE: DNA
<213> ORGANISM: Homo sapiens

<400> SEQUENCE: 1174
tatgatgctg ggaccaggtg                                              20

<210> SEQ ID NO 1175
<211> LENGTH: 23
<212> TYPE: DNA
<213> ORGANISM: Homo sapiens

<400> SEQUENCE: 1175
ccaatctaca gactgggaaa ctg                                          23

<210> SEQ ID NO 1176
<211> LENGTH: 20
<212> TYPE: DNA
<213> ORGANISM: Homo sapiens

<400> SEQUENCE: 1176
gccctcaggc tacagctatc                                              20

<210> SEQ ID NO 1177
<211> LENGTH: 20
<212> TYPE: DNA
<213> ORGANISM: Homo sapiens

<400> SEQUENCE: 1177
aggctgccat ctcatattgg                                              20
```

<210> SEQ ID NO 1178
<211> LENGTH: 20
<212> TYPE: DNA
<213> ORGANISM: Homo sapiens

<400> SEQUENCE: 1178
ctctgccagg gtctctatgc                                               20

<210> SEQ ID NO 1179
<211> LENGTH: 20
<212> TYPE: DNA
<213> ORGANISM: Homo sapiens

<400> SEQUENCE: 1179
agccaggaca tctttgcatc                                               20

<210> SEQ ID NO 1180
<211> LENGTH: 20
<212> TYPE: DNA
<213> ORGANISM: Homo sapiens

<400> SEQUENCE: 1180
catggctctg agacaagcac                                               20

<210> SEQ ID NO 1181
<211> LENGTH: 20
<212> TYPE: DNA
<213> ORGANISM: Homo sapiens

<400> SEQUENCE: 1181
attcccrttt ccttccagag                                               20

<210> SEQ ID NO 1182
<211> LENGTH: 20
<212> TYPE: DNA
<213> ORGANISM: Homo sapiens

<400> SEQUENCE: 1182
gatcacacca tgcactccag                                               20

<210> SEQ ID NO 1183
<211> LENGTH: 20
<212> TYPE: DNA
<213> ORGANISM: Homo sapiens

<400> SEQUENCE: 1183
tgactgaggc acaagaatcg                                               20

<210> SEQ ID NO 1184
<211> LENGTH: 25
<212> TYPE: DNA
<213> ORGANISM: Homo sapiens

<400> SEQUENCE: 1184
ggaaatgtta actcaccaaa aattc                                         25

<210> SEQ ID NO 1185
<211> LENGTH: 21
<212> TYPE: DNA
<213> ORGANISM: Homo sapiens

<400> SEQUENCE: 1185

```
tgtgccttgt ggcaatataa g                                            21

<210> SEQ ID NO 1186
<211> LENGTH: 27
<212> TYPE: DNA
<213> ORGANISM: Homo sapiens

<400> SEQUENCE: 1186
tgcttacccc tactatttca gtaaatc                                      27

<210> SEQ ID NO 1187
<211> LENGTH: 23
<212> TYPE: DNA
<213> ORGANISM: Homo sapiens

<400> SEQUENCE: 1187
tgtcatcatg caaaaattct cag                                          23

<210> SEQ ID NO 1188
<211> LENGTH: 23
<212> TYPE: DNA
<213> ORGANISM: Homo sapiens

<400> SEQUENCE: 1188
caactagcag aggacacttt cac                                          23

<210> SEQ ID NO 1189
<211> LENGTH: 23
<212> TYPE: DNA
<213> ORGANISM: Homo sapiens

<400> SEQUENCE: 1189
caactagcag aggacacttt cac                                          23

<210> SEQ ID NO 1190
<211> LENGTH: 26
<212> TYPE: DNA
<213> ORGANISM: Homo sapiens

<400> SEQUENCE: 1190
tgaaattcac ttatttgtgt tgatcc                                       26

<210> SEQ ID NO 1191
<211> LENGTH: 19
<212> TYPE: DNA
<213> ORGANISM: Homo sapiens

<400> SEQUENCE: 1191
gtccacgatg gtgtggaag                                               19

<210> SEQ ID NO 1192
<211> LENGTH: 19
<212> TYPE: DNA
<213> ORGANISM: Homo sapiens

<400> SEQUENCE: 1192
gggtgcgtac cacttgagc                                               19

<210> SEQ ID NO 1193
<211> LENGTH: 19
<212> TYPE: DNA
<213> ORGANISM: Homo sapiens

<400> SEQUENCE: 1193
```

```
gacactctgg tgggcactc                                              19

<210> SEQ ID NO 1194
<211> LENGTH: 19
<212> TYPE: DNA
<213> ORGANISM: Homo sapiens

<400> SEQUENCE: 1194
aggactttcc aggggtcag                                              19

<210> SEQ ID NO 1195
<211> LENGTH: 19
<212> TYPE: DNA
<213> ORGANISM: Homo sapiens

<400> SEQUENCE: 1195
agcctcagcc ttctgtgtg                                              19

<210> SEQ ID NO 1196
<211> LENGTH: 21
<212> TYPE: DNA
<213> ORGANISM: Homo sapiens

<400> SEQUENCE: 1196
agtccttcca gaacacaggt c                                           21

<210> SEQ ID NO 1197
<211> LENGTH: 20
<212> TYPE: DNA
<213> ORGANISM: Homo sapiens

<400> SEQUENCE: 1197
aagacctccc gtagctgctc                                             20

<210> SEQ ID NO 1198
<211> LENGTH: 20
<212> TYPE: DNA
<213> ORGANISM: Homo sapiens

<400> SEQUENCE: 1198
ctgacagcga ccctgatctc                                             20

<210> SEQ ID NO 1199
<211> LENGTH: 19
<212> TYPE: DNA
<213> ORGANISM: Homo sapiens

<400> SEQUENCE: 1199
gtgaagccac tcccctctg                                              19

<210> SEQ ID NO 1200
<211> LENGTH: 20
<212> TYPE: DNA
<213> ORGANISM: Homo sapiens

<400> SEQUENCE: 1200
tcctctatct gggaatgctg                                             20

<210> SEQ ID NO 1201
<211> LENGTH: 20
<212> TYPE: DNA
<213> ORGANISM: Homo sapiens
```

```
<400> SEQUENCE: 1201
ttcatgccta caccacttcg                                           20

<210> SEQ ID NO 1202
<211> LENGTH: 19
<212> TYPE: DNA
<213> ORGANISM: Homo sapiens

<400> SEQUENCE: 1202
ggctgagagc aaggtcctc                                            19

<210> SEQ ID NO 1203
<211> LENGTH: 20
<212> TYPE: DNA
<213> ORGANISM: Homo sapiens

<400> SEQUENCE: 1203
atgggaggta ggagcaaagg                                           20

<210> SEQ ID NO 1204
<211> LENGTH: 18
<212> TYPE: DNA
<213> ORGANISM: Homo sapiens

<400> SEQUENCE: 1204
tcaggctgat gggaaagc                                             18

<210> SEQ ID NO 1205
<211> LENGTH: 20
<212> TYPE: DNA
<213> ORGANISM: Homo sapiens

<400> SEQUENCE: 1205
gatggaggag gagagctgtg                                           20

<210> SEQ ID NO 1206
<211> LENGTH: 21
<212> TYPE: DNA
<213> ORGANISM: Homo sapiens

<400> SEQUENCE: 1206
ttctcaaaat actgccccaa g                                         21

<210> SEQ ID NO 1207
<211> LENGTH: 24
<212> TYPE: DNA
<213> ORGANISM: Homo sapiens

<400> SEQUENCE: 1207
gaaatgagga tatggattttt gtcc                                     24

<210> SEQ ID NO 1208
<211> LENGTH: 21
<212> TYPE: DNA
<213> ORGANISM: Homo sapiens

<400> SEQUENCE: 1208
tccacagcta agcaatgaca g                                         21

<210> SEQ ID NO 1209
<211> LENGTH: 24
<212> TYPE: DNA
<213> ORGANISM: Homo sapiens
```

<400> SEQUENCE: 1209
ccattaaaca aagtgtcagg tttc                                24

<210> SEQ ID NO 1210
<211> LENGTH: 23
<212> TYPE: DNA
<213> ORGANISM: Homo sapiens

<400> SEQUENCE: 1210
aaaatcccac catttcacta cac                                 23

<210> SEQ ID NO 1211
<211> LENGTH: 22
<212> TYPE: DNA
<213> ORGANISM: Homo sapiens

<400> SEQUENCE: 1211
aactatcaga aagccacagc ag                                  22

<210> SEQ ID NO 1212
<211> LENGTH: 21
<212> TYPE: DNA
<213> ORGANISM: Homo sapiens

<400> SEQUENCE: 1212
gcctaacatc agacgctcaa c                                   21

<210> SEQ ID NO 1213
<211> LENGTH: 19
<212> TYPE: DNA
<213> ORGANISM: Homo sapiens

<400> SEQUENCE: 1213
atgccaccaa agaggaagg                                      19

<210> SEQ ID NO 1214
<211> LENGTH: 20
<212> TYPE: DNA
<213> ORGANISM: Homo sapiens

<400> SEQUENCE: 1214
ctaaaggcaa agggaccaag                                     20

<210> SEQ ID NO 1215
<211> LENGTH: 20
<212> TYPE: DNA
<213> ORGANISM: Homo sapiens

<400> SEQUENCE: 1215
ttggctctac tgcattccac                                     20

<210> SEQ ID NO 1216
<211> LENGTH: 20
<212> TYPE: DNA
<213> ORGANISM: Homo sapiens

<400> SEQUENCE: 1216
tgagtgtgga ggcaatcaag                                     20

<210> SEQ ID NO 1217
<211> LENGTH: 20
<212> TYPE: DNA

<213> ORGANISM: Homo sapiens

<400> SEQUENCE: 1217
gcaggaacga gaaaggtcag         20

<210> SEQ ID NO 1218
<211> LENGTH: 22
<212> TYPE: DNA
<213> ORGANISM: Homo sapiens

<400> SEQUENCE: 1218
aaacactaac aggcaaaagc ag         22

<210> SEQ ID NO 1219
<211> LENGTH: 20
<212> TYPE: DNA
<213> ORGANISM: Homo sapiens

<400> SEQUENCE: 1219
gctttctcct tgtccagtgc         20

<210> SEQ ID NO 1220
<211> LENGTH: 23
<212> TYPE: DNA
<213> ORGANISM: Homo sapiens

<400> SEQUENCE: 1220
gtcattcctc ctgtgaggtc tcc         23

<210> SEQ ID NO 1221
<211> LENGTH: 20
<212> TYPE: DNA
<213> ORGANISM: Homo sapiens

<400> SEQUENCE: 1221
ggttctcccc gtcaaatgtc         20

<210> SEQ ID NO 1222
<211> LENGTH: 25
<212> TYPE: DNA
<213> ORGANISM: Homo sapiens

<400> SEQUENCE: 1222
ccaatagtag cttttcaaag acagc         25

<210> SEQ ID NO 1223
<211> LENGTH: 20
<212> TYPE: DNA
<213> ORGANISM: Homo sapiens

<400> SEQUENCE: 1223
cacagccaca tggttacctc         20

<210> SEQ ID NO 1224
<211> LENGTH: 20
<212> TYPE: DNA
<213> ORGANISM: Homo sapiens

<400> SEQUENCE: 1224
tttggcaaaa tgaaagcatc         20

<210> SEQ ID NO 1225
<211> LENGTH: 20

```
<212> TYPE: DNA
<213> ORGANISM: Homo sapiens

<400> SEQUENCE: 1225 tttccacaa ggggaaagtg                                          20

<210> SEQ ID NO 1226
<211> LENGTH: 19
<212> TYPE: DNA
<213> ORGANISM: Homo sapiens

<400> SEQUENCE: 1226
agggatggct ggcttacag                                          19

<210> SEQ ID NO 1227
<211> LENGTH: 20
<212> TYPE: DNA
<213> ORGANISM: Homo sapiens

<400> SEQUENCE: 1227
atccccaggg cttacacatc                                         20

<210> SEQ ID NO 1228
<211> LENGTH: 21
<212> TYPE: DNA
<213> ORGANISM: Homo sapiens

<400> SEQUENCE: 1228
tgaagaaaac tggaattggt g                                       21

<210> SEQ ID NO 1229
<211> LENGTH: 22
<212> TYPE: DNA
<213> ORGANISM: Homo sapiens

<400> SEQUENCE: 1229
aaggcaggca tttctgtaaa ag                                      22

<210> SEQ ID NO 1230
<211> LENGTH: 18
<212> TYPE: DNA
<213> ORGANISM: Homo sapiens

<400> SEQUENCE: 1230
cccagaagga ggctggtc                                           18

<210> SEQ ID NO 1231
<211> LENGTH: 20
<212> TYPE: DNA
<213> ORGANISM: Homo sapiens

<400> SEQUENCE: 1231
tgggtgaatg acaccatcag                                         20

<210> SEQ ID NO 1232
<211> LENGTH: 20
<212> TYPE: DNA
<213> ORGANISM: Homo sapiens

<400> SEQUENCE: 1232
caagctcaag aatgcacagc                                         20

<210> SEQ ID NO 1233
```

```
<211> LENGTH: 20
<212> TYPE: DNA
<213> ORGANISM: Homo sapiens

<400> SEQUENCE: 1233
acaggaaagg tgagggaagg                                          20

<210> SEQ ID NO 1234
<211> LENGTH: 21
<212> TYPE: DNA
<213> ORGANISM: Homo sapiens

<400> SEQUENCE: 1234
tctgaacccc acttgtcttt g                                        21

<210> SEQ ID NO 1235
<211> LENGTH: 21
<212> TYPE: DNA
<213> ORGANISM: Homo sapiens

<400> SEQUENCE: 1235
gcatccgtga ctaggagtct g                                        21

<210> SEQ ID NO 1236
<211> LENGTH: 20
<212> TYPE: DNA
<213> ORGANISM: Homo sapiens

<400> SEQUENCE: 1236
gtgttcctgg aagcaagtgg                                          20

<210> SEQ ID NO 1237
<211> LENGTH: 19
<212> TYPE: DNA
<213> ORGANISM: Homo sapiens

<400> SEQUENCE: 1237
agagctcctg gccagattg                                           19

<210> SEQ ID NO 1238
<211> LENGTH: 18
<212> TYPE: DNA
<213> ORGANISM: Homo sapiens

<400> SEQUENCE: 1238
tcccttcccc gtttcctc                                            18

<210> SEQ ID NO 1239
<211> LENGTH: 21
<212> TYPE: DNA
<213> ORGANISM: Homo sapiens

<400> SEQUENCE: 1239
aagccattcc tgacctagag c                                        21

<210> SEQ ID NO 1240
<211> LENGTH: 20
<212> TYPE: DNA
<213> ORGANISM: Homo sapiens

<400> SEQUENCE: 1240
agctgtggtt cctgtcttcc                                          20
```

```
<210> SEQ ID NO 1241
<211> LENGTH: 21
<212> TYPE: DNA
<213> ORGANISM: Homo sapiens

<400> SEQUENCE: 1241
ggttcctgtc ttcctgtctc c                                              21

<210> SEQ ID NO 1242
<211> LENGTH: 20
<212> TYPE: DNA
<213> ORGANISM: Homo sapiens

<400> SEQUENCE: 1242
caggcccatg atctcagaag                                                20

<210> SEQ ID NO 1243
<211> LENGTH: 20
<212> TYPE: DNA
<213> ORGANISM: Homo sapiens

<400> SEQUENCE: 1243
ggaagagcat ttgcctgaag                                                20

<210> SEQ ID NO 1244
<211> LENGTH: 20
<212> TYPE: DNA
<213> ORGANISM: Homo sapiens

<400> SEQUENCE: 1244 agaggggtg ctaaggtgac                                                 20

<210> SEQ ID NO 1245
<211> LENGTH: 20
<212> TYPE: DNA
<213> ORGANISM: Homo sapiens

<400> SEQUENCE: 1245
gcttggagga agaggtgagc                                                20

<210> SEQ ID NO 1246
<211> LENGTH: 20
<212> TYPE: DNA
<213> ORGANISM: Homo sapiens

<400> SEQUENCE: 1246
taagaggtca ctggggaacc                                                20

<210> SEQ ID NO 1247
<211> LENGTH: 20
<212> TYPE: DNA
<213> ORGANISM: Homo sapiens

<400> SEQUENCE: 1247
gggtatacat tggggtggtc                                                20

<210> SEQ ID NO 1248
<211> LENGTH: 20
<212> TYPE: DNA
<213> ORGANISM: Homo sapiens

<400> SEQUENCE: 1248
gcctcagggt gaagagaaac                                                20
```

```
<210> SEQ ID NO 1249
<211> LENGTH: 21
<212> TYPE: DNA
<213> ORGANISM: Homo sapiens

<400> SEQUENCE: 1249
ggtctcagac acatggacag g                                              21

<210> SEQ ID NO 1250
<211> LENGTH: 20
<212> TYPE: DNA
<213> ORGANISM: Homo sapiens

<400> SEQUENCE: 1250
gcggcaatat ccctacagag                                                20

<210> SEQ ID NO 1251
<211> LENGTH: 19
<212> TYPE: DNA
<213> ORGANISM: Homo sapiens

<400> SEQUENCE: 1251
cccctgcggt aataactgg                                                 19

<210> SEQ ID NO 1252
<211> LENGTH: 19
<212> TYPE: DNA
<213> ORGANISM: Homo sapiens

<400> SEQUENCE: 1252
agtgggggaa ccaagtgag                                                 19

<210> SEQ ID NO 1253
<211> LENGTH: 20
<212> TYPE: DNA
<213> ORGANISM: Homo sapiens

<400> SEQUENCE: 1253
ccatggttgt gaaggacctc                                                20

<210> SEQ ID NO 1254
<211> LENGTH: 21
<212> TYPE: DNA
<213> ORGANISM: Homo sapiens

<400> SEQUENCE: 1254
cccacaagac caggatgtta g                                              21

<210> SEQ ID NO 1255
<211> LENGTH: 21
<212> TYPE: DNA
<213> ORGANISM: Homo sapiens

<400> SEQUENCE: 1255
aggagtgaat tcagcacatc c                                              21

<210> SEQ ID NO 1256
<211> LENGTH: 18
<212> TYPE: DNA
<213> ORGANISM: Homo sapiens

<400> SEQUENCE: 1256
ttgaggccag aggacagc                                                  18
```

```
<210> SEQ ID NO 1257
<211> LENGTH: 20
<212> TYPE: DNA
<213> ORGANISM: Homo sapiens

<400> SEQUENCE: 1257
cctctccccc tcattctctc                                               20

<210> SEQ ID NO 1258
<211> LENGTH: 20
<212> TYPE: DNA
<213> ORGANISM: Homo sapiens

<400> SEQUENCE: 1258
tttgagcccc tgactaaagg                                               20

<210> SEQ ID NO 1259
<211> LENGTH: 20
<212> TYPE: DNA
<213> ORGANISM: Homo sapiens

<400> SEQUENCE: 1259
tttgagcccc tgactaaagg                                               20

<210> SEQ ID NO 1260
<211> LENGTH: 23
<212> TYPE: DNA
<213> ORGANISM: Homo sapiens

<400> SEQUENCE: 1260
gctacattct ggaaaatcac tcg                                           23

<210> SEQ ID NO 1261
<211> LENGTH: 20
<212> TYPE: DNA
<213> ORGANISM: Homo sapiens

<400> SEQUENCE: 1261
ttcttgcccc agcaattatg                                               20

<210> SEQ ID NO 1262
<211> LENGTH: 20
<212> TYPE: DNA
<213> ORGANISM: Homo sapiens

<400> SEQUENCE: 1262
aggctccatc atgctgtttc                                               20

<210> SEQ ID NO 1263
<211> LENGTH: 24
<212> TYPE: DNA
<213> ORGANISM: Homo sapiens

<400> SEQUENCE: 1263
cagatattga ggatatgcac acac                                          24

<210> SEQ ID NO 1264
<211> LENGTH: 26
<212> TYPE: DNA
<213> ORGANISM: Homo sapiens

<400> SEQUENCE: 1264
```
gagtgtaatt attgtggctc cataaa                                    26

<210> SEQ ID NO 1265
<211> LENGTH: 18
<212> TYPE: DNA
<213> ORGANISM: Homo sapiens

<400> SEQUENCE: 1265
acccaggcca gcagtacc                                             18

<210> SEQ ID NO 1266
<211> LENGTH: 20
<212> TYPE: DNA
<213> ORGANISM: Homo sapiens

<400> SEQUENCE: 1266
ttgaaagaca agcagggatg                                           20

<210> SEQ ID NO 1267
<211> LENGTH: 20
<212> TYPE: DNA
<213> ORGANISM: Homo sapiens

<400> SEQUENCE: 1267
ccagagccag tgaatctcag                                           20

<210> SEQ ID NO 1268
<211> LENGTH: 20
<212> TYPE: DNA
<213> ORGANISM: Homo sapiens

<400> SEQUENCE: 1268
agaagaacag ggccagagtg                                           20

<210> SEQ ID NO 1269
<211> LENGTH: 20
<212> TYPE: DNA
<213> ORGANISM: Homo sapiens

<400> SEQUENCE: 1269
ccagtattcc ggctaaccac                                           20

<210> SEQ ID NO 1270
<211> LENGTH: 20
<212> TYPE: DNA
<213> ORGANISM: Homo sapiens

<400> SEQUENCE: 1270
tggtgcccta acctcatctc                                           20

<210> SEQ ID NO 1271
<211> LENGTH: 19
<212> TYPE: DNA
<213> ORGANISM: Homo sapiens

<400> SEQUENCE: 1271
ttcactcccc agggtcttc                                            19

<210> SEQ ID NO 1272
<211> LENGTH: 19
<212> TYPE: DNA
<213> ORGANISM: Homo sapiens

<400> SEQUENCE: 1272

```
gatacagggt gggggtgac                                          19

<210> SEQ ID NO 1273
<211> LENGTH: 20
<212> TYPE: DNA
<213> ORGANISM: Homo sapiens

<400> SEQUENCE: 1273
agagtaccac gccaaaggac                                         20

<210> SEQ ID NO 1274
<211> LENGTH: 20
<212> TYPE: DNA
<213> ORGANISM: Homo sapiens

<400> SEQUENCE: 1274
agagtaccac gccaaaggac                                         20

<210> SEQ ID NO 1275
<211> LENGTH: 20
<212> TYPE: DNA
<213> ORGANISM: Homo sapiens

<400> SEQUENCE: 1275
tgggggaggg ttgtaggtag                                         20

<210> SEQ ID NO 1276
<211> LENGTH: 20
<212> TYPE: DNA
<213> ORGANISM: Homo sapiens

<400> SEQUENCE: 1276
tgaacattca ggcgtctcag                                         20

<210> SEQ ID NO 1277
<211> LENGTH: 20
<212> TYPE: DNA
<213> ORGANISM: Homo sapiens

<400> SEQUENCE: 1277
ttccctgctc ctgttctctg                                         20

<210> SEQ ID NO 1278
<211> LENGTH: 18
<212> TYPE: DNA
<213> ORGANISM: Homo sapiens

<400> SEQUENCE: 1278 aggggaggc tgtctttg                                            18

<210> SEQ ID NO 1279
<211> LENGTH: 20
<212> TYPE: DNA
<213> ORGANISM: Homo sapiens

<400> SEQUENCE: 1279
ctatctccca gcacccagac                                         20

<210> SEQ ID NO 1280
<211> LENGTH: 20
<212> TYPE: DNA
<213> ORGANISM: Homo sapiens
```

```
<400> SEQUENCE: 1280
gcgtgaagag gagaaacagg                                              20

<210> SEQ ID NO 1281
<211> LENGTH: 19
<212> TYPE: DNA
<213> ORGANISM: Homo sapiens

<400> SEQUENCE: 1281
ccaacagtcg agcatgagc                                               19

<210> SEQ ID NO 1282
<211> LENGTH: 20
<212> TYPE: DNA
<213> ORGANISM: Homo sapiens

<400> SEQUENCE: 1282
cagatctggg gcaatactgg                                              20

<210> SEQ ID NO 1283
<211> LENGTH: 20
<212> TYPE: DNA
<213> ORGANISM: Homo sapiens

<400> SEQUENCE: 1283
atggatctgg acctgtagcc                                              20

<210> SEQ ID NO 1284
<211> LENGTH: 18
<212> TYPE: DNA
<213> ORGANISM: Homo sapiens

<400> SEQUENCE: 1284
agcccctcac gtcctctg                                                18

<210> SEQ ID NO 1285
<211> LENGTH: 18
<212> TYPE: DNA
<213> ORGANISM: Homo sapiens

<400> SEQUENCE: 1285
tgtggtggct cacacctg                                                18

<210> SEQ ID NO 1286
<211> LENGTH: 25
<212> TYPE: DNA
<213> ORGANISM: Homo sapiens

<400> SEQUENCE: 1286
aaaagtgaca tttcaagtat catgc                                        25

<210> SEQ ID NO 1287
<211> LENGTH: 24
<212> TYPE: DNA
<213> ORGANISM: Homo sapiens

<400> SEQUENCE: 1287
tcaagatgtt tgtttaggat ggtg                                         24

<210> SEQ ID NO 1288
<211> LENGTH: 21
<212> TYPE: DNA
<213> ORGANISM: Homo sapiens
```

```
<400> SEQUENCE: 1288
caggagtgag ggttttgaat g                                             21

<210> SEQ ID NO 1289
<211> LENGTH: 20
<212> TYPE: DNA
<213> ORGANISM: Homo sapiens

<400> SEQUENCE: 1289
gcccacagag agtaccttgc                                               20

<210> SEQ ID NO 1290
<211> LENGTH: 22
<212> TYPE: DNA
<213> ORGANISM: Homo sapiens

<400> SEQUENCE: 1290
tgtctgtctt caaagggaaa cc                                            22

<210> SEQ ID NO 1291
<211> LENGTH: 20
<212> TYPE: DNA
<213> ORGANISM: Homo sapiens

<400> SEQUENCE: 1291
aaccctaccc atccaagagg                                               20

<210> SEQ ID NO 1292
<211> LENGTH: 20
<212> TYPE: DNA
<213> ORGANISM: Homo sapiens

<400> SEQUENCE: 1292
attccgaaac tccacacgtc                                               20

<210> SEQ ID NO 1293
<211> LENGTH: 18
<212> TYPE: DNA
<213> ORGANISM: Homo sapiens

<400> SEQUENCE: 1293
ggagagtggc ctgtgagc                                                 18

<210> SEQ ID NO 1294
<211> LENGTH: 18
<212> TYPE: DNA
<213> ORGANISM: Homo sapiens

<400> SEQUENCE: 1294
caggctcggt ggaggaag                                                 18

<210> SEQ ID NO 1295
<211> LENGTH: 20
<212> TYPE: DNA
<213> ORGANISM: Homo sapiens

<400> SEQUENCE: 1295
gctggtgcct cactcctaac                                               20

<210> SEQ ID NO 1296
<211> LENGTH: 19
<212> TYPE: DNA
```

<213> ORGANISM: Homo sapiens

<400> SEQUENCE: 1296
agttggaagg cctgagtgc                                                19

<210> SEQ ID NO 1297
<211> LENGTH: 19
<212> TYPE: DNA
<213> ORGANISM: Homo sapiens

<400> SEQUENCE: 1297
agtgctggcg ttacaggtg                                                19

<210> SEQ ID NO 1298
<211> LENGTH: 20
<212> TYPE: DNA
<213> ORGANISM: Homo sapiens

<400> SEQUENCE: 1298
ctttggctct gcaccctaac                                               20

<210> SEQ ID NO 1299
<211> LENGTH: 19
<212> TYPE: DNA
<213> ORGANISM: Homo sapiens

<400> SEQUENCE: 1299
atgcaggaaa gcgtgaatg                                                19

<210> SEQ ID NO 1300
<211> LENGTH: 20
<212> TYPE: DNA
<213> ORGANISM: Homo sapiens

<400> SEQUENCE: 1300
gtacacccgg tcaaacaagg                                               20

<210> SEQ ID NO 1301
<211> LENGTH: 20
<212> TYPE: DNA
<213> ORGANISM: Homo sapiens

<400> SEQUENCE: 1301
gtacacccgg tcaaacaagg                                               20

<210> SEQ ID NO 1302
<211> LENGTH: 20
<212> TYPE: DNA
<213> ORGANISM: Homo sapiens

<400> SEQUENCE: 1302
atgggctcct cctggtagtc                                               20

<210> SEQ ID NO 1303
<211> LENGTH: 20
<212> TYPE: DNA
<213> ORGANISM: Homo sapiens

<400> SEQUENCE: 1303
gaatgggctc ctcctggtag                                               20

<210> SEQ ID NO 1304
<211> LENGTH: 20

```
<212> TYPE: DNA
<213> ORGANISM: Homo sapiens

<400> SEQUENCE: 1304
ggaggaggag gactggaaag                                            20

<210> SEQ ID NO 1305
<211> LENGTH: 18
<212> TYPE: DNA
<213> ORGANISM: Homo sapiens

<400> SEQUENCE: 1305
aggcagaggg aggtggtg                                              18

<210> SEQ ID NO 1306
<211> LENGTH: 20
<212> TYPE: DNA
<213> ORGANISM: Homo sapiens

<400> SEQUENCE: 1306
tcacgtcact ggtctgttcc                                            20

<210> SEQ ID NO 1307
<211> LENGTH: 21
<212> TYPE: DNA
<213> ORGANISM: Homo sapiens

<400> SEQUENCE: 1307
tcccgtagtt aatggcttct g                                          21

<210> SEQ ID NO 1308
<211> LENGTH: 20
<212> TYPE: DNA
<213> ORGANISM: Homo sapiens

<400> SEQUENCE: 1308
tggggacgtt ggactcatac                                            20

<210> SEQ ID NO 1309
<211> LENGTH: 20
<212> TYPE: DNA
<213> ORGANISM: Homo sapiens

<400> SEQUENCE: 1309
agcactgtcc catttgaagg                                            20

<210> SEQ ID NO 1310
<211> LENGTH: 20
<212> TYPE: DNA
<213> ORGANISM: Homo sapiens

<400> SEQUENCE: 1310
agcactgtcc catttgaagg                                            20

<210> SEQ ID NO 1311
<211> LENGTH: 20
<212> TYPE: DNA
<213> ORGANISM: Homo sapiens

<400> SEQUENCE: 1311
ggggagatag gctgataggg                                            20

<210> SEQ ID NO 1312
```

```
<211> LENGTH: 20
<212> TYPE: DNA
<213> ORGANISM: Homo sapiens

<400> SEQUENCE: 1312
gggactctca tcacctcagc                                          20

<210> SEQ ID NO 1313
<211> LENGTH: 20
<212> TYPE: DNA
<213> ORGANISM: Homo sapiens

<400> SEQUENCE: 1313
gcaggaaagc tcaagaaacc                                          20

<210> SEQ ID NO 1314
<211> LENGTH: 18
<212> TYPE: DNA
<213> ORGANISM: Homo sapiens

<400> SEQUENCE: 1314
cagctggcct ggatgaag                                            18

<210> SEQ ID NO 1315
<211> LENGTH: 19
<212> TYPE: DNA
<213> ORGANISM: Homo sapiens

<400> SEQUENCE: 1315
atcacctgca ggagggaac                                           19

<210> SEQ ID NO 1316
<211> LENGTH: 20
<212> TYPE: DNA
<213> ORGANISM: Homo sapiens

<400> SEQUENCE: 1316
ggaggataac ccttctggtc                                          20

<210> SEQ ID NO 1317
<211> LENGTH: 20
<212> TYPE: DNA
<213> ORGANISM: Homo sapiens

<400> SEQUENCE: 1317
ggaggataac ccttctggtc                                          20

<210> SEQ ID NO 1318
<211> LENGTH: 20
<212> TYPE: DNA
<213> ORGANISM: Homo sapiens

<400> SEQUENCE: 1318
tcagagctga gtcccagagc                                          20

<210> SEQ ID NO 1319
<211> LENGTH: 19
<212> TYPE: DNA
<213> ORGANISM: Homo sapiens

<400> SEQUENCE: 1319
agggtgcttg ggaggtatg                                           19
```

```
<210> SEQ ID NO 1320
<211> LENGTH: 20
<212> TYPE: DNA
<213> ORGANISM: Homo sapiens

<400> SEQUENCE: 1320
catcagttct cccagccaac                                               20

<210> SEQ ID NO 1321
<211> LENGTH: 20
<212> TYPE: DNA
<213> ORGANISM: Homo sapiens

<400> SEQUENCE: 1321
tgggatttcc aaaacaaaac                                               20

<210> SEQ ID NO 1322
<211> LENGTH: 20
<212> TYPE: DNA
<213> ORGANISM: Homo sapiens

<400> SEQUENCE: 1322
caggtcaagt gcaggaaagg                                               20

<210> SEQ ID NO 1323
<211> LENGTH: 20
<212> TYPE: DNA
<213> ORGANISM: Homo sapiens

<400> SEQUENCE: 1323
ctctcttcct gccctgtgag                                               20

<210> SEQ ID NO 1324
<211> LENGTH: 20
<212> TYPE: DNA
<213> ORGANISM: Homo sapiens

<400> SEQUENCE: 1324
cccactgctc cctatcactc                                               20

<210> SEQ ID NO 1325
<211> LENGTH: 19
<212> TYPE: DNA
<213> ORGANISM: Homo sapiens

<400> SEQUENCE: 1325
gcaaagttgc ctgaaccag                                                19

<210> SEQ ID NO 1326
<211> LENGTH: 20
<212> TYPE: DNA
<213> ORGANISM: Homo sapiens

<400> SEQUENCE: 1326
agtgactcat gccagcagac                                               20

<210> SEQ ID NO 1327
<211> LENGTH: 20
<212> TYPE: DNA
<213> ORGANISM: Homo sapiens

<400> SEQUENCE: 1327
tcaatgttag tggggccttg                                               20
```

```
<210> SEQ ID NO 1328
<211> LENGTH: 20
<212> TYPE: DNA
<213> ORGANISM: Homo sapiens

<400> SEQUENCE: 1328
gtgtgaccca tccctactgg                                              20

<210> SEQ ID NO 1329
<211> LENGTH: 20
<212> TYPE: DNA
<213> ORGANISM: Homo sapiens

<400> SEQUENCE: 1329
ccccaagcat tatccctcag                                              20

<210> SEQ ID NO 1330
<211> LENGTH: 18
<212> TYPE: DNA
<213> ORGANISM: Homo sapiens

<400> SEQUENCE: 1330
ctccacctcc agcacacc                                                18

<210> SEQ ID NO 1331
<211> LENGTH: 20
<212> TYPE: DNA
<213> ORGANISM: Homo sapiens

<400> SEQUENCE: 1331
gagagagccc caagtgtgag                                              20

<210> SEQ ID NO 1332
<211> LENGTH: 19
<212> TYPE: DNA
<213> ORGANISM: Homo sapiens

<400> SEQUENCE: 1332
cctggaagcg gaggtagtc                                               19

<210> SEQ ID NO 1333
<211> LENGTH: 20
<212> TYPE: DNA
<213> ORGANISM: Homo sapiens

<400> SEQUENCE: 1333
gtgaatccac ctctggaagg                                              20

<210> SEQ ID NO 1334
<211> LENGTH: 21
<212> TYPE: DNA
<213> ORGANISM: Homo sapiens

<400> SEQUENCE: 1334
ctgaccttcc catctcaaaa g                                            21

<210> SEQ ID NO 1335
<211> LENGTH: 20
<212> TYPE: DNA
<213> ORGANISM: Homo sapiens

<400> SEQUENCE: 1335
cagggaggag aaggaagacc                                              20
```

<210> SEQ ID NO 1336
<211> LENGTH: 22
<212> TYPE: DNA
<213> ORGANISM: Homo sapiens

<400> SEQUENCE: 1336
tttttagcag aaataggcaa gc                                              22

<210> SEQ ID NO 1337
<211> LENGTH: 21
<212> TYPE: DNA
<213> ORGANISM: Homo sapiens

<400> SEQUENCE: 1337
tggggaggat actggtcttt c                                               21

<210> SEQ ID NO 1338
<211> LENGTH: 22
<212> TYPE: DNA
<213> ORGANISM: Homo sapiens

<400> SEQUENCE: 1338
gcctttgtta tccaacactt tg                                              22

<210> SEQ ID NO 1339
<211> LENGTH: 24
<212> TYPE: DNA
<213> ORGANISM: Homo sapiens

<400> SEQUENCE: 1339
gaaaatggag tttaagaacc caag                                            24

<210> SEQ ID NO 1340
<211> LENGTH: 20
<212> TYPE: DNA
<213> ORGANISM: Homo sapiens

<400> SEQUENCE: 1340
gctaaacagc cattccttgg                                                 20

<210> SEQ ID NO 1341
<211> LENGTH: 23
<212> TYPE: DNA
<213> ORGANISM: Homo sapiens

<400> SEQUENCE: 1341
aaacaagtca caagtgagca aag                                             23

<210> SEQ ID NO 1342
<211> LENGTH: 23
<212> TYPE: DNA
<213> ORGANISM: Homo sapiens

<400> SEQUENCE: 1342
aaacaagtca caagtgagca aag                                             23

<210> SEQ ID NO 1343
<211> LENGTH: 21
<212> TYPE: DNA
<213> ORGANISM: Homo sapiens

<400> SEQUENCE: 1343
catgggaggg acttaggttt c                                              21

<210> SEQ ID NO 1344
<211> LENGTH: 21
<212> TYPE: DNA
<213> ORGANISM: Homo sapiens

<400> SEQUENCE: 1344
caacagcttg cttctctcag g                                              21

<210> SEQ ID NO 1345
<211> LENGTH: 19
<212> TYPE: DNA
<213> ORGANISM: Homo sapiens

<400> SEQUENCE: 1345
atgtgcctga gaccccttc                                                 19

<210> SEQ ID NO 1346
<211> LENGTH: 21
<212> TYPE: DNA
<213> ORGANISM: Homo sapiens

<400> SEQUENCE: 1346
cgccaggttt tatggaggta g                                              21

<210> SEQ ID NO 1347
<211> LENGTH: 20
<212> TYPE: DNA
<213> ORGANISM: Homo sapiens

<400> SEQUENCE: 1347
atcccctacc ctgaacactg                                                20

<210> SEQ ID NO 1348
<211> LENGTH: 20
<212> TYPE: DNA
<213> ORGANISM: Homo sapiens

<400> SEQUENCE: 1348
tatgcccctg accatgaaac                                                20

<210> SEQ ID NO 1349
<211> LENGTH: 20
<212> TYPE: DNA
<213> ORGANISM: Homo sapiens

<400> SEQUENCE: 1349
tgacccctag gtgtggtctg                                                20

<210> SEQ ID NO 1350
<211> LENGTH: 20
<212> TYPE: DNA
<213> ORGANISM: Homo sapiens

<400> SEQUENCE: 1350
tctgagcact agcccacttg                                                20

<210> SEQ ID NO 1351
<211> LENGTH: 21
<212> TYPE: DNA
<213> ORGANISM: Homo sapiens

<400> SEQUENCE: 1351

```
tggtggaaag aagatgtttg g                                              21

<210> SEQ ID NO 1352
<211> LENGTH: 19
<212> TYPE: DNA
<213> ORGANISM: Homo sapiens

<400> SEQUENCE: 1352
ctccaatgcc cattcacac                                                 19

<210> SEQ ID NO 1353
<211> LENGTH: 20
<212> TYPE: DNA
<213> ORGANISM: Homo sapiens

<400> SEQUENCE: 1353
tcctggcatc ttggtctttc                                                20

<210> SEQ ID NO 1354
<211> LENGTH: 20
<212> TYPE: DNA
<213> ORGANISM: Homo sapiens

<400> SEQUENCE: 1354
cggttcgtcc ctattttgtg                                                20

<210> SEQ ID NO 1355
<211> LENGTH: 19
<212> TYPE: DNA
<213> ORGANISM: Homo sapiens

<400> SEQUENCE: 1355
ctggtccacc accatgaag                                                 19

<210> SEQ ID NO 1356
<211> LENGTH: 20
<212> TYPE: DNA
<213> ORGANISM: Homo sapiens

<400> SEQUENCE: 1356
gtaacccttc caccttcctg                                                20

<210> SEQ ID NO 1357
<211> LENGTH: 20
<212> TYPE: DNA
<213> ORGANISM: Homo sapiens

<400> SEQUENCE: 1357
atgtgggtga tgtgggaaac                                                20

<210> SEQ ID NO 1358
<211> LENGTH: 20
<212> TYPE: DNA
<213> ORGANISM: Homo sapiens

<400> SEQUENCE: 1358
cctcgtagaa agggttggag                                                20

<210> SEQ ID NO 1359
<211> LENGTH: 20
<212> TYPE: DNA
<213> ORGANISM: Homo sapiens
```

<400> SEQUENCE: 1359
gaaaaagggg tctcggtctc                                       20

<210> SEQ ID NO 1360
<211> LENGTH: 18
<212> TYPE: DNA
<213> ORGANISM: Homo sapiens

<400> SEQUENCE: 1360
gtcacccctg ggtctgtg                                         18

<210> SEQ ID NO 1361
<211> LENGTH: 20
<212> TYPE: DNA
<213> ORGANISM: Homo sapiens

<400> SEQUENCE: 1361
tcacattgtc cgtccatttc                                       20

<210> SEQ ID NO 1362
<211> LENGTH: 20
<212> TYPE: DNA
<213> ORGANISM: Homo sapiens

<400> SEQUENCE: 1362
tttgcatttt cttcctctgg                                       20

<210> SEQ ID NO 1363
<211> LENGTH: 20
<212> TYPE: DNA
<213> ORGANISM: Homo sapiens

<400> SEQUENCE: 1363
tgctttgcat ggtgctactg                                       20

<210> SEQ ID NO 1364
<211> LENGTH: 19
<212> TYPE: DNA
<213> ORGANISM: Homo sapiens

<400> SEQUENCE: 1364
cagcactttg ctgggagac                                        19

<210> SEQ ID NO 1365
<211> LENGTH: 20
<212> TYPE: DNA
<213> ORGANISM: Homo sapiens

<400> SEQUENCE: 1365
tggatcccac agtgttcatc                                       20

<210> SEQ ID NO 1366
<211> LENGTH: 21
<212> TYPE: DNA
<213> ORGANISM: Homo sapiens

<400> SEQUENCE: 1366
tgcctgtaat cccagctact c                                     21

<210> SEQ ID NO 1367
<211> LENGTH: 19
<212> TYPE: DNA
<213> ORGANISM: Homo sapiens

```
<400> SEQUENCE: 1367
cacttttggg aggctgagg                                                    19

<210> SEQ ID NO 1368
<211> LENGTH: 20
<212> TYPE: DNA
<213> ORGANISM: Homo sapiens

<400> SEQUENCE: 1368
gcctgctgag cctaacattc                                                   20

<210> SEQ ID NO 1369
<211> LENGTH: 21
<212> TYPE: DNA
<213> ORGANISM: Homo sapiens

<400> SEQUENCE: 1369
ggtgaaggaa gggagaagtt g                                                 21

<210> SEQ ID NO 1370
<211> LENGTH: 20
<212> TYPE: DNA
<213> ORGANISM: Homo sapiens

<400> SEQUENCE: 1370
gaatttggtg cctgtggaac                                                   20

<210> SEQ ID NO 1371
<211> LENGTH: 20
<212> TYPE: DNA
<213> ORGANISM: Homo sapiens

<400> SEQUENCE: 1371
gttttcgggg cctttcttac                                                   20

<210> SEQ ID NO 1372
<211> LENGTH: 20
<212> TYPE: DNA
<213> ORGANISM: Homo sapiens

<400> SEQUENCE: 1372
tacgacaatg catggggaag                                                   20

<210> SEQ ID NO 1373
<211> LENGTH: 20
<212> TYPE: DNA
<213> ORGANISM: Homo sapiens

<400> SEQUENCE: 1373
cggtgtatgt tcctgcagtc                                                   20

<210> SEQ ID NO 1374
<211> LENGTH: 20
<212> TYPE: DNA
<213> ORGANISM: Homo sapiens

<400> SEQUENCE: 1374
taatgcttgc tcacctgctg                                                   20

<210> SEQ ID NO 1375
<211> LENGTH: 21
<212> TYPE: DNA
```

<213> ORGANISM: Homo sapiens

<400> SEQUENCE: 1375
cccccagagt ttctgcatat c                                              21

<210> SEQ ID NO 1376
<211> LENGTH: 20
<212> TYPE: DNA
<213> ORGANISM: Homo sapiens

<400> SEQUENCE: 1376
ggcaaatggt agaaccaagg                                                20

<210> SEQ ID NO 1377
<211> LENGTH: 25
<212> TYPE: DNA
<213> ORGANISM: Homo sapiens

<400> SEQUENCE: 1377
tgctttagga aattaggctt atcaa                                          25

<210> SEQ ID NO 1378
<211> LENGTH: 25
<212> TYPE: DNA
<213> ORGANISM: Homo sapiens

<400> SEQUENCE: 1378
tgatgatggt gataacatta ttttg                                          25

<210> SEQ ID NO 1379
<211> LENGTH: 20
<212> TYPE: DNA
<213> ORGANISM: Homo sapiens

<400> SEQUENCE: 1379
ttgcagtgag tttgccattg                                                20

<210> SEQ ID NO 1380
<211> LENGTH: 21
<212> TYPE: DNA
<213> ORGANISM: Homo sapiens

<400> SEQUENCE: 1380
gcacatcttt tgtgggtatg g                                              21

<210> SEQ ID NO 1381
<211> LENGTH: 22
<212> TYPE: DNA
<213> ORGANISM: Homo sapiens

<400> SEQUENCE: 1381
ggaaacatgg taagcaaaga cc                                             22

<210> SEQ ID NO 1382
<211> LENGTH: 19
<212> TYPE: DNA
<213> ORGANISM: Homo sapiens

<400> SEQUENCE: 1382
aagggcaggc tcaagagtg                                                 19

<210> SEQ ID NO 1383
<211> LENGTH: 19

```
<212> TYPE: DNA
<213> ORGANISM: Homo sapiens

<400> SEQUENCE: 1383
gttggggtga gggtgtctc                                          19

<210> SEQ ID NO 1384
<211> LENGTH: 20
<212> TYPE: DNA
<213> ORGANISM: Homo sapiens

<400> SEQUENCE: 1384
gcacaacaac tgcagcaaag                                         20

<210> SEQ ID NO 1385
<211> LENGTH: 20
<212> TYPE: DNA
<213> ORGANISM: Homo sapiens

<400> SEQUENCE: 1385
aaatggctct ggagggagac                                         20

<210> SEQ ID NO 1386
<211> LENGTH: 20
<212> TYPE: DNA
<213> ORGANISM: Homo sapiens

<400> SEQUENCE: 1386
tttcccatag cctgaaaagg                                         20

<210> SEQ ID NO 1387
<211> LENGTH: 21
<212> TYPE: DNA
<213> ORGANISM: Homo sapiens

<400> SEQUENCE: 1387
ccactgttgt cgggtgtatt g                                       21

<210> SEQ ID NO 1388
<211> LENGTH: 21
<212> TYPE: DNA
<213> ORGANISM: Homo sapiens

<400> SEQUENCE: 1388
aagaagcata tgtggctctg g                                       21

<210> SEQ ID NO 1389
<211> LENGTH: 18
<212> TYPE: DNA
<213> ORGANISM: Homo sapiens

<400> SEQUENCE: 1389
acgaaggcct cctcatgc                                           18

<210> SEQ ID NO 1390
<211> LENGTH: 20
<212> TYPE: DNA
<213> ORGANISM: Homo sapiens

<400> SEQUENCE: 1390
ctggcacgga ggtagtcttc                                         20

<210> SEQ ID NO 1391
```

```
<211> LENGTH: 26
<212> TYPE: DNA
<213> ORGANISM: Homo sapiens

<400> SEQUENCE: 1391
aaaccataaa aattcattca aaaagg                                               26

<210> SEQ ID NO 1392
<211> LENGTH: 20
<212> TYPE: DNA
<213> ORGANISM: Homo sapiens

<400> SEQUENCE: 1392
ccccacaaag acacacacac                                                      20

<210> SEQ ID NO 1393
<211> LENGTH: 22
<212> TYPE: DNA
<213> ORGANISM: Homo sapiens

<400> SEQUENCE: 1393
ccagacattc cagatcaaag ac                                                   22

<210> SEQ ID NO 1394
<211> LENGTH: 22
<212> TYPE: DNA
<213> ORGANISM: Homo sapiens

<400> SEQUENCE: 1394
tgcttcttgc ctcatatttt cc                                                   22

<210> SEQ ID NO 1395
<211> LENGTH: 22
<212> TYPE: DNA
<213> ORGANISM: Homo sapiens

<400> SEQUENCE: 1395
aaaaggagga cacacaaaaa tc                                                   22

<210> SEQ ID NO 1396
<211> LENGTH: 21
<212> TYPE: DNA
<213> ORGANISM: Homo sapiens

<400> SEQUENCE: 1396
aaaactcatg ccttcaagct c                                                    21

<210> SEQ ID NO 1397
<211> LENGTH: 20
<212> TYPE: DNA
<213> ORGANISM: Homo sapiens

<400> SEQUENCE: 1397
ccttcttcct gatggtgtgg                                                      20

<210> SEQ ID NO 1398
<211> LENGTH: 27
<212> TYPE: DNA
<213> ORGANISM: Homo sapiens

<400> SEQUENCE: 1398
tccttatctt agacacaaaa tgagatg                                              27
```

```
<210> SEQ ID NO 1399
<211> LENGTH: 20
<212> TYPE: DNA
<213> ORGANISM: Homo sapiens

<400> SEQUENCE: 1399
gccacctgag acagaagagc                                               20

<210> SEQ ID NO 1400
<211> LENGTH: 20
<212> TYPE: DNA
<213> ORGANISM: Homo sapiens

<400> SEQUENCE: 1400
taaaaatttc cgggaacagc                                               20

<210> SEQ ID NO 1401
<211> LENGTH: 24
<212> TYPE: DNA
<213> ORGANISM: Homo sapiens

<400> SEQUENCE: 1401
aactgctcaa ggaattaatc acag                                          24

<210> SEQ ID NO 1402
<211> LENGTH: 21
<212> TYPE: DNA
<213> ORGANISM: Homo sapiens

<400> SEQUENCE: 1402
ggaaaattag ctcatgcaac c                                             21

<210> SEQ ID NO 1403
<211> LENGTH: 23
<212> TYPE: DNA
<213> ORGANISM: Homo sapiens

<400> SEQUENCE: 1403
caaaaagatg agccagaaag atg                                           23

<210> SEQ ID NO 1404
<211> LENGTH: 20
<212> TYPE: DNA
<213> ORGANISM: Homo sapiens

<400> SEQUENCE: 1404
gtgtcagttt cctgggaagg                                               20

<210> SEQ ID NO 1405
<211> LENGTH: 23
<212> TYPE: DNA
<213> ORGANISM: Homo sapiens

<400> SEQUENCE: 1405
cagggcaagt taaatttacc aac                                           23

<210> SEQ ID NO 1406
<211> LENGTH: 25
<212> TYPE: DNA
<213> ORGANISM: Homo sapiens

<400> SEQUENCE: 1406
ccacctagtg gagagaatta ctacc                                         25
```

<210> SEQ ID NO 1407
<211> LENGTH: 20
<212> TYPE: DNA
<213> ORGANISM: Homo sapiens

<400> SEQUENCE: 1407
aacttcggct ggtagagtcg                                              20

<210> SEQ ID NO 1408
<211> LENGTH: 20
<212> TYPE: DNA
<213> ORGANISM: Homo sapiens

<400> SEQUENCE: 1408
tccatctacc aagcccaatc                                              20

<210> SEQ ID NO 1409
<211> LENGTH: 20
<212> TYPE: DNA
<213> ORGANISM: Homo sapiens

<400> SEQUENCE: 1409
tgtgcctgtt tttgtgatgg                                              20

<210> SEQ ID NO 1410
<211> LENGTH: 20
<212> TYPE: DNA
<213> ORGANISM: Homo sapiens

<400> SEQUENCE: 1410
tgataggtgc agcaaaccac                                              20

<210> SEQ ID NO 1411
<211> LENGTH: 20
<212> TYPE: DNA
<213> ORGANISM: Homo sapiens

<400> SEQUENCE: 1411
caggggcagc tgtagtcaag                                              20

<210> SEQ ID NO 1412
<211> LENGTH: 20
<212> TYPE: DNA
<213> ORGANISM: Homo sapiens

<400> SEQUENCE: 1412
taggacactg ccctccctac                                              20

<210> SEQ ID NO 1413
<211> LENGTH: 20
<212> TYPE: DNA
<213> ORGANISM: Homo sapiens

<400> SEQUENCE: 1413
tctccctccc tccttcactc                                              20

<210> SEQ ID NO 1414
<211> LENGTH: 18
<212> TYPE: DNA
<213> ORGANISM: Homo sapiens

<400> SEQUENCE: 1414
ctatcccagg ccctccag                                                18

<210> SEQ ID NO 1415
<211> LENGTH: 18
<212> TYPE: DNA
<213> ORGANISM: Homo sapiens

<400> SEQUENCE: 1415
ctatcccagg ccctccag                                                   18

<210> SEQ ID NO 1416
<211> LENGTH: 18
<212> TYPE: DNA
<213> ORGANISM: Homo sapiens

<400> SEQUENCE: 1416
ctatcccagg ccctccag                                                   18

<210> SEQ ID NO 1417
<211> LENGTH: 20
<212> TYPE: DNA
<213> ORGANISM: Homo sapiens

<400> SEQUENCE: 1417
ttgtatctgt gtgcctgctc                                                 20

<210> SEQ ID NO 1418
<211> LENGTH: 20
<212> TYPE: DNA
<213> ORGANISM: Homo sapiens

<400> SEQUENCE: 1418
gcaagagcag ggaatgaatc                                                 20

<210> SEQ ID NO 1419
<211> LENGTH: 24
<212> TYPE: DNA
<213> ORGANISM: Homo sapiens

<400> SEQUENCE: 1419
tggaaaaaga aagaagtcaa acac                                            24

<210> SEQ ID NO 1420
<211> LENGTH: 24
<212> TYPE: DNA
<213> ORGANISM: Homo sapiens

<400> SEQUENCE: 1420
aaacaggaat cagtgtcaac tttc                                            24

<210> SEQ ID NO 1421
<211> LENGTH: 20
<212> TYPE: DNA
<213> ORGANISM: Homo sapiens

<400> SEQUENCE: 1421
gagaggcacc aaagtcacag                                                 20

<210> SEQ ID NO 1422
<211> LENGTH: 20
<212> TYPE: DNA
<213> ORGANISM: Homo sapiens

<400> SEQUENCE: 1422

```
tgctgcttta ggcattccac                                              20

<210> SEQ ID NO 1423
<211> LENGTH: 23
<212> TYPE: DNA
<213> ORGANISM: Homo sapiens

<400> SEQUENCE: 1423
aaaaactgaa agccaaacaa gag                                          23

<210> SEQ ID NO 1424
<211> LENGTH: 19
<212> TYPE: DNA
<213> ORGANISM: Homo sapiens

<400> SEQUENCE: 1424
ttgaaagcca gacgctgtg                                               19

<210> SEQ ID NO 1425
<211> LENGTH: 19
<212> TYPE: DNA
<213> ORGANISM: Homo sapiens

<400> SEQUENCE: 1425
acagagggag ctgctttgc                                               19

<210> SEQ ID NO 1426
<211> LENGTH: 20
<212> TYPE: DNA
<213> ORGANISM: Homo sapiens

<400> SEQUENCE: 1426
tcgctcccct ttttgattag                                              20

<210> SEQ ID NO 1427
<211> LENGTH: 20
<212> TYPE: DNA
<213> ORGANISM: Homo sapiens

<400> SEQUENCE: 1427
cctggtggga ttatgaatgg                                              20

<210> SEQ ID NO 1428
<211> LENGTH: 20
<212> TYPE: DNA
<213> ORGANISM: Homo sapiens

<400> SEQUENCE: 1428
aggtctgtct gcctcctgac                                              20

<210> SEQ ID NO 1429
<211> LENGTH: 20
<212> TYPE: DNA
<213> ORGANISM: Homo sapiens

<400> SEQUENCE: 1429
gggaggttac agctctcctg                                              20

<210> SEQ ID NO 1430
<211> LENGTH: 19
<212> TYPE: DNA
<213> ORGANISM: Homo sapiens

<400> SEQUENCE: 1430
```
aacaccgctg ctacccaac                                                    19

<210> SEQ ID NO 1431
<211> LENGTH: 20
<212> TYPE: DNA
<213> ORGANISM: Homo sapiens

<400> SEQUENCE: 1431
tccagcttca caaaggatgg                                                   20

<210> SEQ ID NO 1432
<211> LENGTH: 20
<212> TYPE: DNA
<213> ORGANISM: Homo sapiens

<400> SEQUENCE: 1432
agccagtgtt ccagcttcac                                                   20

<210> SEQ ID NO 1433
<211> LENGTH: 18
<212> TYPE: DNA
<213> ORGANISM: Homo sapiens

<400> SEQUENCE: 1433
ggagggaaga gggcattc                                                     18

<210> SEQ ID NO 1434
<211> LENGTH: 18
<212> TYPE: DNA
<213> ORGANISM: Homo sapiens

<400> SEQUENCE: 1434
gccctttctc tgcacctg                                                     18

<210> SEQ ID NO 1435
<211> LENGTH: 20
<212> TYPE: DNA
<213> ORGANISM: Homo sapiens

<400> SEQUENCE: 1435
aaccgtatag ccctcaggtg                                                   20

<210> SEQ ID NO 1436
<211> LENGTH: 20
<212> TYPE: DNA
<213> ORGANISM: Homo sapiens

<400> SEQUENCE: 1436
gtcttcgctc tgggactcac                                                   20

<210> SEQ ID NO 1437
<211> LENGTH: 19
<212> TYPE: DNA
<213> ORGANISM: Homo sapiens

<400> SEQUENCE: 1437
cgagccacgg atttatgag                                                    19

<210> SEQ ID NO 1438
<211> LENGTH: 18
<212> TYPE: DNA
<213> ORGANISM: Homo sapiens

```
<400> SEQUENCE: 1438
gccatgccct agatctgc                                                  18

<210> SEQ ID NO 1439
<211> LENGTH: 19
<212> TYPE: DNA
<213> ORGANISM: Homo sapiens

<400> SEQUENCE: 1439
gaggcctggt tggtctcag                                                 19

<210> SEQ ID NO 1440
<211> LENGTH: 19
<212> TYPE: DNA
<213> ORGANISM: Homo sapiens

<400> SEQUENCE: 1440
ctgcagccca gttgtcatc                                                 19

<210> SEQ ID NO 1441
<211> LENGTH: 21
<212> TYPE: DNA
<213> ORGANISM: Homo sapiens

<400> SEQUENCE: 1441
gcaatttcct tgacaaacag g                                              21

<210> SEQ ID NO 1442
<211> LENGTH: 20
<212> TYPE: DNA
<213> ORGANISM: Homo sapiens

<400> SEQUENCE: 1442
cagggtcaga gaggttgctc                                                20

<210> SEQ ID NO 1443
<211> LENGTH: 20
<212> TYPE: DNA
<213> ORGANISM: Homo sapiens

<400> SEQUENCE: 1443
acgagtcaca gaggctttgg                                                20

<210> SEQ ID NO 1444
<211> LENGTH: 20
<212> TYPE: DNA
<213> ORGANISM: Homo sapiens

<400> SEQUENCE: 1444
ggccacagca aaatagaacc                                                20

<210> SEQ ID NO 1445
<211> LENGTH: 20
<212> TYPE: DNA
<213> ORGANISM: Homo sapiens

<400> SEQUENCE: 1445
ttcagcctcc tgtccttgac                                                20

<210> SEQ ID NO 1446
<211> LENGTH: 20
<212> TYPE: DNA
<213> ORGANISM: Homo sapiens
```

<400> SEQUENCE: 1446
acctggcttt gctttgactc                                              20

<210> SEQ ID NO 1447
<211> LENGTH: 20
<212> TYPE: DNA
<213> ORGANISM: Homo sapiens

<400> SEQUENCE: 1447
aagttcccgt cctctggttc                                              20

<210> SEQ ID NO 1448
<211> LENGTH: 21
<212> TYPE: DNA
<213> ORGANISM: Homo sapiens

<400> SEQUENCE: 1448
tccaaagctc atgttgtttc c                                            21

<210> SEQ ID NO 1449
<211> LENGTH: 20
<212> TYPE: DNA
<213> ORGANISM: Homo sapiens

<400> SEQUENCE: 1449
ttcggccttt acagctacag                                              20

<210> SEQ ID NO 1450
<211> LENGTH: 21
<212> TYPE: DNA
<213> ORGANISM: Homo sapiens

<400> SEQUENCE: 1450
catacaacca ggcctacaac c                                            21

<210> SEQ ID NO 1451
<211> LENGTH: 20
<212> TYPE: DNA
<213> ORGANISM: Homo sapiens

<400> SEQUENCE: 1451
tgacaccagt tgccaaagac                                              20

<210> SEQ ID NO 1452
<211> LENGTH: 19
<212> TYPE: DNA
<213> ORGANISM: Homo sapiens

<400> SEQUENCE: 1452
gctgggactt ccaaccttc                                               19

<210> SEQ ID NO 1453
<211> LENGTH: 23
<212> TYPE: DNA
<213> ORGANISM: Homo sapiens

<400> SEQUENCE: 1453
gatttaactg tgattgctgg ttg                                          23

<210> SEQ ID NO 1454
<211> LENGTH: 20
<212> TYPE: DNA

```
<213> ORGANISM: Homo sapiens

<400> SEQUENCE: 1454
attgtgtctg gtggatgtgg                                                   20

<210> SEQ ID NO 1455
<211> LENGTH: 20
<212> TYPE: DNA
<213> ORGANISM: Homo sapiens

<400> SEQUENCE: 1455
ggggcctccg tataattgag                                                   20

<210> SEQ ID NO 1456
<211> LENGTH: 20
<212> TYPE: DNA
<213> ORGANISM: Homo sapiens

<400> SEQUENCE: 1456
ccaaactccg agtcttcagg                                                   20

<210> SEQ ID NO 1457
<211> LENGTH: 20
<212> TYPE: DNA
<213> ORGANISM: Homo sapiens

<400> SEQUENCE: 1457
tcaaagtact cgggctccac                                                   20

<210> SEQ ID NO 1458
<211> LENGTH: 20
<212> TYPE: DNA
<213> ORGANISM: Homo sapiens

<400> SEQUENCE: 1458
tgagggatcc atgacctttc                                                   20

<210> SEQ ID NO 1459
<211> LENGTH: 20
<212> TYPE: DNA
<213> ORGANISM: Homo sapiens

<400> SEQUENCE: 1459
tatgagccac cacactcagc                                                   20

<210> SEQ ID NO 1460
<211> LENGTH: 19
<212> TYPE: DNA
<213> ORGANISM: Homo sapiens

<400> SEQUENCE: 1460
gcctcgatgg tgcagatac                                                    19

<210> SEQ ID NO 1461
<211> LENGTH: 19
<212> TYPE: DNA
<213> ORGANISM: Homo sapiens

<400> SEQUENCE: 1461
gcctcgatgg tgcagatac                                                    19

<210> SEQ ID NO 1462
<211> LENGTH: 20
```

<212> TYPE: DNA
<213> ORGANISM: Homo sapiens

<400> SEQUENCE: 1462
ccacccacaa gatgaaggtc					20

<210> SEQ ID NO 1463
<211> LENGTH: 21
<212> TYPE: DNA
<213> ORGANISM: Homo sapiens

<400> SEQUENCE: 1463
ttccccaact cccatttta c					21

<210> SEQ ID NO 1464
<211> LENGTH: 19
<212> TYPE: DNA
<213> ORGANISM: Homo sapiens

<400> SEQUENCE: 1464
catgccctgg aaatgtgag					19

<210> SEQ ID NO 1465
<211> LENGTH: 20
<212> TYPE: DNA
<213> ORGANISM: Homo sapiens

<400> SEQUENCE: 1465 cccttttca tgggtgaatg					20

<210> SEQ ID NO 1466
<211> LENGTH: 20
<212> TYPE: DNA
<213> ORGANISM: Homo sapiens

<400> SEQUENCE: 1466
caaagggtgg tgactgaacc					20

<210> SEQ ID NO 1467
<211> LENGTH: 20
<212> TYPE: DNA
<213> ORGANISM: Homo sapiens

<400> SEQUENCE: 1467
tacagggagg aggtgagtgg					20

<210> SEQ ID NO 1468
<211> LENGTH: 20
<212> TYPE: DNA
<213> ORGANISM: Homo sapiens

<400> SEQUENCE: 1468
tgagtcgctc aaggtcacac					20

<210> SEQ ID NO 1469
<211> LENGTH: 20
<212> TYPE: DNA
<213> ORGANISM: Homo sapiens

<400> SEQUENCE: 1469
tcaggaccct cacttgttcc					20

<210> SEQ ID NO 1470

```
<211> LENGTH: 19
<212> TYPE: DNA
<213> ORGANISM: Homo sapiens

<400> SEQUENCE: 1470
tcctggaggt ggtggctct                                                  19

<210> SEQ ID NO 1471
<211> LENGTH: 20
<212> TYPE: DNA
<213> ORGANISM: Homo sapiens

<400> SEQUENCE: 1471
agccgtgaag atgctgaaag                                                 20

<210> SEQ ID NO 1472
<211> LENGTH: 22
<212> TYPE: DNA
<213> ORGANISM: Homo sapiens

<400> SEQUENCE: 1472
caaaaacatc atcaacctgc tg                                              22

<210> SEQ ID NO 1473
<211> LENGTH: 19
<212> TYPE: DNA
<213> ORGANISM: Homo sapiens

<400> SEQUENCE: 1473
aggtgtgggt ggagtaggc                                                  19

<210> SEQ ID NO 1474
<211> LENGTH: 21
<212> TYPE: DNA
<213> ORGANISM: Homo sapiens

<400> SEQUENCE: 1474
aagaagacaa ccaacgtgag c                                               21

<210> SEQ ID NO 1475
<211> LENGTH: 19
<212> TYPE: DNA
<213> ORGANISM: Homo sapiens

<400> SEQUENCE: 1475
ctggcctatt cccctggtg                                                  19

<210> SEQ ID NO 1476
<211> LENGTH: 18
<212> TYPE: DNA
<213> ORGANISM: Homo sapiens

<400> SEQUENCE: 1476
cagcccttca ggctgttc                                                   18

<210> SEQ ID NO 1477
<211> LENGTH: 19
<212> TYPE: DNA
<213> ORGANISM: Homo sapiens

<400> SEQUENCE: 1477
ccagagtgct gaggtgtgg                                                  19
```

```
<210> SEQ ID NO 1478
<211> LENGTH: 19
<212> TYPE: DNA
<213> ORGANISM: Homo sapiens

<400> SEQUENCE: 1478
gctggtggaa gtcagaacg                                              19

<210> SEQ ID NO 1479
<211> LENGTH: 22
<212> TYPE: DNA
<213> ORGANISM: Homo sapiens

<400> SEQUENCE: 1479
cagttgggaa taggtgacag ag                                          22

<210> SEQ ID NO 1480
<211> LENGTH: 22
<212> TYPE: DNA
<213> ORGANISM: Homo sapiens

<400> SEQUENCE: 1480
tctttgaccc agaaaaatag cc                                          22

<210> SEQ ID NO 1481
<211> LENGTH: 24
<212> TYPE: DNA
<213> ORGANISM: Homo sapiens

<400> SEQUENCE: 1481
tgtttctgtc agttgacttt tcag                                        24

<210> SEQ ID NO 1482
<211> LENGTH: 26
<212> TYPE: DNA
<213> ORGANISM: Homo sapiens

<400> SEQUENCE: 1482
ttttgttttg ttttgtttta ctttgg                                      26

<210> SEQ ID NO 1483
<211> LENGTH: 20
<212> TYPE: DNA
<213> ORGANISM: Homo sapiens

<400> SEQUENCE: 1483
tccctgaaag ggaaactcac                                             20

<210> SEQ ID NO 1484
<211> LENGTH: 20
<212> TYPE: DNA
<213> ORGANISM: Homo sapiens

<400> SEQUENCE: 1484
attccccctt ttctgctttc                                             20

<210> SEQ ID NO 1485
<211> LENGTH: 22
<212> TYPE: DNA
<213> ORGANISM: Homo sapiens

<400> SEQUENCE: 1485
agaccacatt tggttttgat tc                                          22
```

<210> SEQ ID NO 1486
<211> LENGTH: 20
<212> TYPE: DNA
<213> ORGANISM: Homo sapiens

<400> SEQUENCE: 1486
gaaagagtgg cggtgaaagt                                          20

<210> SEQ ID NO 1487
<211> LENGTH: 24
<212> TYPE: DNA
<213> ORGANISM: Homo sapiens

<400> SEQUENCE: 1487
tgtttggtaa ttttagaccc agac                                     24

<210> SEQ ID NO 1488
<211> LENGTH: 20
<212> TYPE: DNA
<213> ORGANISM: Homo sapiens

<400> SEQUENCE: 1488
ctggcgtgta acaagcactc                                          20

<210> SEQ ID NO 1489
<211> LENGTH: 20
<212> TYPE: DNA
<213> ORGANISM: Homo sapiens

<400> SEQUENCE: 1489
gcgcagccca ttttatctc                                           20

<210> SEQ ID NO 1490
<211> LENGTH: 22
<212> TYPE: DNA
<213> ORGANISM: Homo sapiens

<400> SEQUENCE: 1490
ccggatacag atacccaaaa ag                                       22

<210> SEQ ID NO 1491
<211> LENGTH: 20
<212> TYPE: DNA
<213> ORGANISM: Homo sapiens

<400> SEQUENCE: 1491
gaatgctgtt gtcctgcttg                                          20

<210> SEQ ID NO 1492
<211> LENGTH: 20
<212> TYPE: DNA
<213> ORGANISM: Homo sapiens

<400> SEQUENCE: 1492
agaaacatgc cagtcggaag                                          20

<210> SEQ ID NO 1493
<211> LENGTH: 20
<212> TYPE: DNA
<213> ORGANISM: Homo sapiens

<400> SEQUENCE: 1493
tgcctatttg aggcaatcag                                          20

<210> SEQ ID NO 1494
<211> LENGTH: 20
<212> TYPE: DNA
<213> ORGANISM: Homo sapiens

<400> SEQUENCE: 1494
ttgtggctga ttcaaacgtg                                                 20

<210> SEQ ID NO 1495
<211> LENGTH: 20
<212> TYPE: DNA
<213> ORGANISM: Homo sapiens

<400> SEQUENCE: 1495
ttacagacgt gagccactgc                                                 20

<210> SEQ ID NO 1496
<211> LENGTH: 20
<212> TYPE: DNA
<213> ORGANISM: Homo sapiens

<400> SEQUENCE: 1496 gaatcccta cccaggtttg                                                  20

<210> SEQ ID NO 1497
<211> LENGTH: 20
<212> TYPE: DNA
<213> ORGANISM: Homo sapiens

<400> SEQUENCE: 1497
cacatgggga aaatggagtc                                                 20

<210> SEQ ID NO 1498
<211> LENGTH: 20
<212> TYPE: DNA
<213> ORGANISM: Homo sapiens

<400> SEQUENCE: 1498
gtcctaggga tgctgctgtc                                                 20

<210> SEQ ID NO 1499
<211> LENGTH: 20
<212> TYPE: DNA
<213> ORGANISM: Homo sapiens

<400> SEQUENCE: 1499
caggctggga taggataagg                                                 20

<210> SEQ ID NO 1500
<211> LENGTH: 18
<212> TYPE: DNA
<213> ORGANISM: Homo sapiens

<400> SEQUENCE: 1500
atgtgtggct gggtacgg                                                   18

<210> SEQ ID NO 1501
<211> LENGTH: 19
<212> TYPE: DNA
<213> ORGANISM: Homo sapiens

<400> SEQUENCE: 1501
gatgtgtggc tgggtacgg                                               19

<210> SEQ ID NO 1502
<211> LENGTH: 19
<212> TYPE: DNA
<213> ORGANISM: Homo sapiens

<400> SEQUENCE: 1502
ggtcaagcga gaggaggag                                               19

<210> SEQ ID NO 1503
<211> LENGTH: 20
<212> TYPE: DNA
<213> ORGANISM: Homo sapiens

<400> SEQUENCE: 1503
ttttcaaatg gtccctcacc                                              20

<210> SEQ ID NO 1504
<211> LENGTH: 20
<212> TYPE: DNA
<213> ORGANISM: Homo sapiens

<400> SEQUENCE: 1504
cgtcccactt cctctgtctc                                              20

<210> SEQ ID NO 1505
<211> LENGTH: 20
<212> TYPE: DNA
<213> ORGANISM: Homo sapiens

<400> SEQUENCE: 1505
tacacaccgg aagtgtgagg                                              20

<210> SEQ ID NO 1506
<211> LENGTH: 20
<212> TYPE: DNA
<213> ORGANISM: Homo sapiens

<400> SEQUENCE: 1506
ccccagtagg gatttttgtc                                              20

<210> SEQ ID NO 1507
<211> LENGTH: 20
<212> TYPE: DNA
<213> ORGANISM: Homo sapiens

<400> SEQUENCE: 1507
actcctaggt cagccccttc                                              20

<210> SEQ ID NO 1508
<211> LENGTH: 20
<212> TYPE: DNA
<213> ORGANISM: Homo sapiens

<400> SEQUENCE: 1508
ccctggcttc attctactgg                                              20

<210> SEQ ID NO 1509
<211> LENGTH: 20
<212> TYPE: DNA
<213> ORGANISM: Homo sapiens

<400> SEQUENCE: 1509
ccgtgccaag aaaacgtaag                    20

<210> SEQ ID NO 1510
<211> LENGTH: 18
<212> TYPE: DNA
<213> ORGANISM: Homo sapiens

<400> SEQUENCE: 1510
acagagcggg gaaccaac                      18

<210> SEQ ID NO 1511
<211> LENGTH: 21
<212> TYPE: DNA
<213> ORGANISM: Homo sapiens

<400> SEQUENCE: 1511
catttgctgc ttactcattg c                  21

<210> SEQ ID NO 1512
<211> LENGTH: 20
<212> TYPE: DNA
<213> ORGANISM: Homo sapiens

<400> SEQUENCE: 1512 tccttcctttt ggtgtgtgtg                   20

<210> SEQ ID NO 1513
<211> LENGTH: 21
<212> TYPE: DNA
<213> ORGANISM: Homo sapiens

<400> SEQUENCE: 1513
ggtttggggc taaaagctat g                  21

<210> SEQ ID NO 1514
<211> LENGTH: 19
<212> TYPE: DNA
<213> ORGANISM: Homo sapiens

<400> SEQUENCE: 1514
gattggtgca ggtgagagc                     19

<210> SEQ ID NO 1515
<211> LENGTH: 19
<212> TYPE: DNA
<213> ORGANISM: Homo sapiens

<400> SEQUENCE: 1515
ctgggcgaca gaacaagac                     19

<210> SEQ ID NO 1516
<211> LENGTH: 20
<212> TYPE: DNA
<213> ORGANISM: Homo sapiens

<400> SEQUENCE: 1516 ctaggggaa aaagcagagg                     20

<210> SEQ ID NO 1517
<211> LENGTH: 20
<212> TYPE: DNA
<213> ORGANISM: Homo sapiens

```
<400> SEQUENCE: 1517
cctgagctag ggggaaaaag                                                 20

<210> SEQ ID NO 1518
<211> LENGTH: 20
<212> TYPE: DNA
<213> ORGANISM: Homo sapiens

<400> SEQUENCE: 1518
gctgtggctc ctatcctacc                                                 20

<210> SEQ ID NO 1519
<211> LENGTH: 18
<212> TYPE: DNA
<213> ORGANISM: Homo sapiens

<400> SEQUENCE: 1519
aaggctgggt tccacctc                                                   18

<210> SEQ ID NO 1520
<211> LENGTH: 20
<212> TYPE: DNA
<213> ORGANISM: Homo sapiens

<400> SEQUENCE: 1520
gaggctagga ccgtctcagg                                                 20

<210> SEQ ID NO 1521
<211> LENGTH: 20
<212> TYPE: DNA
<213> ORGANISM: Homo sapiens

<400> SEQUENCE: 1521
cctgtactgg ggacctgttc                                                 20

<210> SEQ ID NO 1522
<211> LENGTH: 21
<212> TYPE: DNA
<213> ORGANISM: Homo sapiens

<400> SEQUENCE: 1522
ggtcattgca tttaggtcag c                                               21

<210> SEQ ID NO 1523
<211> LENGTH: 22
<212> TYPE: DNA
<213> ORGANISM: Homo sapiens

<400> SEQUENCE: 1523
agctcatgcc attaacaatc tc                                              22

<210> SEQ ID NO 1524
<211> LENGTH: 20
<212> TYPE: DNA
<213> ORGANISM: Homo sapiens

<400> SEQUENCE: 1524
cagtaccctc tgagcccttg                                                 20

<210> SEQ ID NO 1525
<211> LENGTH: 21
<212> TYPE: DNA
<213> ORGANISM: Homo sapiens
```

```
<400> SEQUENCE: 1525
tcctaaccta ccccttcttg                                            21

<210> SEQ ID NO 1526
<211> LENGTH: 20
<212> TYPE: DNA
<213> ORGANISM: Homo sapiens

<400> SEQUENCE: 1526
tgtgataagg ggacctgctc                                            20

<210> SEQ ID NO 1527
<211> LENGTH: 25
<212> TYPE: DNA
<213> ORGANISM: Homo sapiens

<400> SEQUENCE: 1527
ttggtgtatt tttagcaggt gtatg                                      25

<210> SEQ ID NO 1528
<211> LENGTH: 20
<212> TYPE: DNA
<213> ORGANISM: Homo sapiens

<400> SEQUENCE: 1528
acctggcctc cattataccc                                            20

<210> SEQ ID NO 1529
<211> LENGTH: 22
<212> TYPE: DNA
<213> ORGANISM: Homo sapiens

<400> SEQUENCE: 1529
tccttcctct ttgcactatt cc                                         22

<210> SEQ ID NO 1530
<211> LENGTH: 27
<212> TYPE: DNA
<213> ORGANISM: Homo sapiens

<400> SEQUENCE: 1530
tggtctagtt catttacaag tgaagac                                    27

<210> SEQ ID NO 1531
<211> LENGTH: 20
<212> TYPE: DNA
<213> ORGANISM: Homo sapiens

<400> SEQUENCE: 1531
gaggcaattt ctgagccaac                                            20

<210> SEQ ID NO 1532
<211> LENGTH: 21
<212> TYPE: DNA
<213> ORGANISM: Homo sapiens

<400> SEQUENCE: 1532
tggacaaaga tgggtaagtg g                                          21

<210> SEQ ID NO 1533
<211> LENGTH: 20
<212> TYPE: DNA
```

```
<213> ORGANISM: Homo sapiens

<400> SEQUENCE: 1533
tagtagtggt gtggggcttg                                           20

<210> SEQ ID NO 1534
<211> LENGTH: 20
<212> TYPE: DNA
<213> ORGANISM: Homo sapiens

<400> SEQUENCE: 1534
ccattctttc acaaccgatg                                           20

<210> SEQ ID NO 1535
<211> LENGTH: 20
<212> TYPE: DNA
<213> ORGANISM: Homo sapiens

<400> SEQUENCE: 1535
tttctcgcct tgttctctgg                                           20

<210> SEQ ID NO 1536
<211> LENGTH: 20
<212> TYPE: DNA
<213> ORGANISM: Homo sapiens

<400> SEQUENCE: 1536
tagccattga gcgaatcaac                                           20

<210> SEQ ID NO 1537
<211> LENGTH: 20
<212> TYPE: DNA
<213> ORGANISM: Homo sapiens

<400> SEQUENCE: 1537
ttttctcttg ggcttgtgtg                                           20

<210> SEQ ID NO 1538
<211> LENGTH: 20
<212> TYPE: DNA
<213> ORGANISM: Homo sapiens

<400> SEQUENCE: 1538
tacctgtagg ggtcgtcctg                                           20

<210> SEQ ID NO 1539
<211> LENGTH: 24
<212> TYPE: DNA
<213> ORGANISM: Homo sapiens

<400> SEQUENCE: 1539
atttttcctc tctgtagttt ttgg                                      24

<210> SEQ ID NO 1540
<211> LENGTH: 20
<212> TYPE: DNA
<213> ORGANISM: Homo sapiens

<400> SEQUENCE: 1540
ttccttatga tgccctgctc                                           20

<210> SEQ ID NO 1541
<211> LENGTH: 24
```

```
<212> TYPE: DNA
<213> ORGANISM: Homo sapiens

<400> SEQUENCE: 1541
gcagaccata ataatgaaca cagg                                           24

<210> SEQ ID NO 1542
<211> LENGTH: 20
<212> TYPE: DNA
<213> ORGANISM: Homo sapiens

<400> SEQUENCE: 1542
tcagcattcc agaaacatgc                                                20

<210> SEQ ID NO 1543
<211> LENGTH: 20
<212> TYPE: DNA
<213> ORGANISM: Homo sapiens

<400> SEQUENCE: 1543
tcaccagaaa gcatgaggag                                                20

<210> SEQ ID NO 1544
<211> LENGTH: 25
<212> TYPE: DNA
<213> ORGANISM: Homo sapiens

<400> SEQUENCE: 1544
aagtgctatc ttagggcaaa ttaac                                          25

<210> SEQ ID NO 1545
<211> LENGTH: 27
<212> TYPE: DNA
<213> ORGANISM: Homo sapiens

<400> SEQUENCE: 1545
aaaaagaaaa ttcagataag ctctgtg                                        27

<210> SEQ ID NO 1546
<211> LENGTH: 23
<212> TYPE: DNA
<213> ORGANISM: Homo sapiens

<400> SEQUENCE: 1546
tttatgtgga agggacattt ttc                                            23

<210> SEQ ID NO 1547
<211> LENGTH: 21
<212> TYPE: DNA
<213> ORGANISM: Homo sapiens

<400> SEQUENCE: 1547
ggttatgtgc cctcaactgt g                                              21

<210> SEQ ID NO 1548
<211> LENGTH: 20
<212> TYPE: DNA
<213> ORGANISM: Homo sapiens

<400> SEQUENCE: 1548
agagcagtct ggagggtgac                                                20

<210> SEQ ID NO 1549
```

```
<210> SEQ ID NO 1549
<211> LENGTH: 20
<212> TYPE: DNA
<213> ORGANISM: Homo sapiens

<400> SEQUENCE: 1549
aggtaagtgg gcatgtctgg                                               20

<210> SEQ ID NO 1550
<211> LENGTH: 20
<212> TYPE: DNA
<213> ORGANISM: Homo sapiens

<400> SEQUENCE: 1550
ccagagtccc atccaaacac                                               20

<210> SEQ ID NO 1551
<211> LENGTH: 20
<212> TYPE: DNA
<213> ORGANISM: Homo sapiens

<400> SEQUENCE: 1551
tcatgctgtt gtctgctgtg                                               20

<210> SEQ ID NO 1552
<211> LENGTH: 20
<212> TYPE: DNA
<213> ORGANISM: Homo sapiens

<400> SEQUENCE: 1552
cccttggcat atctgagcac                                               20

<210> SEQ ID NO 1553
<211> LENGTH: 21
<212> TYPE: DNA
<213> ORGANISM: Homo sapiens

<400> SEQUENCE: 1553
tgcttgatgt aaacccttg g                                              21

<210> SEQ ID NO 1554
<211> LENGTH: 20
<212> TYPE: DNA
<213> ORGANISM: Homo sapiens

<400> SEQUENCE: 1554
actccaacct catgctccac                                               20

<210> SEQ ID NO 1555
<211> LENGTH: 20
<212> TYPE: DNA
<213> ORGANISM: Homo sapiens

<400> SEQUENCE: 1555
agggagggta gatgcaaacc                                               20

<210> SEQ ID NO 1556
<211> LENGTH: 23
<212> TYPE: DNA
<213> ORGANISM: Homo sapiens

<400> SEQUENCE: 1556
cagcctagag taagcaggga gtg                                           23
```

```
<210> SEQ ID NO 1557
<211> LENGTH: 18
<212> TYPE: DNA
<213> ORGANISM: Homo sapiens

<400> SEQUENCE: 1557
agggccctgc cctttaac                                                 18

<210> SEQ ID NO 1558
<211> LENGTH: 20
<212> TYPE: DNA
<213> ORGANISM: Homo sapiens

<400> SEQUENCE: 1558
cgtttctggg gaagattcag                                               20

<210> SEQ ID NO 1559
<211> LENGTH: 20
<212> TYPE: DNA
<213> ORGANISM: Homo sapiens

<400> SEQUENCE: 1559
gggaggtgtg gagaagtgtg                                               20

<210> SEQ ID NO 1560
<211> LENGTH: 18
<212> TYPE: DNA
<213> ORGANISM: Homo sapiens

<400> SEQUENCE: 1560
ggaggactgg aggggttg                                                 18

<210> SEQ ID NO 1561
<211> LENGTH: 20
<212> TYPE: DNA
<213> ORGANISM: Homo sapiens

<400> SEQUENCE: 1561
cagcctggtg acagaatgag                                               20

<210> SEQ ID NO 1562
<211> LENGTH: 22
<212> TYPE: DNA
<213> ORGANISM: Homo sapiens

<400> SEQUENCE: 1562
tttttgcttt tgatttcgat tc                                            22

<210> SEQ ID NO 1563
<211> LENGTH: 24
<212> TYPE: DNA
<213> ORGANISM: Homo sapiens

<400> SEQUENCE: 1563
tgaaaacagc attattgttg aatg                                          24

<210> SEQ ID NO 1564
<211> LENGTH: 24
<212> TYPE: DNA
<213> ORGANISM: Homo sapiens

<400> SEQUENCE: 1564
tctttcaaag tgcctattgg tatg                                          24
```

<210> SEQ ID NO 1565
<211> LENGTH: 20
<212> TYPE: DNA
<213> ORGANISM: Homo sapiens

<400> SEQUENCE: 1565
tacctcccag ctggtactcg                                              20

<210> SEQ ID NO 1566
<211> LENGTH: 20
<212> TYPE: DNA
<213> ORGANISM: Homo sapiens

<400> SEQUENCE: 1566
actcagggtg gggtctagtg                                              20

<210> SEQ ID NO 1567
<211> LENGTH: 21
<212> TYPE: DNA
<213> ORGANISM: Homo sapiens

<400> SEQUENCE: 1567
tttcctttgt gtgtgaagca g                                            21

<210> SEQ ID NO 1568
<211> LENGTH: 24
<212> TYPE: DNA
<213> ORGANISM: Homo sapiens

<400> SEQUENCE: 1568
tgctgttttg cttatctttt cttg                                         24

<210> SEQ ID NO 1569
<211> LENGTH: 24
<212> TYPE: DNA
<213> ORGANISM: Homo sapiens

<400> SEQUENCE: 1569
tggatgatca agaaatacgt caag                                         24

<210> SEQ ID NO 1570
<211> LENGTH: 22
<212> TYPE: DNA
<213> ORGANISM: Homo sapiens

<400> SEQUENCE: 1570
tggtccataa cccacatagt tg                                           22

<210> SEQ ID NO 1571
<211> LENGTH: 17
<212> TYPE: DNA
<213> ORGANISM: Homo sapiens

<400> SEQUENCE: 1571
cttagctagc gccgccg                                                 17

<210> SEQ ID NO 1572
<211> LENGTH: 20
<212> TYPE: DNA
<213> ORGANISM: Homo sapiens

<400> SEQUENCE: 1572
acaacttgcc gtgtttaccc                                              20

<210> SEQ ID NO 1573
<211> LENGTH: 21
<212> TYPE: DNA
<213> ORGANISM: Homo sapiens

<400> SEQUENCE: 1573
aggaggatgg cagaagagtt c                                              21

<210> SEQ ID NO 1574
<211> LENGTH: 20
<212> TYPE: DNA
<213> ORGANISM: Homo sapiens

<400> SEQUENCE: 1574
atctgttggg gagaatgtgg                                                20

<210> SEQ ID NO 1575
<211> LENGTH: 21
<212> TYPE: DNA
<213> ORGANISM: Homo sapiens

<400> SEQUENCE: 1575
gctctccagg tcaccataag c                                              21

<210> SEQ ID NO 1576
<211> LENGTH: 21
<212> TYPE: DNA
<213> ORGANISM: Homo sapiens

<400> SEQUENCE: 1576
tcaaggatgc tgaggaatgt c                                              21

<210> SEQ ID NO 1577
<211> LENGTH: 24
<212> TYPE: DNA
<213> ORGANISM: Homo sapiens

<400> SEQUENCE: 1577
tcctttctaa aatgaccctca cctg                                          24

<210> SEQ ID NO 1578
<211> LENGTH: 23
<212> TYPE: DNA
<213> ORGANISM: Homo sapiens

<400> SEQUENCE: 1578
caaatgtgta aagttggtgt tgc                                            23

<210> SEQ ID NO 1579
<211> LENGTH: 20
<212> TYPE: DNA
<213> ORGANISM: Homo sapiens

<400> SEQUENCE: 1579
tctccattaa cccactgagc                                                20

<210> SEQ ID NO 1580
<211> LENGTH: 22
<212> TYPE: DNA
<213> ORGANISM: Homo sapiens

<400> SEQUENCE: 1580

```
ggggttttga aggaaactat tg                                    22
```

<210> SEQ ID NO 1581
<211> LENGTH: 27
<212> TYPE: DNA
<213> ORGANISM: Homo sapiens

<400> SEQUENCE: 1581

```
tacatgcata tgcatataca tgtatcc                               27
```

<210> SEQ ID NO 1582
<211> LENGTH: 22
<212> TYPE: DNA
<213> ORGANISM: Homo sapiens

<400> SEQUENCE: 1582

```
gggctacttc tttgatttct gg                                    22
```

<210> SEQ ID NO 1583
<211> LENGTH: 23
<212> TYPE: DNA
<213> ORGANISM: Homo sapiens

<400> SEQUENCE: 1583

```
agggctactt ctttgatttc tgg                                   23
```

<210> SEQ ID NO 1584
<211> LENGTH: 20
<212> TYPE: DNA
<213> ORGANISM: Homo sapiens

<400> SEQUENCE: 1584

```
tagccccagg aaaaatgttg                                       20
```

<210> SEQ ID NO 1585
<211> LENGTH: 20
<212> TYPE: DNA
<213> ORGANISM: Homo sapiens

<400> SEQUENCE: 1585

```
tgagactcat ggctgggttc                                       20
```

<210> SEQ ID NO 1586
<211> LENGTH: 20
<212> TYPE: DNA
<213> ORGANISM: Homo sapiens

<400> SEQUENCE: 1586

```
gatcttggct cactgcaacc                                       20
```

<210> SEQ ID NO 1587
<211> LENGTH: 20
<212> TYPE: DNA
<213> ORGANISM: Homo sapiens

<400> SEQUENCE: 1587

```
actgaccttt tggcccaatc                                       20
```

<210> SEQ ID NO 1588
<211> LENGTH: 20
<212> TYPE: DNA
<213> ORGANISM: Homo sapiens

<400> SEQUENCE: 1588
gggcaacaga gtgagactcc                                            20

<210> SEQ ID NO 1589
<211> LENGTH: 26
<212> TYPE: DNA
<213> ORGANISM: Homo sapiens

<400> SEQUENCE: 1589
aaaattagat atttgtccct cagttg                                     26

<210> SEQ ID NO 1590
<211> LENGTH: 23
<212> TYPE: DNA
<213> ORGANISM: Homo sapiens

<400> SEQUENCE: 1590
tgaaacgtaa tggcttaatc aac                                        23

<210> SEQ ID NO 1591
<211> LENGTH: 19
<212> TYPE: DNA
<213> ORGANISM: Homo sapiens

<400> SEQUENCE: 1591
ggcggtgtct agtgacagg                                             19

<210> SEQ ID NO 1592
<211> LENGTH: 20
<212> TYPE: DNA
<213> ORGANISM: Homo sapiens

<400> SEQUENCE: 1592
acctatctgg aagccgaagc                                            20

<210> SEQ ID NO 1593
<211> LENGTH: 19
<212> TYPE: DNA
<213> ORGANISM: Homo sapiens

<400> SEQUENCE: 1593
gagttggagg gtggagcag                                             19

<210> SEQ ID NO 1594
<211> LENGTH: 18
<212> TYPE: DNA
<213> ORGANISM: Homo sapiens

<400> SEQUENCE: 1594
cagcctggct ctggaaag                                              18

<210> SEQ ID NO 1595
<211> LENGTH: 20
<212> TYPE: DNA
<213> ORGANISM: Homo sapiens

<400> SEQUENCE: 1595 acaggggtc acaacaagtg                                             20

<210> SEQ ID NO 1596
<211> LENGTH: 18
<212> TYPE: DNA
<213> ORGANISM: Homo sapiens

```
<400> SEQUENCE: 1596
gctgtggatg ggctggag                                              18

<210> SEQ ID NO 1597
<211> LENGTH: 19
<212> TYPE: DNA
<213> ORGANISM: Homo sapiens

<400> SEQUENCE: 1597
aggtgaggga caggtcagc                                             19

<210> SEQ ID NO 1598
<211> LENGTH: 18
<212> TYPE: DNA
<213> ORGANISM: Homo sapiens

<400> SEQUENCE: 1598
agctccatcc cccttctg                                              18

<210> SEQ ID NO 1599
<211> LENGTH: 20
<212> TYPE: DNA
<213> ORGANISM: Homo sapiens

<400> SEQUENCE: 1599
tccagtcact gtgctgcttc                                            20

<210> SEQ ID NO 1600
<211> LENGTH: 19
<212> TYPE: DNA
<213> ORGANISM: Homo sapiens

<400> SEQUENCE: 1600
ctggctacgg tgcagaaag                                             19

<210> SEQ ID NO 1601
<211> LENGTH: 24
<212> TYPE: DNA
<213> ORGANISM: Homo sapiens

<400> SEQUENCE: 1601
ttttatcttt tgaaacaat ggtg                                        24

<210> SEQ ID NO 1602
<211> LENGTH: 19
<212> TYPE: DNA
<213> ORGANISM: Homo sapiens

<400> SEQUENCE: 1602
caccatggat cagccagtc                                             19

<210> SEQ ID NO 1603
<211> LENGTH: 20
<212> TYPE: DNA
<213> ORGANISM: Homo sapiens

<400> SEQUENCE: 1603
attaagagcc caagggaac                                             20

<210> SEQ ID NO 1604
<211> LENGTH: 19
<212> TYPE: DNA
<213> ORGANISM: Homo sapiens
```

```
<400> SEQUENCE: 1604
tgtgagctcc ttccccatc                                              19

<210> SEQ ID NO 1605
<211> LENGTH: 27
<212> TYPE: DNA
<213> ORGANISM: Homo sapiens

<400> SEQUENCE: 1605
aatggtaagt tctgagtgtc tctattc                                     27

<210> SEQ ID NO 1606
<211> LENGTH: 20
<212> TYPE: DNA
<213> ORGANISM: Homo sapiens

<400> SEQUENCE: 1606
ccaaatttga atgccaaagg                                             20

<210> SEQ ID NO 1607
<211> LENGTH: 20
<212> TYPE: DNA
<213> ORGANISM: Homo sapiens

<400> SEQUENCE: 1607
aggggatgag gaggtagagc                                             20

<210> SEQ ID NO 1608
<211> LENGTH: 21
<212> TYPE: DNA
<213> ORGANISM: Homo sapiens

<400> SEQUENCE: 1608
tcattcatta ccagcctttg g                                           21

<210> SEQ ID NO 1609
<211> LENGTH: 26
<212> TYPE: DNA
<213> ORGANISM: Homo sapiens

<400> SEQUENCE: 1609
tgatttttat ttttgggtgt actgaa                                      26

<210> SEQ ID NO 1610
<211> LENGTH: 20
<212> TYPE: DNA
<213> ORGANISM: Homo sapiens

<400> SEQUENCE: 1610
ccacatttca gcaacagcag                                             20

<210> SEQ ID NO 1611
<211> LENGTH: 20
<212> TYPE: DNA
<213> ORGANISM: Homo sapiens

<400> SEQUENCE: 1611
tgatccttgc caaagacaac                                             20

<210> SEQ ID NO 1612
<211> LENGTH: 20
<212> TYPE: DNA
```

```
<213> ORGANISM: Homo sapiens

<400> SEQUENCE: 1612
gctggatgcc catacatttg                                                    20

<210> SEQ ID NO 1613
<211> LENGTH: 25
<212> TYPE: DNA
<213> ORGANISM: Homo sapiens

<400> SEQUENCE: 1613
tttccatcag ttagttgtga tcttg                                              25

<210> SEQ ID NO 1614
<211> LENGTH: 20
<212> TYPE: DNA
<213> ORGANISM: Homo sapiens

<400> SEQUENCE: 1614
tgctcaagcg taagttcctg                                                    20

<210> SEQ ID NO 1615
<211> LENGTH: 21
<212> TYPE: DNA
<213> ORGANISM: Homo sapiens

<400> SEQUENCE: 1615
cacccttggg tatttttatg g                                                  21

<210> SEQ ID NO 1616
<211> LENGTH: 20
<212> TYPE: DNA
<213> ORGANISM: Homo sapiens

<400> SEQUENCE: 1616
aagttgcctg gtgaaggaag                                                    20

<210> SEQ ID NO 1617
<211> LENGTH: 20
<212> TYPE: DNA
<213> ORGANISM: Homo sapiens

<400> SEQUENCE: 1617
tatcttgcca ggcttttcc                                                     20

<210> SEQ ID NO 1618
<211> LENGTH: 27
<212> TYPE: DNA
<213> ORGANISM: Homo sapiens

<400> SEQUENCE: 1618
cactgatagc tcatacattc aaaattc                                            27

<210> SEQ ID NO 1619
<211> LENGTH: 25
<212> TYPE: DNA
<213> ORGANISM: Homo sapiens

<400> SEQUENCE: 1619
tgaagcagat tatagatgaa tgagg                                              25

<210> SEQ ID NO 1620
<211> LENGTH: 26
```

```
<212> TYPE: DNA
<213> ORGANISM: Homo sapiens

<400> SEQUENCE: 1620
tctctctaaa ttttgaagtg aagcag                                    26

<210> SEQ ID NO 1621
<211> LENGTH: 23
<212> TYPE: DNA
<213> ORGANISM: Homo sapiens

<400> SEQUENCE: 1621
cagaccttaa atctttgcca aag                                       23

<210> SEQ ID NO 1622
<211> LENGTH: 20
<212> TYPE: DNA
<213> ORGANISM: Homo sapiens

<400> SEQUENCE: 1622
cggattcctt gcaatgtgtg                                           20

<210> SEQ ID NO 1623
<211> LENGTH: 20
<212> TYPE: DNA
<213> ORGANISM: Homo sapiens

<400> SEQUENCE: 1623
actgctggct agaggagagc                                           20

<210> SEQ ID NO 1624
<211> LENGTH: 24
<212> TYPE: DNA
<213> ORGANISM: Homo sapiens

<400> SEQUENCE: 1624
gaggtggttc attttaaact atgc                                      24

<210> SEQ ID NO 1625
<211> LENGTH: 21
<212> TYPE: DNA
<213> ORGANISM: Homo sapiens

<400> SEQUENCE: 1625
ccacgttttt cctctctttc a                                         21

<210> SEQ ID NO 1626
<211> LENGTH: 20
<212> TYPE: DNA
<213> ORGANISM: Homo sapiens

<400> SEQUENCE: 1626
tctgaggccg agtagtgtcc                                           20

<210> SEQ ID NO 1627
<211> LENGTH: 20
<212> TYPE: DNA
<213> ORGANISM: Homo sapiens

<400> SEQUENCE: 1627
gggggtagga agagatgacc                                           20

<210> SEQ ID NO 1628
```

```
<211> LENGTH: 20
<212> TYPE: DNA
<213> ORGANISM: Homo sapiens

<400> SEQUENCE: 1628
tcattggctc actgttctgg                                                   20

<210> SEQ ID NO 1629
<211> LENGTH: 20
<212> TYPE: DNA
<213> ORGANISM: Homo sapiens

<400> SEQUENCE: 1629
attggcaatt ccacctgacc                                                   20

<210> SEQ ID NO 1630
<211> LENGTH: 20
<212> TYPE: DNA
<213> ORGANISM: Homo sapiens

<400> SEQUENCE: 1630
ctgccatgtg ctgctttaac                                                   20

<210> SEQ ID NO 1631
<211> LENGTH: 18
<212> TYPE: DNA
<213> ORGANISM: Homo sapiens

<400> SEQUENCE: 1631
acggctgtga ggagcaag                                                     18

<210> SEQ ID NO 1632
<211> LENGTH: 20
<212> TYPE: DNA
<213> ORGANISM: Homo sapiens

<400> SEQUENCE: 1632
ctcatatcct gtgcccttgc                                                   20

<210> SEQ ID NO 1633
<211> LENGTH: 26
<212> TYPE: DNA
<213> ORGANISM: Homo sapiens

<400> SEQUENCE: 1633
tgtcagtgat atgtgaatga aatgac                                            26

<210> SEQ ID NO 1634
<211> LENGTH: 22
<212> TYPE: DNA
<213> ORGANISM: Homo sapiens

<400> SEQUENCE: 1634
aaccgaagag gtgattttc ag                                                 22

<210> SEQ ID NO 1635
<211> LENGTH: 24
<212> TYPE: DNA
<213> ORGANISM: Homo sapiens

<400> SEQUENCE: 1635
gaaatttcac cttaatctgt ttgg                                              24
```

```
<210> SEQ ID NO 1636
<211> LENGTH: 27
<212> TYPE: DNA
<213> ORGANISM: Homo sapiens

<400> SEQUENCE: 1636
ctagtcttta aggaaaagtc attgcat                                          27

<210> SEQ ID NO 1637
<211> LENGTH: 20
<212> TYPE: DNA
<213> ORGANISM: Homo sapiens

<400> SEQUENCE: 1637
atcctgcact tccacactcc                                                  20

<210> SEQ ID NO 1638
<211> LENGTH: 20
<212> TYPE: DNA
<213> ORGANISM: Homo sapiens

<400> SEQUENCE: 1638
atgatggagt ggaggtggag                                                  20

<210> SEQ ID NO 1639
<211> LENGTH: 20
<212> TYPE: DNA
<213> ORGANISM: Homo sapiens

<400> SEQUENCE: 1639
gccagattgg atgggtagtg                                                  20

<210> SEQ ID NO 1640
<211> LENGTH: 20
<212> TYPE: DNA
<213> ORGANISM: Homo sapiens

<400> SEQUENCE: 1640
gagctaggct tgcacagagg                                                  20

<210> SEQ ID NO 1641
<211> LENGTH: 20
<212> TYPE: DNA
<213> ORGANISM: Homo sapiens

<400> SEQUENCE: 1641
ggaggaggtg cagatgtgtc                                                  20

<210> SEQ ID NO 1642
<211> LENGTH: 20
<212> TYPE: DNA
<213> ORGANISM: Homo sapiens

<400> SEQUENCE: 1642
acccatgaac ctgggtattg                                                  20

<210> SEQ ID NO 1643
<211> LENGTH: 20
<212> TYPE: DNA
<213> ORGANISM: Homo sapiens

<400> SEQUENCE: 1643
ctctaaaatg cccccagtcc                                                  20
```

```
<210> SEQ ID NO 1644
<211> LENGTH: 20
<212> TYPE: DNA
<213> ORGANISM: Homo sapiens

<400> SEQUENCE: 1644
ggcctccttt aagggtcttg                                              20

<210> SEQ ID NO 1645
<211> LENGTH: 20
<212> TYPE: DNA
<213> ORGANISM: Homo sapiens

<400> SEQUENCE: 1645
ctgacctggt atggtcatgg                                              20

<210> SEQ ID NO 1646
<211> LENGTH: 20
<212> TYPE: DNA
<213> ORGANISM: Homo sapiens

<400> SEQUENCE: 1646
gtccaccccc ttactcattg                                              20

<210> SEQ ID NO 1647
<211> LENGTH: 19
<212> TYPE: DNA
<213> ORGANISM: Homo sapiens

<400> SEQUENCE: 1647
ctggtcacac caggctgag                                               19

<210> SEQ ID NO 1648
<211> LENGTH: 20
<212> TYPE: DNA
<213> ORGANISM: Homo sapiens

<400> SEQUENCE: 1648
ctgaaagctc agggataggg                                              20

<210> SEQ ID NO 1649
<211> LENGTH: 20
<212> TYPE: DNA
<213> ORGANISM: Homo sapiens

<400> SEQUENCE: 1649 gtggtgggggg tggatatctg                                             20

<210> SEQ ID NO 1650
<211> LENGTH: 18
<212> TYPE: DNA
<213> ORGANISM: Homo sapiens

<400> SEQUENCE: 1650
tgtggtgggc tgtccttc                                                18

<210> SEQ ID NO 1651
<211> LENGTH: 20
<212> TYPE: DNA
<213> ORGANISM: Homo sapiens

<400> SEQUENCE: 1651
aggtggagac acagccagag                                              20
```

```
<210> SEQ ID NO 1652
<211> LENGTH: 20
<212> TYPE: DNA
<213> ORGANISM: Homo sapiens

<400> SEQUENCE: 1652
actgaaacct cctcgtgtgc                                              20

<210> SEQ ID NO 1653
<211> LENGTH: 20
<212> TYPE: DNA
<213> ORGANISM: Homo sapiens

<400> SEQUENCE: 1653
gcttcctcca gcaattgacc                                              20

<210> SEQ ID NO 1654
<211> LENGTH: 20
<212> TYPE: DNA
<213> ORGANISM: Homo sapiens

<400> SEQUENCE: 1654
tcctccttca tccctgtctg                                              20

<210> SEQ ID NO 1655
<211> LENGTH: 20
<212> TYPE: DNA
<213> ORGANISM: Homo sapiens

<400> SEQUENCE: 1655
gggtacccac gaagactgac                                              20

<210> SEQ ID NO 1656
<211> LENGTH: 20
<212> TYPE: DNA
<213> ORGANISM: Homo sapiens

<400> SEQUENCE: 1656 cctcacccgtt agggcttgtg                                             20

<210> SEQ ID NO 1657
<211> LENGTH: 20
<212> TYPE: DNA
<213> ORGANISM: Homo sapiens

<400> SEQUENCE: 1657 cctcacccgtt agggcttgtg                                             20

<210> SEQ ID NO 1658
<211> LENGTH: 20
<212> TYPE: DNA
<213> ORGANISM: Homo sapiens

<400> SEQUENCE: 1658
catcttgggc aggtagaagc                                              20

<210> SEQ ID NO 1659
<211> LENGTH: 20
<212> TYPE: DNA
<213> ORGANISM: Homo sapiens

<400> SEQUENCE: 1659
```
tgggagatag tgagccttgg                                              20

<210> SEQ ID NO 1660
<211> LENGTH: 20
<212> TYPE: DNA
<213> ORGANISM: Homo sapiens

<400> SEQUENCE: 1660
cctcagcttt gatccctgtg                                              20

<210> SEQ ID NO 1661
<211> LENGTH: 20
<212> TYPE: DNA
<213> ORGANISM: Homo sapiens

<400> SEQUENCE: 1661
ccccaaggag aaaaagaagc                                              20

<210> SEQ ID NO 1662
<211> LENGTH: 25
<212> TYPE: DNA
<213> ORGANISM: Homo sapiens

<400> SEQUENCE: 1662
ttgtgtaaga atccgtttta gttcc                                        25

<210> SEQ ID NO 1663
<211> LENGTH: 20
<212> TYPE: DNA
<213> ORGANISM: Homo sapiens

<400> SEQUENCE: 1663 tccctgaag aagtgattcg                                               20

<210> SEQ ID NO 1664
<211> LENGTH: 23
<212> TYPE: DNA
<213> ORGANISM: Homo sapiens

<400> SEQUENCE: 1664
caggctacct agaattgaac acg                                          23

<210> SEQ ID NO 1665
<211> LENGTH: 21
<212> TYPE: DNA
<213> ORGANISM: Homo sapiens

<400> SEQUENCE: 1665
aggattcttt ctgagggaag g                                            21

<210> SEQ ID NO 1666
<211> LENGTH: 20
<212> TYPE: DNA
<213> ORGANISM: Homo sapiens

<400> SEQUENCE: 1666
ggattctttc tgagggaagg                                              20

<210> SEQ ID NO 1667
<211> LENGTH: 20
<212> TYPE: DNA
<213> ORGANISM: Homo sapiens

<400> SEQUENCE: 1667
tgggtacacc atgcttttg                                    20

<210> SEQ ID NO 1668
<211> LENGTH: 26
<212> TYPE: DNA
<213> ORGANISM: Homo sapiens

<400> SEQUENCE: 1668
tcagtatcca gaatgagcat tacttc                            26

<210> SEQ ID NO 1669
<211> LENGTH: 20
<212> TYPE: DNA
<213> ORGANISM: Homo sapiens

<400> SEQUENCE: 1669
gcgtcatctg atgctgtttc                                   20

<210> SEQ ID NO 1670
<211> LENGTH: 20
<212> TYPE: DNA
<213> ORGANISM: Homo sapiens

<400> SEQUENCE: 1670
tcatctgatg ctgtttcctg                                   20

<210> SEQ ID NO 1671
<211> LENGTH: 20
<212> TYPE: DNA
<213> ORGANISM: Homo sapiens

<400> SEQUENCE: 1671
gatgagtttg ctcccagctc                                   20

<210> SEQ ID NO 1672
<211> LENGTH: 20
<212> TYPE: DNA
<213> ORGANISM: Homo sapiens

<400> SEQUENCE: 1672
tggctcctag ttgcttttgg                                   20

<210> SEQ ID NO 1673
<211> LENGTH: 20
<212> TYPE: DNA
<213> ORGANISM: Homo sapiens

<400> SEQUENCE: 1673
agggcaggtg aggtacagag                                   20

<210> SEQ ID NO 1674
<211> LENGTH: 20
<212> TYPE: DNA
<213> ORGANISM: Homo sapiens

<400> SEQUENCE: 1674
agcgttggaa cgagtgtctc                                   20

<210> SEQ ID NO 1675
<211> LENGTH: 19
<212> TYPE: DNA
<213> ORGANISM: Homo sapiens

```
<400> SEQUENCE: 1675
ctatgtggcc tgggagctg                                           19

<210> SEQ ID NO 1676
<211> LENGTH: 20
<212> TYPE: DNA
<213> ORGANISM: Homo sapiens

<400> SEQUENCE: 1676
aactgtgggg acccagaaac                                          20

<210> SEQ ID NO 1677
<211> LENGTH: 20
<212> TYPE: DNA
<213> ORGANISM: Homo sapiens

<400> SEQUENCE: 1677
ctaaatccag gctccctgtg                                          20

<210> SEQ ID NO 1678
<211> LENGTH: 19
<212> TYPE: DNA
<213> ORGANISM: Homo sapiens

<400> SEQUENCE: 1678
gtgatggctg ctgtgtgtg                                           19

<210> SEQ ID NO 1679
<211> LENGTH: 20
<212> TYPE: DNA
<213> ORGANISM: Homo sapiens

<400> SEQUENCE: 1679
agagcttgga ggcagatgag                                          20

<210> SEQ ID NO 1680
<211> LENGTH: 18
<212> TYPE: DNA
<213> ORGANISM: Homo sapiens

<400> SEQUENCE: 1680
atcaccgtcc cactgctg                                            18

<210> SEQ ID NO 1681
<211> LENGTH: 18
<212> TYPE: DNA
<213> ORGANISM: Homo sapiens

<400> SEQUENCE: 1681
gatggctggt gtggcttc                                            18

<210> SEQ ID NO 1682
<211> LENGTH: 20
<212> TYPE: DNA
<213> ORGANISM: Homo sapiens

<400> SEQUENCE: 1682
ctgagccaga ccccttagtg                                          20

<210> SEQ ID NO 1683
<211> LENGTH: 18
<212> TYPE: DNA
<213> ORGANISM: Homo sapiens
```

```
<400> SEQUENCE: 1683
gtgtgtgctg gggacagg                                              18

<210> SEQ ID NO 1684
<211> LENGTH: 19
<212> TYPE: DNA
<213> ORGANISM: Homo sapiens

<400> SEQUENCE: 1684
ctgctgtcca accctcaag                                             19

<210> SEQ ID NO 1685
<211> LENGTH: 19
<212> TYPE: DNA
<213> ORGANISM: Homo sapiens

<400> SEQUENCE: 1685
gaaggtgacg tgggtggac                                             19

<210> SEQ ID NO 1686
<211> LENGTH: 18
<212> TYPE: DNA
<213> ORGANISM: Homo sapiens

<400> SEQUENCE: 1686
aaggtcagcg gaggctct                                              18

<210> SEQ ID NO 1687
<211> LENGTH: 18
<212> TYPE: DNA
<213> ORGANISM: Homo sapiens

<400> SEQUENCE: 1687
caagggcagg cagatgac                                              18

<210> SEQ ID NO 1688
<211> LENGTH: 19
<212> TYPE: DNA
<213> ORGANISM: Homo sapiens

<400> SEQUENCE: 1688
aggccttcct ggacgagac                                             19

<210> SEQ ID NO 1689
<211> LENGTH: 20
<212> TYPE: DNA
<213> ORGANISM: Homo sapiens

<400> SEQUENCE: 1689
attgtcatgg agcacgtgag                                            20

<210> SEQ ID NO 1690
<211> LENGTH: 20
<212> TYPE: DNA
<213> ORGANISM: Homo sapiens

<400> SEQUENCE: 1690
gaggctttgt gagcttgtgg                                            20

<210> SEQ ID NO 1691
<211> LENGTH: 20
<212> TYPE: DNA
```

```
<213> ORGANISM: Homo sapiens

<400> SEQUENCE: 1691 agtgaggtc aacccaggag                                          20

<210> SEQ ID NO 1692
<211> LENGTH: 20
<212> TYPE: DNA
<213> ORGANISM: Homo sapiens

<400> SEQUENCE: 1692
ggctccgtac cctaaaatgg                                         20

<210> SEQ ID NO 1693
<211> LENGTH: 21
<212> TYPE: DNA
<213> ORGANISM: Homo sapiens

<400> SEQUENCE: 1693
tgtccgtctg tctctctgtc c                                       21

<210> SEQ ID NO 1694
<211> LENGTH: 21
<212> TYPE: DNA
<213> ORGANISM: Homo sapiens

<400> SEQUENCE: 1694
tcataatgca gcctcggtaa c                                       21

<210> SEQ ID NO 1695
<211> LENGTH: 24
<212> TYPE: DNA
<213> ORGANISM: Homo sapiens

<400> SEQUENCE: 1695
tttgacagta cactgcttca gttg                                    24

<210> SEQ ID NO 1696
<211> LENGTH: 20
<212> TYPE: DNA
<213> ORGANISM: Homo sapiens

<400> SEQUENCE: 1696
agcctgggtg acagaacaag                                         20

<210> SEQ ID NO 1697
<211> LENGTH: 21
<212> TYPE: DNA
<213> ORGANISM: Homo sapiens

<400> SEQUENCE: 1697
tgggtgacag aacaagactc c                                       21

<210> SEQ ID NO 1698
<211> LENGTH: 22
<212> TYPE: DNA
<213> ORGANISM: Homo sapiens

<400> SEQUENCE: 1698
gctgaagctt taggattgtg ag                                      22

<210> SEQ ID NO 1699
<211> LENGTH: 22
```

```
<212> TYPE: DNA
<213> ORGANISM: Homo sapiens

<400> SEQUENCE: 1699
aaattattct tggccaaagt gg                                        22

<210> SEQ ID NO 1700
<211> LENGTH: 23
<212> TYPE: DNA
<213> ORGANISM: Homo sapiens

<400> SEQUENCE: 1700
tctgcctata acacaaaacc aag                                       23

<210> SEQ ID NO 1701
<211> LENGTH: 24
<212> TYPE: DNA
<213> ORGANISM: Homo sapiens

<400> SEQUENCE: 1701
ctctgcctat aacacaaaac caag                                      24

<210> SEQ ID NO 1702
<211> LENGTH: 21
<212> TYPE: DNA
<213> ORGANISM: Homo sapiens

<400> SEQUENCE: 1702
ctcagttgtg tgccttttct g                                         21

<210> SEQ ID NO 1703
<211> LENGTH: 20
<212> TYPE: DNA
<213> ORGANISM: Homo sapiens

<400> SEQUENCE: 1703
tgtaatggtg aggccacaag                                           20

<210> SEQ ID NO 1704
<211> LENGTH: 22
<212> TYPE: DNA
<213> ORGANISM: Homo sapiens

<400> SEQUENCE: 1704
ccacctcaga agtagtggaa gg                                        22

<210> SEQ ID NO 1705
<211> LENGTH: 18
<212> TYPE: DNA
<213> ORGANISM: Homo sapiens

<400> SEQUENCE: 1705
aagggccagt ggcttctc                                             18

<210> SEQ ID NO 1706
<211> LENGTH: 20
<212> TYPE: DNA
<213> ORGANISM: Homo sapiens

<400> SEQUENCE: 1706
tgagtcacca ctgtgggaag                                           20

<210> SEQ ID NO 1707
```

-continued

```
<211> LENGTH: 22
<212> TYPE: DNA
<213> ORGANISM: Homo sapiens

<400> SEQUENCE: 1707
cccccataaa ttacttgctt tg                                               22

<210> SEQ ID NO 1708
<211> LENGTH: 20
<212> TYPE: DNA
<213> ORGANISM: Homo sapiens

<400> SEQUENCE: 1708
aggtagtgca aggcgtaacc                                                  20

<210> SEQ ID NO 1709
<211> LENGTH: 20
<212> TYPE: DNA
<213> ORGANISM: Homo sapiens

<400> SEQUENCE: 1709
gaaggcacca gtgagtaggg                                                  20

<210> SEQ ID NO 1710
<211> LENGTH: 20
<212> TYPE: DNA
<213> ORGANISM: Homo sapiens

<400> SEQUENCE: 1710
acctgagcat accagggttc                                                  20

<210> SEQ ID NO 1711
<211> LENGTH: 20
<212> TYPE: DNA
<213> ORGANISM: Homo sapiens

<400> SEQUENCE: 1711
agcctctcag cctttgacag                                                  20

<210> SEQ ID NO 1712
<211> LENGTH: 25
<212> TYPE: DNA
<213> ORGANISM: Homo sapiens

<400> SEQUENCE: 1712
tctagtgaga cacacaaaca aactg                                            25

<210> SEQ ID NO 1713
<211> LENGTH: 25
<212> TYPE: DNA
<213> ORGANISM: Homo sapiens

<400> SEQUENCE: 1713
tctgaaacaa aacacatttt attgg                                            25

<210> SEQ ID NO 1714
<211> LENGTH: 24
<212> TYPE: DNA
<213> ORGANISM: Homo sapiens

<400> SEQUENCE: 1714
tccaatttgt tcctgatcct aagg                                             24
```

```
<210> SEQ ID NO 1715
<211> LENGTH: 20
<212> TYPE: DNA
<213> ORGANISM: Homo sapiens

<400> SEQUENCE: 1715
tgtgaccatc tgctgaaatg                                              20

<210> SEQ ID NO 1716
<211> LENGTH: 20
<212> TYPE: DNA
<213> ORGANISM: Homo sapiens

<400> SEQUENCE: 1716
agagcaaaag caggttggag                                              20

<210> SEQ ID NO 1717
<211> LENGTH: 20
<212> TYPE: DNA
<213> ORGANISM: Homo sapiens

<400> SEQUENCE: 1717 cagggagtg aatcaactgg                                               20

<210> SEQ ID NO 1718
<211> LENGTH: 21
<212> TYPE: DNA
<213> ORGANISM: Homo sapiens

<400> SEQUENCE: 1718
cttgccttaa tcactcccat c                                            21

<210> SEQ ID NO 1719
<211> LENGTH: 18
<212> TYPE: DNA
<213> ORGANISM: Homo sapiens

<400> SEQUENCE: 1719
gcagcggtgg tgacacag                                                18

<210> SEQ ID NO 1720
<211> LENGTH: 20
<212> TYPE: DNA
<213> ORGANISM: Homo sapiens

<400> SEQUENCE: 1720
ctacacctgt gcccaccttc                                              20

<210> SEQ ID NO 1721
<211> LENGTH: 19
<212> TYPE: DNA
<213> ORGANISM: Homo sapiens

<400> SEQUENCE: 1721
ccttcgggta aggatgtgg                                               19

<210> SEQ ID NO 1722
<211> LENGTH: 19
<212> TYPE: DNA
<213> ORGANISM: Homo sapiens

<400> SEQUENCE: 1722
tcaggaggca gaacacctg                                               19
```

<210> SEQ ID NO 1723
<211> LENGTH: 18
<212> TYPE: DNA
<213> ORGANISM: Homo sapiens

<400> SEQUENCE: 1723
cctgcccacc tccatagg                                                        18

<210> SEQ ID NO 1724
<211> LENGTH: 20
<212> TYPE: DNA
<213> ORGANISM: Homo sapiens

<400> SEQUENCE: 1724
tcatccaggt tagggagcag                                                      20

<210> SEQ ID NO 1725
<211> LENGTH: 19
<212> TYPE: DNA
<213> ORGANISM: Homo sapiens

<400> SEQUENCE: 1725
accgagtcct gtccccacc                                                       19

<210> SEQ ID NO 1726
<211> LENGTH: 20
<212> TYPE: DNA
<213> ORGANISM: Homo sapiens

<400> SEQUENCE: 1726
tttcagctgt gctgcttttg                                                      20

<210> SEQ ID NO 1727
<211> LENGTH: 20
<212> TYPE: DNA
<213> ORGANISM: Homo sapiens

<400> SEQUENCE: 1727
attctggaga ggtggggaag                                                      20

<210> SEQ ID NO 1728
<211> LENGTH: 24
<212> TYPE: DNA
<213> ORGANISM: Homo sapiens

<400> SEQUENCE: 1728
gctactatgt tagccagaat gttg                                                 24

<210> SEQ ID NO 1729
<211> LENGTH: 20
<212> TYPE: DNA
<213> ORGANISM: Homo sapiens

<400> SEQUENCE: 1729
aaaaaggttg gggaccactg                                                      20

<210> SEQ ID NO 1730
<211> LENGTH: 18
<212> TYPE: DNA
<213> ORGANISM: Homo sapiens

<400> SEQUENCE: 1730
gcgacagagc gagactcc                                                        18

<210> SEQ ID NO 1731
<211> LENGTH: 18
<212> TYPE: DNA
<213> ORGANISM: Homo sapiens

<400> SEQUENCE: 1731
gcgacagagc gagactcc                                                 18

<210> SEQ ID NO 1732
<211> LENGTH: 20
<212> TYPE: DNA
<213> ORGANISM: Homo sapiens

<400> SEQUENCE: 1732
ttctgccttc ccttcacttc                                               20

<210> SEQ ID NO 1733
<211> LENGTH: 21
<212> TYPE: DNA
<213> ORGANISM: Homo sapiens

<400> SEQUENCE: 1733
gctgggatta taggtgtgag c                                             21

<210> SEQ ID NO 1734
<211> LENGTH: 21
<212> TYPE: DNA
<213> ORGANISM: Homo sapiens

<400> SEQUENCE: 1734
agggagtagg aggtgctaag g                                             21

<210> SEQ ID NO 1735
<211> LENGTH: 22
<212> TYPE: DNA
<213> ORGANISM: Homo sapiens

<400> SEQUENCE: 1735
ttggagacat tattgcaaga gc                                            22

<210> SEQ ID NO 1736
<211> LENGTH: 23
<212> TYPE: DNA
<213> ORGANISM: Homo sapiens

<400> SEQUENCE: 1736
cttggagaca ttattgcaag agc                                           23

<210> SEQ ID NO 1737
<211> LENGTH: 20
<212> TYPE: DNA
<213> ORGANISM: Homo sapiens

<400> SEQUENCE: 1737
gctgagctca acgtagcaag                                               20

<210> SEQ ID NO 1738
<211> LENGTH: 19
<212> TYPE: DNA
<213> ORGANISM: Homo sapiens

<400> SEQUENCE: 1738
cactgggggt ggacaagac                                                19

<210> SEQ ID NO 1739
<211> LENGTH: 19
<212> TYPE: DNA
<213> ORGANISM: Homo sapiens

<400> SEQUENCE: 1739
cctctggcgg tatctgagg                                                19

<210> SEQ ID NO 1740
<211> LENGTH: 19
<212> TYPE: DNA
<213> ORGANISM: Homo sapiens

<400> SEQUENCE: 1740
ggtgctggtt ctggctctc                                                19

<210> SEQ ID NO 1741
<211> LENGTH: 20
<212> TYPE: DNA
<213> ORGANISM: Homo sapiens

<400> SEQUENCE: 1741
agcctggtga gagctaggtg                                               20

<210> SEQ ID NO 1742
<211> LENGTH: 19
<212> TYPE: DNA
<213> ORGANISM: Homo sapiens

<400> SEQUENCE: 1742
ctgggaggat gacatgcag                                                19

<210> SEQ ID NO 1743
<211> LENGTH: 20
<212> TYPE: DNA
<213> ORGANISM: Homo sapiens

<400> SEQUENCE: 1743
tgtgtgtgca tgtgtgtgtg                                               20

<210> SEQ ID NO 1744
<211> LENGTH: 20
<212> TYPE: DNA
<213> ORGANISM: Homo sapiens

<400> SEQUENCE: 1744
ctcactcaac cgggagacac                                               20

<210> SEQ ID NO 1745
<211> LENGTH: 20
<212> TYPE: DNA
<213> ORGANISM: Homo sapiens

<400> SEQUENCE: 1745
cccctagcca ggaaccttag                                               20

<210> SEQ ID NO 1746
<211> LENGTH: 18
<212> TYPE: DNA
<213> ORGANISM: Homo sapiens

<400> SEQUENCE: 1746
cctggtctgc ctgaggtg                                                    18

<210> SEQ ID NO 1747
<211> LENGTH: 20
<212> TYPE: DNA
<213> ORGANISM: Homo sapiens

<400> SEQUENCE: 1747
gtgggctctc tctcctctcc                                                  20

<210> SEQ ID NO 1748
<211> LENGTH: 20
<212> TYPE: DNA
<213> ORGANISM: Homo sapiens

<400> SEQUENCE: 1748
ggatctgggg cttccaatag                                                  20

<210> SEQ ID NO 1749
<211> LENGTH: 19
<212> TYPE: DNA
<213> ORGANISM: Homo sapiens

<400> SEQUENCE: 1749
ctgagtggag cccagagtg                                                   19

<210> SEQ ID NO 1750
<211> LENGTH: 20
<212> TYPE: DNA
<213> ORGANISM: Homo sapiens

<400> SEQUENCE: 1750
gaaggggcag agttgtcatc                                                  20

<210> SEQ ID NO 1751
<211> LENGTH: 20
<212> TYPE: DNA
<213> ORGANISM: Homo sapiens

<400> SEQUENCE: 1751
ggaacagtag ttgggggttg                                                  20

<210> SEQ ID NO 1752
<211> LENGTH: 21
<212> TYPE: DNA
<213> ORGANISM: Homo sapiens

<400> SEQUENCE: 1752
aggctcagaa ccaagttctc c                                                21

<210> SEQ ID NO 1753
<211> LENGTH: 20
<212> TYPE: DNA
<213> ORGANISM: Homo sapiens

<400> SEQUENCE: 1753
tggtaaccca gtggtgtgtg                                                  20

<210> SEQ ID NO 1754
<211> LENGTH: 20
<212> TYPE: DNA
<213> ORGANISM: Homo sapiens

```
<400> SEQUENCE: 1754
atttctgtgg ggcattccag                                        20

<210> SEQ ID NO 1755
<211> LENGTH: 23
<212> TYPE: DNA
<213> ORGANISM: Homo sapiens

<400> SEQUENCE: 1755
gcatctatgt gtgaagagtg cag                                    23

<210> SEQ ID NO 1756
<211> LENGTH: 20
<212> TYPE: DNA
<213> ORGANISM: Homo sapiens

<400> SEQUENCE: 1756
gggaagttgt tgctttttgc                                        20

<210> SEQ ID NO 1757
<211> LENGTH: 23
<212> TYPE: DNA
<213> ORGANISM: Homo sapiens

<400> SEQUENCE: 1757
tgaaattgca taacatcttc agg                                    23

<210> SEQ ID NO 1758
<211> LENGTH: 21
<212> TYPE: DNA
<213> ORGANISM: Homo sapiens

<400> SEQUENCE: 1758
tccagattgc ctttctgtct g                                      21

<210> SEQ ID NO 1759
<211> LENGTH: 18
<212> TYPE: DNA
<213> ORGANISM: Homo sapiens

<400> SEQUENCE: 1759
cccattgagc tggacacc                                          18

<210> SEQ ID NO 1760
<211> LENGTH: 18
<212> TYPE: DNA
<213> ORGANISM: Homo sapiens

<400> SEQUENCE: 1760
gtgtcagggg ccaccatc                                          18

<210> SEQ ID NO 1761
<211> LENGTH: 19
<212> TYPE: DNA
<213> ORGANISM: Homo sapiens

<400> SEQUENCE: 1761
caggcatctc accatgctc                                         19

<210> SEQ ID NO 1762
<211> LENGTH: 20
<212> TYPE: DNA
<213> ORGANISM: Homo sapiens
```

```
<400> SEQUENCE: 1762
tttggaccct gcttgaactc                                               20

<210> SEQ ID NO 1763
<211> LENGTH: 20
<212> TYPE: DNA
<213> ORGANISM: Homo sapiens

<400> SEQUENCE: 1763
accaacccaa gtggatgaag                                               20

<210> SEQ ID NO 1764
<211> LENGTH: 20
<212> TYPE: DNA
<213> ORGANISM: Homo sapiens

<400> SEQUENCE: 1764
tgtgaggaga ggagacatgc                                               20

<210> SEQ ID NO 1765
<211> LENGTH: 21
<212> TYPE: DNA
<213> ORGANISM: Homo sapiens

<400> SEQUENCE: 1765
ttgtgaggag aggagacatg c                                             21

<210> SEQ ID NO 1766
<211> LENGTH: 21
<212> TYPE: DNA
<213> ORGANISM: Homo sapiens

<400> SEQUENCE: 1766
ggggccttga gaattaacat c                                             21

<210> SEQ ID NO 1767
<211> LENGTH: 22
<212> TYPE: DNA
<213> ORGANISM: Homo sapiens

<400> SEQUENCE: 1767
tgcccaactt tatttctttt cc                                            22

<210> SEQ ID NO 1768
<211> LENGTH: 20
<212> TYPE: DNA
<213> ORGANISM: Homo sapiens

<400> SEQUENCE: 1768
ggactgcctc tccttgtctg                                               20

<210> SEQ ID NO 1769
<211> LENGTH: 20
<212> TYPE: DNA
<213> ORGANISM: Homo sapiens

<400> SEQUENCE: 1769
cttcattgcc tttttcatgg                                               20

<210> SEQ ID NO 1770
<211> LENGTH: 28
<212> TYPE: DNA
```

<213> ORGANISM: Homo sapiens

<400> SEQUENCE: 1770
actactctgt gaatatacta aaacccac                      28

<210> SEQ ID NO 1771
<211> LENGTH: 20
<212> TYPE: DNA
<213> ORGANISM: Homo sapiens

<400> SEQUENCE: 1771
gcctggaagc tcaggtacag                               20

<210> SEQ ID NO 1772
<211> LENGTH: 21
<212> TYPE: DNA
<213> ORGANISM: Homo sapiens

<400> SEQUENCE: 1772
ggctgttttc tcatcttttg c                             21

<210> SEQ ID NO 1773
<211> LENGTH: 19
<212> TYPE: DNA
<213> ORGANISM: Homo sapiens

<400> SEQUENCE: 1773 gtggggtga ggagcttag                                 19

<210> SEQ ID NO 1774
<211> LENGTH: 19
<212> TYPE: DNA
<213> ORGANISM: Homo sapiens

<400> SEQUENCE: 1774
aaacagtgtc ccccagcag                                19

<210> SEQ ID NO 1775
<211> LENGTH: 20
<212> TYPE: DNA
<213> ORGANISM: Homo sapiens

<400> SEQUENCE: 1775
aaaagccctc tcttctgctg                               20

<210> SEQ ID NO 1776
<211> LENGTH: 21
<212> TYPE: DNA
<213> ORGANISM: Homo sapiens

<400> SEQUENCE: 1776
tgtgtcttct cccacatacg g                             21

<210> SEQ ID NO 1777
<211> LENGTH: 20
<212> TYPE: DNA
<213> ORGANISM: Homo sapiens

<400> SEQUENCE: 1777
ttttcatctg gtgtggatgc                               20

<210> SEQ ID NO 1778
<211> LENGTH: 21

-continued

<212> TYPE: DNA
<213> ORGANISM: Homo sapiens

<400> SEQUENCE: 1778
ttgatggtga ctgagggtag c                                           21

<210> SEQ ID NO 1779
<211> LENGTH: 20
<212> TYPE: DNA
<213> ORGANISM: Homo sapiens

<400> SEQUENCE: 1779
ggcaatttcc acagcacatc                                             20

<210> SEQ ID NO 1780
<211> LENGTH: 20
<212> TYPE: DNA
<213> ORGANISM: Homo sapiens

<400> SEQUENCE: 1780
ttctttcctg ttccccaaag                                             20

<210> SEQ ID NO 1781
<211> LENGTH: 21
<212> TYPE: DNA
<213> ORGANISM: Homo sapiens

<400> SEQUENCE: 1781
cctgttcccc aaagttttca g                                           21

<210> SEQ ID NO 1782
<211> LENGTH: 19
<212> TYPE: DNA
<213> ORGANISM: Homo sapiens

<400> SEQUENCE: 1782
ttgtggagcc acagctcag                                              19

<210> SEQ ID NO 1783
<211> LENGTH: 20
<212> TYPE: DNA
<213> ORGANISM: Homo sapiens

<400> SEQUENCE: 1783
tctcagaaag ggtgggtctc                                             20

<210> SEQ ID NO 1784
<211> LENGTH: 21
<212> TYPE: DNA
<213> ORGANISM: Homo sapiens

<400> SEQUENCE: 1784
ttgccatacc atgtcttcct c                                           21

<210> SEQ ID NO 1785
<211> LENGTH: 20
<212> TYPE: DNA
<213> ORGANISM: Homo sapiens

<400> SEQUENCE: 1785
ttgggtggct tcattctctc                                             20

<210> SEQ ID NO 1786

```
<211> LENGTH: 19
<212> TYPE: DNA
<213> ORGANISM: Homo sapiens

<400> SEQUENCE: 1786
gagactgctg caggaaacg                                                   19

<210> SEQ ID NO 1787
<211> LENGTH: 20
<212> TYPE: DNA
<213> ORGANISM: Homo sapiens

<400> SEQUENCE: 1787
agggtggtga aggatgtttg                                                  20

<210> SEQ ID NO 1788
<211> LENGTH: 20
<212> TYPE: DNA
<213> ORGANISM: Homo sapiens

<400> SEQUENCE: 1788
gctgtggttt gtgatggttg                                                  20

<210> SEQ ID NO 1789
<211> LENGTH: 20
<212> TYPE: DNA
<213> ORGANISM: Homo sapiens

<400> SEQUENCE: 1789
tatgtccaca aggggctagg                                                  20

<210> SEQ ID NO 1790
<211> LENGTH: 20
<212> TYPE: DNA
<213> ORGANISM: Homo sapiens

<400> SEQUENCE: 1790
taggatgggg actcttgctg                                                  20

<210> SEQ ID NO 1791
<211> LENGTH: 20
<212> TYPE: DNA
<213> ORGANISM: Homo sapiens

<400> SEQUENCE: 1791
tagcccatgg gagaactctg                                                  20

<210> SEQ ID NO 1792
<211> LENGTH: 20
<212> TYPE: DNA
<213> ORGANISM: Homo sapiens

<400> SEQUENCE: 1792
ctcctgagca gaacctctgg                                                  20

<210> SEQ ID NO 1793
<211> LENGTH: 18
<212> TYPE: DNA
<213> ORGANISM: Homo sapiens

<400> SEQUENCE: 1793
agactggagg gggagtgg                                                    18
```

```
<210> SEQ ID NO 1794
<211> LENGTH: 20
<212> TYPE: DNA
<213> ORGANISM: Homo sapiens

<400> SEQUENCE: 1794
tgggaaggag agatgagtcc                                              20

<210> SEQ ID NO 1795
<211> LENGTH: 20
<212> TYPE: DNA
<213> ORGANISM: Homo sapiens

<400> SEQUENCE: 1795
ttaaggctca gccaaactgg                                              20

<210> SEQ ID NO 1796
<211> LENGTH: 20
<212> TYPE: DNA
<213> ORGANISM: Homo sapiens

<400> SEQUENCE: 1796
aggacgagta tgcgctgaag                                              20

<210> SEQ ID NO 1797
<211> LENGTH: 21
<212> TYPE: DNA
<213> ORGANISM: Homo sapiens

<400> SEQUENCE: 1797
tgaggagcag agtcagaatc c                                            21

<210> SEQ ID NO 1798
<211> LENGTH: 20
<212> TYPE: DNA
<213> ORGANISM: Homo sapiens

<400> SEQUENCE: 1798
ttccattgtc agcattgcac                                              20

<210> SEQ ID NO 1799
<211> LENGTH: 20
<212> TYPE: DNA
<213> ORGANISM: Homo sapiens

<400> SEQUENCE: 1799
atcccttctg aggtctgctg                                              20

<210> SEQ ID NO 1800
<211> LENGTH: 21
<212> TYPE: DNA
<213> ORGANISM: Homo sapiens

<400> SEQUENCE: 1800
caggattgga atgttgcttt c                                            21

<210> SEQ ID NO 1801
<211> LENGTH: 20
<212> TYPE: DNA
<213> ORGANISM: Homo sapiens

<400> SEQUENCE: 1801
agaatcggat cctggggtag                                              20
```

<210> SEQ ID NO 1802
<211> LENGTH: 20
<212> TYPE: DNA
<213> ORGANISM: Homo sapiens

<400> SEQUENCE: 1802
ggtattccga aaggatctgc                                              20

<210> SEQ ID NO 1803
<211> LENGTH: 20
<212> TYPE: DNA
<213> ORGANISM: Homo sapiens

<400> SEQUENCE: 1803
ctctgctggg ctcaaggtag                                              20

<210> SEQ ID NO 1804
<211> LENGTH: 18
<212> TYPE: DNA
<213> ORGANISM: Homo sapiens

<400> SEQUENCE: 1804
ctcctggctg ctcaggtc                                                18

<210> SEQ ID NO 1805
<211> LENGTH: 20
<212> TYPE: DNA
<213> ORGANISM: Homo sapiens

<400> SEQUENCE: 1805
gtctcaggtg agggcttcag                                              20

<210> SEQ ID NO 1806
<211> LENGTH: 20
<212> TYPE: DNA
<213> ORGANISM: Homo sapiens

<400> SEQUENCE: 1806
ccctgtgagg tgagacttcc                                              20

<210> SEQ ID NO 1807
<211> LENGTH: 24
<212> TYPE: DNA
<213> ORGANISM: Homo sapiens

<400> SEQUENCE: 1807
ttgcatttct tagcactcac tctc                                         24

<210> SEQ ID NO 1808
<211> LENGTH: 29
<212> TYPE: DNA
<213> ORGANISM: Homo sapiens

<400> SEQUENCE: 1808
acctgataca taaatatgtt cttatcatg                                    29

<210> SEQ ID NO 1809
<211> LENGTH: 27
<212> TYPE: DNA
<213> ORGANISM: Homo sapiens

<400> SEQUENCE: 1809
tttcattact cttaaatgcc atatttc                                      27

<210> SEQ ID NO 1810
<211> LENGTH: 20
<212> TYPE: DNA
<213> ORGANISM: Homo sapiens

<400> SEQUENCE: 1810 cctttacac aggggaggtg                      20

<210> SEQ ID NO 1811
<211> LENGTH: 20
<212> TYPE: DNA
<213> ORGANISM: Homo sapiens

<400> SEQUENCE: 1811
ggcctatggt gacctcaatg                      20

<210> SEQ ID NO 1812
<211> LENGTH: 20
<212> TYPE: DNA
<213> ORGANISM: Homo sapiens

<400> SEQUENCE: 1812
gtgaggagca tggttgtttg                      20

<210> SEQ ID NO 1813
<211> LENGTH: 20
<212> TYPE: DNA
<213> ORGANISM: Homo sapiens

<400> SEQUENCE: 1813
tcccaaagtg ctgggattac                      20

<210> SEQ ID NO 1814
<211> LENGTH: 21
<212> TYPE: DNA
<213> ORGANISM: Homo sapiens

<400> SEQUENCE: 1814
ctccttcatg tcttggagtg g                    21

<210> SEQ ID NO 1815
<211> LENGTH: 26
<212> TYPE: DNA
<213> ORGANISM: Homo sapiens

<400> SEQUENCE: 1815
tgcaaaagtt aaactgtgat tattgg               26

<210> SEQ ID NO 1816
<211> LENGTH: 22
<212> TYPE: DNA
<213> ORGANISM: Homo sapiens

<400> SEQUENCE: 1816
agatcatgtt cttggaagga tg                   22

<210> SEQ ID NO 1817
<211> LENGTH: 20
<212> TYPE: DNA
<213> ORGANISM: Homo sapiens

<400> SEQUENCE: 1817

```
caggtatttc cgtgggactg                                              20

<210> SEQ ID NO 1818
<211> LENGTH: 22
<212> TYPE: DNA
<213> ORGANISM: Homo sapiens

<400> SEQUENCE: 1818
gggtcactca ttagtgccta tc                                           22

<210> SEQ ID NO 1819
<211> LENGTH: 21
<212> TYPE: DNA
<213> ORGANISM: Homo sapiens

<400> SEQUENCE: 1819
gcagtgtgtg actcaggatt g                                            21

<210> SEQ ID NO 1820
<211> LENGTH: 20
<212> TYPE: DNA
<213> ORGANISM: Homo sapiens

<400> SEQUENCE: 1820 tttggghhtgg gagaagagac                                             20
```

```
tttgggttgg gagaagagac                                              20

<210> SEQ ID NO 1821
<211> LENGTH: 24
<212> TYPE: DNA
<213> ORGANISM: Homo sapiens

<400> SEQUENCE: 1821
gaaatgtctg aaaggaggtt catc                                         24

<210> SEQ ID NO 1822
<211> LENGTH: 22
<212> TYPE: DNA
<213> ORGANISM: Homo sapiens

<400> SEQUENCE: 1822
caggtgatct tttaatgcct tg                                           22

<210> SEQ ID NO 1823
<211> LENGTH: 26
<212> TYPE: DNA
<213> ORGANISM: Homo sapiens

<400> SEQUENCE: 1823
tgtcatttaa aaagaaaatt tacacg                                       26

<210> SEQ ID NO 1824
<211> LENGTH: 27
<212> TYPE: DNA
<213> ORGANISM: Homo sapiens

<400> SEQUENCE: 1824
atgtcattta aaagaaaat ttacacg                                       27

<210> SEQ ID NO 1825
<211> LENGTH: 19
<212> TYPE: DNA
<213> ORGANISM: Homo sapiens

<400> SEQUENCE: 1825
```
ggtggggact ggatgaatg                                    19

<210> SEQ ID NO 1826
<211> LENGTH: 20
<212> TYPE: DNA
<213> ORGANISM: Homo sapiens

<400> SEQUENCE: 1826
tagtttgggc atgtgtaggc                                   20

<210> SEQ ID NO 1827
<211> LENGTH: 20
<212> TYPE: DNA
<213> ORGANISM: Homo sapiens

<400> SEQUENCE: 1827
gaagattttg gctggaggtg                                   20

<210> SEQ ID NO 1828
<211> LENGTH: 18
<212> TYPE: DNA
<213> ORGANISM: Homo sapiens

<400> SEQUENCE: 1828
gcagcaccga tgatgacc                                     18

<210> SEQ ID NO 1829
<211> LENGTH: 20
<212> TYPE: DNA
<213> ORGANISM: Homo sapiens

<400> SEQUENCE: 1829
aaacaaggag ggcaagaatg                                   20

<210> SEQ ID NO 1830
<211> LENGTH: 20
<212> TYPE: DNA
<213> ORGANISM: Homo sapiens

<400> SEQUENCE: 1830
gctggttggt ttgaggtttc                                   20

<210> SEQ ID NO 1831
<211> LENGTH: 20
<212> TYPE: DNA
<213> ORGANISM: Homo sapiens

<400> SEQUENCE: 1831
cagttgaggg actggtttcc                                   20

<210> SEQ ID NO 1832
<211> LENGTH: 23
<212> TYPE: DNA
<213> ORGANISM: Homo sapiens

<400> SEQUENCE: 1832
tgttggtttg ttttatgttt tgc                               23

<210> SEQ ID NO 1833
<211> LENGTH: 21
<212> TYPE: DNA
<213> ORGANISM: Homo sapiens

```
<400> SEQUENCE: 1833
cacagcatgt gaaatggatt c                                             21

<210> SEQ ID NO 1834
<211> LENGTH: 21
<212> TYPE: DNA
<213> ORGANISM: Homo sapiens

<400> SEQUENCE: 1834
ccgtatgtta tctgggaggt g                                             21

<210> SEQ ID NO 1835
<211> LENGTH: 20
<212> TYPE: DNA
<213> ORGANISM: Homo sapiens

<400> SEQUENCE: 1835
tgaattgtcc cctcttggtc                                               20

<210> SEQ ID NO 1836
<211> LENGTH: 20
<212> TYPE: DNA
<213> ORGANISM: Homo sapiens

<400> SEQUENCE: 1836
tgacagccct cccttttgtag                                              20

<210> SEQ ID NO 1837
<211> LENGTH: 22
<212> TYPE: DNA
<213> ORGANISM: Homo sapiens

<400> SEQUENCE: 1837
caaccaagat tgtgcaaatg ac                                            22

<210> SEQ ID NO 1838
<211> LENGTH: 24
<212> TYPE: DNA
<213> ORGANISM: Homo sapiens

<400> SEQUENCE: 1838
cgattatttt ggtcaacttg aatg                                          24

<210> SEQ ID NO 1839
<211> LENGTH: 25
<212> TYPE: DNA
<213> ORGANISM: Homo sapiens

<400> SEQUENCE: 1839
aagacagtct gctaattcca gctac                                         25

<210> SEQ ID NO 1840
<211> LENGTH: 33
<212> TYPE: DNA
<213> ORGANISM: Homo sapiens

<400> SEQUENCE: 1840 ataaagttttt gtcatcttag atttcatata tgt                               33

<210> SEQ ID NO 1841
<211> LENGTH: 27
<212> TYPE: DNA
<213> ORGANISM: Homo sapiens
```

```
<400> SEQUENCE: 1841 ataaaggaa tatatagggt taagacc                                          27

<210> SEQ ID NO 1842
<211> LENGTH: 24
<212> TYPE: DNA
<213> ORGANISM: Homo sapiens

<400> SEQUENCE: 1842
aaaataggcc tgattattca aatg                                            24

<210> SEQ ID NO 1843
<211> LENGTH: 21
<212> TYPE: DNA
<213> ORGANISM: Homo sapiens

<400> SEQUENCE: 1843
aggcctgctg tgataactct t                                               21

<210> SEQ ID NO 1844
<211> LENGTH: 22
<212> TYPE: DNA
<213> ORGANISM: Homo sapiens

<400> SEQUENCE: 1844
ccattgactg gaggaaattg ag                                              22

<210> SEQ ID NO 1845
<211> LENGTH: 22
<212> TYPE: DNA
<213> ORGANISM: Homo sapiens

<400> SEQUENCE: 1845
ttatgacatg tgccctgtat tg                                              22

<210> SEQ ID NO 1846
<211> LENGTH: 20
<212> TYPE: DNA
<213> ORGANISM: Homo sapiens

<400> SEQUENCE: 1846
tgcttccact gctctctagc                                                 20

<210> SEQ ID NO 1847
<211> LENGTH: 26
<212> TYPE: DNA
<213> ORGANISM: Homo sapiens

<400> SEQUENCE: 1847
aagagaaagg tcctcttatg tagtgg                                          26

<210> SEQ ID NO 1848
<211> LENGTH: 20
<212> TYPE: DNA
<213> ORGANISM: Homo sapiens

<400> SEQUENCE: 1848 cagggtggg aaggatagac                                                  20

<210> SEQ ID NO 1849
<211> LENGTH: 20
<212> TYPE: DNA
```

```
<213> ORGANISM: Homo sapiens

<400> SEQUENCE: 1849
agctagccag tgcccatctc                                               20

<210> SEQ ID NO 1850
<211> LENGTH: 20
<212> TYPE: DNA
<213> ORGANISM: Homo sapiens

<400> SEQUENCE: 1850
tatagggatg agcccaggtg                                               20

<210> SEQ ID NO 1851
<211> LENGTH: 20
<212> TYPE: DNA
<213> ORGANISM: Homo sapiens

<400> SEQUENCE: 1851
acctcagccc caaaggtaag                                               20

<210> SEQ ID NO 1852
<211> LENGTH: 20
<212> TYPE: DNA
<213> ORGANISM: Homo sapiens

<400> SEQUENCE: 1852
aacagttgca gcttcaggag                                               20

<210> SEQ ID NO 1853
<211> LENGTH: 20
<212> TYPE: DNA
<213> ORGANISM: Homo sapiens

<400> SEQUENCE: 1853
gatagcccct gcactaccac                                               20

<210> SEQ ID NO 1854
<211> LENGTH: 27
<212> TYPE: DNA
<213> ORGANISM: Homo sapiens

<400> SEQUENCE: 1854
gtcagtcttg ttacaaaatt caatatg                                       27

<210> SEQ ID NO 1855
<211> LENGTH: 21
<212> TYPE: DNA
<213> ORGANISM: Homo sapiens

<400> SEQUENCE: 1855
tgagaaattc tgtccggttt c                                             21

<210> SEQ ID NO 1856
<211> LENGTH: 19
<212> TYPE: DNA
<213> ORGANISM: Homo sapiens

<400> SEQUENCE: 1856
cgcccatgaa aacgtaaac                                                19

<210> SEQ ID NO 1857
<211> LENGTH: 20
```

```
<212> TYPE: DNA
<213> ORGANISM: Homo sapiens

<400> SEQUENCE: 1857
ccgcccatga aaacgtaaac                                              20

<210> SEQ ID NO 1858
<211> LENGTH: 20
<212> TYPE: DNA
<213> ORGANISM: Homo sapiens

<400> SEQUENCE: 1858
ttcctgccga tgttagtgtc                                              20

<210> SEQ ID NO 1859
<211> LENGTH: 21
<212> TYPE: DNA
<213> ORGANISM: Homo sapiens

<400> SEQUENCE: 1859
gttcctgccg atgttagtgt c                                            21

<210> SEQ ID NO 1860
<211> LENGTH: 24
<212> TYPE: DNA
<213> ORGANISM: Homo sapiens

<400> SEQUENCE: 1860
tgcaaattgt gctaattgaa aatc                                         24

<210> SEQ ID NO 1861
<211> LENGTH: 19
<212> TYPE: DNA
<213> ORGANISM: Homo sapiens

<400> SEQUENCE: 1861
tgcaccttat ggggtaggg                                               19

<210> SEQ ID NO 1862
<211> LENGTH: 24
<212> TYPE: DNA
<213> ORGANISM: Homo sapiens

<400> SEQUENCE: 1862
caaaggcaca aatattttaa atgg                                         24

<210> SEQ ID NO 1863
<211> LENGTH: 27
<212> TYPE: DNA
<213> ORGANISM: Homo sapiens

<400> SEQUENCE: 1863
tctctataat cctcaggtaa atccaac                                      27

<210> SEQ ID NO 1864
<211> LENGTH: 25
<212> TYPE: DNA
<213> ORGANISM: Homo sapiens

<400> SEQUENCE: 1864
gaaaaataat tcaacgcatt tactc                                        25

<210> SEQ ID NO 1865
```

```
<211> LENGTH: 21
<212> TYPE: DNA
<213> ORGANISM: Homo sapiens

<400> SEQUENCE: 1865
catgtgtttt attgggggat g                                             21

<210> SEQ ID NO 1866
<211> LENGTH: 21
<212> TYPE: DNA
<213> ORGANISM: Homo sapiens

<400> SEQUENCE: 1866
gcacgcagat atttttcatg g                                             21

<210> SEQ ID NO 1867
<211> LENGTH: 21
<212> TYPE: DNA
<213> ORGANISM: Homo sapiens

<400> SEQUENCE: 1867
gatgctgctg aactaccaac c                                             21

<210> SEQ ID NO 1868
<211> LENGTH: 20
<212> TYPE: DNA
<213> ORGANISM: Homo sapiens

<400> SEQUENCE: 1868
tgtgcctcat tcttctctgg                                               20

<210> SEQ ID NO 1869
<211> LENGTH: 22
<212> TYPE: DNA
<213> ORGANISM: Homo sapiens

<400> SEQUENCE: 1869
ttttatatgg gccaaaacat tc                                            22

<210> SEQ ID NO 1870
<211> LENGTH: 24
<212> TYPE: DNA
<213> ORGANISM: Homo sapiens

<400> SEQUENCE: 1870
aaacagttga tgacagttta gtgc                                          24

<210> SEQ ID NO 1871
<211> LENGTH: 26
<212> TYPE: DNA
<213> ORGANISM: Homo sapiens

<400> SEQUENCE: 1871
ttaaacagtt gatgacagtt tagtgc                                        26

<210> SEQ ID NO 1872
<211> LENGTH: 19
<212> TYPE: DNA
<213> ORGANISM: Homo sapiens

<400> SEQUENCE: 1872
atggaggaca cagcccttc                                                19
```

```
<210> SEQ ID NO 1873
<211> LENGTH: 20
<212> TYPE: DNA
<213> ORGANISM: Homo sapiens

<400> SEQUENCE: 1873
caggggtagg aagcagaatg                                               20

<210> SEQ ID NO 1874
<211> LENGTH: 19
<212> TYPE: DNA
<213> ORGANISM: Homo sapiens

<400> SEQUENCE: 1874
cttggaggcc aagctcttc                                                19

<210> SEQ ID NO 1875
<211> LENGTH: 18
<212> TYPE: DNA
<213> ORGANISM: Homo sapiens

<400> SEQUENCE: 1875
agcttgtgca gggtgagc                                                 18

<210> SEQ ID NO 1876
<211> LENGTH: 20
<212> TYPE: DNA
<213> ORGANISM: Homo sapiens

<400> SEQUENCE: 1876
gcttttgtcc ttggctttcc                                               20

<210> SEQ ID NO 1877
<211> LENGTH: 20
<212> TYPE: DNA
<213> ORGANISM: Homo sapiens

<400> SEQUENCE: 1877
tccctgtcta ccctggactc                                               20

<210> SEQ ID NO 1878
<211> LENGTH: 20
<212> TYPE: DNA
<213> ORGANISM: Homo sapiens

<400> SEQUENCE: 1878
tcatggtatc ccccagagtc                                               20

<210> SEQ ID NO 1879
<211> LENGTH: 20
<212> TYPE: DNA
<213> ORGANISM: Homo sapiens

<400> SEQUENCE: 1879
tagcttgcca agtgcctttc                                               20

<210> SEQ ID NO 1880
<211> LENGTH: 20
<212> TYPE: DNA
<213> ORGANISM: Homo sapiens

<400> SEQUENCE: 1880
cacatgcaga cgcaaagaag                                               20
```

```
<210> SEQ ID NO 1881
<211> LENGTH: 20
<212> TYPE: DNA
<213> ORGANISM: Homo sapiens

<400> SEQUENCE: 1881
gaggagaggg gaattcatgg                                              20

<210> SEQ ID NO 1882
<211> LENGTH: 20
<212> TYPE: DNA
<213> ORGANISM: Homo sapiens

<400> SEQUENCE: 1882
atgtgtgtgt gcatccttgg                                              20

<210> SEQ ID NO 1883
<211> LENGTH: 19
<212> TYPE: DNA
<213> ORGANISM: Homo sapiens

<400> SEQUENCE: 1883
gccgctagtg tgggtttac                                               19

<210> SEQ ID NO 1884
<211> LENGTH: 22
<212> TYPE: DNA
<213> ORGANISM: Homo sapiens

<400> SEQUENCE: 1884
caaatagctg gtggtcaaaa cc                                           22

<210> SEQ ID NO 1885
<211> LENGTH: 24
<212> TYPE: DNA
<213> ORGANISM: Homo sapiens

<400> SEQUENCE: 1885
aagaaaacca aatacagctc tctg                                         24

<210> SEQ ID NO 1886
<211> LENGTH: 20
<212> TYPE: DNA
<213> ORGANISM: Homo sapiens

<400> SEQUENCE: 1886
tgcagggtaa cttgatgtgc                                              20

<210> SEQ ID NO 1887
<211> LENGTH: 20
<212> TYPE: DNA
<213> ORGANISM: Homo sapiens

<400> SEQUENCE: 1887
caagtgggtt ttgaaggatg                                              20

<210> SEQ ID NO 1888
<211> LENGTH: 20
<212> TYPE: DNA
<213> ORGANISM: Homo sapiens

<400> SEQUENCE: 1888
agttcctgga ggtggaggag                                              20
```

<210> SEQ ID NO 1889
<211> LENGTH: 20
<212> TYPE: DNA
<213> ORGANISM: Homo sapiens

<400> SEQUENCE: 1889
aagggcagac tgacatccag                                           20

<210> SEQ ID NO 1890
<211> LENGTH: 20
<212> TYPE: DNA
<213> ORGANISM: Homo sapiens

<400> SEQUENCE: 1890
tatgcagatg gaggttgcac                                           20

<210> SEQ ID NO 1891
<211> LENGTH: 19
<212> TYPE: DNA
<213> ORGANISM: Homo sapiens

<400> SEQUENCE: 1891
agctgggcaa ggtaaggtg                                            19

<210> SEQ ID NO 1892
<211> LENGTH: 19
<212> TYPE: DNA
<213> ORGANISM: Homo sapiens

<400> SEQUENCE: 1892
acagctgggc aaggtaagg                                            19

<210> SEQ ID NO 1893
<211> LENGTH: 20
<212> TYPE: DNA
<213> ORGANISM: Homo sapiens

<400> SEQUENCE: 1893
gcaaaactga ggtcgagagg                                           20

<210> SEQ ID NO 1894
<211> LENGTH: 20
<212> TYPE: DNA
<213> ORGANISM: Homo sapiens

<400> SEQUENCE: 1894
gaggtcgaga gggacacaag                                           20

<210> SEQ ID NO 1895
<211> LENGTH: 20
<212> TYPE: DNA
<213> ORGANISM: Homo sapiens

<400> SEQUENCE: 1895
atagttgggg tctgggttgg                                           20

<210> SEQ ID NO 1896
<211> LENGTH: 20
<212> TYPE: DNA
<213> ORGANISM: Homo sapiens

<400> SEQUENCE: 1896

```
cacctaccct gaccagttcc                                          20

<210> SEQ ID NO 1897
<211> LENGTH: 19
<212> TYPE: DNA
<213> ORGANISM: Homo sapiens

<400> SEQUENCE: 1897
atcacagatg gccectacc                                           19

<210> SEQ ID NO 1898
<211> LENGTH: 20
<212> TYPE: DNA
<213> ORGANISM: Homo sapiens

<400> SEQUENCE: 1898
gtcacttggg aggaaggttg                                          20

<210> SEQ ID NO 1899
<211> LENGTH: 20
<212> TYPE: DNA
<213> ORGANISM: Homo sapiens

<400> SEQUENCE: 1899
tgggaagcct aggacatctg                                          20

<210> SEQ ID NO 1900
<211> LENGTH: 20
<212> TYPE: DNA
<213> ORGANISM: Homo sapiens

<400> SEQUENCE: 1900
ctagagatgg gacccagcag                                          20

<210> SEQ ID NO 1901
<211> LENGTH: 20
<212> TYPE: DNA
<213> ORGANISM: Homo sapiens

<400> SEQUENCE: 1901
tccagtgatt ctggggacag                                          20

<210> SEQ ID NO 1902
<211> LENGTH: 20
<212> TYPE: DNA
<213> ORGANISM: Homo sapiens

<400> SEQUENCE: 1902
ctatgcatgg gggtagcttg                                          20

<210> SEQ ID NO 1903
<211> LENGTH: 20
<212> TYPE: DNA
<213> ORGANISM: Homo sapiens

<400> SEQUENCE: 1903
ccaggttgtg cttgtctcag                                          20

<210> SEQ ID NO 1904
<211> LENGTH: 22
<212> TYPE: DNA
<213> ORGANISM: Homo sapiens

<400> SEQUENCE: 1904
```

```
ccctagtgcc atatgatgaa gg                                          22

<210> SEQ ID NO 1905
<211> LENGTH: 23
<212> TYPE: DNA
<213> ORGANISM: Homo sapiens

<400> SEQUENCE: 1905
aaccctagtg ccatatgatg aag                                         23

<210> SEQ ID NO 1906
<211> LENGTH: 29
<212> TYPE: DNA
<213> ORGANISM: Homo sapiens

<400> SEQUENCE: 1906
cagtagtgtt aagtatattc acattgttg                                   29

<210> SEQ ID NO 1907
<211> LENGTH: 20
<212> TYPE: DNA
<213> ORGANISM: Homo sapiens

<400> SEQUENCE: 1907
ctttccactg gctcaaatgc                                             20

<210> SEQ ID NO 1908
<211> LENGTH: 20
<212> TYPE: DNA
<213> ORGANISM: Homo sapiens

<400> SEQUENCE: 1908
aagcacctcc tcctctttgg                                             20

<210> SEQ ID NO 1909
<211> LENGTH: 26
<212> TYPE: DNA
<213> ORGANISM: Homo sapiens

<400> SEQUENCE: 1909
aggctttact cgtttgtata catcca                                      26

<210> SEQ ID NO 1910
<211> LENGTH: 23
<212> TYPE: DNA
<213> ORGANISM: Homo sapiens

<400> SEQUENCE: 1910
tgtgtaatgc attttgctct gtc                                         23

<210> SEQ ID NO 1911
<211> LENGTH: 23
<212> TYPE: DNA
<213> ORGANISM: Homo sapiens

<400> SEQUENCE: 1911
caaatgtgta atgcattttg ctc                                         23

<210> SEQ ID NO 1912
<211> LENGTH: 23
<212> TYPE: DNA
<213> ORGANISM: Homo sapiens
```

-continued

```
<400> SEQUENCE: 1912
tgcaaatgta aaatgcaaa gtg                                          23

<210> SEQ ID NO 1913
<211> LENGTH: 21
<212> TYPE: DNA
<213> ORGANISM: Homo sapiens

<400> SEQUENCE: 1913
ccacacaact caagggagaa g                                           21

<210> SEQ ID NO 1914
<211> LENGTH: 19
<212> TYPE: DNA
<213> ORGANISM: Homo sapiens

<400> SEQUENCE: 1914
ccagctgggt cagagaagc                                              19

<210> SEQ ID NO 1915
<211> LENGTH: 19
<212> TYPE: DNA
<213> ORGANISM: Homo sapiens

<400> SEQUENCE: 1915
gtaagcctct gcccctgtg                                              19

<210> SEQ ID NO 1916
<211> LENGTH: 19
<212> TYPE: DNA
<213> ORGANISM: Homo sapiens

<400> SEQUENCE: 1916
ctacggccag aagccctac                                              19

<210> SEQ ID NO 1917
<211> LENGTH: 20
<212> TYPE: DNA
<213> ORGANISM: Homo sapiens

<400> SEQUENCE: 1917
tctacctcag ccaagcacag                                             20

<210> SEQ ID NO 1918
<211> LENGTH: 20
<212> TYPE: DNA
<213> ORGANISM: Homo sapiens

<400> SEQUENCE: 1918
tgcaatttac atcccacagg                                             20

<210> SEQ ID NO 1919
<211> LENGTH: 21
<212> TYPE: DNA
<213> ORGANISM: Homo sapiens

<400> SEQUENCE: 1919
gcaatttaca tcccacagga g                                           21

<210> SEQ ID NO 1920
<211> LENGTH: 21
<212> TYPE: DNA
<213> ORGANISM: Homo sapiens
```

```
<400> SEQUENCE: 1920
tctccactgt ctctgggagt c                                           21

<210> SEQ ID NO 1921
<211> LENGTH: 18
<212> TYPE: DNA
<213> ORGANISM: Homo sapiens

<400> SEQUENCE: 1921
ccttgtctgg ggcaggtg                                               18

<210> SEQ ID NO 1922
<211> LENGTH: 20
<212> TYPE: DNA
<213> ORGANISM: Homo sapiens

<400> SEQUENCE: 1922
ccgttgtgcc aattagtgtg                                             20

<210> SEQ ID NO 1923
<211> LENGTH: 23
<212> TYPE: DNA
<213> ORGANISM: Homo sapiens

<400> SEQUENCE: 1923
cactcatcct taccaacctt cac                                         23

<210> SEQ ID NO 1924
<211> LENGTH: 20
<212> TYPE: DNA
<213> ORGANISM: Homo sapiens

<400> SEQUENCE: 1924
gcaaagccag gactcaaacc                                             20

<210> SEQ ID NO 1925
<211> LENGTH: 22
<212> TYPE: DNA
<213> ORGANISM: Homo sapiens

<400> SEQUENCE: 1925
gggctcctga atcaatactt tg                                          22

<210> SEQ ID NO 1926
<211> LENGTH: 20
<212> TYPE: DNA
<213> ORGANISM: Homo sapiens

<400> SEQUENCE: 1926
taggttttgt caccggcttc                                             20

<210> SEQ ID NO 1927
<211> LENGTH: 20
<212> TYPE: DNA
<213> ORGANISM: Homo sapiens

<400> SEQUENCE: 1927
gcagggaaat gagtgagagc                                             20

<210> SEQ ID NO 1928
<211> LENGTH: 20
<212> TYPE: DNA
```

<213> ORGANISM: Homo sapiens

<400> SEQUENCE: 1928
cgtccaaacc tatcccagtc                                              20

<210> SEQ ID NO 1929
<211> LENGTH: 29
<212> TYPE: DNA
<213> ORGANISM: Homo sapiens

<400> SEQUENCE: 1929
agtaagagag agtgaaacaa ctaaaggta                                    29

<210> SEQ ID NO 1930
<211> LENGTH: 25
<212> TYPE: DNA
<213> ORGANISM: Homo sapiens

<400> SEQUENCE: 1930
gaaaggactt ctgtttttgt ttttc                                        25

<210> SEQ ID NO 1931
<211> LENGTH: 26
<212> TYPE: DNA
<213> ORGANISM: Homo sapiens

<400> SEQUENCE: 1931
tgtttcaata tttaagagaa gtgctg                                       26

<210> SEQ ID NO 1932
<211> LENGTH: 19
<212> TYPE: DNA
<213> ORGANISM: Homo sapiens

<400> SEQUENCE: 1932
gtgatttggg gtggaggag                                               19

<210> SEQ ID NO 1933
<211> LENGTH: 27
<212> TYPE: DNA
<213> ORGANISM: Homo sapiens

<400> SEQUENCE: 1933
tttcagtgac acaatttgat attaacc                                      27

<210> SEQ ID NO 1934
<211> LENGTH: 20
<212> TYPE: DNA
<213> ORGANISM: Homo sapiens

<400> SEQUENCE: 1934
tcagctgtca ttcctcatgg                                              20

<210> SEQ ID NO 1935
<211> LENGTH: 18
<212> TYPE: DNA
<213> ORGANISM: Homo sapiens

<400> SEQUENCE: 1935
ccctcnccat cagcttcc                                                18

<210> SEQ ID NO 1936
<211> LENGTH: 20

<212> TYPE: DNA
<213> ORGANISM: Homo sapiens

<400> SEQUENCE: 1936
gtgtgcatct ggcatgtagg                                           20

<210> SEQ ID NO 1937
<211> LENGTH: 18
<212> TYPE: DNA
<213> ORGANISM: Homo sapiens

<400> SEQUENCE: 1937
ggaggccaca gctgacac                                             18

<210> SEQ ID NO 1938
<211> LENGTH: 20
<212> TYPE: DNA
<213> ORGANISM: Homo sapiens

<400> SEQUENCE: 1938
atgggttttg ggaatcactg                                           20

<210> SEQ ID NO 1939
<211> LENGTH: 18
<212> TYPE: DNA
<213> ORGANISM: Homo sapiens

<400> SEQUENCE: 1939
aaggggtggt tggctctc                                             18

<210> SEQ ID NO 1940
<211> LENGTH: 22
<212> TYPE: DNA
<213> ORGANISM: Homo sapiens

<400> SEQUENCE: 1940
tttcacattt tgtgcgtgat ac                                        22

<210> SEQ ID NO 1941
<211> LENGTH: 24
<212> TYPE: DNA
<213> ORGANISM: Homo sapiens

<400> SEQUENCE: 1941
tgctgtgatt accattttag ttgc                                      24

<210> SEQ ID NO 1942
<211> LENGTH: 27
<212> TYPE: DNA
<213> ORGANISM: Homo sapiens

<400> SEQUENCE: 1942
tcttctctgg agaaaaaaag attaaac                                   27

<210> SEQ ID NO 1943
<211> LENGTH: 25
<212> TYPE: DNA
<213> ORGANISM: Homo sapiens

<400> SEQUENCE: 1943
tctatgacaa agaatgatgt ttgag                                     25

<210> SEQ ID NO 1944

```
<211> LENGTH: 21
<212> TYPE: DNA
<213> ORGANISM: Homo sapiens

<400> SEQUENCE: 1944
agccattgtt tcagaatcac c                                          21

<210> SEQ ID NO 1945
<211> LENGTH: 23
<212> TYPE: DNA
<213> ORGANISM: Homo sapiens

<400> SEQUENCE: 1945 gcactttttcc tttgagaact gtg                                       23

<210> SEQ ID NO 1946
<211> LENGTH: 27
<212> TYPE: DNA
<213> ORGANISM: Homo sapiens

<400> SEQUENCE: 1946
tgaacctaaa actaaaaagc tacattg                                    27

<210> SEQ ID NO 1947
<211> LENGTH: 24
<212> TYPE: DNA
<213> ORGANISM: Homo sapiens

<400> SEQUENCE: 1947
aaaatgaagc tcataaaggg tttg                                       24

<210> SEQ ID NO 1948
<211> LENGTH: 21
<212> TYPE: DNA
<213> ORGANISM: Homo sapiens

<400> SEQUENCE: 1948
tgtggtttac catttcattg c                                          21

<210> SEQ ID NO 1949
<211> LENGTH: 26
<212> TYPE: DNA
<213> ORGANISM: Homo sapiens

<400> SEQUENCE: 1949
ccaaactaat ttttgagaca agataa                                     26

<210> SEQ ID NO 1950
<211> LENGTH: 24
<212> TYPE: DNA
<213> ORGANISM: Homo sapiens

<400> SEQUENCE: 1950
gatttcaaat actgaagcca cttg                                       24

<210> SEQ ID NO 1951
<211> LENGTH: 23
<212> TYPE: DNA
<213> ORGANISM: Homo sapiens

<400> SEQUENCE: 1951
ccaagaccta ctgatttcct ttc                                        23
```

```
<210> SEQ ID NO 1952
<211> LENGTH: 21
<212> TYPE: DNA
<213> ORGANISM: Homo sapiens

<400> SEQUENCE: 1952
gcccagaccc cttgtaagta g                                         21

<210> SEQ ID NO 1953
<211> LENGTH: 20
<212> TYPE: DNA
<213> ORGANISM: Homo sapiens

<400> SEQUENCE: 1953
aggccatcga tattctttgc                                           20

<210> SEQ ID NO 1954
<211> LENGTH: 20
<212> TYPE: DNA
<213> ORGANISM: Homo sapiens

<400> SEQUENCE: 1954
cacctctctg ctgcttttgg                                           20

<210> SEQ ID NO 1955
<211> LENGTH: 20
<212> TYPE: DNA
<213> ORGANISM: Homo sapiens

<400> SEQUENCE: 1955
gttcccccac cttagcagag                                           20

<210> SEQ ID NO 1956
<211> LENGTH: 20
<212> TYPE: DNA
<213> ORGANISM: Homo sapiens

<400> SEQUENCE: 1956
aggtgaggtg gggagtgatg                                           20

<210> SEQ ID NO 1957
<211> LENGTH: 20
<212> TYPE: DNA
<213> ORGANISM: Homo sapiens

<400> SEQUENCE: 1957
cggtagcctt acagggtgtc                                           20

<210> SEQ ID NO 1958
<211> LENGTH: 20
<212> TYPE: DNA
<213> ORGANISM: Homo sapiens

<400> SEQUENCE: 1958
ggagagatcc agtggaccag                                           20

<210> SEQ ID NO 1959
<211> LENGTH: 18
<212> TYPE: DNA
<213> ORGANISM: Homo sapiens

<400> SEQUENCE: 1959
cagctgggcc ttctaggg                                             18
```

<210> SEQ ID NO 1960
<211> LENGTH: 25
<212> TYPE: DNA
<213> ORGANISM: Homo sapiens

<400> SEQUENCE: 1960
gaaaaatctt caccacacac taaag                                   25

<210> SEQ ID NO 1961
<211> LENGTH: 20
<212> TYPE: DNA
<213> ORGANISM: Homo sapiens

<400> SEQUENCE: 1961
catgacaggg aacaggaagg                                         20

<210> SEQ ID NO 1962
<211> LENGTH: 21
<212> TYPE: DNA
<213> ORGANISM: Homo sapiens

<400> SEQUENCE: 1962
ttcccattat gaggatgatg c                                       21

<210> SEQ ID NO 1963
<211> LENGTH: 21
<212> TYPE: DNA
<213> ORGANISM: Homo sapiens

<400> SEQUENCE: 1963
cccattatga ggatgatgca g                                       21

<210> SEQ ID NO 1964
<211> LENGTH: 20
<212> TYPE: DNA
<213> ORGANISM: Homo sapiens

<400> SEQUENCE: 1964
tgaggtgcct catgagattg                                         20

<210> SEQ ID NO 1965
<211> LENGTH: 20
<212> TYPE: DNA
<213> ORGANISM: Homo sapiens

<400> SEQUENCE: 1965
tgcaatgtac tgggggtaag                                         20

<210> SEQ ID NO 1966
<211> LENGTH: 20
<212> TYPE: DNA
<213> ORGANISM: Homo sapiens

<400> SEQUENCE: 1966
acgtgcacat tcacgcatac                                         20

<210> SEQ ID NO 1967
<211> LENGTH: 20
<212> TYPE: DNA
<213> ORGANISM: Homo sapiens

<400> SEQUENCE: 1967
cttgctttgc catcttcctc                                         20

```
<210> SEQ ID NO 1968
<211> LENGTH: 19
<212> TYPE: DNA
<213> ORGANISM: Homo sapiens

<400> SEQUENCE: 1968 cagggggtgtg gcttctagg                                              19

<210> SEQ ID NO 1969
<211> LENGTH: 19
<212> TYPE: DNA
<213> ORGANISM: Homo sapiens

<400> SEQUENCE: 1969
ccacatggga gtggatttc                                               19

<210> SEQ ID NO 1970
<211> LENGTH: 20
<212> TYPE: DNA
<213> ORGANISM: Homo sapiens

<400> SEQUENCE: 1970
aacaccctga agggaaggac                                              20

<210> SEQ ID NO 1971
<211> LENGTH: 20
<212> TYPE: DNA
<213> ORGANISM: Homo sapiens

<400> SEQUENCE: 1971
ggctgaggta gcaagtcagg                                              20

<210> SEQ ID NO 1972
<211> LENGTH: 20
<212> TYPE: DNA
<213> ORGANISM: Homo sapiens

<400> SEQUENCE: 1972
cacctggtga gacccttgtc                                              20

<210> SEQ ID NO 1973
<211> LENGTH: 19
<212> TYPE: DNA
<213> ORGANISM: Homo sapiens

<400> SEQUENCE: 1973
aggaacagcc cttccacac                                               19

<210> SEQ ID NO 1974
<211> LENGTH: 19
<212> TYPE: DNA
<213> ORGANISM: Homo sapiens

<400> SEQUENCE: 1974
gaaggctctt gctccaagg                                               19

<210> SEQ ID NO 1975
<211> LENGTH: 20
<212> TYPE: DNA
<213> ORGANISM: Homo sapiens

<400> SEQUENCE: 1975
```

-continued ctgtcctttc cagcaacctc                                              20

<210> SEQ ID NO 1976
<211> LENGTH: 20
<212> TYPE: DNA
<213> ORGANISM: Homo sapiens

<400> SEQUENCE: 1976
gggcctgtgt gagttgagtg                                              20

<210> SEQ ID NO 1977
<211> LENGTH: 20
<212> TYPE: DNA
<213> ORGANISM: Homo sapiens

<400> SEQUENCE: 1977
cagggcctgt gtgagttgag                                              20

<210> SEQ ID NO 1978
<211> LENGTH: 20
<212> TYPE: DNA
<213> ORGANISM: Homo sapiens

<400> SEQUENCE: 1978
atcctggtct tgtgggtcag                                              20

<210> SEQ ID NO 1979
<211> LENGTH: 21
<212> TYPE: DNA
<213> ORGANISM: Homo sapiens

<400> SEQUENCE: 1979
tttgggggat tgaatacaga c                                            21

<210> SEQ ID NO 1980
<211> LENGTH: 20
<212> TYPE: DNA
<213> ORGANISM: Homo sapiens

<400> SEQUENCE: 1980
tcagtgaggc aacactgtcc                                              20

<210> SEQ ID NO 1981
<211> LENGTH: 21
<212> TYPE: DNA
<213> ORGANISM: Homo sapiens

<400> SEQUENCE: 1981
ttcagtgagg caacactgtc c                                            21

<210> SEQ ID NO 1982
<211> LENGTH: 23
<212> TYPE: DNA
<213> ORGANISM: Homo sapiens

<400> SEQUENCE: 1982
ggacagtggg acatttttaa agc                                          23

<210> SEQ ID NO 1983
<211> LENGTH: 33
<212> TYPE: DNA
<213> ORGANISM: Homo sapiens

<400> SEQUENCE: 1983
cctctataaa tatacttaca gactcaaaga tcc                                    33

<210> SEQ ID NO 1984
<211> LENGTH: 27
<212> TYPE: DNA
<213> ORGANISM: Homo sapiens

<400> SEQUENCE: 1984
aatctgcata tacaagtcaa aataatg                                           27

<210> SEQ ID NO 1985
<211> LENGTH: 25
<212> TYPE: DNA
<213> ORGANISM: Homo sapiens

<400> SEQUENCE: 1985
gccttagtag tctaagaggg catac                                             25

<210> SEQ ID NO 1986
<211> LENGTH: 28
<212> TYPE: DNA
<213> ORGANISM: Homo sapiens

<400> SEQUENCE: 1986
tttgacacta ataaaattt ctgggtaa                                           28

<210> SEQ ID NO 1987
<211> LENGTH: 20
<212> TYPE: DNA
<213> ORGANISM: Homo sapiens

<400> SEQUENCE: 1987
aagacagtcc ccgctacaac                                                   20

<210> SEQ ID NO 1988
<211> LENGTH: 19
<212> TYPE: DNA
<213> ORGANISM: Homo sapiens

<400> SEQUENCE: 1988
ctgacatggc tggataccg                                                    19

<210> SEQ ID NO 1989
<211> LENGTH: 20
<212> TYPE: DNA
<213> ORGANISM: Homo sapiens

<400> SEQUENCE: 1989
ccagtctcct ctcccatcac                                                   20

<210> SEQ ID NO 1990
<211> LENGTH: 20
<212> TYPE: DNA
<213> ORGANISM: Homo sapiens

<400> SEQUENCE: 1990
taatgatggg gctggggtag                                                   20

<210> SEQ ID NO 1991
<211> LENGTH: 21
<212> TYPE: DNA
<213> ORGANISM: Homo sapiens

```
<400> SEQUENCE: 1991
gagtagtgtg agctgccttg g                                              21

<210> SEQ ID NO 1992
<211> LENGTH: 21
<212> TYPE: DNA
<213> ORGANISM: Homo sapiens

<400> SEQUENCE: 1992
agcccttcag aagaggagaa g                                              21

<210> SEQ ID NO 1993
<211> LENGTH: 20
<212> TYPE: DNA
<213> ORGANISM: Homo sapiens

<400> SEQUENCE: 1993
agggtcaggt ttggtgtctg                                                20

<210> SEQ ID NO 1994
<211> LENGTH: 20
<212> TYPE: DNA
<213> ORGANISM: Homo sapiens

<400> SEQUENCE: 1994
accctgggga gtgaaagaag                                                20

<210> SEQ ID NO 1995
<211> LENGTH: 21
<212> TYPE: DNA
<213> ORGANISM: Homo sapiens

<400> SEQUENCE: 1995
ggatgagaag attgggagag g                                              21

<210> SEQ ID NO 1996
<211> LENGTH: 21
<212> TYPE: DNA
<213> ORGANISM: Homo sapiens

<400> SEQUENCE: 1996
ttggtgactc tggaggatga g                                              21

<210> SEQ ID NO 1997
<211> LENGTH: 18
<212> TYPE: DNA
<213> ORGANISM: Homo sapiens

<400> SEQUENCE: 1997 gaacacccccc atcccttg                                                 18

<210> SEQ ID NO 1998
<211> LENGTH: 19
<212> TYPE: DNA
<213> ORGANISM: Homo sapiens

<400> SEQUENCE: 1998
ctcagtgcag gaggctgag                                                 19

<210> SEQ ID NO 1999
<211> LENGTH: 20
<212> TYPE: DNA
<213> ORGANISM: Homo sapiens
```

```
<400> SEQUENCE: 1999
caccaactga ccctcagtgc                                               20

<210> SEQ ID NO 2000
<211> LENGTH: 18
<212> TYPE: DNA
<213> ORGANISM: Homo sapiens

<400> SEQUENCE: 2000
agggcctggg aggctggg                                                 18

<210> SEQ ID NO 2001
<211> LENGTH: 20
<212> TYPE: DNA
<213> ORGANISM: Homo sapiens

<400> SEQUENCE: 2001
gtatgctcct ggggtctctg                                               20

<210> SEQ ID NO 2002
<211> LENGTH: 20
<212> TYPE: DNA
<213> ORGANISM: Homo sapiens

<400> SEQUENCE: 2002
acagatggga ggtgttcctg                                               20

<210> SEQ ID NO 2003
<211> LENGTH: 20
<212> TYPE: DNA
<213> ORGANISM: Homo sapiens

<400> SEQUENCE: 2003
cctctggact ggaaaacagg                                               20

<210> SEQ ID NO 2004
<211> LENGTH: 18
<212> TYPE: DNA
<213> ORGANISM: Homo sapiens

<400> SEQUENCE: 2004
gaccaaccgg gatgtgag                                                 18

<210> SEQ ID NO 2005
<211> LENGTH: 20
<212> TYPE: DNA
<213> ORGANISM: Homo sapiens

<400> SEQUENCE: 2005
cttcctcagc ctgcttcttc                                               20

<210> SEQ ID NO 2006
<211> LENGTH: 20
<212> TYPE: DNA
<213> ORGANISM: Homo sapiens

<400> SEQUENCE: 2006
gaggctacag gtccagatcc                                               20

<210> SEQ ID NO 2007
<211> LENGTH: 20
<212> TYPE: DNA
```

<213> ORGANISM: Homo sapiens

<400> SEQUENCE: 2007
agcaatcctc tcacctcagc                                                    20

<210> SEQ ID NO 2008
<211> LENGTH: 20
<212> TYPE: DNA
<213> ORGANISM: Homo sapiens

<400> SEQUENCE: 2008
ctcactgcag ccttgaactc                                                    20

<210> SEQ ID NO 2009
<211> LENGTH: 20
<212> TYPE: DNA
<213> ORGANISM: Homo sapiens

<400> SEQUENCE: 2009
atggtgctga agctcacttg                                                    20

<210> SEQ ID NO 2010
<211> LENGTH: 20
<212> TYPE: DNA
<213> ORGANISM: Homo sapiens

<400> SEQUENCE: 2010
ctggggttcc agagatgttc                                                    20

<210> SEQ ID NO 2011
<211> LENGTH: 20
<212> TYPE: DNA
<213> ORGANISM: Homo sapiens

<400> SEQUENCE: 2011
gcgagactcc gtctcaaaag                                                    20

<210> SEQ ID NO 2012
<211> LENGTH: 20
<212> TYPE: DNA
<213> ORGANISM: Homo sapiens

<400> SEQUENCE: 2012
gccttgtacc cctatgatgg                                                    20

<210> SEQ ID NO 2013
<211> LENGTH: 20
<212> TYPE: DNA
<213> ORGANISM: Homo sapiens

<400> SEQUENCE: 2013
cacctccctg gagtgtcaac                                                    20

<210> SEQ ID NO 2014
<211> LENGTH: 20
<212> TYPE: DNA
<213> ORGANISM: Homo sapiens

<400> SEQUENCE: 2014
ttggatgggt agggtttgag                                                    20

<210> SEQ ID NO 2015
<211> LENGTH: 20

```
<212> TYPE: DNA
<213> ORGANISM: Homo sapiens

<400> SEQUENCE: 2015
tacagaggtg ggcaggagtc                                              20

<210> SEQ ID NO 2016
<211> LENGTH: 19
<212> TYPE: DNA
<213> ORGANISM: Homo sapiens

<400> SEQUENCE: 2016
agaggctgct gggtaggtg                                               19

<210> SEQ ID NO 2017
<211> LENGTH: 19
<212> TYPE: DNA
<213> ORGANISM: Homo sapiens

<400> SEQUENCE: 2017
ggagttcgga ggtgagctg                                               19

<210> SEQ ID NO 2018
<211> LENGTH: 21
<212> TYPE: DNA
<213> ORGANISM: Homo sapiens

<400> SEQUENCE: 2018
cttcctggct gaagcctcag t                                            21

<210> SEQ ID NO 2019
<211> LENGTH: 18
<212> TYPE: DNA
<213> ORGANISM: Homo sapiens

<400> SEQUENCE: 2019
gtgcgctgag ctgtgtgg                                                18

<210> SEQ ID NO 2020
<211> LENGTH: 19
<212> TYPE: DNA
<213> ORGANISM: Homo sapiens

<400> SEQUENCE: 2020
agtgctgctt gtcctgcac                                               19

<210> SEQ ID NO 2021
<211> LENGTH: 19
<212> TYPE: DNA
<213> ORGANISM: Homo sapiens

<400> SEQUENCE: 2021
gtctgcaccc aggaaggtg                                               19

<210> SEQ ID NO 2022
<211> LENGTH: 21
<212> TYPE: DNA
<213> ORGANISM: Homo sapiens

<400> SEQUENCE: 2022
tcctctgtaa agtgggtgga g                                            21

<210> SEQ ID NO 2023
```

```
<211> LENGTH: 20
<212> TYPE: DNA
<213> ORGANISM: Homo sapiens

<400> SEQUENCE: 2023
cctctgtaaa gtgggtggag                                               20

<210> SEQ ID NO 2024
<211> LENGTH: 18
<212> TYPE: DNA
<213> ORGANISM: Homo sapiens

<400> SEQUENCE: 2024
agggagatgg ggcagaac                                                 18

<210> SEQ ID NO 2025
<211> LENGTH: 20
<212> TYPE: DNA
<213> ORGANISM: Homo sapiens

<400> SEQUENCE: 2025
agatggggca gaactggatg                                               20

<210> SEQ ID NO 2026
<211> LENGTH: 20
<212> TYPE: DNA
<213> ORGANISM: Homo sapiens

<400> SEQUENCE: 2026
tgtggtgggt catgtctgtg                                               20

<210> SEQ ID NO 2027
<211> LENGTH: 20
<212> TYPE: DNA
<213> ORGANISM: Homo sapiens

<400> SEQUENCE: 2027
tcaaactccc caccaaactc                                               20

<210> SEQ ID NO 2028
<211> LENGTH: 20
<212> TYPE: DNA
<213> ORGANISM: Homo sapiens

<400> SEQUENCE: 2028
ctcccagttg gaggagaaag                                               20

<210> SEQ ID NO 2029
<211> LENGTH: 20
<212> TYPE: DNA
<213> ORGANISM: Homo sapiens

<400> SEQUENCE: 2029
gacatggcag cccaagtaag                                               20

<210> SEQ ID NO 2030
<211> LENGTH: 19
<212> TYPE: DNA
<213> ORGANISM: Homo sapiens

<400> SEQUENCE: 2030
cagggagggt acgtgtgag                                                19
```

```
<210> SEQ ID NO 2031
<211> LENGTH: 20
<212> TYPE: DNA
<213> ORGANISM: Homo sapiens

<400> SEQUENCE: 2031
ttttggattg gtgctcacac                                          20

<210> SEQ ID NO 2032
<211> LENGTH: 20
<212> TYPE: DNA
<213> ORGANISM: Homo sapiens

<400> SEQUENCE: 2032
attccgaaca ttacccttgc                                          20

<210> SEQ ID NO 2033
<211> LENGTH: 18
<212> TYPE: DNA
<213> ORGANISM: Homo sapiens

<400> SEQUENCE: 2033
ctgggtgagc ccaaggtg                                            18

<210> SEQ ID NO 2034
<211> LENGTH: 20
<212> TYPE: DNA
<213> ORGANISM: Homo sapiens

<400> SEQUENCE: 2034
cccccttgct agtccacttc                                          20

<210> SEQ ID NO 2035
<211> LENGTH: 19
<212> TYPE: DNA
<213> ORGANISM: Homo sapiens

<400> SEQUENCE: 2035
caggactgcc tgggaagag                                           19

<210> SEQ ID NO 2036
<211> LENGTH: 19
<212> TYPE: DNA
<213> ORGANISM: Homo sapiens

<400> SEQUENCE: 2036
ggaatgaggt ggcttgagg                                           19

<210> SEQ ID NO 2037
<211> LENGTH: 20
<212> TYPE: DNA
<213> ORGANISM: Homo sapiens

<400> SEQUENCE: 2037
tggcaagagt gtgagtgtcc                                          20

<210> SEQ ID NO 2038
<211> LENGTH: 20
<212> TYPE: DNA
<213> ORGANISM: Homo sapiens

<400> SEQUENCE: 2038
cagatggtga gcagatccag                                          20
```

<210> SEQ ID NO 2039
<211> LENGTH: 20
<212> TYPE: DNA
<213> ORGANISM: Homo sapiens

<400> SEQUENCE: 2039
cagatggtga gcagatccag                                              20

<210> SEQ ID NO 2040
<211> LENGTH: 24
<212> TYPE: DNA
<213> ORGANISM: Homo sapiens

<400> SEQUENCE: 2040
aaagaggact tttgtgaaag atgg                                         24

<210> SEQ ID NO 2041
<211> LENGTH: 20
<212> TYPE: DNA
<213> ORGANISM: Homo sapiens

<400> SEQUENCE: 2041
gcggagctcc tctttattcc                                              20

<210> SEQ ID NO 2042
<211> LENGTH: 21
<212> TYPE: DNA
<213> ORGANISM: Homo sapiens

<400> SEQUENCE: 2042
ggcacatagc ctagtgagct g                                            21

<210> SEQ ID NO 2043
<211> LENGTH: 21
<212> TYPE: DNA
<213> ORGANISM: Homo sapiens

<400> SEQUENCE: 2043
aagtttactg tcccccaaag c                                            21

<210> SEQ ID NO 2044
<211> LENGTH: 20
<212> TYPE: DNA
<213> ORGANISM: Homo sapiens

<400> SEQUENCE: 2044
cattggccca ctgagacttc                                              20

<210> SEQ ID NO 2045
<211> LENGTH: 20
<212> TYPE: DNA
<213> ORGANISM: Homo sapiens

<400> SEQUENCE: 2045
cctgactcta gggcacagac                                              20

<210> SEQ ID NO 2046
<211> LENGTH: 20
<212> TYPE: DNA
<213> ORGANISM: Homo sapiens

<400> SEQUENCE: 2046
tggtgcacag aggctgtaac                                              20

```
<210> SEQ ID NO 2047
<211> LENGTH: 20
<212> TYPE: DNA
<213> ORGANISM: Homo sapiens

<400> SEQUENCE: 2047
ggctgcagac ggtaagtagg                                               20

<210> SEQ ID NO 2048
<211> LENGTH: 20
<212> TYPE: DNA
<213> ORGANISM: Homo sapiens

<400> SEQUENCE: 2048
gcagcccrta cagttcttcc                                               20

<210> SEQ ID NO 2049
<211> LENGTH: 19
<212> TYPE: DNA
<213> ORGANISM: Homo sapiens

<400> SEQUENCE: 2049
gtgccgaggg tcttgtctg                                                19

<210> SEQ ID NO 2050
<211> LENGTH: 20
<212> TYPE: DNA
<213> ORGANISM: Homo sapiens

<400> SEQUENCE: 2050
ctggagggag aagaatggtg                                               20

<210> SEQ ID NO 2051
<211> LENGTH: 22
<212> TYPE: DNA
<213> ORGANISM: Homo sapiens

<400> SEQUENCE: 2051
aatcaaagag cgttgtatga cc                                            22

<210> SEQ ID NO 2052
<211> LENGTH: 20
<212> TYPE: DNA
<213> ORGANISM: Homo sapiens

<400> SEQUENCE: 2052
agcaagaagc ctgtcctcag                                               20

<210> SEQ ID NO 2053
<211> LENGTH: 19
<212> TYPE: DNA
<213> ORGANISM: Homo sapiens

<400> SEQUENCE: 2053
gtggctccaa tgaggtgtg                                                19

<210> SEQ ID NO 2054
<211> LENGTH: 19
<212> TYPE: DNA
<213> ORGANISM: Homo sapiens

<400> SEQUENCE: 2054
```

```
ctgtttcccc gtgtgtgtc                                           19

<210> SEQ ID NO 2055
<211> LENGTH: 20
<212> TYPE: DNA
<213> ORGANISM: Homo sapiens

<400> SEQUENCE: 2055
agccctcctc tcagagttcc                                          20

<210> SEQ ID NO 2056
<211> LENGTH: 19
<212> TYPE: DNA
<213> ORGANISM: Homo sapiens

<400> SEQUENCE: 2056
aggaaatgcc cagcaagag                                           19

<210> SEQ ID NO 2057
<211> LENGTH: 20
<212> TYPE: DNA
<213> ORGANISM: Homo sapiens

<400> SEQUENCE: 2057
ataggccttg gtgtgcattc                                          20

<210> SEQ ID NO 2058
<211> LENGTH: 23
<212> TYPE: DNA
<213> ORGANISM: Homo sapiens

<400> SEQUENCE: 2058
gagctttcaa ccctagtttg ttg                                      23

<210> SEQ ID NO 2059
<211> LENGTH: 19
<212> TYPE: DNA
<213> ORGANISM: Homo sapiens

<400> SEQUENCE: 2059
ggtgggggaa ggggtatag                                           19

<210> SEQ ID NO 2060
<211> LENGTH: 20
<212> TYPE: DNA
<213> ORGANISM: Homo sapiens

<400> SEQUENCE: 2060
ggcaaatcaa accatgatgc                                          20

<210> SEQ ID NO 2061
<211> LENGTH: 20
<212> TYPE: DNA
<213> ORGANISM: Homo sapiens

<400> SEQUENCE: 2061 ttgcttttc agccactttg                                           20

<210> SEQ ID NO 2062
<211> LENGTH: 21
<212> TYPE: DNA
<213> ORGANISM: Homo sapiens

<400> SEQUENCE: 2062
```
tcccattgga gaagaaatca c                                          21

<210> SEQ ID NO 2063
<211> LENGTH: 20
<212> TYPE: DNA
<213> ORGANISM: Homo sapiens

<400> SEQUENCE: 2063 gtggggtgg gaattaaaac                                             20

<210> SEQ ID NO 2064
<211> LENGTH: 19
<212> TYPE: DNA
<213> ORGANISM: Homo sapiens

<400> SEQUENCE: 2064 tggggtggg aattaaaac                                              19

<210> SEQ ID NO 2065
<211> LENGTH: 24
<212> TYPE: DNA
<213> ORGANISM: Homo sapiens

<400> SEQUENCE: 2065
ttgctgagaa ttctactcaa aagg                                       24

<210> SEQ ID NO 2066
<211> LENGTH: 20
<212> TYPE: DNA
<213> ORGANISM: Homo sapiens

<400> SEQUENCE: 2066
ctgagactct gggtggcttc                                            20

<210> SEQ ID NO 2067
<211> LENGTH: 20
<212> TYPE: DNA
<213> ORGANISM: Homo sapiens

<400> SEQUENCE: 2067
tgacccatag ccttcctgac                                            20

<210> SEQ ID NO 2068
<211> LENGTH: 27
<212> TYPE: DNA
<213> ORGANISM: Homo sapiens

<400> SEQUENCE: 2068
cattttaaaa gttgctagct ttaggac                                    27

<210> SEQ ID NO 2069
<211> LENGTH: 20
<212> TYPE: DNA
<213> ORGANISM: Homo sapiens

<400> SEQUENCE: 2069
ggaagaatgt gcatgccaag                                            20

<210> SEQ ID NO 2070
<211> LENGTH: 21
<212> TYPE: DNA
<213> ORGANISM: Homo sapiens

```
<400> SEQUENCE: 2070
cagggaggct ccatataaag g                                              21

<210> SEQ ID NO 2071
<211> LENGTH: 20
<212> TYPE: DNA
<213> ORGANISM: Homo sapiens

<400> SEQUENCE: 2071
ccatgaagtc agctgtcagg                                                20

<210> SEQ ID NO 2072
<211> LENGTH: 18
<212> TYPE: DNA
<213> ORGANISM: Homo sapiens

<400> SEQUENCE: 2072
gggtgagccc ctatctgg                                                  18

<210> SEQ ID NO 2073
<211> LENGTH: 20
<212> TYPE: DNA
<213> ORGANISM: Homo sapiens

<400> SEQUENCE: 2073
caggaatgcc cttagtgctg                                                20

<210> SEQ ID NO 2074
<211> LENGTH: 21
<212> TYPE: DNA
<213> ORGANISM: Homo sapiens

<400> SEQUENCE: 2074
ggcaccattg ttctccatta g                                              21

<210> SEQ ID NO 2075
<211> LENGTH: 20
<212> TYPE: DNA
<213> ORGANISM: Homo sapiens

<400> SEQUENCE: 2075
cagaagctga caagcagcag                                                20

<210> SEQ ID NO 2076
<211> LENGTH: 20
<212> TYPE: DNA
<213> ORGANISM: Homo sapiens

<400> SEQUENCE: 2076
taaggctcag aggggctacc                                                20

<210> SEQ ID NO 2077
<211> LENGTH: 20
<212> TYPE: DNA
<213> ORGANISM: Homo sapiens

<400> SEQUENCE: 2077
ggtggagtca gtgtgaaagg                                                20

<210> SEQ ID NO 2078
<211> LENGTH: 19
<212> TYPE: DNA
<213> ORGANISM: Homo sapiens
```

```
<400> SEQUENCE: 2078
gcccacagca actacaagg                                                19

<210> SEQ ID NO 2079
<211> LENGTH: 20
<212> TYPE: DNA
<213> ORGANISM: Homo sapiens

<400> SEQUENCE: 2079
agatgccacc ggttctacag                                               20

<210> SEQ ID NO 2080
<211> LENGTH: 20
<212> TYPE: DNA
<213> ORGANISM: Homo sapiens

<400> SEQUENCE: 2080
cccctctctc tggttgtctg                                               20

<210> SEQ ID NO 2081
<211> LENGTH: 16
<212> TYPE: DNA
<213> ORGANISM: Homo sapiens

<400> SEQUENCE: 2081
ggagaaggcc cggcgt                                                   16

<210> SEQ ID NO 2082
<211> LENGTH: 20
<212> TYPE: DNA
<213> ORGANISM: Homo sapiens

<400> SEQUENCE: 2082
tgcacacctt cgagaaacag                                               20

<210> SEQ ID NO 2083
<211> LENGTH: 23
<212> TYPE: DNA
<213> ORGANISM: Homo sapiens

<400> SEQUENCE: 2083
ggctatttct ggtgtaggaa atc                                           23

<210> SEQ ID NO 2084
<211> LENGTH: 20
<212> TYPE: DNA
<213> ORGANISM: Homo sapiens

<400> SEQUENCE: 2084
aaggtcgagg atgcagtgag                                               20

<210> SEQ ID NO 2085
<211> LENGTH: 20
<212> TYPE: DNA
<213> ORGANISM: Homo sapiens

<400> SEQUENCE: 2085
agaaggtcga ggatgcagtg                                               20

<210> SEQ ID NO 2086
<211> LENGTH: 22
<212> TYPE: DNA
```

```
<213> ORGANISM: Homo sapiens

<400> SEQUENCE: 2086
aagatggagt ctcactctga cg                                          22

<210> SEQ ID NO 2087
<211> LENGTH: 21
<212> TYPE: DNA
<213> ORGANISM: Homo sapiens

<400> SEQUENCE: 2087
gagctgctga gaagaatttg c                                           21

<210> SEQ ID NO 2088
<211> LENGTH: 20
<212> TYPE: DNA
<213> ORGANISM: Homo sapiens

<400> SEQUENCE: 2088
cgggagtgtt gcttttattg                                             20

<210> SEQ ID NO 2089
<211> LENGTH: 21
<212> TYPE: DNA
<213> ORGANISM: Homo sapiens

<400> SEQUENCE: 2089
acgggagtgt tgctttttatt g                                          21

<210> SEQ ID NO 2090
<211> LENGTH: 20
<212> TYPE: DNA
<213> ORGANISM: Homo sapiens

<400> SEQUENCE: 2090
ttccagctct tcctgcattc                                             20

<210> SEQ ID NO 2091
<211> LENGTH: 21
<212> TYPE: DNA
<213> ORGANISM: Homo sapiens

<400> SEQUENCE: 2091
aatgaccatt ggctattttg g                                           21

<210> SEQ ID NO 2092
<211> LENGTH: 20
<212> TYPE: DNA
<213> ORGANISM: Homo sapiens

<400> SEQUENCE: 2092
gcactgcagt aaagcaaagg                                             20

<210> SEQ ID NO 2093
<211> LENGTH: 20
<212> TYPE: DNA
<213> ORGANISM: Homo sapiens

<400> SEQUENCE: 2093
ccggtgaagt ctcaggaatg                                             20

<210> SEQ ID NO 2094
<211> LENGTH: 21
```

```
<212> TYPE: DNA
<213> ORGANISM: Homo sapiens

<400> SEQUENCE: 2094
ttctagaggc aggttggttt g                                        21

<210> SEQ ID NO 2095
<211> LENGTH: 20
<212> TYPE: DNA
<213> ORGANISM: Homo sapiens

<400> SEQUENCE: 2095
gcaagaaagt ggagctggag                                          20

<210> SEQ ID NO 2096
<211> LENGTH: 25
<212> TYPE: DNA
<213> ORGANISM: Homo sapiens

<400> SEQUENCE: 2096
ccttgtgaga ggttataaga caaag                                    25

<210> SEQ ID NO 2097
<211> LENGTH: 22
<212> TYPE: DNA
<213> ORGANISM: Homo sapiens

<400> SEQUENCE: 2097
gctttatagt cccctggtat cc                                       22

<210> SEQ ID NO 2098
<211> LENGTH: 21
<212> TYPE: DNA
<213> ORGANISM: Homo sapiens

<400> SEQUENCE: 2098
ttaggcactt ccaactgaag g                                        21

<210> SEQ ID NO 2099
<211> LENGTH: 30
<212> TYPE: DNA
<213> ORGANISM: Homo sapiens

<400> SEQUENCE: 2099
aagactcaca tttaggaaat acatatagaa                               30

<210> SEQ ID NO 2100
<211> LENGTH: 20
<212> TYPE: DNA
<213> ORGANISM: Homo sapiens

<400> SEQUENCE: 2100
ttggtgtttg gattgacctg                                          20

<210> SEQ ID NO 2101
<211> LENGTH: 23
<212> TYPE: DNA
<213> ORGANISM: Homo sapiens

<400> SEQUENCE: 2101
caacattttt caaacttttg ctc                                      23

<210> SEQ ID NO 2102
```

<211> LENGTH: 24
<212> TYPE: DNA
<213> ORGANISM: Homo sapiens

<400> SEQUENCE: 2102 tgaattttc aaccatttgt tatg                                          24

<210> SEQ ID NO 2103
<211> LENGTH: 20
<212> TYPE: DNA
<213> ORGANISM: Homo sapiens

<400> SEQUENCE: 2103
tacgacccat gtggcttttc                                              20

<210> SEQ ID NO 2104
<211> LENGTH: 19
<212> TYPE: DNA
<213> ORGANISM: Homo sapiens

<400> SEQUENCE: 2104
gcctctcgtg tttgtccac                                               19

<210> SEQ ID NO 2105
<211> LENGTH: 19
<212> TYPE: DNA
<213> ORGANISM: Homo sapiens

<400> SEQUENCE: 2105
tggcttgcgg actctgtag                                               19

<210> SEQ ID NO 2106
<211> LENGTH: 21
<212> TYPE: DNA
<213> ORGANISM: Homo sapiens

<400> SEQUENCE: 2106
tcctgttcct cccagtttaa g                                            21

<210> SEQ ID NO 2107
<211> LENGTH: 20
<212> TYPE: DNA
<213> ORGANISM: Homo sapiens

<400> SEQUENCE: 2107
agccagcatt tcagatttcc                                              20

<210> SEQ ID NO 2108
<211> LENGTH: 20
<212> TYPE: DNA
<213> ORGANISM: Homo sapiens

<400> SEQUENCE: 2108
aatcctagtg atggccgttg                                              20

<210> SEQ ID NO 2109
<211> LENGTH: 21
<212> TYPE: DNA
<213> ORGANISM: Homo sapiens

<400> SEQUENCE: 2109
ttgccacttt ctcaactttc c                                            21

```
<210> SEQ ID NO 2110
<211> LENGTH: 20
<212> TYPE: DNA
<213> ORGANISM: Homo sapiens

<400> SEQUENCE: 2110
tctgtgtgcc tgtgtgtgtg                                              20

<210> SEQ ID NO 2111
<211> LENGTH: 19
<212> TYPE: DNA
<213> ORGANISM: Homo sapiens

<400> SEQUENCE: 2111
catcttcccc gccaactac                                               19

<210> SEQ ID NO 2112
<211> LENGTH: 19
<212> TYPE: DNA
<213> ORGANISM: Homo sapiens

<400> SEQUENCE: 2112
cctggtgctg gagttcgcc                                               19

<210> SEQ ID NO 2113
<211> LENGTH: 20
<212> TYPE: DNA
<213> ORGANISM: Homo sapiens

<400> SEQUENCE: 2113
catgccacag aaaaattgtg                                              20

<210> SEQ ID NO 2114
<211> LENGTH: 23
<212> TYPE: DNA
<213> ORGANISM: Homo sapiens

<400> SEQUENCE: 2114
ggaatggatg aaggtactga agg                                          23

<210> SEQ ID NO 2115
<211> LENGTH: 25
<212> TYPE: DNA
<213> ORGANISM: Homo sapiens

<400> SEQUENCE: 2115
ttaggaatgg atgaaggtac tgaag                                        25

<210> SEQ ID NO 2116
<211> LENGTH: 24
<212> TYPE: DNA
<213> ORGANISM: Homo sapiens

<400> SEQUENCE: 2116
tttggaatga caaatgttaa gttg                                         24

<210> SEQ ID NO 2117
<211> LENGTH: 18
<212> TYPE: DNA
<213> ORGANISM: Homo sapiens

<400> SEQUENCE: 2117
ggggtcgcca gtgtagtg                                                18
```

```
<210> SEQ ID NO 2118
<211> LENGTH: 20
<212> TYPE: DNA
<213> ORGANISM: Homo sapiens

<400> SEQUENCE: 2118
ttgtcctgta gctggctgtg                                           20

<210> SEQ ID NO 2119
<211> LENGTH: 20
<212> TYPE: DNA
<213> ORGANISM: Homo sapiens

<400> SEQUENCE: 2119 cccacctttta gacaggcaac                                          20

<210> SEQ ID NO 2120
<211> LENGTH: 21
<212> TYPE: DNA
<213> ORGANISM: Homo sapiens

<400> SEQUENCE: 2120
tcattcctgt gacctgagtc c                                         21

<210> SEQ ID NO 2121
<211> LENGTH: 27
<212> TYPE: DNA
<213> ORGANISM: Homo sapiens

<400> SEQUENCE: 2121
tgttttatgt tatattgtgc cagaaag                                   27

<210> SEQ ID NO 2122
<211> LENGTH: 19
<212> TYPE: DNA
<213> ORGANISM: Homo sapiens

<400> SEQUENCE: 2122
ggggttctct gcgagtcac                                            19

<210> SEQ ID NO 2123
<211> LENGTH: 20
<212> TYPE: DNA
<213> ORGANISM: Homo sapiens

<400> SEQUENCE: 2123
tggagagaca ctgtggttgc                                           20

<210> SEQ ID NO 2124
<211> LENGTH: 22
<212> TYPE: DNA
<213> ORGANISM: Homo sapiens

<400> SEQUENCE: 2124
gagtttcctg tagcatgtga cc                                        22

<210> SEQ ID NO 2125
<211> LENGTH: 20
<212> TYPE: DNA
<213> ORGANISM: Homo sapiens

<400> SEQUENCE: 2125 aggttcttttt tccccctctc                                          20
```

```
<210> SEQ ID NO 2126
<211> LENGTH: 20
<212> TYPE: DNA
<213> ORGANISM: Homo sapiens

<400> SEQUENCE: 2126
tttttccccc tctctgattc                                              20

<210> SEQ ID NO 2127
<211> LENGTH: 23
<212> TYPE: DNA
<213> ORGANISM: Homo sapiens

<400> SEQUENCE: 2127
catctttctg gctcatcttt ttg                                          23

<210> SEQ ID NO 2128
<211> LENGTH: 25
<212> TYPE: DNA
<213> ORGANISM: Homo sapiens

<400> SEQUENCE: 2128
tctgcaaatg ttgactaggt tacac                                        25

<210> SEQ ID NO 2129
<211> LENGTH: 22
<212> TYPE: DNA
<213> ORGANISM: Homo sapiens

<400> SEQUENCE: 2129
aactgtgttt ttgattgcaa gg                                           22

<210> SEQ ID NO 2130
<211> LENGTH: 21
<212> TYPE: DNA
<213> ORGANISM: Homo sapiens

<400> SEQUENCE: 2130
gatccatgtt tcctcatgtc c                                            21

<210> SEQ ID NO 2131
<211> LENGTH: 20
<212> TYPE: DNA
<213> ORGANISM: Homo sapiens

<400> SEQUENCE: 2131
ggagttggag cagtgagagg                                              20

<210> SEQ ID NO 2132
<211> LENGTH: 21
<212> TYPE: DNA
<213> ORGANISM: Homo sapiens

<400> SEQUENCE: 2132
aggagttgga gcagtgagag g                                            21

<210> SEQ ID NO 2133
<211> LENGTH: 20
<212> TYPE: DNA
<213> ORGANISM: Homo sapiens

<400> SEQUENCE: 2133
```
gttggcaaga gtggaagacc                                          20

<210> SEQ ID NO 2134
<211> LENGTH: 20
<212> TYPE: DNA
<213> ORGANISM: Homo sapiens

<400> SEQUENCE: 2134
ccactgtggg agaggctagg                                          20

<210> SEQ ID NO 2135
<211> LENGTH: 20
<212> TYPE: DNA
<213> ORGANISM: Homo sapiens

<400> SEQUENCE: 2135
gagcacctgc ttggtctgag                                          20

<210> SEQ ID NO 2136
<211> LENGTH: 20
<212> TYPE: DNA
<213> ORGANISM: Homo sapiens

<400> SEQUENCE: 2136
aaacgctacc aagggttgtg                                          20

<210> SEQ ID NO 2137
<211> LENGTH: 20
<212> TYPE: DNA
<213> ORGANISM: Homo sapiens

<400> SEQUENCE: 2137
cctacgcagc acaccaatag                                          20

<210> SEQ ID NO 2138
<211> LENGTH: 20
<212> TYPE: DNA
<213> ORGANISM: Homo sapiens

<400> SEQUENCE: 2138
cctacgcagc acaccaatag                                          20

<210> SEQ ID NO 2139
<211> LENGTH: 20
<212> TYPE: DNA
<213> ORGANISM: Homo sapiens

<400> SEQUENCE: 2139
gttccagatg gggagatgag                                          20

<210> SEQ ID NO 2140
<211> LENGTH: 20
<212> TYPE: DNA
<213> ORGANISM: Homo sapiens

<400> SEQUENCE: 2140
gcaaggtcca caaagtgttg                                          20

<210> SEQ ID NO 2141
<211> LENGTH: 19
<212> TYPE: DNA
<213> ORGANISM: Homo sapiens

<400> SEQUENCE: 2141
tggacaacac agcaagacc                                              19

<210> SEQ ID NO 2142
<211> LENGTH: 25
<212> TYPE: DNA
<213> ORGANISM: Homo sapiens

<400> SEQUENCE: 2142
tttcataatc ccatattgaa gacag                                       25

<210> SEQ ID NO 2143
<211> LENGTH: 26
<212> TYPE: DNA
<213> ORGANISM: Homo sapiens

<400> SEQUENCE: 2143
tcccatattg aagacagaaa tagaag                                      26

<210> SEQ ID NO 2144
<211> LENGTH: 23
<212> TYPE: DNA
<213> ORGANISM: Homo sapiens

<400> SEQUENCE: 2144
tgatggagta ttgaaggtag gac                                         23

<210> SEQ ID NO 2145
<211> LENGTH: 20
<212> TYPE: DNA
<213> ORGANISM: Homo sapiens

<400> SEQUENCE: 2145
ccttcagata cggtgtttgc                                             20

<210> SEQ ID NO 2146
<211> LENGTH: 20
<212> TYPE: DNA
<213> ORGANISM: Homo sapiens

<400> SEQUENCE: 2146
ttttgtgatg gtgggttgag                                             20

<210> SEQ ID NO 2147
<211> LENGTH: 20
<212> TYPE: DNA
<213> ORGANISM: Homo sapiens

<400> SEQUENCE: 2147
ggaaagggga gaagcagacc                                             20

<210> SEQ ID NO 2148
<211> LENGTH: 20
<212> TYPE: DNA
<213> ORGANISM: Homo sapiens

<400> SEQUENCE: 2148
tctttgagac cgcctacagc                                             20

<210> SEQ ID NO 2149
<211> LENGTH: 20
<212> TYPE: DNA
<213> ORGANISM: Homo sapiens

```
<400> SEQUENCE: 2149
tctaggacgc ttgcctcttc                                              20

<210> SEQ ID NO 2150
<211> LENGTH: 19
<212> TYPE: DNA
<213> ORGANISM: Homo sapiens

<400> SEQUENCE: 2150
ggagcagagg gagttcctg                                               19

<210> SEQ ID NO 2151
<211> LENGTH: 20
<212> TYPE: DNA
<213> ORGANISM: Homo sapiens

<400> SEQUENCE: 2151
gttctctggg ctgtctacgg                                              20

<210> SEQ ID NO 2152
<211> LENGTH: 18
<212> TYPE: DNA
<213> ORGANISM: Homo sapiens

<400> SEQUENCE: 2152
ctggtcccct gccttttg                                                18

<210> SEQ ID NO 2153
<211> LENGTH: 18
<212> TYPE: DNA
<213> ORGANISM: Homo sapiens

<400> SEQUENCE: 2153
cacctgccct caaaccac                                                18

<210> SEQ ID NO 2154
<211> LENGTH: 18
<212> TYPE: DNA
<213> ORGANISM: Homo sapiens

<400> SEQUENCE: 2154
ctgccctcaa accacctg                                                18

<210> SEQ ID NO 2155
<211> LENGTH: 20
<212> TYPE: DNA
<213> ORGANISM: Homo sapiens

<400> SEQUENCE: 2155
gaagccatct gcacatctcc                                              20

<210> SEQ ID NO 2156
<211> LENGTH: 20
<212> TYPE: DNA
<213> ORGANISM: Homo sapiens

<400> SEQUENCE: 2156
gagccactca caccagagag                                              20

<210> SEQ ID NO 2157
<211> LENGTH: 19
<212> TYPE: DNA
<213> ORGANISM: Homo sapiens
```

```
<400> SEQUENCE: 2157
acagctcctt ccccagcag                                                19

<210> SEQ ID NO 2158
<211> LENGTH: 20
<212> TYPE: DNA
<213> ORGANISM: Homo sapiens

<400> SEQUENCE: 2158
gcttgatgga aggacagcag                                               20

<210> SEQ ID NO 2159
<211> LENGTH: 18
<212> TYPE: DNA
<213> ORGANISM: Homo sapiens

<400> SEQUENCE: 2159
gggcactgct gtcccttg                                                 18

<210> SEQ ID NO 2160
<211> LENGTH: 21
<212> TYPE: DNA
<213> ORGANISM: Homo sapiens

<400> SEQUENCE: 2160
ttaccccgat tttggttaag g                                             21

<210> SEQ ID NO 2161
<211> LENGTH: 19
<212> TYPE: DNA
<213> ORGANISM: Homo sapiens

<400> SEQUENCE: 2161
ttcctggcag caaaatctg                                                19

<210> SEQ ID NO 2162
<211> LENGTH: 20
<212> TYPE: DNA
<213> ORGANISM: Homo sapiens

<400> SEQUENCE: 2162
cccagctaga agagcaaagg                                               20

<210> SEQ ID NO 2163
<211> LENGTH: 21
<212> TYPE: DNA
<213> ORGANISM: Homo sapiens

<400> SEQUENCE: 2163
tcccagctag aagagcaaag g                                             21

<210> SEQ ID NO 2164
<211> LENGTH: 18
<212> TYPE: DNA
<213> ORGANISM: Homo sapiens

<400> SEQUENCE: 2164
gggaagggtc aggggttg                                                 18

<210> SEQ ID NO 2165
<211> LENGTH: 20
<212> TYPE: DNA
```

<213> ORGANISM: Homo sapiens

<400> SEQUENCE: 2165
tccctggctt agattcttgg                                          20

<210> SEQ ID NO 2166
<211> LENGTH: 20
<212> TYPE: DNA
<213> ORGANISM: Homo sapiens

<400> SEQUENCE: 2166
cccaggctaa gggtcttcag                                          20

<210> SEQ ID NO 2167
<211> LENGTH: 20
<212> TYPE: DNA
<213> ORGANISM: Homo sapiens

<400> SEQUENCE: 2167
actgagtgct aatggcgatg                                          20

<210> SEQ ID NO 2168
<211> LENGTH: 20
<212> TYPE: DNA
<213> ORGANISM: Homo sapiens

<400> SEQUENCE: 2168
ggcctccacg aagtacaaag                                          20

<210> SEQ ID NO 2169
<211> LENGTH: 20
<212> TYPE: DNA
<213> ORGANISM: Homo sapiens

<400> SEQUENCE: 2169
atgttcccct tggtgagttg                                          20

<210> SEQ ID NO 2170
<211> LENGTH: 27
<212> TYPE: DNA
<213> ORGANISM: Homo sapiens

<400> SEQUENCE: 2170
cctctctgtc aaataataga tacttcc                                  27

<210> SEQ ID NO 2171
<211> LENGTH: 27
<212> TYPE: DNA
<213> ORGANISM: Homo sapiens

<400> SEQUENCE: 2171
ttgataatga gagtgataaa tagatgg                                  27

<210> SEQ ID NO 2172
<211> LENGTH: 20
<212> TYPE: DNA
<213> ORGANISM: Homo sapiens

<400> SEQUENCE: 2172
agtgtggggt ccaaataacc                                          20

<210> SEQ ID NO 2173
<211> LENGTH: 27

```
<212> TYPE: DNA
<213> ORGANISM: Homo sapiens

<400> SEQUENCE: 2173
caacttagag ttaactaaag ggatttg                                        27

<210> SEQ ID NO 2174
<211> LENGTH: 21
<212> TYPE: DNA
<213> ORGANISM: Homo sapiens

<400> SEQUENCE: 2174
cctggagcac aaaaataatg c                                              21

<210> SEQ ID NO 2175
<211> LENGTH: 20
<212> TYPE: DNA
<213> ORGANISM: Homo sapiens

<400> SEQUENCE: 2175
gcttagcgtt ccaaaaatgg                                                20

<210> SEQ ID NO 2176
<211> LENGTH: 22
<212> TYPE: DNA
<213> ORGANISM: Homo sapiens

<400> SEQUENCE: 2176
ccttatcaag gtgtgtgtct gg                                             22

<210> SEQ ID NO 2177
<211> LENGTH: 18
<212> TYPE: DNA
<213> ORGANISM: Homo sapiens

<400> SEQUENCE: 2177
agggttggtg gtgtctgg                                                  18

<210> SEQ ID NO 2178
<211> LENGTH: 20
<212> TYPE: DNA
<213> ORGANISM: Homo sapiens

<400> SEQUENCE: 2178
cctcccacat cttggtcttc                                                20

<210> SEQ ID NO 2179
<211> LENGTH: 20
<212> TYPE: DNA
<213> ORGANISM: Homo sapiens

<400> SEQUENCE: 2179
agtgaacagc cccatgagag                                                20

<210> SEQ ID NO 2180
<211> LENGTH: 20
<212> TYPE: DNA
<213> ORGANISM: Homo sapiens

<400> SEQUENCE: 2180
ccaaaactca gcctgacctc                                                20

<210> SEQ ID NO 2181
```

```
<211> LENGTH: 20
<212> TYPE: DNA
<213> ORGANISM: Homo sapiens

<400> SEQUENCE: 2181
gtgagccaat ggaaatgagg                                              20

<210> SEQ ID NO 2182
<211> LENGTH: 22
<212> TYPE: DNA
<213> ORGANISM: Homo sapiens

<400> SEQUENCE: 2182
aaatctcatc ttctgggtct gg                                           22

<210> SEQ ID NO 2183
<211> LENGTH: 19
<212> TYPE: DNA
<213> ORGANISM: Homo sapiens

<400> SEQUENCE: 2183
gggctctctt caggacctc                                               19

<210> SEQ ID NO 2184
<211> LENGTH: 20
<212> TYPE: DNA
<213> ORGANISM: Homo sapiens

<400> SEQUENCE: 2184
gggaacaagt gagggtcctg                                              20

<210> SEQ ID NO 2185
<211> LENGTH: 20
<212> TYPE: DNA
<213> ORGANISM: Homo sapiens

<400> SEQUENCE: 2185
ggtccctgaa gctagtgagc                                              20

<210> SEQ ID NO 2186
<211> LENGTH: 21
<212> TYPE: DNA
<213> ORGANISM: Homo sapiens

<400> SEQUENCE: 2186
cacatcagta ggaccctgca c                                            21

<210> SEQ ID NO 2187
<211> LENGTH: 20
<212> TYPE: DNA
<213> ORGANISM: Homo sapiens

<400> SEQUENCE: 2187
atgcccctaa gcacctattg                                              20

<210> SEQ ID NO 2188
<211> LENGTH: 20
<212> TYPE: DNA
<213> ORGANISM: Homo sapiens

<400> SEQUENCE: 2188
atgcatccag atcagtttcg                                              20
```

```
<210> SEQ ID NO 2189
<211> LENGTH: 20
<212> TYPE: DNA
<213> ORGANISM: Homo sapiens

<400> SEQUENCE: 2189
atgccttggt cttggacttc                                                 20

<210> SEQ ID NO 2190
<211> LENGTH: 20
<212> TYPE: DNA
<213> ORGANISM: Homo sapiens

<400> SEQUENCE: 2190
ccatctctga gtgcatggtg                                                 20

<210> SEQ ID NO 2191
<211> LENGTH: 20
<212> TYPE: DNA
<213> ORGANISM: Homo sapiens

<400> SEQUENCE: 2191
accagagcac aagcaatcag                                                 20
```

TYROSINE KINOME

This invention was made using funds from the United States government under grants NIH Award CA 43460 and CA 62924. The U.S. government therefore retains certain rights in the invention according to the terms of the grants.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of cancer genetics and therapeutics. In particular, it relates to genetic changes that affect protein kinase gene families or other gene families. These genetic changes are useful in diagnostic, prognostic, drag discovery, and clinical drug testing applications.

BACKGROUND OF THE INVENTION

Tyrosine kinases (TKs) are central regulators of signaling pathways that control differentiation, transcription, cell cycle progression, apoptosis, motility, and invasion (1). Although genetic alterations in a few TK genes have been linked to human cancer (2), most TK genes have not been directly implicated in tumorigenesis. Additionally, it is not known how many or how often members of the TK gene family are altered in any particular cancer type.

BRIEF SUMMARY OF THE INVENTION

In a first embodiment of the invention a method is provided for detecting mutations involved in cancer. Members of a family of genes in a database of human nucleotide sequences are identified based on homology to a known member of the family. Nucleotide sequence differences in a selected region of each of the members of the family of genes are identified in matched pairs of an individual's cancer cells and normal cells. Such differences identify members of heightened interest. Additional nucleotide sequence differences in the members of heightened interest are determined, either in one or more additional regions outside of the selected region, or in matched pairs of cancer cells and normal cells of additional individuals, or in both.

Another embodiment of the invention provides a method of screening test substances for use as anti-cancer agents. A test substance is contacted with an activated protein kinase selected from the group consisting of: NTRK3, FES, MCCK/MLK4, EPHA3, NTRK2, INSRR, JAK1, PDGFRA, EPHA7, EPHA8, KDR, FGFR1, and ERBB4. Activity of the activated protein kinase is assayed. A test substance which inhibits the activity of the activated protein kinase is a potential anti-cancer agent.

Another embodiment of the invention provides a method of screening test substances for use as anti-cancer agents. A test substance is contacted with a mutated GUCY2F guanylate cyclase. Activity of the mutated GUCY2F guanylate cyclase is assayed. A test substance which increases the activity of the mutated GUCY2F guanylate cyclase is a potential anti-cancer agent.

Another embodiment of the invention provides an isolated, activated protein kinase. The kinase is selected from the group consisting of NTRK3, FES, MCCK/MLK4, GUCY2F, EPHA3, NTRK2, INSRR, JAK1, PDGFRA, EPHA7, EPHA8, KDR, FGFR1, and ERBB4.

Another embodiment of the invention provides an isolated, mutated GUCY2F protein.

Still another embodiment of the invention is a method of categorizing cancers. The sequence of one or more protein kinase family members in a sample of a cancer tissue is determined. The one or more members is selected from the group consisting of NTRK3, FES, MCCK/MLK4, EPHA3, NTRK2, INSRR, JAK1, PDGFRA, EPHA7, EPHA8, GUCY2F, KDR, FGFR1, and ERBB4. A somatic mutation of said one or more protein kinase family members is identified in the cancer tissue. The cancer tissue is assigned to a group based on the presence of the somatic mutation.

BRIEF DESCRIPTION OF THE DRAWINGS

FIG. 3 shows sequence conservation and location of mutations in altered genes. Alignment of amino acid sequences for (FIG. 3A) NTRK3 (SEQ ID NO: 1-5, respectively), (FIG. 3B) FES, NTRK2 and EPHA3 (SEQ ID NO: 6-15, respectively), and (FIG. 3C) MCCK/MLK4 (SEQ ID NO: 16-21, respectively). Conserved residues are indicated by a dot, while nonconserved residues are indicated by a letter. The positions of identified mutations in each gene are highlighted in yellow, while positions of mutations in MET and BRAF are highlighted in blue. Underlined regions represent the activation loop (subdomain VII and VIII).

DETAILED DESCRIPTION OF THE INVENTION

Figure 1A:
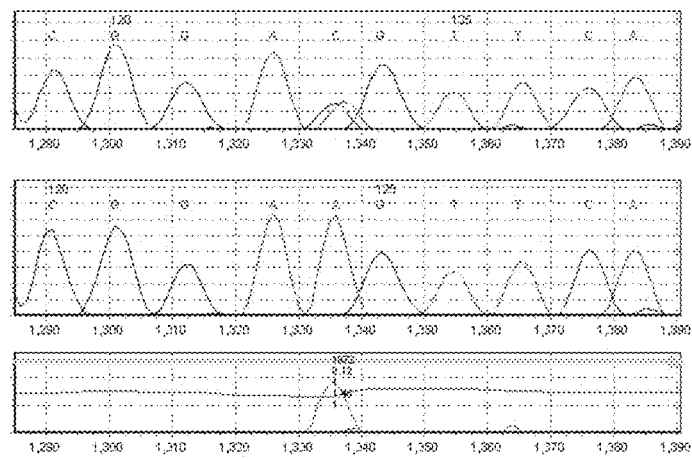
FIG. 1 shows detection of mutations in tyrosine kinase genes. Representative examples of mutations in NTRK3 (FIG. 1A) and MCCK/MLK4 (FIG. 1B) identified using the Mutation Explorer software package (SoftGenetics, State College, Pa.). In each case, the top box contains the sequence chromatogram from tumor DNA, the middle box contains the sequence chromatogram from normal tissue from the same patient, and the lower box contains a computed comparison between the tumor and normal traces displaying a peak at the observed alteration.

Any database can be used in the present invention, whether public, subscription, or proprietary to identify members of a family of genes. Databases can be of nucleotide sequences or protein sequences. They can be of genomic sequences or expressed sequence tags or cDNA sequences. Preferably the sequences are human sequences although the same methods can be used for other species. Homology to a known member may be based on limited portions of the known member, such as a catalytic domain or a regulatory domain. Alternatively homology may be based on the whole protein. Any algorithm or program known in the art can be used. Suitable programs are available publicly and commercially, or they can be made by the individual worker in the art.

Nucleotide sequence differences in a family member can be determined between a sample of cancer cells and normal cells. Cancer and normal cells typically are matched pairs, i.e., they are derived from the same individual and optionally from the same organ. Any technique can be used to determine nucleotide sequence differences. Sequencing of genomic DNA or cDNA can be used. Other techniques which detect differences between two sequences can also be used, without limitation. Techniques which detect differences between the encoded proteins can also be used, since a change in the amino acid of a protein indicates that the nucleotide sequence has been changed.

Selected regions of the family members can be initially screened for nucleotide differences. Any basis for selecting a region can be used. Regions can be selected based on knowledge of mutations in similar regions of other proteins, or based on predictions of particularly important domains of the encoded proteins. Examples of important domains include, but are not limited to catalytic domains and regulatory domains.

One method for determining the functional significance of any mutation which is found is to determine the effect that the mutation has on the encoded protein. A synonymous mutation creates no change in the encoded protein and is sometimes termed silent. Such a mutation is less likely to be functionally relevant to cancer than a non-synonymous mutation. One can determine an encoded protein by identifying an mRNA transcribed from a gene containing a mutation and translating the mRNA (or derived cDNA).

Another method for determining functional significance of a mutation is to determine if the mutation affects an evolutionarily conserved amino acid residue. This can be done by aligning sequences of the same protein from different species and assessing which ones are invariant or predominantly so. The mutation is then compared with this determination of evolutionarily conserved residues to identify if the mutation affects such a residue.

Another method for attributing functional significance to a mutation is to determine if it affects an important domain of the protein. Such domains include but are not limited to catalytic domains and regulatory domains. Another index of functional significance of a new mutation can be found by comparing the amino acid residue affected by the new mutation with equivalent residues in other proteins. If mutations have been found affecting the equivalent residues and those mutations have been determined to be associated with disease, then the new mutation is more likely to be functionally significant. The equivalent mutation may be in the positionally equivalent amino acid residue, or in a close neighbor, perhaps within 5, within 3, within 2, or within 1 residue of the positionally equivalent amino acid residue.

The identified protein kinase family members which have been found to harbor cancer-associated mutations can be used to screen test substances for use as anti-cancer agents. The encoded mutant proteins can be isolated from cells and used in vitro in a cell-free assay. Alternatively, cancer cell lines harboring the mutant protein kinase family members can be used. Cells which have been genetically modified to express the encoded mutant protein can also be used. Regardless of the form in which the mutant protein is presented, it can be contacted with a test substance and the affect on enzymatic activity assessed. If the mutant protein is an activated protein kinase, then test substances will desirably inhibit the activity. If the mutant protein is enzymatically less active than its wild-type cognate, then the test substance will desirably restore activity. Although the family members were selected as being homologous to a tyrosine kinase, all family members are not tyrosine kinases. Some phosphorylate other residues of proteins, such as serine and/or threonine. Others contain inactive kinase domains and have other catalytic domains, such as guanylate cyclase activity. Assays for tyrosine, serine, or threonine kinase activity are well known in the art. See, e.g., the HitHunter™ Enzyme Fragment Complementation Assay of Applied Biosystems, Foster City, Calif., Tyrosine Kinase Assay Kits, (Green or Red) of Panvera, Madison Wis.

Any such assay can be used. Assays for guanylate cyclase are also well known. One commercially availably assay kit which may be used is a cGMP RIA assay (Amersham, Bucks., UK).

An isolated protein, whether an activated protein kinase or a mutant guanylate cyclase can be obtained from cancer cells which express such proteins. Alternatively, they can be obtained from cells which have been genetically modified to express such cancer-specific forms of the protein. Any means for isolating the enzymes from the cells can be used to form a cell-free preparation. Further purification of the enzymes can be used as desired. Any purification methods known in the art can be used without limitation, including immunoaffinity methods and chromatography methods.

Mutations in the kinase family members taught herein can be used to categorize cancers. Such mutations can be identified in cancer tissue and not in corresponding non-cancer tissue of an individual. This pattern indicates that the mutations are somatic mutations. The cancers can be categorized based on the kinase family member which is mutated, based on the particular mutation in the kinase family member, or based on the residue mutated within the family member. Such categorization can be correlated with mortality data to enable prognosis on the basis of the category. Such categorization can be correlated with recurrence data to enable prognosis on the basis of the category. Such categorization can be correlated with efficacy of a therapeutic agent to enable prescription of drugs for individuals with higher probability of successful treatment. Patients can be assigned to clinical trials on the basis of the categorization of their cancers. Correlations of the categories of cancers are not limited by this list.

EXAMPLES

Example 1

Identification of Genes Encoding a Protein Family

Using a combination of hidden Markov models and global homology searches similar to those recently described (3), we identified 98 genes encoding proteins that contained tyrosine kinase domains in the Celera (Rockville, Md.) and public genome databases (4). Seven of these represented previously uncharacterized genes that were identified solely on the basis of sequence similarity to other human tyrosine kinase genes.

Example 2

Initial Screen for Mutations in Catalytic Domain

As an initial screen to evaluate whether these genes were genetically altered in colorectal cancer, we analyzed all exons encoding the predicted kinase domain. This region has been found to harbor the great majority of previously observed tyrosine kinase gene alterations in other cancers (2, 5). A total of 589 exons containing this domain were extracted from genomic databases (6). To identify coding changes in these genes, the identified exons were amplified using polymerase chain reaction on template DNA derived from 35 colorectal cancers and directly sequenced (7). Six of the selected cancer cell lines had deficiencies in mismatch repair (MMR). Inclusion of these cancers allowed identification of genes that might be preferentially implicated in different forms of sporadic colorectal cancer, as was observed with the BRAF kinase (8, 9).

A total of 249 alterations not present in the normal human genome sequence were identified in the cancers. Of these 249, 15 alterations proved to be somatic, while the others were found to be present in normal cells of the same patients.

Figure 1B:
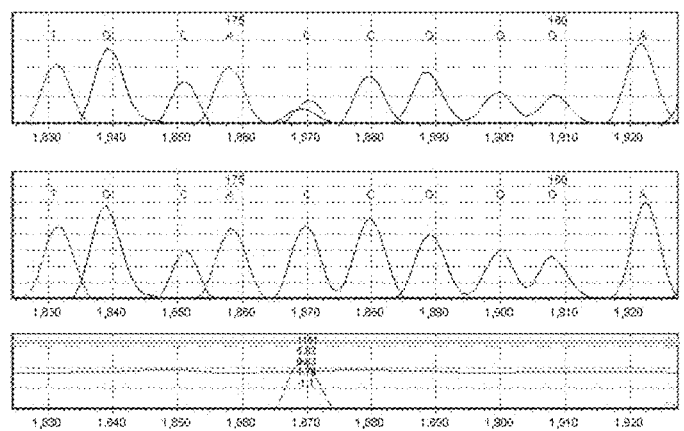

The 15 alterations affected 13 different genes (examples in FIG. 1). One MMR-deficient and one MMR proficient tumor were observed to have mutations in the TGF-β receptor Type II (TGFBR2) gene. These comprised two different transitions affecting the same codon, C to T change at nucleotide position 1582 resulting in a R528C substitution, and G to A at 1583 resulting in a R528H substitution. As the prevalence of mutations in the kinase domain of TGFBR2 is known to be quite rare (10, 11), these data indicated that our methods were sufficiently sensitive to detect mutations even when present at low frequencies.

Example 3

Expanded Screen for Mutations in Other Cancers and/or Domains

The 12 remaining mutant genes were further analyzed for mutations in another 155 colorectal cancers. Two or more additional mutations were found in only four of the genes, and all coding exons of these four genes were then analyzed in all 190 cancers (12). We thereby identified a total of 42 non-synonymous mutations (Table 1). There were six mutations in the neurotrophic receptor NTRK3, four in the feline sarcoma oncogene (FES), ten in the guanylate cyclase 2F gene (GUCY2F), and ten in a predicted tyrosine kinase like gene with no known function, hereafter called MCCK/MLK4. Two additional genes, EPHA3 and NTRK2, had two alterations each (Table 1). Seven of ten mutations in GUCY2F, which is on the X chromosome, were homozygous, while 29 of the 34 alterations in the remaining genes were heterozygous. All of these mutations were shown to be somatic in the cancers that could be assessed; in three of the 42 cases, no normal tissue was available for comparison.

TABLE 1

Mutations observed in the tyrosine kinome

| Gene | Celera Accession | Genbank Accession | Number of Mutations* | Nucleotide | Amino acid[+] | Residue Properties[‡] |
|---|---|---|---|---|---|---|
| NTRK3 | hCT17758 | NM_002530 | 6 | A2083G | I695V | C, K, M |
| | | | | G1822A | G608S | K, M |
| | | | | C2278A | L760I | C, K |
| | | | | A2195C | K732T | K |
| | | | | G2192A | R731Q | K |
| | | | | G2192A | R731Q | K |
| FES | hCT23770 | NM_002005 | 4 | A2110G | M704V | C, K, M |
| | | | | G2117A | R706Q | C, K, M |
| | | | | G2227A | V743M | C, K |
| | | | | C2283T | S759F | C, K |
| MCCK/MLK4 | hCT6856 | NM_032435 | 10 | C781T | H261Y | C, K |
| | | | | C783G | H261Q | C, K |
| | | | | G872A | G291E | C, K, M |
| | | | | C878A | A293E | C, K, M |
| | | | | G888A | W296STP | K |
| | | | | C1408T | R470C | C |
| | | | | C1408T | R470C | C |
| | | | | C1657T | R553Stp | C |
| | | | | A1787T | N596I | C |
| | | | | A1885G | K629E | |
| GUCY2F | hCT11696 | NM_001522 | 10 | G673T | D225Y | |
| | | | | G1078A | A360T | C |
| | | | | A1083T | Q361H | |
| | | | | C1170A | F390L | C |
| | | | | G1475A | R492H | C |
| | | | | A1635T | R545S | K |
| | | | | A1872T | E624D | C, K |
| | | | | A2333G | E778G | K |
| | | | | +2T > C | Splice site* | |
| | | | | G3226A | V1026M | C |
| TGFBR2 | hCT17988 | NM_003242 | 2 | C1582T | R528C | C, K |
| | | | | G1583A | R528H | C, K |
| EPHA3 | hCT23516 | NM_005233 | 2 | T2374C | S792P | K |
| | | | | G2416A | D806N | C, K |
| NTRK2 | hCT18879 | NM_006180 | 2 | C2084T | T695I | C, K |
| | | | | G2251A | D751N | C, K |
| INSRR | hCT31077 | XM_043563 | 1 | C2863T | T985M | C, K |
| JAK1 | hCT13272 | NM_002227 | 1 | A2656A | E886K | K |
| PDGFRA | hCT13252 | NM_006206 | 1 | +1G > A | Splice site* | K |
| EPHA7 | hCT23587 | NM_004440 | 1 | G2303T | S768I | K |
| EPHA8 | hCT31226 | NM_020526 | 1 | G2617A | D873N | C, K |
| ERBB4 | hCT6470 | NM_005235 | 1 | C3090G | I1030M | K |

*Number of mutations observed in panel of 190 colorectal cancers. For TGFBR2 only the initial panel of 36 tumors was analyzed for mutations.
[+]Amino acid change resulting from mutation. Splice site alterations affected position 2 of the donor splice site of exon 17 of GUCY2F, and position 1 of the donor site of exon 15 of PDGFRA.
[‡]C, residue is evolutionarily conserved, K, residue is within kinase domain, M, mutation of equivalent residue in other kinases is disease causing.

Example 4

Evidence of Functional Relevance of Mutations

One of the most difficult issues confronting the sequence analysis of cancer genomes is the distinction between functionally relevant and "passenger" mutations. Each of the clonal expansions driving the neoplastic process leads to fixation of any mutation that had previously occurred in the clone's-progenitor cell, whether or not the mutation was responsible for the clonal expansion. Several observations support the hypothesis that the six genes mutated more than once among the tumors in our cohort (NTRK3, FES, MCCK/MLK4, GUCY2F, EPHA3, NTRK2) were functional rather than coincidental.

The first observation involved comparison of synonymous vs. non-synonymous alterations identified during sequencing. Synonymous mutations are likely to be passengers, as they would not be expected to exert a selective growth advantage. Only one somatic synonymous mutation was identified in these six genes, yielding a N:S (non-synonymous:synonymous) ratio of 34:1, far higher than the N:S ratio of 2:1 predicted for non-functional mutations ($p<1\times10^{-4}$).

Figure 2:
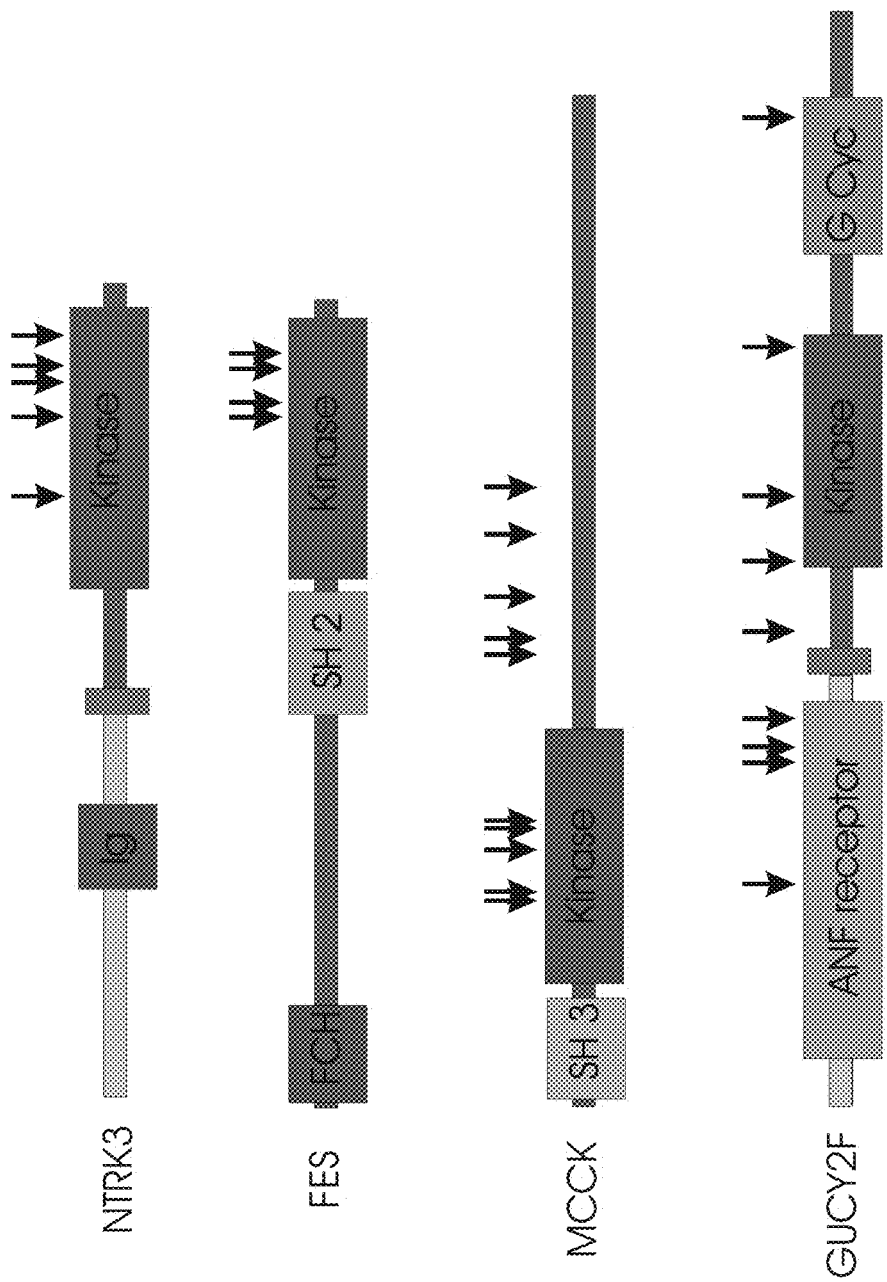
FIG. 2 shows distribution of mutations in NTRK3, FES, MCCK/MLK4 and GUCY2F. Arrows indicate location of mutations while boxes represent functional domains.

Second, most of the non-synonymous mutations identified in these genes occurred in conserved residues in key regions in the kinase domain (Table 1, examples in FIG. 2). All mutated residues in FES, two of six mutated residues in NTRK3, eight of ten mutated residues in MCCK/MLK4, five of ten mutated residues in GUCY2F, both mutated residues in NTRK2, and one of two mutated residues in EPHA3 were identical in all species analyzed. Based on comparisons to related tyrosine kinase genes (13, 14), these alterations were predicted to affect residues in functionally important regions of the kinase domain. In NTRK3, three alterations were located in two subdomains predicted to affect kinase activity: the I695V alteration was localized in subdomain VII, while the cluster of R732Q and K733T mutations was directly adjacent to subdomain VIII. These subdomains comprise the activation loop, normally responsible for autoinhibition of tyrosine kinase activity (13, 14). An additional substitution in FES (R706Q), two alterations in MCCK/MLK4 (G291E, A293E), and an alteration in EPHA3 (S792P) also occurred in the activation loop. Mutations in the activation loop have been shown to lead to ligand-independent tyrosine kinase activation in other genes by relief of the autoinhibitory function of these domains (2). Identical alterations at equivalent residues in NTRK2 (D751N) and EPHA3 (D806N), as well as an alteration in FES (V743M) were in subdomain IX, a region known to stabilize the catalytic loop. Finally, two substitutions in MCCK/MLK4 at position 261 were located in subdomain VIB, the catalytic loop of the kinase domain, but did not affect the invariant aspartate and asparagine residues required for phosphoryl transfer.

Many of the mutations we detected corresponded to those previously shown to be functionally mutated in other protein kinase genes (15) (Table 1, examples in FIG. 3). In NTRK3, the I695V mutation corresponded to a homologous position in the MET oncogene that is altered in renal cell carcinoma (5), while G608S represented an equivalent residue that is affected in the RET oncogene in Hirschsprung's disease (16). Two mutations in FES, M704V and R706Q, and two mutations in MCCK/MLK4 corresponded to or were just adjacent to residues that are altered in the BRAF oncogene in a variety of cancers (6), and are in a region surrounded by three previously reported mutations in MET in renal cell carcinoma (5). Additionally, one mutation in EPHA3 (S792P) was just adjacent to a previously reported alteration in MET in renal cell and hepatocellular carcinomas (5). No mutations in GUCY2F corresponded to alterations in other protein kinase genes, but two alterations (E596K and V1026M) were located near equivalent mutations of the homologous GUCY2D gene that is inactivated in Leber's congenital amaurosis (17).

It was of interest to compare the non-synonymous alterations in these six genes with the three synonymous mutations that were discovered in the study (one in the six genes noted above and two others identified during the sequencing of other tyrosine kinase genes). None of the 3 synonymous mutations occurred in residues that had previously been shown to be functionally altered in other cancers or inherited conditions. Moreover, the prevalence of these synonymous mutations, calculated to be 1.1 alterations per Mb (95% confidence interval 0.23 to 3.3 alterations per Mb) was consistent with previous estimates of the prevalence of nonfunctional alterations in tumor DNA (18). In contrast, the prevalence of non-synonymous alterations in the kinase domain of the six analyzed genes was estimated to be significantly higher at 55 alterations per Mb (95% confidence interval 33 to 85 alterations per Mb; $p<0.001$). We conclude that the three synonymous mutations observed were likely to be passengers while the 34 non-synonymous mutations identified among six genes were likely to be functional.

Based on their positions and analogous mutations in homologous genes, the majority of alterations we observed are expected to act in a dominant fashion, leading to increased kinase activity. In this respect, the observation of nonsense alterations in MCCK/MLK4 is not unprecedented. Truncations in Src and Met resulting in constitutively active kinase activity have been previously reported (19, 20). Interestingly, MCCK/MLK4 contains an SH3 domain whose homolog has been shown to autoinhibit kinase activity (21). Such kinase autoinhibition would be relieved by the nonsense codons between the kinase and SH3-binding domains at the C-terminus that we observed in two cancers.

Example 5

Significance

This study represents the first systematic mutational analysis of any gene family in a human cancer. Despite decades of research on tyrosine kinase genes, only a few of the genes we had found mutated had been previously linked to tumorigenesis. A fusion gene of NTRK3 with ETV6 has been identified in congenital fibrosarcoma (22), and neurotrophin ligands, including those for NTRK2 and NTRK3, appear to stimulate the invasive behavior of at least several cancer types (23, 24). The v-fes transforming oncogene was identified as a causative agent of feline and avian sarcomas (25), but its human equivalent (FES) has not been found to be altered in any human neoplasia. A homolog of MCCK/MLK4, MLK3, as well as a homolog of EPHA3, EPHA1, have transforming abilities in NIH3T3 cells (26, 27), but their roles in tumorigenesis are otherwise unknown. GUCY2F has only been known to function in light-mediated signal transduction in photoreceptor cells of the retina (28), and had not been thought to play a role in any tissue outside the eye. Using quantitative PCR, we found that all four commonly mutated genes, including GUCY2F, were expressed in both primary cancers as well as cell lines derived from the colon (29).

One reason for attempting to identify tyrosine kinase mutations is that the altered proteins provide attractive targets for therapeutic intervention. This has been convincingly demonstrated with ST1571 in patients with chronic myelogenous leukemia (30). The number of colorectal cancer patients with mutations in the six tyrosine kinase genes noted above outnumbers the number of patients with CML or with any cancer type previously associated with tyrosine kinase mutations. These results thereby provide substantial new opportunities for drug development. Moreover, future investigation of the pathways through which these kinases act in colorectal cancer may yield new insights into pathogenesis as well as additional drug targets. Personalized therapeutics can be based on the kinases that are mutationally activated in an individual's cancer. Finally, the large scale sequencing-based approach we used to find novel gene mutations can readily be applied to other enzyme-encoding genes in any common tumor type.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

REFERENCES AND NOTES

1. T. Hunter, *Philos Trans R Soc Lond B Biol Sci* 353, 583-605. (1998).
2. P. Blume-Jensen, T. Hunter, *Nature* 411, 355-65. (2001).
3. G. Manning, D. B. Whyte, R. Martinez, T. Hunter, S. Sudarsanam, *Science* 298, 1912-34. (2002).
4. All annotated genes present in the draft human genome sequence (CHGD Assembly 25H, Jun. 19, 2001) were initially analyzed using both hidden Markov models and global homology searches using the Panther protein classification system (world wide web domain name: celera, top level domain name: com) to identify protein families of receptor and non-receptor tyrosine kinases. To eliminate potential artifactual clustering of related proteins lacking a kinase domain in these families, all identified proteins were further analyzed by blast analysis against the catalytic domain of the SRC protooncogene. From this analysis, only those proteins showing similarities with an E score of <1.times.10.sup.-14 were retained. All identified tyrosine kinase genes are available in Supplemental Table 1.
5. A. Danilkovitch-Miagkova, B. Zbar, *J Clin Invest* 109, 863-7. (2002).
6. Sequences for all available annotated exons and adjacent intronic sequences of identified TK genes were extracted from Celera draft human genome sequence (CHGD Assembly 25H, Jun. 19, 2001) or from Genbank (world wide web domain name: genbank.nlm.nih, top level domain name: gov). All exons encoding the catalytic domain of each kinase were identified by pairwise homology analyses to canonical tyrosine kinase catalytic domains.
7. Primers for PCR amplification and sequencing were designed using the Primer 3 program (world wide web sub-domain name: www domain name: genome.wi.mit, top level domain name: edu folder: cgi-bin/primer/primer3_www.cgi), and were synthesized by MWG (High Point, N.C.) and IDT (Coralville, Iowa). PCR amplification and sequencing were performed on tumor DNA from early passage cell lines as previously described (18) using 384 capillary automated sequencing apparatuses (Spectrumedix, State College, Pa.). Of the 589 exons extracted, 556 (94%) were successfully analyzed, each in an average of 33 tumor samples. Sequence traces were assembled and analyzed to identify potential genomic alterations using Mutation Explorer software package (SoftGenetics, State College, Pa.). Sequences of all primers used for PCR amplification and sequencing are available in Supplemental Table 2.
8. H. Davies et al., *Nature* (Jun. 9, 2002).
9. H. Rajagopalan et al., *Nature* 418, 934. (2002).
10. W. M. Grady et al., *Cancer Res* 59, 320-4 (1999).
11. S. J. Kim, Y. H. Im, S. D. Markowitz, Y. J. Bang, *Cytokine Growth Factor Rev* 11, 159-68. (2000).
12. All available annotated exons and adjacent intronic regions were extracted for NTRK3, FES, GUCY2F and MCCK from the Celera draft human genome sequence (CHGD Assembly 25H, Jun. 19, 2001). Tumor DNA from 142 MMR proficient and 48 MMR deficient early-passage colorectal cancer cell lines passaged in vitro or as xenografts in nude mice were analyzed for each exon.
13. S. K. Hanks, T. Hunter, *Faseb J* 9, 576-96. (1995).
14. S. R. Hubbard, J. H. Till, *Annu Rev Biochem* 69, 373-98. (2000).
15. Altered tyrosine kinase genes identified were aligned to other protein kinase genes using CLUSTAL and identified alterations were compared to previously observed mutations reported in the literature or at the Human Gene Mutation Database at Cardiff University (world wide web domain name: archive.uwcm.ac, top level domain name: uk folder: uwcm/mg/hgmd0.html).
16. M. Sancandi et al., *J Pediatr Surg* 35, 139-42; discussion 142-3. (2000).
17. I. Perrault et al., *Eur J Hum Genet* 8, 578-82. (2000).
18. T. L. Wang et al., *Proc Natl Acad Sci USA* 99, 3076-80. (2002).
19. R. B. Irby et al., *Nat Genet* 21, 187-90. (1999).
20. V. Wallenius et al., *Am J Pathol* 156, 821-9. (2000).
21. H. Zhang, K. A. Gallo, *J Biol Chem* 276, 45598-603. (2001).
22. S. R. Knezevich, D. E. McFadden, W. Tao, J. F. Lim, P. H. Sorensen, *Nat Genet* 18, 184-7. (1998).
23. S. J. Miknyoczki et al., *Int J Cancer* 81, 417-27. (1999).
24. D. Marchetti, D. J. McQuillan, W. C. Spohn, D. D. Carson, G. L. Nicolson, *Cancer Res* 56, 2856-63. (1996).
25. B. Scheijen, J. D. Griffin, *Oncogene* 21, 3314-33. (2002).
26. J. Hartkamp, J. Troppmair, U. R. Rapp, *Cancer Res* 59, 2195-202. (1999).
27. M. Nakamoto, A. D. Bergemann, *Microsc Res Tech* 59, 58-67. (2002).
28. K. A. Lucas et al., *Pharmacol Rev* 52, 375-414. (2000).
29. Total RNA was isolated from two primary colorectal cancers and two colorectal cancer cell lines using RNAgents (Promega, Madison, Wis.) and mRNA was selected using the MessageMaker Reagent Assembly (Gibco BRL). Single-stranded cDNA was generated using Superscript II Reverse Transcriptase (Gibco BRL) following the manufacturer's directions. Mock template preparations were prepared in parallel without the addition of reverse transcriptase. Quantitative PCR was performed with an iCycler (Bio-Rad, Hercules, Calif.) using SYBR Green dye (Molecular Probes, Eugene, Oreg.), as previously described (31).
30. B. J. Druker, *Cancer Cell* 1, 31-6. (2002).
31. S. Saha et al., *Science* 294, 1343-6 (Nov. 9, 2001).

We claim:

1. A method of screening test substances and identifying potential anti-cancer agents, comprising:
contacting a test substance with protein kinase MLK4, wherein the protein kinase MLK4 has a mutation selected from the group consisting of H261Y, H261Q, G291E, A293E, W296STP, R470C, R553Stp, N596I, and K629E;
testing activity of the protein kinase;
identifying a test substance which inhibits the activity of the protein kinase as a potential anti-cancer agent; and
testing the test substance for anti-cancer activity in a cancer cell that has an MLK4 mutation.

2. The method of claim 1 wherein the protein kinase is MLK4 protein kinase with a H261Y mutation.

3. The method of claim 1 wherein the protein kinase is MLK4 protein kinase with a H261Q mutation.

4. The method of claim 1 wherein the protein kinase is MLK4 protein kinase with a G291E mutation.

5. The method of claim 1 wherein the protein kinase is MLK4 protein kinase with a A293E mutation.

6. The method of claim 1 wherein the protein kinase is MLK4 protein kinase with a W296STP mutation.

7. The method of claim 1 wherein the protein kinase is MLK4 protein kinase with a R470C mutation.

8. The method of claim 1 wherein the protein kinase is MLK4 protein kinase with a R553Stp mutation.

9. The method of claim 1 wherein the protein kinase is MLK4 protein kinase with a N596I mutation.

10. The method of claim 1 wherein the protein kinase is MLK4 protein kinase with a K629E mutation.

11. The method of claim 2 wherein the potential anti-cancer agent is identified as a potential anti-cancer agent for a cancer that has a MLK4 H261Y mutation.

12. The method of claim 3 wherein the potential anti-cancer agent is identified as a potential anti-cancer agent for a cancer that has a MLK4 H261Q mutation.

13. The method of claim 4 wherein the potential anti-cancer agent is identified as a potential anti-cancer agent for a cancer that has a MLK4 G291E mutation.

14. The method of claim 5 wherein the potential anti-cancer agent is identified as a potential anti-cancer agent for a cancer that has a MLK4 A293E mutation.

15. The method of claim 6 wherein the potential anti-cancer agent is identified as a potential anti-cancer agent for a cancer that has a MLK4 W296Stp mutation.

16. The method of claim 7 wherein the potential anti-cancer agent is identified as a potential anti-cancer agent for a cancer that has a MLK4 R470C mutation.

17. The method of claim 8 wherein the potential anti-cancer agent is identified as a potential anti-cancer agent for a cancer that has a MLK4 R553Stp mutation.

18. The method of claim 9 wherein the potential anti-cancer agent is identified as a potential anti-cancer agent for a cancer that has a MLK4 N561I mutation.

19. The method of claim 10 wherein the potential anti-cancer agent is identified as a potential anti-cancer agent for a cancer that has a MLK4 K629E mutation.

20. The method of claim 1 wherein the protein kinase is in a cell.

21. The method of claim 1 wherein the protein kinase is isolated from a cell.

22. The method of claim 1 wherein the protein kinase is in a cell of a cancer cell line.

23. The method of claim 1 wherein the protein kinase is in a cell which has been modified to express the protein kinase.

24. The method of claim 1 wherein the cancer cell is a cancer cell line.

25. The method of claim 1 wherein the cancer cell is a human cancer cell.

26. The method of claim 1 wherein the potential anti-cancer agent is identified as a potential anti-cancer agent for a cancer that expresses a mutant MLK4.

27. The method of claim 1 wherein the potential anti-cancer agent is identified as a potential anti-colorectal cancer agent.

28. A method of screening test substances and identifying potential anti-cancer agents, comprising:
contacting a test substance with protein kinase MLK4, wherein the protein kinase MLK4 has a mutation selected from the group consisting of H261Y, H261Q, G291E, A293E, W296STP, R470C, R553Stp, N596I, and K629E;
testing activity of the protein kinase; and
testing the test substance for anti-cancer activity in a cancer cell that has an MLK4 mutation.

* * * * *